US007871611B2

(12) United States Patent
Calzone et al.

(10) Patent No.: US 7,871,611 B2
(45) Date of Patent: Jan. 18, 2011

(54) COMPOSITIONS AND METHODS RELATING TO ANTI IGF-1 RECEPTOR ANTIBODIES

(75) Inventors: Frank J. Calzone, Westlake Village, CA (US); Rajendra V. Deshpande, Thousand Oaks, CA (US); Mei-Mei Tsai, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 1413 days.

(21) Appl. No.: 11/313,209

(22) Filed: Dec. 20, 2005

(65) Prior Publication Data
US 2009/0285824 A1 Nov. 19, 2009

Related U.S. Application Data

(60) Provisional application No. 60/638,961, filed on Dec. 22, 2004.

(51) Int. Cl.
*A61K 39/395* (2006.01)
*A61K 39/00* (2006.01)
*C12P 21/08* (2006.01)

(52) U.S. Cl. .............. 424/130.1; 424/133.1; 424/135.1; 424/141.1; 424/142.1; 424/143.1; 530/387.1; 530/387.3; 530/388.1; 530/388.15; 530/388.22

(58) Field of Classification Search ........................ None
See application file for complete search history.

(56) References Cited

U.S. PATENT DOCUMENTS

| 6,084,085 | A  |   | 7/2000  | Baserga |  |
|---|---|---|---|---|---|
| 6,300,129 | B1 |   | 10/2001 | Lonberg |  |
| 6,403,764 | B1 |   | 6/2002  | Dubaquie |  |
| 7,020,563 | B1 |   | 3/2006  | Bentley |  |
| 7,037,498 | B2 |   | 5/2006  | Cohen |  |
| 7,147,851 | B1 | * | 12/2006 | Ponath et al. | ............ 424/133.1 |
| 7,217,796 | B2 |   | 5/2007  | Wang |  |
| 7,241,444 | B2 | * | 7/2007  | Goetsch et al. | .......... 424/130.1 |
| 7,378,503 | B2 | * | 5/2008  | Graus et al. | ............. 530/387.1 |
| 7,521,053 | B2 | * | 4/2009  | Oliner | .................... 424/155.1 |
| 2003/0092631 | A1 |   | 5/2003  | Deshayes |  |
| 2003/0165502 | A1 |   | 9/2003  | Fujita-Yamaguchi |  |
| 2003/0235582 | A1 |   | 12/2003 | Singh |  |
| 2004/0018191 | A1 |   | 1/2004  | Wang |  |
| 2004/0086503 | A1 |   | 5/2004  | Cohen |  |
| 2004/0202655 | A1 |   | 10/2004 | Morton |  |
| 2004/0228859 | A1 |   | 11/2004 | Graus |  |
| 2004/0265307 | A1 |   | 12/2004 | Singh |  |
| 2005/0008642 | A1 |   | 1/2005  | Graus |  |
| 2005/0059021 | A1 |   | 3/2005  | Farid |  |
| 2005/0084906 | A1 |   | 4/2005  | Goetsch |  |
| 2005/0136063 | A1 |   | 6/2005  | Wang |  |
| 2005/0147612 | A1 |   | 7/2005  | Yayon |  |
| 2005/0186203 | A1 |   | 8/2005  | Singh |  |
| 2005/0244408 | A1 |   | 11/2005 | Cohen |  |
| 2005/0249728 | A1 |   | 11/2005 | Singh |  |
| 2005/0249730 | A1 |   | 11/2005 | Goetsch |  |

| 2005/0272637 | A1 | 12/2005 | Clinton |
|---|---|---|---|
| 2006/0040358 | A1 | 2/2006  | Ligensa |

FOREIGN PATENT DOCUMENTS

| EP | 463151 A1 | 6/1996 |
|---|---|---|
| EP | 1054018 A1 | 11/2000 |
| WO | WO90/00562 A1 | 1/1990 |
| WO | WO93/17105 A1 | 9/1993 |
| WO | WO96/33735 A1 | 10/1996 |
| WO | WO99/28347 A1 | 6/1999 |
| WO | WO99/60023 A1 | 11/1999 |
| WO | WO02/053596 A2 | 7/2002 |
| WO | WO02/072780 S2 | 9/2002 |
| WO | WO02/102973 A2 | 12/2002 |
| WO | WO03/059951 A2 | 7/2003 |
| WO | WO03/100008 A2 | 12/2003 |
| WO | WO03/106621 A2 | 12/2003 |
| WO | WO2004/050850 A2 | 12/2003 |
| WO | WO2004/071529 A2 | 8/2004 |
| WO | WO2004/083248 C2 | 9/2004 |
| WO | WO2004/087756 A2 | 10/2004 |
| WO | WO2005/005635 A2 | 1/2005 |
| WO | WO2005/016967 A2 | 2/2005 |
| WO | WO2005/016970 A2 | 2/2005 |

(Continued)

OTHER PUBLICATIONS

Brown et al, J Immunol 156(9): 3285-91, May 1996.*
Barrios et al, J Molecular Recognition 17: 332-338, 2004.*
Vajdos et al, J Mol Biol 320(2): 415-428, Jul. 5, 2002.*
Caldas et al, Mol. Immunol. 39 (15): 941-952, May 2003.*
Aburatani et al., "Importance of a CDR H3 basal residue in VH/VL interaction of human antibodies." J. Biochem., 2002, 132(5):75-782.
Adams et al., "Structure and function of the type 1 insulin-like growth factor receptor" Cell. Mol. Life Sci., 2000, 57:1050-1093.
Arteaga et al., 1989, Cancer Res 49 :6237-6241.
Arteaga et al., 1989, J Clinical Investigation 84:1418-1423.

(Continued)

*Primary Examiner*—Phuong Huynh
(74) *Attorney, Agent, or Firm*—Nathan A. Machin

(57) ABSTRACT

The present invention provides compositions and methods relating to or derived from anti-IGF-1R antibodies. In particular embodiments, the invention provides fully human, humanized, or chimeric anti-IGF-1R antibodies that bind human IGF-R, IGF-1R-binding fragments and derivatives of such antibodies, and IGF-1R-binding polypeptides comprising such fragments. Other embodiments provide nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having IGF-1R-related disorders or conditions.

16 Claims, 32 Drawing Sheets

FOREIGN PATENT DOCUMENTS

| | | |
|---|---|---|
| WO | WO2005/052005 A1 | 6/2005 |
| WO | WO2005/058967 A2 | 6/2005 |
| WO | WO2005/061541 A1 | 7/2005 |
| WO | WO2005/112969 A2 | 12/2005 |
| WO | WO2006/068953 A2 | 12/2005 |
| WO | WO2006/013472 A2 | 2/2006 |
| WO | WO2006/047639 A2 | 5/2006 |
| WO | WO03/027246 A2 | 10/2009 |
| WO | WO2005/026386 A1 | 10/2009 |

OTHER PUBLICATIONS

Bartucci Monica et al. "Differential insulin-like growth factor 1 receptor signaling and function in estrogen receptor (ER)-positive MCF-7 and ER-negative MDA-MB-231 breast cancer cells." 2001, Cancer Res. 61(18):6747-6754.
Brunner et al., "Effect of Endocrine Therapy on Growth of T61 Human Breast Cancer Xenografts is Directly Correlated to Specific Down-regulation of IGF-II" 1993, Euro J Cancer 29A:562-569.
Burtrum et al., 2003, Cancer Research 63:8912-8921.
C. Mitsiades et al. "The IGF/IGF-1R system is a major therapeutic target for multiple myeloma, other hematologic malignancies and solid tumors" 2002, Blood, 100(11):170A.
C. Mitsiades et al. "Gene expression and proteomic profiling of multiple myeloma (MM) cells co-cultured with bone marrow (BM) stromal cells or stimulated with BM-derived cytokines: Implications for therapeutic targeting of the BM milieu in MM." 2002, Blood, 100(11):811A.
Conover et al., 1987, J Cell Physiol 133:560-566.
Cullen et al., "Insulin-like growth factor receptor expression and function in human breast cancer." 1990, Cancer Res 50(1): 48-53.
Cullen et al., "Insulin-Like Growth Factor-II Overexpression in MCF-7 Cells Induces Phenotypic Changes Associated with Malignant Progression" 1992, Mol Endocrinol 6:91-100.
Fishwild et al. "High-avidity human IgGk monoclonal antibodies from a novel strain of minilocus transgenic mice." 1996, Nature Biotechnology 14(7):845-851.
Database EPO Proteins Aug. 6, 2002, EBI accession No. EPOP:AX470348. Database accession No. AX470348.
De Haard et al. 1999, J Biological Chemistry, 274:26 pp. 18218-18230.
De Meyts et al., 2002, Nature Reviews 1:769-783.
Elagib et al. "Immunoglobulin variable genes and epitope recognition of human monoclonal anti-Ro 52-kd in primary Sjögren's syndrome." 1999, Arthritis and Rheumatism, 42(11):2471-2481.
Emery et al. Expert Opinion on Investigational Drugs 3(3):241-251 (Mar. 1994).
Flier et al., 1986, Proc Natl Acad Sci USA 83:664-668.
Furlanetto et al., 1993, Cancer Res 53:2522-2526.
Gansler et al., 1989, American J Pathol 135:961-966.
Garrett et al. "Crystal Structure of the first 3 domains of the type-1 insulin-like growth factor-1 receptor" 1998, Nature, 394(Jul.):395-399.
Gustafson et al., 1990, J Biol Chem 265:18663-18667.
Hailey et al., 2002, Mol Cancer Therapeutics 1 :1349-1353.
Happerfield et al. "The localization of the insulin-like growth factor receptor 1 (IGFR-1) in benigh and malignant breast tissue." 1997, J. Pathology, 183:412-417.
Harumi et al. "Cloning of porcine IGF1 receptor cDNA and detection of sequence polymorphisms using TR-PCR." 2001, Animal Genetics, 32(6):387 right column, lines 17-19; and p. 388 left column, line 3 to right col. line 1.
Hekimi et al. "Molecular genetics of life span in *C. elegans*: how much does it teach us?" 1998, TIG 14(1):14-20.
Hermanto et al., 2000, Cell Growth & Differentiation 11:12, p. 659.
Holzenberger et al. "IGF-1 receptor regulates lifespan and resistance to oxidative stress in mice." 2003, Nature, 421 (6919):182-187.
Hsin et al. "Signals from reproductive system regulate the life span of *C. elegans*." 1999, Nature 399:pp. 362-366.
Jansson et al., 1997, J Biol Chem 272:8189-8197.
Kalebic et al., 1994, Cancer Res 54:5531-5534.
Karavitaki et al., 2004, Hormones 3:27-36.
Kull et al., 1983, J Biol Chem 258:6561-6566.
Lahm et al., 1994, Intl J Cancer 58 :452-459.
Li et al., 1993, Biochem Biophys Res Comm 196:92-98.
Li et al., 2000, Cancer Immunol Immunotherapy 49:243-252.
Logie et al., 1999, J Mol Endocrinol 23 :23-32.
Lu Dan et al. "Simultaneous blockade of both the epidermal growth factor receptor and the insulin-like growth factor receptor signaling pathways in cancer cells with a fully human recombinant bispecific antibody." 2004, J. Biol. Chem. 279(4):2856-2865.
Lu Yuhong et al. "Insulin-like growth factor-1 receptor signaling and resistance to trastuzumab (Herceptin)" 2001, J. the Nat Cancer Inst 93(24):1852-1857.
Maloney et al., 2003, Cancer Research 63:5073-5083.
McKern NM et al. "Crystallization of the first 3 domains of the human insulin-like growth factor-1 receptor" 1997, Protein Science No. 6, pp. 2663-2666.
Pillutla et al., J. Biol. Chem., 2002, 277(25), pp. 22590-22594.
Rohlik et al., 1987, Biochem Biophys Res Comm, 1987, v149, pp. 276-281.
Rubini et al., Experimental Cell Res, 1999, v251, pp. 22-32.
Sachdev D. et al., Cancer Res, 2003, v63, p. 627-635.
Shamieh et al., FEBS Letters, 2004, v568, pp. 163-166.
Soo et al., J Biol Chem, 1992, v267, pp. 12955-12963.
Steele-Perkins et al., Biochem Biophys Res Comm, 1990, v171, pp. 1244-1251.
Stephen R. et al., J Biol Chem, 2001, 276(43), pp. 40080-40086.
Surmacz, Onocgene, 2003, v22, pp. 6589-6597.
Tissenbaum et al., Genetics, 1998, v148, pp. 703-717.
Ullrich et al., EMBO Journal, 1986, 5(10), pp. 2503-2512.
Vajdos et al., Biochemistry, 2001, 40(37), pp. 11022-11029.
Vanraden et al., J. Dairy Sci., 1993, v76, pp. 2758-2764.
Vaughan T J et al., Nature Biotechnology, 1996, 14(1), pp. 309-314.
Xiong et al., Proc Natl Acad Sci USA, 1992, v89, pp. 5356-5360.
Ye J. et al., Horm Metab Res, 2003, v35, pp. 836-842.
Zhang H et al., Expert Opinion on Investigational Drugs, 2004, 13(12), pp. 1569-1577.
Zia et al., J. Cell Biochem Supp., 1996, v24, pp. 269-275.
Scotlandi et al., Cancer Res., 2006, v58, pp. 4127-4131.

\* cited by examiner

FIG. 1A

L1 (SEQ ID NO:1)
```
     GAT GTTGTGATGA CTCAGTCTCC ACTCTCCCTG CCCGTCACCC CTGGAGAGCC GGCCTCCATC
TCCTGCAGGT CTAGTCAGAG CCTCCTGCAT AGTAGTGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACTCCGATC ACCTTCGGCC AAGGGACACG ACTGGAGATT AAA
```
L2 (SEQ ID NO:3)
```
     GAT GTTGTGATGA CTCAGTCTCC ACTCTCCCTG CCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACTCCGATC ACCTTCGGCC AAGGGACACG ACTGGAGATT AAA
```
L3 (SEQ ID NO:5)
```
     GAT GTTGTGATGA CTCAGTCTCC ACTCTCCCTG CCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACTCCACTC ACTTTCGGCG GCGGGACCAA GGTGGAGATC AAA
```
L4 (SEQ ID NO:7)
```
      GA AATTGTGATG ACGCAGTCTC CACTCTCCCT GCCCGTCACC CCTGGAGAGC CGGCCTCCAT
CTCCTGCAGG TCTAGTCAGA GCCTCCTGCA TAGTAATGGA TACAACTATT TGGATTGGTA CCTGCAGAAG
CCAGGGCAGT CTCCACAGCT CCTGATCTAT TTGGGTTCTA ATCGGGCCTC CGGGGTCCCT GACAGGTTCA
GTGGCAGTGG ATCAGGCACA GATTTTACAC TGAAAATCAG CAGAGTGGAG CTGAGGATG TTGGGGTTTA
TTACTGCATG CAAGCTCTAC AAACTCCTCA CACTTTCGGC GGAGGGACCA AGGTGGAGAT CAAA
```
L5 (SEQ ID NO:9)
```
    GAAA TTGTGCTGAC TCAGTCTCCA CTCTCCCTGC CCGTCACCCC TGGAGAGCCG GCCTCCATCT
CCTGCAGGTC TAGTCAGAGC CTCCTGCATA GTAATGGATA CAACTATTTG GATTGGTACC TGCAGAAGCC
AGGGCAGTCT CCACAGCTCC TGATCTATTT GGGTTCTAAT CGGGCCTCCG GGTCCCTGA CAGGTTCAGT
GGCAGTGGAT CAGGCACAGA TTTTACACTG AAAATCAGCA GAGTGGAGGC TGAGGATGTT GGGGTTTATT
ACTGCATGCA AGCTCTACAA ACCCCTCTCA CTTTCGGCCC TGGGACCAAA GTGGATATCA AA
```
L6 (SEQ ID NO:11)
```
     GAT GTTGTGATGA CTCAGTCTCC ACTCTCCCTG GCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACTCCGCTC ACTTTCGGCG GAGGGACCAA GGTGGAGATC AAA
```
L7 (SEQ ID NO:13)
```
     GAT GTTGTGATGA CTCAGTCTCC ACTCTCCCTG CCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACTCCTCTC ACTTTCGGCG GAGGGACCAA GGTGGAGATC AAA
```
L8 (SEQ ID NO:15)
```
 GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAG AAGCCAGGGC
AGTCTCCACA GCTCCTGATC TATTTGGGTT CTAATCGGGC CTCCGGGGTC CCTGACAGGT TCAGTGGCAG
TGGATCAGGC ACAGATTTTA CACTGAAAAT CAGCAGAGTG GAGGCTGAAG ATGTTGGGGT TTATTACTGT
ATGCAAGCTC TACAAACCCC CCTCACTTTC GGCGGAGGGA CCAAGGTGGA GATCAAA
```
L9 (SEQ ID NO:17)
```
   GATG TTGTGATGAC TCAGTCTCCA CTCTCCCTGC CCGTCACCCC TGGAGAGCCG GCCTCCATCT
CCTGCAGGTC TAGTCAGAGC CTCCTGCATA GTAATGGATA CAACTATTTG GATTGGTACC TGCAGAAGCC
AGGGCAGTCT CCACAGCTCC TGATCTATTT GGGTTCTAAT CGGGCCTCCG GGGTCCCTGA CAGGTTCAGT
GGCAGTGGAT CAGGCACAGA TTTTACACTG AAAATCAGCA GAGTGGAGGC TGAGGATGTT GGGGTTTATT
ACTGCATGCA AGCTCTACAA ACTCCGTTCA CCTTCGGCCA AGGGACACGA CTGGAGATTA AA
```

FIG. 1B

L10 (SEQ ID NO:19)
GATGTTGTGA TGACTCAGTC TCCACTCTCC CTGCCCGTCA CCCCTGGAGA GCCGGCCTCC ATCTCCTGCA
GGTCTAGTCA GAGCCTCCTG CATAGTAATG GATACAACTA TTTGGATTGG TACCTGCAGA AGCCAGGGCA
GTCTCCACAG CTCCTGATCT ATTTGGGTTC TAATCGGGCC TCCGGGGTCC CTGACAGGTT CAGTGGCAGT
GGATCAGGCA CAGATTTTAC ACTGAAAATC AGCAGAGTGG AGGCTGAGGA TGTTGGGGTT TATTACTGCA
TGCAAGCTCT ACAAACTCCT CTGGCGTTCG GCCAAGGGAC CAAGGTGGAA ATCAAA

L11 (SEQ ID NO:21)
GAAATTGT GCTGACTCAG TCTCCACTCT CCCTGCCCGT CACCCCTGGA GAGCCGGCCT CCATCTCCTG
CAGGTCTAGT CAGAGCCTCC TGCATAGTAA TGGATACAAC TATTTGAATT GGTACCTGCA GAAGCCAGGG
CAGTCTCCAC AGCTCCTGAT CTATTTGGGT TCTAATCGGG CCTCCGGGGT CCCTGACAGG TTCAGTGCCA
GTGGATCAGG CACAGATTTT ACACTGAAAA TCAGCAGAGT GGAGGCTGAG GATGTTGGGG TTTATTACTG
CATGCAAGCT CTACAAACTC CTATCACCTT CGGCCAAGGG ACACGACTGG AGATTAAA

L12 (SEQ ID NO:23)
AATT TTATGCTGAC TCAGCCCCAC TCTGTGTCGG AGTCTCCGGG AAGACGGTA ACCATCTCCT
GCACCCGCAG CAGTGGCAGC ATTGCCAGCA ACTATGTGCA GTGGTACCAG CAGCGCCCGG GCAGTTCCCC
CACCACTGTG ATCTATGAGG ATAACCAAAG ACCCTCTGGG GTCCCTGATC GGTTCTCTGG CTCCATCGAC
AGCTCCTCCA ACTCTGCCTC CCTCACCATC TCTGGACTGA AGACTGAGGA CGAGGCTGAC TACTACTGTC
AGTCTTATGA TAGCAGCAAT CAGAGAGTGT TCGGCGGAGG GACCAAGCTG ACCGTCCTA

L13 (SEQ ID NO:25)
GAT GTTGTGATGA CTCAGTCTCC ACTCTCCCTG CCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACCCCGCTC ACTTTCGGCG GAGGGACCAA GGTGGAGATC AAA

L14 (SEQ ID NO:27)
G ATGTTGTGAT GACTCAGTCT CCACTCTCCC TGCCCGTCAC CCTGGAGAG CCGGCCTCCA
TCTCCTGCAG GTCTAGTCAG AGCCTCCTGC ATAGTAATGG ATACAACTAT TTGGATTGGT ACCTGCAGAA
GCCAGGGCAG TCTCCACAGC TCCTGATCTA TTTGGGTTCT AATCGGGCCT CCGGGGTCCC TGACAGGTTC
AGTGGCAGTG GATCAGGCAC AGATTTTACA CTGAAAATCA GCAGAGTGGA GGCTGAGGAT GTTGGGGTTT
ATTACTGCAT GCAAGCTCTA CAAACTCCTC TTACTTTCGG CGGAGGGACC AAGGTGGAGA TCAAA

L15 (SEQ ID NO:29)
GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAA AAGCCAGGGC
AGTCTCCACA GCTCCTGATC TATTTGGGTT CTTATCGGGC CTCCGGGGTC CCTGACAGGT TCAGTGCCAG
TGGATCAGGC ACAGATTTTA CACTGAAAAT CAGCAGAGTG GAGGCTGAGG ATGTTGGGGT TTATTACTGC
ATGCAAGCTC TACAAACTCC GATCACCTTC GGCCAAGGGA CACGACTGGA GATTAAA

L16 (SEQ ID NO:31)
GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAG AAGCCAGGGC
AGTCTCCACA GCTCCTGATC TATTTGGGTT CTAATCGGGC CTCCGGGGTC CCTGACAGGT TCAGTGGCAG
TGGATCAGGC ACAGATTTTA CACTGAAAAT CAGCAGGGTG GAGGCTGAGG ATGTTGGGGT TTATTACTGC
ATGCAAGGTA CACACTGGCC TCTGACGTTC GGCCAAGGGA CCAAGGTGGA GATCAAA

L17 (SEQ ID NO:33)
GAAATTG TGATGACGCA GTCTCCACTC TCCCTGCCCG TCACCCCTGG AGAGCCGGCC TCCATCTCCT
GCAGGTCTAG TCAGAGCCTC CTGCATAGTA ATGGATACAA CTATTTGGAT TGGTACCTGC AGAAGCCAGG
GCAGTCTCCA CAGCTCCTGA TCTATTTGGG TTCTAATCGG CCTCCGGGG TCCTGACAG GTTCAGTGGC
AGTGGATCAG GCACAGATTT TACACTGAAA ATCAGCAGAG TGGAGGCTGA GGATGTTGGG GTTTATTACT
GCATGCAAGC TCTACAAACT CCTCTCACTT TCGGCGGAGG GACCAAGGTG GAGATCAAA

L18 (SEQ ID NO:35)
GAC ATCCAGTTGA CCCAGTCTCC ATCTTCCGTG TCTGCGTCTG TCGGAGACAG AGTCACCATC
ACTTGTCGGG CGAGTCAGGG TATTAGCAGG TGGTTAGCCT GGTATCAACA GAAACCAGGG AAAGCCCCTA
GACTCCTGAT CTATGCTGCG TCCGGTTTAC AAAGTGGGGT CCCATCAAGG TTCAGCGGCA GTGGATCTGG
GACAGATTTC ACTCTCACCA TCAGCAACCT GCAGCCTGAA GATTTTGCAA CTTACTATTG TCAACAGGCT
AGCAGTTTTC CAATCACCTT CGGCCAAGGG ACACGACTGG AGACTAAA

FIG. 1C

L19 (SEQ ID NO:37)
```
        GAT GTTGTGATGA CTCAGTCTCC ACTCTCCCTG CCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGAGTTTAT
TACTGCATGC AAGCTCTACA AACTCCGTAC ACTTTTGGCC AGGGGACCAA GCTGGAGATC AAA
```
L20 (SEQ ID NO:39)
```
 GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAG AAGCCAGGGC
AGTCTCCACA GCTCCTGATC TATTTGGGTT CTAATCGGGC CTCCGGGGTC CCTAACAGGT TCAGTGGCAG
TGGATCAGGC ACAGATTTTA CACTGAAAAT CAGCAGAGTG GAGGCTGAGG ATGTTGGGGT TTATTACTGC
ATGCAAGCTC TACAAACTCC ATTCACTTTC GGCCCTGGGA CCAAAGTGGA TATCAAA
```
L21 (SEQ ID NO:41)
```
 GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTCAT GGATACAACT ATTTGGATTG GTACCTGCAG AAGCCAGGGC
AGTCTCCACA ACTTCTGATC TATTTGGGTT CTTATCGGGC CTCCGGGGTC CCTGACAGGT TCAGTGGCAG
TGGATCAGGC ACAGATTTTA CACTGAAAAT CAGCAGAGTG GAGGCTGAGG ATGTTGGGGT TTATTACTGC
ATGCAATCTC TAGAAGTTCC GTTCACTTTT GGCCAGGGGA CCAAGCTGGA GATCAAA
```
L22 (SEQ ID NO:43)
```
        TCT TCTGAGCTGA CTCAGGACCC TGCTGTGTCT GTGGCCTTGG GACAGACAGT CAGGATCACA
TGCCAAGGAG ACAGCCTCAG AATTTATTAT ACAGGCTGGT ACCAACAGAA GCCAGGACAG GCCCCTGTGC
TTGTCCTCTT TGGTAAGAAC AATCGGCCCT CAGGGATCCC AGACCGATTC TCTGGCTCCC ACTCAGGGAA
CACAGCTTCC TTGACCATCA CTGGGGCTCA AGCGGAAGAT GAGGCTGACT ATTACTGTAA CTCCCGGGAC
ATCACTGGTG TCCATCGATT CGGCGGAGGG ACCAAGCTGA CCGTCCTA
```
L23 (SEQ ID NO:45)
```
        GAA ATTGTGCTGA CTCAGTCTCC ACTCTCCCTG CCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACTCCCTCT ACTTTCGGCG GAGGGACCAA GGTGGAGATC AAA
```
L24 (SEQ ID NO:47)
```
        GAT GTTGTGATGA CTCAGTCTCC ACTCTCCCTG CCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTACACT GAAAATCAGC AGAGTGGAGG CTGAGGATGT TGGGGTTTAT
TACTGCATGC AAGCTCTACA AACTCCTAAC ACTTTCGGCG GAGGGACCAA GGTGGAGATC AAA
```
L25 (SEQ ID NO:49)
```
 GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAG AAGCCAGGGC
AGTCTCCACA GCTCCTGATC TATTTGGGTT CTAATCGGGC CTCCGGGGTC CCTGACAGGT TCAGTGGCAG
TGGATCAGGC ACAGATTTTA CACTGAAAAT CAGCAGAGTG GAGGCTGAGG ATGTTGGGGT TTATTACTGC
ATGCAAGCTC TACAAACTCC AATCACTTTC GGCCCTGGGA CCAAAGTGGA TATCAAA
```
L26 (SEQ ID NO:51)
```
 GATGTTGT GATGACTCAG TCTCCACTCT CCCTGCCCGT CACCCCTGGA GAGCCGGCCT CCATCTCCTG
CAGGTCTAGT CAGAGCCTCC TGCATAGTAA TGGATACACC TATTTGGATT GGTACCTGCA GAAGCCAGGG
CAGTCTCCAC AACTCCTGAT CTATTTGGGT TCTAATCGGG CCTCCGGGGT CCCTGACAGG TTCAGCGGCA
GTGGATCAGG CACAGATTTT ACACTGAAAA TCAGCAGAGT GGAGCCTGAG GATGTTGGGG TCTATTACTG
CATGCAAGCT CTAGAAATGC CCCTCACTTT CGGCGGAGGG ACCAAGGTGG AGATCAAA
```
L27 (SEQ ID NO:53)
```
        GAC ATCCAGTTGA CCCAGTCTCC ATCCTTCCTG TCTGCATCTG TAGGAGACAG AGTCACCATC
ACTTGCCGGG CCAGTCAGGG CATTAGCAGT TATTTAGCCT GGTATCAGCA AAAACCAGGG AAAGCCCCTA
AGCTCCTGAT CTATGCTGCA TCCACTTTGC AAAGTGGGGT CCCATCAAGG TTCAGCGGCA GTGGATCTGG
GACAGAATTC ACTCTCACAA TCAGCAGCCT GCAGCCTGAA GATTTTGCAA CTTATTACTG TCAACAGCTT
AATAGTTACC CCCTCACTTT CGGCGGAGGG ACCAAGGTGG AGATCAAA
```

FIG. 1D

L28 (SEQ ID NO:55)
```
         TC CTATGTGCTG ACTCAGCCAC CCTCAGTGTC CGTGTCCCCA GGACAGACAG CCAGCATCAC
CTGCTCTGGA GATAAATTGG GGGATAAATA TGTTGGCTGG TATCAGCAAA AGGCAGGCCA AGCCCCTGTT
TTGGTCATCT ATCAAGACAA CAAGCGACCC TCAGGGATCC CTGAGCGATT CTCTGGCTCC AACTCTGGGA
ACACAGCCAG TCTGACCATC AGCGGGACCC AGGCTATGGA TGAGGCTGAC TATTACTGTC AGGCGTGGGA
CAGCGGCACG GTGTTCGGCG GAGGGACCAA GCTGACCGTC CTA
```

L29 (SEQ ID NO:57)
```
        GATG TTGTGATGAC TCAGTCTCCA CTCTCCCTGC CCGTCACCCC TGGAGAGCCG GCCTCCATCT
CCTGCAGGTC TAGTCAGAGC CTCCTGCATA GTAATGGATA CAACTATTTG GATTGGTACC TGCAGAAGCC
AGGGCAGTCT CCACAGCTCC TGATCTATTT GGGTTCTAAT CGGGCCTCCG GGGTCCCTGA CAGGTTCAGT
GGCAGTGGAT CAGGCACAGA TTTTACACTG AAAATCAGCA GAGTGGAGGC TGAGGATGTT GGGGTTTATT
ACTGCATGCA AGCTCTACAA ACCCCCCTCA CTTTCGGCGG AGGGACCAAG GTGGAGATCA AA
```

L30 (SEQ ID NO:59)
```
GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAG AAGCCAGGGC
AGTCTCCACA GCTCCTGATC TATTTGGGTT CTAATCGGGC CTCCGGGGTC CCTGACAGGT TCAGTGGCAG
TGGATCAGGC ACAGATTTTA CACTGAAAAT CAGCAGAGTG GAGGCTGAGG ATGTTGGGGT TTATTACTGC
ATGGAAGCTC TACAAACTCC ATTCACTTTC GGCCCTGGGA CCAAGGTGGA AATCAAA
```

L31 (SEQ ID NO:61)
```
   GACATC CAGTTGACCC AGTCTCCATC CTCCCTGTCT GCGTCTGTGG GAGACAGAGT CACCATCACT
TGCCGGTCAA GTCAAGGCAT TGGTTACTTC TTAAATTGGT ATCAGCAGGA ACCAGGGAAA GCCCCAAAGA
TCCTGATCTC TGCTGCATCC ACTTTGCAAA GTGGGGTCCC ATCAAGGTTC AGTGGCAGTG GATCTGGGAC
AGATTTCACA CTCTCCATCA ACAATCTGCA ACCCGCAGAT TTTGCGACAT ACTACTGTCA ACAGAGTCAC
AGTCCCCCGT ACACTTTCGG CCAGGGGACC AAGGTGGAGA TCAAA
```

L32 (SEQ ID NO:63)
```
       GAT GTTGTGATGA CTCAGTCTCC ACTCTCCCTG CCCGTCACCC TGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTATT TGGGTTCTAA TCGGGCCTCC GGGGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACTCCGCTC ACTTTCGGCG GAGGGACCAA GGTGGAGATC AAA
```

L33 (SEQ ID NO:65)
```
  GAAATTGTG CTGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAG AAGCCAGGGC
AGTCTCCACA GCTCCTGATG TATTTGGTTT CTAATCGGGC CTCCGGGGTC CCTGACAGGT TCAGTGGCAG
TGGATCAGGC ACAGATTTTA CACTGAAAAT CAGCAGAGTG GAGGCTGAGG ATGTTGGGGT TTATTACTGC
ATGCAAACTC TACAAACTCC TCTCAGTTTT GGCCAGGGA CCAAGCTGGA GATCAAA
```

L34 (SEQ ID NO:67)
```
GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAG AAGCCAGGGC
AGTCTCCACA GCTCCTGATC TATTTGGGTT CTAATCGGGC CTCCGGGGTC CCTGACAGGT TCAGTGGCAG
TGGATCAGGC ACAGATTTTA CACTGAAAAT CAGCAGAGTG GAGGCTGAGG ATGTTGGGGT TTATTACTGC
ATGCAAGCTC TACAAACTCC GCTCACTTTC GGCGGAGGGA CCAAGGTGGA GATCAAA
```

L35 (SEQ ID NO:69)
```
  AATTTTATG CTGACTCAGC CCCACTCTGT GTCGGCGTCT CCGGGGAAGA CGGTTACCAT CTCCTGCACC
CGCAGCAGTG GCGACATTGA CAACAACTAT GTGCAGTGGT ACCAGCAGCG CCCGGGCAAT TCCCCCACCA
ATGTGATTTA TGAGGATAAC CGAAGACCCT CTGGGGTCCC GGATCGCTTC TCTGGCTCCA TCGACAGCTC
CTCCAACTCT GCCTCCCTCA CCATCTCTGG ACTGCAGCCT GAGGACGAGG CTGACTACTA TTGTCAGTCT
TATCAAAGCG ACAATTGGGT GTTCGGCGGA GGGACCAAGG TGACCGTCCT A
```

L36 (SEQ ID NO:71)
```
  AATTTTATG CTGACTCAGC CCCACTCTGT GTCGGAGTCT CCGGGGAAGA CGGTAACCAT CTCCTGCACC
CGCAGCAGTG GCAGCATTGC CAGCAACTAT GTGCAGTGGT ACCAGCAGCG CCCGGGCAGT TCCCCCACCA
CTGTGATCTA TGAGGATAAC CAAAGACCCT CTGGGGTCCC TGATCGATTC TCTGGCTCCA TCGACAGCTC
CTCCAACTCT GCCTCCCTCA CCATCTCTGG ACTGAAGACT GAGGACGAGG CTGACTACTA CTGTCAGTCT
TATGATAGCA GCAATGTGGT GTTCGGCGGA GGGACCAAGC TGACCGTCCT A
```

FIG. 1E

L37 (SEQ ID NO:73)
GATGTTGTGA TGACTCAGTC TCCACTCTCC CTGCCCGTCA CCCCTGGGGA GCCGGCCTCC ATCTCCTGCA
GGTCTAGTCA GAGCCTCCTG CATAGTAATG GATACAACTA TTTGGATTGG TACCTGCAGA AGCCAGGGCA
GTCTCCACAG CTCCTGATCT ATTTGGGTTC TAACCGGGAC TCTGGGGTCC CAGACAGATT CAGCGGCAGT
GGGTCAGGCA CTGATTTCAC ACTGAAAATC AGCAGGGTGG AGGCTGAGGA TGTTGGGGTT TATTACTGCA
TGCAAGGTAC ACACTGGCCG TACACTTTTG GCCAGGGGAC CAGGCTGGAG ATCAAA

L38 (SEQ ID NO:75)
GATGTTGT GATGACTCAG TCTCCACTCT CCCTGCCCGT CACCCCTGGA GAGTCGGCCT CCATCTCCTG
CAGGTCTAGT CAGAGCCTCC TGCATAGTAA TGGATACAAC TTTTTGGATT GGTACCTGCA GAAGCCAGGG
CAGTCTCCAC AGCTCCTGAT CTATTTGGGT TCTAATCGGG CCTCCGGGGT CCCTGACAGG TTCAGTGGCA
GTGGATCAGG CACAGATTTT ACACTGAAAA TCAGCAGAGT GGAGGCTGAG GATGTTGGGG TTTATTACTG
CATGCAAGCT CTACAAACTC CTCTCACTTT CGGCGGAGGG ACCAAGGTGG AGATCAAA

L39 (SEQ ID NO:77)
GA TGTTGTGATG ACTCAGTCTC CACTCTCCCT GCCCGTCACC CTGGAGAGC CGGCCTCCAT
CTCCTGCAGG TCTAGTCAGA GCCTCCTGCA TAGTAATGGA TACAACTATT TGGATTGGTA CCTGCAGAAG
CCAGGGCAGT CTCCACAGCT CCTGATCTAT TTGGGTTCTA ATCGGGCCTC CGGGGTCCCT GACAGGTTCA
GTGGCAGTGG ATCAGGCACA GATTTTACAC TGAAAATCAG CAGAGTGGAG GCTGAGGATG TTGGGGTTTA
TTACTGCATG CAAGCTCTAC AAACCCCCCT CACTTTCGGC GGAGGGACCA AGGTGGAGAT CAAA

L40 (SEQ ID NO:79)
GAAACGAC ACTCACGCAG TCTCCAGCCA CCCTGTCTTT GTCTCCAGGG CAAAGAGCCA CCCTCTCCTG
CAGGGCCAGT CAGAGTGTCT ACAACTACTT AGCCTGGTAC CAACAGAAGC CTGGCCAGGC TCCCAGGCTC
CTCATCTATG ATGCATCCAG AAGGGCAACT GGCATCCCAG CCAGGTTCAG TGGCAGTGGG TCTGGGACAG
ACTTCACTCT CACCATCAGC AGCCTAGAGC CTGAAGATTT TGCACTTTAT TACTGTCAGC AGCGTAACAA
CTGGCCGCTC ACTTTCGGTG GAGGGACCAA GGTGGAGATC AAA

L41 (SEQ ID NO:81)
GACAT CCAGTTGACC CAGTCTCCAT CCTCCCTGTC TGCTTCTGTT GGAGACAGCG TCACCATCTC
TTGCCGGGCA AGTCAGAGTC CTGGCATCTT TTTAAATTGG TATCAGCAGA TACCAGGGAA AGCCCCTAAA
CTCCTGATCT ACGCTACATC CACTCTGCAA AGTGGGGTCC CCCCAGGTT CACCGGCAGT GGATCTGGGA
CAGATTTCAC TCTCACCATC AGCAGTCTGC AACCTGAGGA CTTTGCAACT TACTACTGTC AACAGAGTAA
CAGTGTTCCG CTCACTTTCG GCGGCGGGAC CAAGGTGGAG ATCAAA

L42 (SEQ ID NO:83)
GATGT TGTGATGACT CAGTCTCCAC TCTCCCTGCC CGTCACCCCT GGAGAGCCGG CCTCCATCTC
CTGCAGGTCT AGTCAGAGCC TCCTGCATAG TAATGGATAC AACTATTTGG ATTGGTACCT GCAGAAGCCA
GGGCAGTCTC CACAGCTCCT GATCTATTTG GGTTCTAATC GGGCCTCCGG GGTCCCTGAC AGGTTCAGTG
GCAGTGGATC AGGCACAGAT TTTACACTAA AAATCAGCAG AGTGGAGGCT GAGGATGTTG GGGTTTATTA
CTGCATGCAA GCTCTACAAA CTCCTCTAAC CTTCGGCCAA GGGACACGAC TGGAGATTAA A

L43 (SEQ ID NO:85)
GAAATT GTGATGACGC AGTCTCCAGC CACCCTGTCT GTGTCTCCAG GGGAAAGAGC CACCTTCTCC
TGTAGGGCCA GTCAGAGTGT TGGCAGCAAC TTAGCCTGGT ACCAGCAGAA ACCTGGCCAG GCTCCCAGGC
TCCTCATCTA TGATGCATCC AACAGGGCCA CTGGCATCCC AGCCAGGTTC AGTGGCAGTG GTCTGGGAC
AGACTTCACT CTCACCATCA GCAGACTGGA GCCTGAAGAT TTGCAGTGT ATTACTGTCA GCAGCGTAGC
AACTGGCCCC TCACTTTCGG CGGAGGGACC AAGGTGGAGA TCAAA

L44 (SEQ ID NO:87)
GATGT TGTGATGACT CAGTCTCCAC TCTCCCTGCC CGTCACCCCT GGAGAGCCGG CCTCCATCTC
CTGCAGGTCT AGTCAGAGCC TCCTGCATAG TAATGGATAC AACTATTTGG ATTGGTACCT GCAGAAGCCA
GGGCAGTCTC CACAGCTCCT GATCTATTTG GGTTCTAATC GGGCCTCCGG GGTCCCTGAC AGGTTCAGTG
GCAGTGGATC AGGCACAGAT TTTACACTGA AAATCAGCAG AGTGGAGGCT GAGGATGTTG GGGTTTATTA
CTGCATGCAA GCTCTACAAA CTCCGCTCAC TTTCGGCGGA GGGACCAAGG TGGAGATCAA A

L45 (SEQ ID NO:89)
GAT GTTGTGATGA CTCAGTCTCC ACTCTCCCTG CCCGTCACCC CTGGAGAGCC GGCCTCCATC
TCCTGCAGGT CTAGTCAGAG CCTCCTGCAT AGTAATGGAT ACAACTATTT GGATTGGTAC CTGCAGAAGC
CAGGGCAGTC TCCACAGCTC CTGATCTACT TGGGTTCTAC TCGGGCCTCC GGCGTCCCTG ACAGGTTCAG
TGGCAGTGGA TCAGGCACAG ATTTTACACT GAAAATCAGC AGAGTGGAGG CTGAGGATGT TGGGGTTTAT
TACTGCATGC AAGCTCTACA AACTCCTTAC ACTTTCGGCG GAGGGACCAA GGTGGAGATC AAA

FIG. 1F

L46 (SEQ ID NO:91)
```
     GATGT TGTGATGACT CAGTCTCCAC TCTCCCTGCC CGTCACCCCT GGAGAGCCGG CCTCCATCTC
CTGCAGGTCT AGTCAGAGCC TCCTGCATAG TAATGGATAC AACTATTTGG ATTGGTACCT GCAGAAGCCA
GGGCAGTCTC CACAGCTCCT GATCTATTTG GGTTCTAATC GGGCCTCCGG GGTCCCTGAC AGGTTCAGTG
GCAGTGGATC AGGCACAGAT TTTACACTGA AAATCAGCAG AGTGGAGGCT GAGGATGTTG GGGTTTATTA
CTGCATGCAA GCTCTACAAA CTCCCCTCAC TTTCGGCGGA GGGACCAAGG TGGAGATCAA A
```

L47 (SEQ ID NO:93)
```
     GATGT TGTGATGACT CAGTCTCCAC TCTCCCTGCC CGTCACCCCT GGAGAGCCGG CCTCCATCTC
CTGCAGGTCT AGTCAGAGCC TCCTGCATAC TAATGGATAC AACTATTTGG ATTGGTACCT GCAGAAGCCA
GGGCAGTCTC CACGGCTCCT GATCTATTTG GGTTTTAATC GGGCCTCCGG GGTCCCTGAC AGGTTCAGTG
GCAGTGGATC AGGCACAGAT TTTACACTGA AAATCAGCAG AGTGGAGGCT GAGGATGTTG GGGTTTATTA
CTGTATGCAA GGTCTACAAA CTCCCCTCAC TTTCGGCGGA GGGACCAAGG TGGAGATCAA A
```

L48 (SEQ ID NO:95)
```
  GATGTTGTG ATGACTCAGT CTCCACTCTC CCTGCCCGTC ACCCCTGGAG AGCCGGCCTC CATCTCCTGC
AGGTCTAGTC AGAGCCTCCT GCATAGTAAT GGATACAACT ATTTGGATTG GTACCTGCAG AAGCCAGGGC
AGTCTCCACA GCTCCTGATC TATTTGGGTT CTAATCGGGC CTCCGGGGTC CCTGACAGGT TCAGTGGCAG
TGGATCAGGC ACAGATTTTA CACTGAAAAT CAGCAGGGTG GAGGCTGAGG ATGTTGGGGT TTATTATTGC
ATGCAAGCTA CACACTGGCC GTACACTTTT GGCCAGGGGA CCAAGCTGGA GATCAAA
```

L49 (SEQ ID NO:97)
```
    AATTTTA TGCTGACTCA GCCCCACTCT GTGTCGGAGT CTCCGGGGAA GACGGTAAGC ATCTCCTGCA
CCCGCAACAG TGGCAGCATT GCCAGCAACT TTGTGCAGTG GTACCAGCAG CGCCCGGGCA GTGCCCCAC
CATTGTAATC TATGAGGATA ACCAAAGACC CTCTGCGGTC CCTACTCGGT TCTCTGGCTC CATCGACAGG
TCCTCCAACT CTGCCTCCCT CACCATCTCT GGACTCACGA CTGAGGACGA GGCTGACTAC TACTGTCAGT
CTTATGATAG CGCCAATGTC ATTTTCGGCG GGGGACCAA GCTGACCGTC CTA
```

L50 (SEQ ID NO:99)
```
     GAAACG ACACTCACGC AGTCTCCAGG CACCCTGTCT TTGTCTCCAG GGGAGAGAGC CACCCTCTCC
TGCAGGGCCA GTCAGACTAT CAGCAGCAGC CACTTAGCCT GGTACCAGCA GAAACCTGGC CAGTCTCCCA
GGCTCCTCAT CTATGGTGCG GGCTACAGGG CCACCGGCAT TCCAGACAGG TTCAGTGGCA GTGGGTCTGG
CACAGACTTC ACTCTCACCA TCAGCAGACT GGAGCCTGAA GATTTTGCAG TGTATTACTG TCAGCACTAT
GGTAGTTCAC TCCGGACGTT CGGCCAAGGG ACCAAGGTGG AAATCAAA
```

L51 (SEQ ID NO:101)
```
     AATTTT ATGCTGACTC AGCCCCACTC TGTGTCGGAG TCTCCGGGGA AGACGGTAAC CATCTCCTGC
ACCGGCAGCG GTGGCAACAT TGCCAGCAAT TATGTGCAGT GGTACCAGCA GCGCCCGGGC AGGGCCCCCA
CCACTGTGAT CTATGAGGAT AATCGAAGAC CCTCTGGGGT CCCTGATCGG TTCTCTGGCT CCATCGACAG
CTCCTCCAAC TCTGCCTCCC TCACCATCTC TGGACTGAAG ACTGAAGACG AGGCTGACTA CTACTGTCAG
TCTTATGATC CCTACAATCG AGTGTTCGGC GGAGGGACCA AGCTGACCGT CCTA
```

L51 (SEQ ID NO:103)
```
      GAAA TTGTGATGAC GCAGTCTCCA CTCTCCCTGC CCGTCACCCC TGGAGAGCCG GCCTCCATCT
CCTGCAGGTC TAGTCAGAGC CTCCTGCATA CTAATGGATA CGACTATTTG GATTGGTACC TGCAGAAGCC
AGGGCAGTCT CCACAGCTTC TGATCTATTT GGGTTCTACT CGGGCCTCCG GGGTCCCTGA CAGGTTCAGT
GGCAGTGGAT CGGGCACAGA TTTTACACTG AAAATCAGCA GAGTGGAGGC TGAGGATGTT GGGGTTTATT
ACTGCATGCA AGCTTTTCAA ACTCCGCTCA CTTTCGGCGG AGGGACCAAG ATGGAGATCA AA
```

H1 (SEQ ID NO:105)
```
GAGGTGCAGC TGGTGGAGAC CGGCCAGGA CTGGTGAAGC CTTCGGGGAC CCTGTCCCTC ACCTGCGCTG
TCTCTGGTGG CTCCATCAGC AGTAGTAACT GGTGGAGTTG GGTCCGCCAG CCCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCCGCGGAC ACGGCCGTGT
ATTACTGTGC GAGATTTAAT TACTATGATA GTAGTGTCTG GGGCCAGGGA ACCCTGGTCA CCGTCTCAAG
C
```

FIG. 1G

H2 (SEQ ID NO:107)
```
GAGGTGCAGC TGGTGGAGAC CGGCCCAGGA CTGGTGAAGC CTTCGGGGAC CCTGTCCCTC ACCTGCGCTG
TCTCTGGTGG CTCCATCAGC AGTAGTAACT GGTGGAGTTG GGTCCGCCAG CCCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCCGCGGAC ACGGCCGTGT
ATTACTGTGC GAGAGGGGTT GAGCAGATTG ACTACTGGGG CCAGGGAACC CTGGTCACCG TCTCAAGC
```

H3 (SEQ ID NO:109)
```
CAGGTGCAGC TGCAGGAGTC GGGCCCAGGA CTGGTGAAGC CTTCGGGGAC CCTGTCCCTC ACCTGCGCTG
TCTCTGGTGG CTCCATCAGC AGTAGTAACT GGTGGAGTTG GGTCCGCCAG CCCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC TGCCGCGGAC ACGGCCGTGT
ATTACTGTGC GAAAAATTTA GCAGCAGGGG CGGTTGCCTA CTGGGGCCAG GGCACCCTGG TCACCGTCTC
AAGC
```

H4 (SEQ ID NO:111)
```
 CAGGTGCAG CTACAGCAGT GGGGCGCAGG ACTGTTGAAG CCTTCGGAGA CCCTGTCCCT CACCTGCGCT
GTCTCTGGTG GGTCCTTCAG TGGTTACTAC TGGAGCTGGA TCCGTCAGCC CCCAGGGAAG GGCTGGAGT
GGATTGGGGA AATCAATCAT AGTGGAAGTA CCAACTACAA CCGGTCCCTC AAGAGTCGAG TCACCATATC
AGTAGACACG TCCAAGAACC AGTTCTCCCT GAAGCTGAGC TCTGTGACCG CCGCGGACAC GGCTGTGTAT
TACTGTGCGA GACTTTCATA TGGTTCGGGC GTTGACTACT GGGGCCAGGG CACCCTGGTC ACCGTCTCAA
GC
```

H5 (SEQ ID NO:113)
```
         C AGCTGCAGCT GCAGGAGTCG GGCCCAGGAC TGGTGAAGCC TTCACAGACC CTGTCCCTCA
CCTGCACTGT CTCTGGTGGC TCCATCAGCA GTAGTAACTG GTGGAGTTGG GTCCGCCAGC CCCCAGGGAA
GGGGCTGGAG TGGATTGGGG AAATCTATCA TAGTGGGAGC ACCAACTACA ACCCGTCCCT CAAGAGTCGA
GTCACCATAT CAGTAGACAA GTCCAAGAAC CAGTTCTCCC TGAAGCTGAG CTCTGTGACC GCCGCGGACA
CGGCCGTGTA TTACTGTGCG AGGTATAGCA GCAGCCGCAA TGATGCTTTT GATATCTGGG GCCAAGGGAC
AATGGTCACC GTCTCAAGC
```

H6 (SEQ ID NO:115)
```
CAGGTGCAGC TGCAGGAGTC GGGCCCAGGA CTGGTGAAGC CTTCGGGGAC CCTGTCCCTC ACCTGCGCTG
TCTCTGGTGG CTCCATCAGC AGTAGTAACT GGTGGAGTTG GGTCCGCCAG CCCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCCGCGGAC ACGGCCGTGT
ATTACTGTGC GAGAGATGGG CAGCTGGATG CTTTTGATAT CTGGGGCCAA GGGACAATGG TCACCGTCTC
AAGC
```

H7 (SEQ ID NO:117)
```
CAGGTGCAGC TGCAGGAGTC GGGCCCAGGA CTGGTGAAGC CTTCGGGGAC CCTGTCCCTC ACCTGCGCTG
TCTCTGGTGG CTCCATCAGC AGTAGTAACT GGTGGAGTTG GGTCCGCCAG CCCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCCGCGGAC ACGGCCGTGT
ATTACTGTGC GAGATTTTGG GACTACTACG GTATGGACGT CTGGGGCCAA GGGACCACGG TCACCGTCTC
AAGC
```

H8 (SEQ ID NO:119)
```
      CAGGTG CAGCTACAGC AGTGGGGCCC AGGACTGGTG AAGCCTTCGG GGACCCTGTC CCTCACCTGC
GCTGTCTCTG GTGGCTCCAT CAGCAGTAGT AACTGGTGGA GTTGGGTCCG CCAGCCCCCA GGGAAGGGGC
TGGAGTGGAT TGGGGAAATC TATCATAGTG GGAGCACCAA CTACAACCCG TCCCTCGAGA GTCGAGTCAC
CATATCAGTA GACAAGTCCA AGAACCAGTT CTCCCTGAAG CTGAGCTCTG TGACCGCCGC AGACACGGCC
GTGTATTACT GTGCGAGAGA TCGGTACTAC GGTATGGACG TCTGGGCCCA AGGGACCACG GTCACCGTCT
CAAGC
```

H9 (SEQ ID NO:121)
```
        G AGGTGCAGCT GGTCGAGTCT GGCCCAGGAC TGGTGAAGCC TTCGGGACC CTGTCCCTCA
CCTGCGCTGT CTCTGGTGGC TCCATCAGCA GTAGTAACTG GTGGAGTTGG GTCCGCCAGC CCCCAGGGAA
GGGGCTGGAG TGGATTGGGT ACATCTATTA TAGTGGGAGC ACCTACTACA ACCCGTCCCT CAAGAGTCGA
GTCACCATGT CAGTAGACAC GTCCAAGAAC CAGTTCTCCC TGAAGCTGAG CTCTGTGACC GCCGCAGACA
CGGCCGTGTA TTACTGTGCG AGATGGAGCT ACTTGGATGC TTTTGATATC TGGGGCCAAG GGACAATGGT
CACCGTCTCA AGC
```

FIG. 1H

H10 (SEQ ID NO:123)
```
     GAGGTGC AGCTGGTGGA GTCTGGCCCA GGACTGGTGA AGCCTTCGGG GACCCTGTCC CTCACCTGCG
CTGTCTCTGG TGGCTCCATC AGCAGTAGTA ACTGGTGGAG TTGGGTCCGC CAGCCCCAG GGAAGGGGCT
GGAGTGGATT GGGGAAATCT ATCATAGTGG GAGCACCAAC TACAACCCGT CCCTCAAGAG TCGAGTCACC
ATATCAGTAG ACAAGTCCAA GAACCAGTTC TCCCTGAAGC TGAGCTCTGT GACCGCCGCG GACACGGCCG
TGTATTACTG TGCGAGAGAT TACGATATTT TCGGTATGGA CGTCTGGGGC CAAGGGACCA CGGTCACCGT
CTCAAGC
```

H11 (SEQ ID NO:125)
```
       CAGCT GCAGCTGCAG GAGTCGGGCC CAGGACTGGT GAAGCCTTCG GGGACCCTGT CCCTCACCTG
CGCTGTCTCT GGTGGCTCCA TCAGCAGTAG TAACTGGTGG AGTTGGGTCC GCCAGCCCCC AGGGAAGGGG
CTGGAGTGGA TTGGGGAAAT CTATCATAGT GGGAGCACCA ACTACAACCC GTCCCTCAAG AGTCGAGTCA
CCATATCAGT AGACAAGTCC AAGAACCAGT CCTCCCTGAA GCTGAGCTCT GTGACCGCCG CGGACACGGC
CGTGTATTAC TGTGCGAGAG CCAACAGAGA TGATGCTTTT GATATCTGGG GCCAAGGGAC AATGGTCACC
GTCTCAAGC
```

H12 (SEQ ID NO:127)
```
     GAGGTGC AGCTGGTGGA GTCTGGGGGA GGCTTGGTAC AGCCGGGGGG GTCCCTGAGA CTCTCCTGTG
CAGCCTCTGG ATTCACCTTT AGCAGCTATG CCATGAGCTG GGTCCGCCAG GCTCCAGGGA AGGGGCTGGA
GTGGGTCTCA GCTATTAGTG GTAGTGGTGG TAGCACATAC TACGCAGACT CCGTGAAGGG CCGGTTCACC
ATCTCCAGAG ACAATTCCAA GAACACGCTG TATCTGCAAA TGAACAGTCT GAGCGCCGAC GACACGGCCG
TATATTTCTG TGCGTCGGGT GGCTGGTACG GGGACTACTT TGACTACTGG GGCCAGGGAA CCCTGGTCAC
CGTCTCAAGC
```

H13 (SEQ ID NO:129)
```
CAGGTGCAGC TGCAGGAGTC CGGCCCAGGA CTGGTGAAGC CTTCGGAGAC CCTGTCCCTC ACCTGCACTG
TCTCTGGTGG CTCCATCAGC AGTAGTAACT GGTGGAGTTG GGTCCGCCAG CCCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCCGCGGAC ACGGCCGTGT
ATTACTGTGC GAGAGAAGGG AACCGAACGG TGACTAGTGC TTTTGATATC TGGGGCCAAG GGACAATGGT
CACCGTCTCA AGC
```

H14 (SEQ ID NO:131)
```
   CAGGTGCA GCTGCAGGAG TCCGGCCCAG GACTGGTGAA GCCTTCGGGG ACCCTGTCCC TCACCTGCGC
TGTCTCTGGT GGCTCCATCA GCAGTAGTAA CTGGTGGAGT TGGGTCCGCC AGCCCCAGG GAAGGGGCTG
GAGTGGATTG GGGAAATCTA TCATAGTGGG AGCACCAACT ACAACCCGTC CCTCAAGAGT CGAGTCACCA
TATCAGTAGA CAAGTCCAA AACCAGTTCT CCCTGAAGCT GAGCTCTGTG ACCGCTGCGG ACACGGCCGT
GTACTACTGT GCGAGAGGGC TGGGGGATAG TAGTGGTTAT ATCCTTTGGG CCAAGGGAC AATGGTCACC
GTCTCAAGC
```

H15 (SEQ ID NO:133)
```
      CAGGTG CAGCTGCAGG AGTCCGGCCC AGGACTGGTG AAGCCTTCGG GGACCCTGTC CCTCACCTGC
GCTGTCTCTG GTGGCTCCAT CAGCAGTAGT AACTGGTGGA GTTGGGTCCG CCAGCCCCA GGGAAGGGGC
TGGAGTGGAT TGGGGAAATC TATCATAGTG GAGCACCAA CTACAACCCG TCCCTCAAGA GTCGAGTCAC
CATATCAGTA GACAAGTCCA AGAACCAGTT CTCCCTGAAG CTGAGCTCTG TGACCGCTGC GGACACGGCC
GTGTACTACT GTGCGAGAGG GCTGGGGGAT AGTAGTGGTT ATATCCTTTG GGGCCAAGGG ACAATGGTCA
CCGTCTCAAG C
```

H16 (SEQ ID NO:135)
```
      CAGGTG CAGCTGCAGG AGTCGGGCCC AGGACTGGTG AAGCCTTCGG GGACCCTGTC CCTCACCTGC
GCTGTCTCTG GTGGCTCCAT CAGCAGTAGT AACTGGTGGA GTTGGGTCCG CCAGCCCCCA GGGAAGGGGC
TGGAGTGGAT TGGGGAAATC TATCATAGTG GGAGCACCAA CTACAACCCG TCCCTCAAGA GTCGAGTCAC
CATATCAGTA GACAAGTCCA AGAACCAGTT CTCCCTGAAG CTGAGCTCTG TGACCGCCGC GGACACGGCC
GTGTATTACT GTGCGAGATG GACCGGGCGT ACTGATGCTT TTGATATCTG GGGCCAAGGG ACAATGGTCA
CCGTCTCAAG C
```

FIG. 1I

H17 (SEQ ID NO:137)
```
     CAGG TGCAGCTGCA GGAGTCCGGC CCAGGACTGG TGAAGCCTTC GGGGACCCTG TCCCTCACCT
GCGCTGTCTC TGGTGGCTCC ATCAGCAGTA GTAACTGGTG GAGTTGGGTC CGCCAGCCCC CAGGGAAGGG
GCTGGAGTGG ATTGGGGAAA TCTATCATAG TGGGAGCACC AACTACAACC CGTCCCTCAA GAGTCGAGTC
ACCATATCAG TAGACAAGTC CAAGAACCAG TTCTCCCTGA AGCTGAGCTC TGTGACCGCC GCGGACACGG
CCGTGTATTA CTGTGCGAGA CAAGGGGCGT TAGATGCTTT TGATATCTGG GGCAAGGGA CCACGGTCAC
CGTCTCAAGC
```

H18 (SEQ ID NO:139)
```
GCAGCTGGTG GAGTCCGGGG GAGGCGTGGT CCGACCTGGG GGGTCCCTGA GACTCTCCTG TGCAGCGTCT
GGATTCACCT TTAGCAGCTA TGCCATGAGC TGGGTCCGCC AGGCTCCAGG GAAGGGGCTG GAGTGGGTCT
CAACTATTAG TGGTAGTGGT GGTAGCACAT ACTACGCAGA CTCCGTGAAG GGCCGGTTCA CCATCTCCAG
AGACAATTCC AAGAACACGC TGTATCTGCA GATGAACAGC CTGAGAGCCG AGGACACGGC CGTATATTAC
TGTGCGAAAG AGCGTGGCAG TGGCTGGTCC TTAGACAATA TGGACGTCTG GGGCCAAGGG ACCACGGTCA
CCGTCTCAAG C
```

H19 (SEQ ID NO:141)
```
CAGGTGCAGC TGGTGGAGTC TGGCCCAGGA CTGGTGAAGC CTTCGGGGAC CCTGTCCCTC ACCTGCGCTG
TCTCTGGTGG CTCCATCAGC AGTAGTAACT GGTGGAGTTG GGTCCGCCAG CCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCTGCGGAC ACGGCCGTGT
ATTACTGTGC GAGAGATAGC AGTGGGTTCT ACGGTATGGA CGTCTGGGGC CAAGGGACCA CGGTCACCGT
CTCAAGC
```

H20 (SEQ ID NO:143)
```
     CAGGTG CAGCTGCAGG AGTCGGGCCC AGGACTGGTG AAGCCTTCGG GGACCCTGTC CCTCACCTGC
GCTGTCTCTG GTGGCTCCAT CAGCAGTAGT AACTGGTGGA GTTGGGTCCG CCAGCCCCA GGGAAGGGGC
TGGAGTGGAT TGGGGAAATC TATCATAGTG GGAGCACCAA CTACAACCCG TCCCTCAAGA GTCGAGTCAC
CATATCAGTA GACAAGTCCA AGAACCAGTT CTCCCTGAAG CTGAGCTCT TGACTGCCGC GGACACGGCC
GTGTATTACT GTGCGAGAAG CAGCAGCTGG TACTGGAATG CTTTTGATAT CTGGGGCCAA GGGACAATGG
TCACCGTCTC AAGC
```

H21 (SEQ ID NO:145)
```
     CAGGTG CAGCTACAGC AGTGGGGCCC AGCACTGGTG AAGCCTTCGG GGACCCTGTC CCTCACCTGC
TCTGTCTCTG GTGTCTCCAT CACCAGTAAT ATCTGGTGGA GTTGGGTCCG CCAGTCCCA GGGAAGGGGC
TGGAGTGGAT TGGGGAAGTC TATCATAGTG GGAGCACCAA CTACAACCCG TCCCTCAAGA GTCGAGTCAC
CATATCAGTA GACAAGTCCA AGAACCAGTT CTCCCTGAAG CTGAGCTCTG TGACCGCCGC GGACACGGCT
GTGTATTACT GTGCGGGGTA CCGTAGCTTC GGGGAGTCCT ACTGGGGCCA GGGAACCCTG GTCACCGTCT
CAAGC
```

H22 (SEQ ID NO:147)
```
     CAGGTGCA GCTACAGCAG TGGGGCGCAG GGCTGTTGAA GCCTTCGGAG ACCCTGTCTC TCACCTGCGT
TGTCTATGGT GGGTCCTTCA GCGATTTCTA CTGGAGCTGG ATCCGCCAGC CCCCAGGGAA GGGGCCAGAG
TGGATTGGGG AAGTCAATCC TAGAGGAAGC ACCAACTACA ACCCGTCCCT CAAGAGTCGA GCCACCATAT
CACTAGACAC GTCCAAGAAC CAGTTCTCCC TGAAGCTGAG TTCTGTGACC GCCGCGGACA CGGCTGTGTA
TTTCTGTGCG AGAGGTCCTC GGCCGGGAG AGATGGCTAC AATTACTTTG ACAACTGGGG CCAGGGCACC
CTGGTCACCG TCTCAAGC
```

H23 (SEQ ID NO:149)
```
CAGGTGCAGC TGCAGGAGTC CGGCCCAGGA CTGGTCAAGC CTTCGGAGAC CCTGTCCCTC ACCTGCACTG
TCTCTGGTGG CTCCATCAGC AGTAGTAACT GGTGGAGTTG GGTCCGCCAG CCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCCGCGGAC ACGGCCGTGT
ATTACTGTGC GAGAGGTATA GCAGCAGCTG GTCAAGGTGA CTACTGGGGC CAGGGAACCC TGGTCACCGT
CTCAAGC
```

FIG. 1J

H24 (SEQ ID NO:151)
CAGGTGCAGC TGCAGGAGTC GGGCCCAGGA CTGGTGAAGC CTTCGGAGAC CCTGTCCCTC ACCTGCACTG
TCTCTGGTGG CTCCATCAGC AGTAGTAGTT ACTACTGGGG CTGGATCCGC CAGCCCCAG GGAAGGGGCT
GGAGTGGATT GGGAGTATCT ATTATAGTGG GAGCACCTAC TACAACCCGT CCCTCAAGAG TCGAGTCACC
ATATCCGTAG ACACGTCCAA GAACCAGTTC TCCCTGAAGC TGAGCTCTGT GACCGCCGCG GACACGGCCG
TGTATTACTG TGCGAGAGAT GGGGGATACT ACTACTACGG TATGGACGTC TGGGGCCAAG GGACCACGGT
CACCGTCTCA AGC

H25 (SEQ ID NO:153)
CAGGTG CAGCTGCAGG AGTCGGGCCC AGGACTGGTG AAGCCTTCGG GGACCCTGTC CCTCACCTGC
GCTGTCTCTG GTGGCTCCAT CAGCAGTAGT AACTGGTGGA GTTGGGTCCG CCAGCCCCCA GGGAAGGGGC
TGGAGTGGAT TGGGGAAATC TATCATAGTG GGAGCACCAA CTACAACCCG TCCCTCAAGA GTCGAGTCAC
CATATCAGTA GACAAGTCCA AGAACCAGTT CTCCCTGAAG CTGAGCTCTG TGACCGCCGC GGACACGGCC
GTGTATTACT GTGCGAGTAG TGGTTATGAT GCTTTTGATA TCTGGGGCCA AGGGACCACG GTCACCGTCT
CAAGC

H26 (SEQ ID NO:155)
CAGGT GCAGCTGCAG GAGTCGGGCC CAGGACTGGT GAAGCCTTCG GGGACCCTGT CCCTCACCTG
CGCTGTCTCT GGTGGCTCCA TCAGCAGTAG TAATTGGTGG AGTTGGGTCC GCCAGCCCCC AGGGAAGGGG
CTGGAGTGGA TTGGGGAAAT CTATCATACT GGGAGCACCA ACTACAACCC GTCCCTCAAG AGTCGAGTCA
CCATATCAGT AGACAAGTCC AAGAACCAGT TCTCCCTGAA GCTGAGCTCT GTGACCGCCG CGGACACGGC
CGTGTATTAC TGTGCACGAT ACAGCTATGG AACGGTAGGA ATTGACTACT GGGGCCAGGG AACCCTGGTC
ACCGTCTCAA GC

H27 (SEQ ID NO:157)
GAGGT GCAGCTGGTG CAGTCTGGGG GAGGCGTGGT CCAGCCTGGG ACGTCCCTGA GACTCTCCTG
TGCAGCCTCT GGATTCAGCT TCAGAAGTCA TGGCATGCAC TGGGTCCGCC AGGCTCCAGG CAAGGGGCTG
GAGTGGGTGG CAGTTATATC ATATGATGGA AGTAATAAAT ACTATGCAGA CTCCGTGAAG GGCCGATTCA
CCATCTCCAG AGACAATTCC AAGAACACGC TGTATCTGCA AATGAACAGC CTGAGAGCTG AGGACACGGC
TGTGTATTAC TGTGCGACTA TAGGGCCGGG GGGATTTGAC TACTGGGGCC AGGGCACCCT GGTCACCGTC
TCAAGC

H28 (SEQ ID NO:159)
CAG GTGCAGCTGC AGGAGTCCGG CCCAGGACTG GTGAAGCCTT CGGAGACCCT GTCCCTCACC
TGCACTGTCT CTGGTGGCTC CATTAGAAAT TACTACTGGA GTTGGATCCG GCAGCCCCCA GGGAAGGGAC
TGGAGTGGAT TGGGTATATT TCTGACAGTG GGAATACCAA CTACAATCCC TCCCTCAAGA GTCGAGTCAC
CATATCAGTA GACACGTCCA AGAACCAGTT CTCCCTAAAG CTGACCTCTG TGACCGCCAC AGACACGGCT
GCGTATTTCT GTGCGAGACA TCGAAGCAGC TGGGCATGGT ACTTCGATCT CTGGGGCCGT GGCACCCTGG
TCACCGTCTC AAGC

H29 (SEQ ID NO:161)
C AGGTGCAGCT GCAGGAGTCG GGCCCAGGAC TGGTGAAGCC TTCGGAGACC CTGTCCCTCA
CCTGCGCTGT CTCTGGTGGC TCCATCAGCA GTAGTAACTG GTGGAGTTGG GTCCGCCAGC CCCCAGGGAA
GGGGCTGGAG TGGATTGGGG AAATCTATCA TAGTGGGAGC ACCAACTACA ACCGTCCCT CAAGAGTCGA
GTCACCATAT CAGTAGACAA GTCCAAGAAC CAGTTCTCCC TGAAGCTGAG CTCTGTGACC GCCGCGGACA
CGGCCGTGTA TTACTGTGCG AGACTGGGCA GTGGCTGGTA CGTTGACTAC TGGGGCCAGG GAACCCTGGT
CACCGTCTCA AGC

H30 (SEQ ID NO:163)
CAGGTG CAGCTGCAGG AGTCCGGCCC AGGACTGGTG AAGCCTTCGG GGACCCTGTC CCTCACCTGC
GCTGTCTCTG GTGGCTCCAT CAGCAGTAGT AACTGGTGGA GTTGGGTCCG CCAGCCCCCA GGGAAGGGGC
TGGAGTGGAT TGGGGAAATC TATCATAGTG GGAGCACCAA CTACAACCCG TCCCTCAAGA GTCGAGTCAC
CATATCAGTA GACAAGTCCA AGAACCAGTT CTCCCTGAAG CTGAGCTCTG TGACCGCCGC GGACACGGCC
GTGTATTACT GTGCGAGAGT TTCTGGCTAC TACTACTACG GTATGGACGT CTGGGGCCAA GGGACCACGG
TCACCGTCTC AAGC

FIG. 1K

H31 (SEQ ID NO:165)
```
   GAGGTCCA GCTGGTACAG TCTGGGGGAG GCGTGGTCCA GCCTGGGAGG TCCCTGAGAC TCTCCTGTGC
AGCCTCTGGA TTCACCTTCA GTAGCTATGG CATGCACTGG GTCCGCCAGG CTCCAGGCAA GGGGCTGGAG
TGGGTGGCAG TTATATCATA TGATGGAAGT AATAAATACT ATGCAGACTC CGTGAAGGGC CGATTCACCA
TCTCCAGAGA CAATTCCAAG AACACGCTGT ATCTGCAAAT GAACAGCCTG AGAGCTGAGG ACACGGCTGT
GTATTACTGT GCGAAAGCGT ATAGCAGTGG CTGGTACGAC TACTACGGTA TGGACGTCTG GGGCCAAGGG
ACCACGGTCA CCGTCTCAAG C
```
H32 (SEQ ID NO:167)
```
CAGGTGCAGC TGCAGGAGTC GGGCCCAGGA CTGGTGAAGC CTTCGGGGAC CCTGTCCCTC ACCTGCGCTG
TCTCTGGTGG CTCCATCAGC AGTAGTAACT GGTGGAGTTG GGTCCGCCAG CCCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCCGCGGAC ACGGCCGTGT
ATTACTGTGC GAGAGCCAGC GTTGATGCTT TTGATATCTG GGGCCAAGGG ACAATGGTCA CCGTCTCAAG
C
```
H33 (SEQ ID NO:169)
```
   CAGGTG CAGCTGCAGG AGTCCGGCCC AGGACTGGTG AAGCCTTCGG GGACCCTGTC CCTCACCTGC
GCTGTCTCTG GTGGCTCCAT CAGCAGTAGT AACTGGTGGA GTTGGGTCCG CCAGCCCCCA GGGAAGGGGC
TGGAGTGGAT TGGGGAAATC TATCATAGTG GGAGCACCAA CTACAACCCG TCCCTCAAGA GTCGAGTCAC
CATATCAGTA GACAAGTCCA AGAACCAGTT CTCCCTGAAG CTGAGCTCTG TGACCGCTGC GGACACGGCC
GTGTACTACT GTGCGAGAGG GCTGGGGGAT AGTAGTGGTT ATATCCTTTG GGGCCAAGGG ACAATGGTCA
CCGTCTCAAG C
```
H34 (SEQ ID NO:171)
```
   CAGGTA CAGCTGCAGC AGTCAGGCCC AGGACTGGTG AAGCCTTCGG GGACCCTGTC CCTCACCTGC
GCTGTCTCTG GTGGCTCCAT CAGCAGTAGT AACTGGTGGA GTTGGGTCCG CCAGCCCCCA GGGAAGGGGC
TGGAGTGGAT TGGGGAAATC TATCATAGTG GGAGCACCAA CTACAACCCG TCCCTCAAGA GTCGAGTCAC
CATATCAGTA GACAAGTCCA AGAACCAGTT CTCCCTGAAG CTGAGCTCTG TGACTCCGA GGACACGGCT
GTGTATTACT GTGCAAGAGA TCACGGCCCC TTTGACTACT GGGGCCGGGG AACCCTGGTC ACCGTCTCAA
GC
```
H35 (SEQ ID NO:173)
```
    CAGGT GCAGCTGGTG CAATCTGGGG GAGGCGTGGT CCAGCCTGGG AGGTCCCTGA GACTCTCCTG
TGCAGCCTCT GGATTCGCCT TCAGTAGCTA TGGCATGCAC TGGGTCCGCC AGGCTCCAGG GAAGGGGCTG
GAGTGGGTTT CATACATTAG TAGTAGTAGT AGTACCATAT ACTACGCAGA CTCTGTGAAG GGCCGATTCA
CCATCTCCAG AGACAATTCC AAGAACACGC TGTATCTGCA AATGAACAGC CTGAGAGCCG AGGACACGGC
TGTGTATTAC TGTGCGAGAG ATCGATTTGG GTCGGGCAC TTGCCCGACT ACTGGGGCCA GGGAACCCTG
GTCACCGTCT CAAGC
```
H36 (SEQ ID NO:175)
```
    CAGGT GCAGCTACAG CAGTGGGGCG CAGGACTGTT GAAGCCTTCG GAGACCCTGT CCCTCACCTG
CGCTGTCTAT GGTGGGTCCT TCAGTGGTTA CTACTGGAGC TGGATCCGCC AGCCCCCAGG GAAGGGGCTG
GAGTGGATTG GGGAAATCAA TCATAGTGGA AGCACCAACT ACAACCCGTC CCTCAAGAGT CGAGTCACCA
TATCAGTAGA CACGTCCAAG AACCAGTTCT CCCTGAAGCT GAGCTCTGTG ACCGCCGCGG ACACGGCTGT
GTATTACTGT GCGAGAGTTG GGTATAGCAG TGGCCGTGAC GTTGACTACT GGGGCCAGGG CACCCTGGTC
ACCGTCTCAA GC
```
H37 (SEQ ID NO:177)
```
    GAGGTCC AGCTGGTGGA GTCTGGCCCA GGACTGGTGA AGCCTTCGGG GACCCTGTCC CTCACCTGCG
CTGTCTCTGG TGGCTCCATC AGCAGTAGTA ACTGGTGGAG TTGGATCCGG CAGCCCCCAG GAAGGGGCT
GGAGTGGATT GGGGAAATCT ATCATAGTGG GAGCACCAAC TACAACCCGT CCCTCAAGAG TCGAGTCACC
ATATCAGTAG ACAAGTCCAA GAACCAGTTC TCCCTGAAGC TGAGCTCTGT GACCGCCGCG GACACGGCCG
TGTATTACTG TGCGAGAGAT AGCAGCAGCT GGTACTACGG TATGGACGTC TGGGGCCAAG GACCACGGT
CACCGTCTCA AGC
```

FIG. 1L

H38 (SEQ ID NO:179)
```
      GAGGT CCAGCTGGTG GAGTCCGGCC CAGGACTGGT GAAGCCTTCG GAGACCCTGT CCCTCACCTG
CGCTGTCTCT GGTGGCTCCA TCAGCAGTAC TAACTGGTGG AGTTGGGTCC GCCAGCCCCC AGGGAAGGGG
CTGGAGTGGA TTGGGGAAAT CTATCATAGT GGGAGCACCA ACTACAACCC GTCCCTCAAG AGTCGAGTCA
CCATATCAGT AGACAAGTCC AAGAACCAGT TCTCCCTGAA GCTGAGCTCT GTGACCGCTG CGGACACGGC
CGTATATTAT TGTGCGAGAT CGACGTGGTC CCTTGACTAC TGGGGCCAGG GCACCCTGGT CACCGTCTCA
AGC
```
H39 (SEQ ID NO:181)
```
  GAGGTCCAG CTGGTGGAGT CTGGCCCAGG ACTGGTGAAG CCTTCGGGGA CCCTGTCCCT CACCTGCGCT
GTCTCTGGTG GCTCCATCAG CAGTAGTAAC TGGTGGAGTT GGGTCCGCCA GCCCCCAGGG AAGGGGCTGG
AGTGGATTGG GGAAATCTAT CATAGTGGGA GCACCAACTA CAACCCGTCC CTCAAGAGTC GAGTCACCAT
ATCAGTAGAC AAGTCCAAGA ACCAGTTCTC CCTGAAGCTG AGCTCTGTGA CCGCTGCGGA CACGGCCGTA
TATTACTGTG CGAGACTCTC GTTTGCCGAT CCTTTTGATA TCTGGGGCCA AGGGACAATG GTCACCGTCT
CAAGC
```
H40 (SEQ ID NO:183)
```
CAGGTCCAGC TGGTGCAGTC TGGGGCTGAG GTGAAGAAGC CTGGGTCCTC GGTGAAGGTC TCCTGCAAGG
CTTCTGGAGG CACCTTCAGC AGCTATGCTA TCAGCTGGGT GCGACAGGCC CCTGGACAAG GGCTTGAGTG
GATGGGAAGG ATCATCCCCA TCCTTGGTAT AGCAAACTAC GCACAGAAGT TCCAGGGCAG AGTCACGATT
ACCGCGGACA AATCCACGAG CACAGCCTAC ATGGAGCTGA GCAGCCTGAG ATCTGAGGAC ACGGCCGTGT
ATTACTGTGC ATATGGTTCG GGGAGTTATT ACGACTACTA CTACATGGAC GTCTGGGGCA AAGGGACCAC
GGTCACCGTC TCAAGC
```
H41 (SEQ ID NO:185)
```
     GAGGTCC AGCTGGTGCA GTCTGGGGGA GGCTTGGTCC AGCCTGGGGG GTCCCTGAGA CTCTCCTGTT
CAGCCTCCGG ATTCACCTTC AGTAGCTATG CTATGCACTG GGTCCGCCAG GCTCCAGGGA AGGGACTGGA
ATATGTTTCA ACTATTAGTA GTAATGGGGA TAGCACATAC TACGCAGACT CCGTGAAGGG CAGATTCACC
ATCTCCAGAG ACAATTCCAA GAACACGCTG TATCTGCAAA TGAACAGCCT GAGAGCTGAG GACACGGCTG
TGTATTACTG TGCGAAAGAA GAAGTATGGC TACAGGCTTT TGATATCTGG GGCCAAGGGA CAATGGTCAC
CGTCTCAAGC
```
H42 (SEQ ID NO:187)
```
        CA GCTGCAGCTG CAGGAGTCGG GCCCAGGACT GGTGAAGCCT TCGGAGACCC TGTCCCTCAC
CTGCACTGTC TCTGGTGGCT CCATCAGTAG TAACTGGTGG AGTTGGGTCC GCCAGCCCCC AGGGAAGGGG
CTGGAGTGGA TTGGGGAAAT CTATCATAGT GGGAGCACCA ACTACAACCC CTCCCTCAAG AGTCGAGTCA
CCATCTCAGT AGACACGTCC AAGAACCAGT TCTCCCTGAA GCTGAGCTCT GTGACCGCTG CGGACACGGC
CGTGTATTAC TGTGCGAGAG ATAAGGGATA CATGGACGTC TGGGGCAAAG GGACCACGGT CACCGTCTCA
AGC
```
H43 (SEQ ID NO:189)
```
    CAGGTACA GCTGCAGCAG TCAGGGGCTG AGGTGAAGAA GCCTGGGTCC TCGGTGAAGG TCTCCTGCAA
GGCTTCTGGA GGCACCTTCA GCAGCTATGC TATCAGCTGG GTGCGACAGG CCCCTGGACA AGGGCTTGAG
TGGATGGGAA GGATCATCCC TATCCTTGGT ATAGCAAACT ACGCACAGAA GTTCCAGGGC AGAGTCACGA
TTACCGCGGA CAAATCCACG AGCACAGCCT ACATGGAGCT GAGCAGCCTG AGATCTGAGG ACACGGCCGT
GTATTACTGT GCGAGAGATC ATAGGTTCGA CTACGGCTGG TACTTCGATC TCTGGGGCCG TGGCACCCTG
GTCACCGTCT CAAGC
```
H44 (SEQ ID NO:191)
```
        CA GGTGCAGCTG CAGGAGTCGG GCCCAGGACT GCTGAAGCCT TCGGGGACCC TGTCCCTCAC
CTGCGCTGTC TCTGGTGGCT CCATCAGCAG TAGCAACTGG TGGAGTTGGG TCCGCCAGCC CCCAGGGGAG
GGGCTGGAGT GGATTGGGGA AATCTATCAT AGTGGGAGCA CCAACTACAA CCCGTCCCTC AAGAGTCGAG
TCACCATATC AGTAGACAAG TCCAAGAACC AGTTCTCCCT GAAGCTGAGC TCTGTGACCG CCGCGGACAC
GGCCGTCTAT TACTGTGCGA GAGATCTAAC GGGGAGTCTT GACTACTGGG GCCAGGGAAC CCTGGTCACC
GTCTCAAGC
```

FIG. 1M

H45 (SEQ ID NO:193)
CAGGTGCAGC TGCAGGAGTC CGGCCCAGGA CTGGTGAAGC CTTCGGGGAC CCTGTCCCTC ACCTGCGCTG
TCTCTGGTGG CTCCATCAGC AGTAGTAACT GGTGGAGTTG GGTCCGCCAG CCCCCAGGGA AGGGGCTGGA
GTGGATTGGG GAAATCTATC ATAGTGGGAG CACCAACTAC AACCCGTCCC TCAAGAGTCG AGTCACCATA
TCAGTAGACA AGTCCAAGAA CCAGTTCTCC CTGAAGCTGA GCTCTGTGAC CGCCGCGGAC ACGGCCGTGT
ATTACTGTGC GAGAATACGC TATGATGCTT TTGATATCTG GGGCCAAGGG ACAATGGTCA CCGTCTCAAG
C

H46 (SEQ ID NO:195)
CA GGTGCAGCTG CAGGAGTCGG GCCCAGGACT GGTGAAGCCT TCGGAGACCC TGTCCCTCAC
CTGCGCTGTC TCTGGTGGCT CCATCAGCAG TAGTAACTGG TGGAGTTGGG TCCGCCAGCC CCAGGGAAG
GGGCTGGAGT GGATTGGGGA AATCTATCAT AGTGGGAGCA CCAACTACAA CCCGTCCCTC AAGAGTCGAG
TCACCATATC AGTAGACAAG TCCAAGAACC AGTTCTCCCT GAAGCTGAGC TCTGTGACCG CTGCGGACAC
GGCCGTGTAT TACTGTGCCG TGACGGCAGC CCATGATGCT TTTGATATCT GGGGCCAAGG GACAATGGTC
ACCGTCTCAA GC

H47 (SEQ ID NO:197)
CA GGTGCAGCTA CAGCAGTGGG GCCCAGGACT GGTGAAGCCT TCGGGGACCC TGTCCCTCAC
CTGCGCTGTC TCTGGTGGCT CCATCAGCAG TAGTAACTGG TGGAGTTGGG TCCGCCAGCC CCAGGGAAG
GGGCTGGAGT GGATTGGGGA AATCTATCAT AGTGGGAGCA CCAACTACAA CCCGTCCCTC AAGAGTCGAG
TCACCATATC AGTAGACAAG TCCAAGAACC AGTTCTCCCT GAAGCTGAGC TCTGTGACCG CCGCGGACAC
GGCCGTGTAT TACTGTGCGA GAGACAGCAG TGGCCAAGGG TACTTTGACT ACTGGGGCCA GGGCACCCTG
GTCACCGTCT CAAGC

H48 (SEQ ID NO:199)
GAGGTG CAGCTGGTGC AGTCTGGGGC TGAGGTGAAG AAGCCTGGGG CCTCAGTGAA GGTCTCCTGC
AAGGCTTCTG GATACACCTT CACTAGCTAT GCTATGCATT GGGTGCGCCA GGCCCCCGGA CAAAGGCTTG
AGTGGATGGG ATGGATCAAC GCTGGCAATG GTAACACAAA ATATTCACAG AAGTTCCAGG GCAGAGTCAC
CATGACCAGG GACACGTCCA CGAGCACAGT CTACATGGAG CTGAGCAGCC TGAGATCTGA GGACACGGCC
GTGTATTACT GTGCTAGACA CTCGTACTAC TACGGTATGG ACGTCTGGGG CCAAGGCACC CTGGTCACCG
TCTCAAGC

H49 (SEQ ID NO:201)
CAG GTGCAGCTAC AGCAGTGGGG CGCAGGACTG TTGAAGCCTT CGGAGACCCT GTCCCTCACC
TGCGCTGTCT ATGGTGGGTC CTTCAGTGGT TACTACTGGA GCTGGATCCG CCAGCCCCCA GGGAAGGGGC
TGGAGTGGAT TGGGAAATC AATCATAGTG GAAGCACCAA CTACAACCCG TCCCTCAAGA GTCGAGTCAC
CATATCGGTA GACACGTCCA AGAACCAGTT CTCCCTGAAG CTGAGCTCTG TGACCGCCGC GGACACGGCT
GTGTATTACT GTGCGAGAGT CGGGTATAGC ACGGCGAAG AAGTCCTGGA CGTCTGGGGC AAAGGGACCA
CGGTCACCGT CTCAAGC

H50 (SEQ ID NO:203)
CAGGT GCAGCTGCAG GAGTCGGGCC CAGGACTGGT GAAGCCTTCG GAGACCCTGT CCCTCACCTG
CACTGTCTCT GGTGGCTCCA TCGGCAATTA TGACTGGAGT TGGATCCGGC AGCCCCCAGG GAAGGGACTG
GAGTGGATTG GGACTATCTA CTCTAGTGGG AGTACGTACT ACAGTCCGTC CCTCAAGAGT CGACTCACCA
TATCAGTAGA CAAGTCCAAG AACCGGTTCT CCCTGAAGCT GAGCTCTGTG ACCGCCGCGG ACACGGCCGT
GTATTACTGT GCGAGAGCAC GAGGGTATAG CAGCCCCTTC GACCCCTGGG GCCAGGGCAC CCTGGTCACC
GTCTCAAGC

H51 (SEQ ID NO:205)
CA GGTCCAGCTG GTACAGTCTG GGGCTGAGGT GAAGAAGCCT GGGTCCTCGG TGAAGGTCTC
CTGCAAGGCT TCTGGAGGCA CCTTCAGCAG CTATGCTATC AGCTGGGTGC GACAGGCCCC TGGACAAGGG
CTTGAGTGGA TGGGAATAAT CAACCCTAGT GGTGGTAGCA CAAGCTACGC ACAGAAGTTC CAGGGCAGAG
TCACCATTAC CAGGGACACA TCCGCGAGCA CAGCCTACAT GGAGCTGAGC AGCCTGAGAT CTGAAGACAC
GGCTGTGTAT TACTGTGCGA GAGATCGGTG GAGCTACCAT GCTTTTGATA TCTGGGGCCA AGGGACAATG
GTCACCGTCT CAAGC

H52 (SEQ ID NO:207)
G AGGTGCAGCT GGTGCAGTCT GGCCCAGGAC TGGTGAAGCC TTCGGGGACC CTGTCCCTCA
CCTGCGCTGT CTCTGGTGGC TCCATCAGCA GTAGTAACTG GTGGAGTTGG TCCGCCAGC CCCCAGGGAA
GGGGCTGGAG TGGATTGGGG AAATCTATCA TAGTGGGAGC ACCAACTACA CCCGTCCCT CAAGAGTCGA
GTCACCATAT CAGTAGACAA GTCCAAGAAC CAGTTCTCCC TGAAGCTGAG CTCTGTGACC GCCGCGGACA
CGGCCGTGTA TTACTGTGCG AGAGAAAAAT CGGGTATGGA CGTCTGGGGC CAAGGGACCA CGGTCACCGT
CTCAAGC

FIG. 2A

LIGHT CHAIN VARIABLE REGION SEQUENCES (Sequence alignment table of light chain variable regions L1–L35, showing framework regions FR1, FR2, FR3, FR4 and complementarity determining regions CDR1, CDR2, CDR3, with corresponding SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70.)

Light Chain      CDR1 Sequence

| Light Chain | | | | | | | | | | | | | | | |
|---|---|---|---|---|---|---|---|---|---|---|---|---|---|---|---|
| L2, L3, L4, L5, L6, L7, L8, L9, L10, L13, L14, L15, L16, L17, L19, L20, L23, L24, L25, L29, L30, L32, L33, L34, L37, L39, L42, L44, L45, L46, L48 | R | S | S | Q | S | L | L | H | S | N | G | Y | N | Y | L | D |
| L1  | R | S | S | Q | S | L | L | H | S | S | G | Y | N | Y | L | D |
| L11 | R | S | S | Q | S | L | L | H | S | N | G | Y | N | Y | L | N |
| L21 | R | S | S | Q | S | L | L | H | S | H | G | Y | N | Y | L | D |
| L26 | R | S | S | Q | S | L | L | H | S | N | G | Y | T | Y | L | D |
| L38 | R | S | S | Q | S | L | L | H | S | N | G | Y | N | F | L | D |
| L47 | R | S | S | Q | S | L | L | H | T | N | G | Y | N | Y | L | D |
| L52 | R | S | S | Q | S | L | L | H | T | N | G | Y | D | Y | L | D |
| CONSENSUS | R | S | S | Q | S | L | L | H | S | N | G | Y | N | Y | L | D |

| | | | | | | | | | | | | | | |
|---|---|---|---|---|---|---|---|---|---|---|---|---|---|---|
| L51 | T | G | S | G | G | N | I | A | S | N | Y | V | Q | | |
| L12, L36 | T | R | S | S | G | S | I | A | S | N | Y | V | Q | | |
| L35 | T | R | S | S | G | D | I | D | N | N | Y | V | Q | | |
| L49 | T | R | N | S | G | S | I | A | S | N | F | V | Q | W | Y | Q |

| | | | | | | | | | | |
|---|---|---|---|---|---|---|---|---|---|---|
| | | | | | | | | H | | |
| L50 | R | A | S | Q | T | I | S | S | S | L | A |
| L18 | R | A | S | Q | G | I | S | R | W | L | A |
| L27 | R | A | S | Q | G | I | S | S | Y | L | A |
| L40 | R | A | S | Q | S | V | Y | N | Y | L | A |
| L43 | R | A | S | Q | S | V | G | S | N | L | A |
| L31 | R | S | S | Q | G | I | G | Y | P | L | N |
| L41 | R | A | S | Q | S | P | G | I | F | L | N |
| CONSENSUS | R | A | S | Q | G | I | G | X | Y | L | A |
| | | | | S | V | S | | F | | | N |

| | | | | | | | | | | |
|---|---|---|---|---|---|---|---|---|---|---|
| L28 | S | G | D | K | L | G | D | K | Y | V | G |
| L22 | Q | G | D | S | L | R | I | Y | Y | T | G |

| | | | | | | | | | | | | | | | |
|---|---|---|---|---|---|---|---|---|---|---|---|---|---|---|---|
| OVERALL CONSENSUS | R | S | S | Q | S | L | X | X | X | X | X | X | X | X | X |

FIG. 5

| Light Chain | CDR2 Sequence | | | | | | |
|---|---|---|---|---|---|---|---|
| L1, L2, L3, L4, L5, L6, L7, L8, L9, L10, L11, L13, L14, L16, L17, L19, L20, L23, L24, L25, L26, L29, L30, L32, L34, L38, L39, L42, L44, L46, L48 | L | G | S | N | R | A | S |
| L15, L21 | L | G | S | Y | R | A | S |
| L33 | L | V | S | N | R | A | S |
| L37 | L | G | S | N | R | D | S |
| L45, L52 | L | G | S | T | R | A | S |
| L47 | L | G | F | N | R | A | S |
| CONSENSUS | L | G | S | N | R | A | S |
| L27, L31 | A | A | S | T | L | Q | S |
| L18 | A | A | S | G | L | Q | S |
| L41 | A | T | S | T | L | E | S |
| CONSENSUS | A | A | S | T | L | Q | S |
| L12, L36, L49 | E | D | N | Q | R | P | S |
| L35, L51 | E | D | N | R | R | P | S |
| L28 | Q | D | N | K | R | P | S |
| L22 | G | K | N | N | R | P | S |
| CONSENSUS | E | D | N | X | R | P | S |
| L40 | D | A | S | R | R | A | T |
| L43 | D | A | S | N | R | A | T |
| L50 | G | A | G | Y | R | A | T |

FIG. 6

| Light Chain | CDR3 Sequence |
|---|---|

| Light Chain | | | | | | | | |
|---|---|---|---|---|---|---|---|---|
| L3, L5, L6, L7, L8, L13, L14, L17, L23, L29, L32, L34, L38, L39, L42, L44, L46 | M | Q | A | L | Q | T | P | L | T |
| L52 | M | Q | A | F | Q | T | P | L | T |
| L1, L2, L11, L15, L25 | M | Q | A | L | Q | T | P | I | T |
| L19, L45 | M | Q | A | L | Q | T | P | Y | T |
| L9, L20 | M | Q | A | L | Q | T | P | F | T |
| L4 | M | Q | A | L | Q | T | P | H | T |
| L24 | M | Q | A | L | Q | T | P | N | T |
| L10 | M | Q | A | L | Q | T | P | L | A |
| L47 | M | Q | G | L | Q | T | P | L | T |
| L26 | M | Q | A | L | E | M | P | L | T |
| L30 | M | E | A | L | Q | T | P | F | T |
| L33 | M | Q | T | L | Q | T | P | L | S |
| L16 | M | Q | G | T | H | W | P | L | T |
| L21 | M | Q | S | L | E | V | P | F | T |
| L48 | M | Q | A | T | H | W | P | Y | T |
| L37 | M | Q | G | T | H | W | P | Y | T |
| CONSENSUS | M | Q | A | L | Q | T | P | * | T |

"*" = nonpolar side chain amino acid

| | | | | | | | | |
|---|---|---|---|---|---|---|---|---|
| L40 | Q | Q | R | N | N | W | P | L | T |
| L43 | Q | Q | R | S | N | W | P | L | T |
| L41 | Q | Q | S | N | S | V | P | L | T |
| L27 | Q | Q | L | N | S | Y | P | L | T |
| L31 | Q | Q | S | H | S | P | P | Y | T |
| L18 | Q | Q | A | S | S | F | P | I | T |
| CONSENSUS | Q | Q | R | N | S | * | P | L | T |
| | | | S | S | | | | | |
| | | | N | | | | | | |

"*" = nonpolar side chain amino acid

| | | | | | | | | |
|---|---|---|---|---|---|---|---|---|
| L12 | Q | S | Y | D | S | S | N | Q | R | V |
| L51 | Q | S | Y | D | P | Y | N | R | V |
| L36 | Q | S | Y | D | S | S | N | V | – | V |
| L35 | Q | S | Y | Q | S | D | N | W | – | V |
| L49 | Q | S | Y | D | S | A | N | V | I |
| | Q | S | Y | D | S | S | N | K | V |

| | | | | | | | |
|---|---|---|---|---|---|---|---|---|
| L28 | Q | A | W | D | S | G | T | V |
| L50 | Q | H | Y | G | S | S | L | R | T |
| L22 | N | S | R | D | I | T | G | V | H | R |

FIG. 7

| Heavy Chain | CDR1 Sequence |
|---|---|
| H1, H2, H3, H5, H6, H7, H8, H9, H10, H11, H13, H14, H15, H16, H17, H19, H20, H23, H25, H26, H29, H30, H32, H33, H34, H37, H38, H39, H44, H46, H47, H52 | S S N W W S |
| H42, H45 | - S N W W S |
| H21 | S N I W W S |
| CONSENSUS | S S N W W S |
| | |
| H4, H36, H49 | G Y Y W S |
| H50 | N Y D W S |
| H28 | N Y Y W S |
| H22 | D F Y W S |
| CONSENSUS | X Y Y W S |
| | |
| H12, H18 | S Y A M S |
| H40, H43, H51 | S Y A I S |
| H31, H35 | S Y G M H |
| H41, H48 | S Y A M H |
| CONSENSUS | S Y A M S/H |
| | |
| H27 | S H G M H |
| | |
| H24 | S S S Y Y W G |

FIG. 8

| Heavy Chain | CDR2 Sequence | | | | | | | | | | | | | | | |
|---|---|---|---|---|---|---|---|---|---|---|---|---|---|---|---|---|
| H1, H2, H3, H5, H6, H7, H10, H11, H13, H14, H15, H16, H17, H19, H20, H23, H25, H26, H29, H30, H32, H33, H34, H37, H38, H39, H42, H44, H45, H46, H47, H52 | E | I | Y | H | S | G | S | T | N | Y | N | P | S | L | K | S |
| H8 | E | I | Y | H | S | G | S | T | N | Y | N | P | S | L | E | S |
| H36, H49 | E | I | N | H | S | G | S | T | N | Y | N | P | S | L | K | S |
| H21 | E | V | Y | H | S | G | S | T | N | Y | N | P | S | L | K | S |
| H4 | E | I | N | H | S | G | S | T | N | Y | N | R | S | L | K | S |
| H9 | Y | I | Y | Y | S | G | S | T | Y | Y | N | P | S | L | K | S |
| H50 | T | I | Y | S | S | G | S | T | Y | Y | S | P | S | L | K | S |
| H24 | S | I | Y | Y | S | G | S | T | Y | Y | N | P | S | L | K | S |
| H28 | Y | I | S | D | S | G | N | T | N | Y | N | P | S | L | K | S |
| H22 | E | V | N | P | R | G | S | T | N | Y | N | P | S | L | K | S |
| CONSENSUS | E | I | Y | H | S | G | S | T | N | Y | N | P | S | L | K | S |
|  | Y | V | N | Y |   |   |   |   | Y |   |   |   |   |   |   |   |

| | | | | | | | | | | | | | | | | |
|---|---|---|---|---|---|---|---|---|---|---|---|---|---|---|---|---|
| H18 | T | I | S | G | S | G | G | S | T | Y | Y | A | D | S | V | K | G |
| H12 | A | I | S | G | S | G | G | S | T | Y | Y | A | D | S | V | K | G |
| H41 | T | I | S | S | N | G | D | S | T | Y | Y | A | D | S | V | K | G |
| H27, H31 | V | I | S | Y | D | G | S | N | K | Y | Y | A | D | S | V | K | G |
| H35 | Y | I | S | S | S | S | S | T | I | Y | Y | A | D | S | V | K | G |
| CONSENSUS | X | I | S | G | S | G | G | S | T | Y | Y | A | D | S | V | K | G |
|  |   |   |   | S |   | S |   |   |   |   |   |   |   |   |   |   |   |

| | | | | | | | | | | | | | | | |
|---|---|---|---|---|---|---|---|---|---|---|---|---|---|---|---|---|
| H40, H43 | R | I | I | P | I | L | G | I | A | N | Y | A | Q | K | F | Q | G |
| H48 | W | I | N | A | G | N | G | N | T | K | Y | S | Q | K | F | Q | G |
| H51 | I | I | N | P | S | G | G | S | T | S | Y | A | Q | K | F | Q | G |

FIG. 9A

| Heavy Chain | | | | CDR3 Sequence | | | | | | | | | |
|---|---|---|---|---|---|---|---|---|---|---|---|---|---|
| H5  | - | Y | S | S | S | R | N | D | A | F | D | I | |
| H6  | - | - | - | D | G | Q | L | D | A | F | D | I | |
| H9  | - | - | - | W | S | Y | L | D | A | F | D | I | |
| H11 | - | - | - | A | N | R | D | D | A | F | D | I | |
| H13 | E | G | N | R | T | V | T | S | A | F | D | I | |
| H16 | - | - | W | T | G | R | T | D | A | F | D | I | |
| H17 | - | - | - | Q | G | A | L | D | A | F | D | I | |
| H20 | - | S | S | S | W | Y | W | N | A | F | D | I | |
| H25 | - | - | - | - | S | G | Y | D | A | F | D | I | |
| H32 | - | - | - | - | A | S | V | D | A | F | D | I | |
| H39 | - | - | - | L | S | F | A | D | P | F | D | I | |
| H41 | - | - | E | E | V | W | L | Q | A | F | D | I | |
| H45 | - | - | - | - | I | R | Y | D | A | F | D | I | |
| H46 | - | - | - | T | A | A | H | D | A | F | D | I | |
| H51 |   |   | D | R | W | R | Y | D | A | F | D | I | |
| CONSENSUS | - | - | - | X | S | R | L | D | A | F | D | I | |
| | | | | | | | | | | | | | |
| H7  | | | - | - | - | - | - | F | W | D | Y | Y | G | M | D | V |
| H52 | | | | | | | | | E | K | S | G | M | D | V |
| H8  | | | - | - | - | - | - | - | D | R | Y | Y | G | M | D | V |
| H10 | | | - | - | - | - | - | D | Y | D | I | F | G | M | D | V |
| H18 | | | - | E | R | G | S | G | W | S | L | D | N | M | D | V |
| H19 | | | - | - | - | - | D | S | S | G | F | Y | G | M | D | V |
| H24 | | | - | - | - | D | G | G | Y | Y | Y | Y | G | M | D | V |
| H48 | | | | | | H | S | Y | Y | Y | G | M | D | V |
| H30 | | | - | - | - | V | S | G | Y | Y | Y | Y | G | M | D | V |
| H31 | | | A | Y | S | S | G | W | Y | D | Y | Y | G | M | D | V |
| H37 | | | - | - | - | D | S | S | W | Y | Y | G | M | D | V |
| H40 | | | - | G | S | G | S | Y | Y | D | Y | Y | Y | M | D | V |
| H42 | | | - | - | - | - | - | - | D | K | G | Y | M | D | V |
| CONSENSUS | | | - | - | - | - | S | X | Y | D | Y | Y | G | M | D | V |
| | | | | | | | | | | | | | |
| H2  | - | - | - | - | G | V | E | Q | I | D | Y | | |
| H3  | - | - | N | L | A | A | G | A | V | A | Y | | |
| H4  | - | - | L | S | Y | G | S | G | V | D | Y | | |
| H12 | - | G | G | W | Y | G | D | Y | F | D | Y | | |
| H23 | - | G | I | A | A | A | G | Q | G | D | Y | | |
| H26 | - | Y | S | Y | G | T | V | G | I | D | Y | | |
| H27 | - | - | - | I | G | P | G | G | F | D | Y | | |
| H29 | - | - | V | G | S | G | W | Y | V | D | Y | | |
| H34 | - | - | - | - | D | H | G | P | F | D | Y | | |
| H35 | D | R | F | G | S | G | H | L | P | D | Y | | |
| H36 | V | G | Y | S | S | G | R | D | V | D | Y | | |
| H38 | - | - | - | - | S | T | W | S | L | D | Y | | |
| H44 | - | - | - | D | L | T | G | S | L | D | Y | | |
| H47 | - | D | S | S | G | Q | G | Y | F | D | Y | | |
| CONSENSUS | - | - | X | X | G | G | G | X | * | D | Y | | |

"*" = nonpolar side chain amino acids

FIG. 9B

| | | | | | | | | | | | | | |
|---|---|---|---|---|---|---|---|---|---|---|---|---|---|
| H22 | G | P | R | P | G | R | D | G | Y | N | Y | F | D | N |
| H28 | - | - | - | H | R | S | S | W | A | W | Y | F | D | L |
| H43 | - | - | D | H | R | F | D | Y | A | W | Y | F | D | L |
| CONSENSUS | - | - | X | H | R | X | D | X | A | W | Y | F | D | L |

| | | | | | | | | | | | | | |
|---|---|---|---|---|---|---|---|---|---|---|---|---|---|
| H1 | F | N | Y | Y | D | S | S | V | | | | | |
| H14, H15, H33 | - | G | L | G | D | S | S | G | Y | I | L | | |
| H19 | - | - | - | - | D | S | S | G | F | Y | G | M | D | V |
| H37 | - | - | - | - | D | S | S | S | W | Y | Y | G | M | D | V |
| H47 | - | - | - | - | D | S | S | G | Q | G | Y | F | D | Y |
| CONSENSUS | - | - | - | - | D | S | S | G | X | X | X | - | - | - |

| | | | | | | | | | | |
|---|---|---|---|---|---|---|---|---|---|---|
| H21 | Y | R | S | F | G | E | S | Y | | |
| H49 | V | G | Y | S | H | G | E | E | V | L | D | V |
| H50 | A | R | G | Y | S | S | P | F | D | P |

FIG. 10

```
  1  MKSGSGGGSP TSLWGLLFLS AALSLWPTSG EICGPGIDIR NDYQQLKRLE NCTVIEGYLH
 61  ILLISKAEDY RSYRFPKLTV ITEYLLLFRV AGLESLGDLF PNLTVIRGWK LFYNYALVIF
121  EMTNLKDIGL YNLRNITRGA IRIEKNADLC YLSTVDWSLI LDAVSNNYIV GNKPPKECGD
181  LCPGTMEEKP MCEKTTINNE YNYRCWTTNR CQKMCPSTCG KRACTENNEC CHPECLGSCS
241  APDNDTACVA CRHYYYAGVC VPACPPNTYR FEGWRCVDRD FCANILSAES SDSEGFVIHD
301  GECMQECPSG FIRNGSQSMY CIPCEGPCPK VCEEEKKTKT IDSVTSAQML QGCTIFKGNL
361  LINIRRGNNI ASELENFMGL IEVVTGYVKI RHSHALVSLS FLKNLRLTLG EEQLEGNYSF
421  YVLDNQNLQQ LWDWDHRNLT IKAGKMYFAF NPKLCVSEIY RMEEVTGTKG RQSKGDINTR
481  NNGERASCES DVLHFTSTTT SKNRIIITWH RYRPPDYRDL ISFTVYYKEA PFKNVTEYDG
541  QDACGSNSWN MVDVDLPPNK DVEPGILLHG LKPWTQYAVY VKAVTLTMVE NDHIRGAKSE
601  ILYIRTNASV PSIPLDVLSA SNSSSQLIVK WNPPSLPNGN LSYYIVRWQR QPQDGYLYRH
661  NYCSKDKIFI RKYADGTIDI EEVTENPKTE VCGGEKGPCC ACPKTEAEKQ AEKEEAEYRK
721  VFENFLHNSI FVPRPERKRR DVMQVANTTM SSRSRNTTAA DTYNITDPEE LETEYPFFES
781  RVDNKERTVI SNLRPFTLYR IDIHSCNHEA EKLGCSASNF VFARTMPAEG ADDIPGPVTW
841  EPRPENSIFL KWPEPENPNG LILMYEIKYG SQVEDQRECV SRQEYRKYGG AKLNRLNPGN
901  YTARIQATSL SGNGSWTDPV FFYVQAKTGY ENFIHLDEVD GCKPCICTVP EVSSVFIFPP
961  KPKDVLTITL TPKVTCVVVD ISKDDPEVQF SWFVDDVEVH TAQTQPREEQ FNSTFRSVSE
1021 LPIMHQDWLN GKEFKCRVNS AAFPAPIEKT ISKTKGRPKA PQVYTIPPPK EQMAKDKVSL
1081 TCMITDFFPE DITVEWQWNG QPAENYKNTQ PIMDTDGSYF VYSKLNVQKS NWEAGNTFTC
1141 SVLHEGLHNH HTEKSLSHSP GK
```

FIG. 11

```
   1 MGTGGRRGAA AAPLLVAVAA LLLGAAGHLY PGEVCPGMDI RNNLTRLHEL ENCSVIEGHL
  61 QILLMFKTRP EDFRDLSFPK LIMITDYLLL FRVYGLESLK DLFPNLTVIR GSRLFFNYAL
 121 VIFEMVHLKE LGLYNLMNIT RGSVRIEKNN ELCYLATIDW SRILDSVEDN HIVLNKDDNE
 181 ECGDICPGTA KGKTNCPATV INGQFVERCW THSHCQKVCP TICKSHGCTA EGLCCHSECL
 241 GNCSQPDDPT KCVACRNFYL DGRCVETCPP PYYHFQDWRC VNFSFCQDLH HKCKNSRRQG
 301 CHQYVIHNNK CIPECPSGYT MNSSNLLCTP CLGPCPKVCH LLEGEKTIDS VTSAQELRGC
 361 TVINGSLIIN IRGGNNLAAE LEANLGLIEE ISGYLKIRRS YALVSLSFFR KLRLIRGETL
 421 EIGNYSFYAL DNQNLRQLWD WSKHNLTTTQ GKLFFHYNPK LCLSEIHKME EVSGTKGRQE
 481 RNDIALKTNG DKASCENELL KFSYIRTSFD KILLRWEPYW PPDFRDLLGF MLFYKEAPYQ
 541 NVTEFDGQDA CGSNSWTVVD IDPPLRSNDP KSQNHPGWLM RGLKPWTQYA IFVKTLVTFS
 601 DERRTYGAKS DIIYVQTDAT NPSVPLDPIS VSNSSSQIIL KWKPPSDPNG NITHYLVFWE
 661 RQAEDSELFE LDYCLKGLKI PSRTWSPPFE SEDSQKHNQS EYEDSAGECC SCPKTDSQIL
 721 KELEESSFRK TFEDYLHNVV FVPRKTSSGT GAEDFRPSRK RRSLGDVGNV TVAVPTVAAF
 781 PNTSSTSVPT SPEEHRPFEK VVNKESLVIS GLRHFTGYRI ELQACNQDTP EERCSVAAYV
 841 SARTMPEAKA DDIVGPVTHE IFENNVVHLM WQEPKEPNGL IVLYEVSYRR YGDEELHLCV
 901 SRKHFALERG CRLRGLSPGN YSVRIRATSL AGNGSWTEPT YFYVTDYLDV PSNIAKVDGC
 961 KPCICTVPEV SSVFIFPPKP KDVLTITLTP KVTCVVVDIS KDDPEVQFSW FVDDVEVHTA
1021 QTQPREEQFN STFRSVSELP IMHQDWLNGK EFKCRVNSAA FPAPIEKTIS KTKGRPKAPQ
1081 VYTIPPPKEQ MAKDKVSLTC MITDFFPEDI TVEWQWNGQP AENYKNTQPI MDTDGSYFVY
1141 SKLNVQKSNW EAGNTFTCSV LHEGLHNHHT EKSLSHSPGK
```

FIG. 12

```
   1  MKSGSGGG SPTSLWGLLF LSAALSLWPT SGEICGPGID IRNDYQQLKR
  51  LENCTVIEGY LHILLISKAE DYRSYRFPKL TVITEYLLLF RVAGLESLGD
 101  LFPNLTVIRG WKLFYNYALV IFEMTNLKDI GLYNLRNITR GAIRIEKNAD
 151  LCYLSTVDWS LILDAVSNNY IVGNKPPKEC GDLCPGTMEE KPMCEKTTIN
 201  NEYNYRCWTT NRCQKMCPST CGKRACTENN ECCHPECLGS CSAPDNDTAC
 251  VACRHYYYAG VCVPACPPNT YRFEGWRCVD RDFCANILSA ESSDSEGFVI
 301  HDGECMQECP SGFIRNGSQS MYCIPCEGPC PKVCEEEKKT KTIDSVTSAQ
 351  MLQGCTIFKG NLLINIRRGN NIASELENFM GLIEVVTGYV KIRHSHALVS
 401  LSFLKNLRLI LGEEQLEGNY SFYVLDNQNL QQLWDWDHRN LTIKAGKMYF
 451  AFNPKLCVSE IYRMEEVTGT KGRQSKGDIN TRNNGERASC ESDVLHFTST
 501  TTSKNRIIIT WHRYRPPDYR DLISFTVYYK EAPFKNVTEY DGQDACGSNS
 551  WNMVDVDLPP NKDVEPGILL HGLKPWTQYA VYVKAVTLTM VENDHIRGAK
 601  SEILYIRTNA SVPSIPLDVL SASNSSSQLI VKWNPPSLPN GNLSYYIVRW
 651  QRQPQDGYLY RHNYCSKDKI PIRKYADGTI DIEEVTENPK TEVCGGEKGP
 701  CCACPKTEAE KQAEKEEAEY RKVFENFLHN SIFVPRPERK RRDVMQVANT
 751  TMSSRSRNTT AADTYNITDP EELETEYPFF ESRVDNKERT VISNLRPFTL
 801  YRIDIHSCNH EAEKLGCSAS NFVFARTMPA EGADDIPGPV TWEPRPENSI
 851  FLKWPEPENP NGLILMYEIK YGSQVEDQRE CVSRQEYRKY GGAKLNRLNP
 901  GNYTARIQAT SLSGNGSWTD PVFFYVQAKT GYEAAAARKC SLTGKWTNDL
 951  GSNMTIGAVN SKGEFTGTYT TAVTATSNEI KESPLHGTQN TINKRTQPTF
1001  GETVNWKPSE STTVFTGQCF IDRNGKEVLK TMWLLRSSVN DIGDDWKATR
1101  VGINIFTRLR TQKE
```

FIG. 13

Kappa light chain constant region

*Nucleotide Sequence* cgaactgtggctgcaccatctgtcttcatcttcccgccatctgatgagcagttgaaatctggaac
tgcctctgttgtgtgcctgctgaataacttctatcccagagaggccaaagtacagtggaaggtgg
ataacgcctccaatcgggtaactcccaggagagtgtcacagagcaggacagcaaggacagcacc
tacagcctcagcagcaccctgacgctgagcaaagcagactacgagaaacacaaagtctacgcctg
cgaagtcacccatcagggcctgagctcgcccgtcacaaagagcttcaacaggggagagtgt

*Amino acid sequence* rtvaapsvfifppsdeqlksgtasvvcllnnfypreakvqwkvdnalqsgnsqesvteqdskdst
yslsstltlskadyekhkvyacevthqglsspvtksfnrgec

IgG1 heavy chain constant region

*Nucleotide Sequence* gcctccaccaagggcccatcggtcttccccctggcaccctcctccaagagcacctctgggggcac
agcggccctgggctgcctggtcaaggactacttccccgaaccggtgacggtgtcgtggaactcag
gcgccctgaccagcggcgtgcacaccttcccggctgtcctacagtcctcaggactctactccctc
agcagcgtggtgaccgtgccctccagcagcttgggcacccagacctacatctgcaacgtgaatca
caagcccagcaacaccaaggtggacaagaaagttgagcccaaatcttgtgacaaaactcacacat
gcccaccgtgcccagcacctgaactcctggggggaccgtcagtcttcctcttccccccaaaaccc
aaggacaccctcatgatctcccggacccctgaggtcacatgcgtggtggtggacgtgagccacga
agaccctgaggtcaagttcaactggtacgtggacggcgtggaggtgcataatgccaagacaaagc
cgcgggaggagcagtacaacagcacgtaccgtgtggtcagcgtcctcaccgtcctgcaccaggac
tggctgaatggcaaggagtacaagtgcaaggtctccaacaaagccctcccagcccccatcgagaa
aaccatctccaaagccaaagggcagccccgagaaccacaggtgtacaccctgcccccatcccggg
atgagctgaccaagaaccaggtcagcctgacctgcctggtcaaaggcttctatcccagcgacatc
gccgtggagtgggagagcaatgggcagccggagaacaactacaagaccacgcctcccgtgctgga
ctccgacggctccttcttcctctatagcaagctcaccgtggacaagagcaggtggcagcagggga
acgtcttctcatgctccgtgatgcatgaggctctgcacaaccactacacgcagaagagcctctcc
ctgtctccgggtaaa

*Amino acid sequence* astkgpsvfplapsskstsggtaalgclvkdyfpepvtvswnsgaltsgvhtfpavlqssglysl
ssvvtvpssslgtqtyicnvnhkpsntkvdkkvepkscdkthtcppcpapellggpsvflfppkp
kdtlmisrtpevtcvvvdvshedpevkfnwyvdgvevhnakttkpreeqynstyrvvsvltvlhqd
wlngkeykckvsnkalpapiektiskakgqprepqvytlppsrdeltknqvsltclvkgfypsdi
avewesngqpennykttppvldsdgsfflysklt vdksrwqqgnvfscsvmhealhnhytqksls
lspgk

US 7,871,611 B2

COMPOSITIONS AND METHODS RELATING TO ANTI IGF-1 RECEPTOR ANTIBODIES

REFERENCE TO RELATED APPLICATION

This application claims the benefit of U.S. Provisional Application Ser. No. 60/638,961, filed on Dec. 22, 2004, and is incorporated by reference herein.

SEQUENCE LISTING APPENDIX ON COMPACT DISC

This application includes the sequence listing submitted on the enclosed three compact discs identified as "Compact Disc 1", and duplicate copies, "Copy 1", and "Copy 2". Each disc was created on Dec. 19, 2005, document named A-954 (US) st25.TXT, having 376 K bytes of data, using an IBM-PC Compatible computer, MS-DOS/Windows NT, and Patentin software version 3.2. The content of each disc is identical, all of which are incorporated by reference herein.

FIELD OF THE INVENTION

This application provides compositions and methods relating to anti-IGF-1 receptor antibodies.

BACKGROUND OF THE INVENTION

Insulin-like growth factors 1 and 2 (IGF-1 and IGF-2, respectively) promote the differentiation and proliferation of a wide variety of mammalian cell types.

IGF-1 and IGF-2 both circulate widely throughout the body in plasma. They exert their effects on cells by binding to and activating the IGF-1 receptor (IGF-1R). IGF-1R is a member of the family of tyrosine kinase growth factor receptors. Its amino acid sequence is about 70% identical to that of the insulin receptor.

Abnormal IGF-1, IGF-2, and/or IGF-1R activities are associated with a number of medical conditions, including various types of cancer, growth defects (e.g., acromegaly, gigantism, and small stature), psoriasis, atherosclerosis, post angioplasty smooth muscle restonsis of blood vessels, diabetes, microvasular proliferation, neuropathy, loss of muscle mass, and osteoporosis.

BRIEF DESCRIPTION OF THE DRAWINGS

FIG. 1 provides nucleotide sequences encoding light chain variable domains L1 through L52 and heavy chain variable domains H1 through H52.

FIG. 2 provides amino acid sequences of light chain variable domains L1 through L52. CDR and FR regions are indicated.

FIG. 3 provides amino acid sequences of heavy chain variable domains H1 through H52. CDR and FR regions are indicated.

FIG. 4 provides amino acid sequences of the light chain CDR1 regions of light chain variable domains L1 through L52. Consensus sequences for groups of related CDR sequences are also provided.

FIG. 5 provides amino acid sequences of the light chain CDR2 regions of light chain variable domains L1 through L52. Consensus sequences for groups of related CDR sequences are also provided.

FIG. 6 provides amino acid sequences of the light chain CDR3 regions of light chain variable domains L1 through L52. Consensus sequences for groups of related CDR sequences are also provided.

FIG. 7 provides amino acid sequences of the heavy chain CDR1 regions of heavy chain variable domains H1 through H52. Consensus sequences for groups of related CDR sequences are also provided.

FIG. 8 provides amino acid sequences of the heavy chain CDR2 regions of heavy chain variable domains H1 through H52. Consensus sequences for groups of related CDR sequences are also provided.

FIG. 9 provides amino acid sequences of the heavy chain CDR3 regions of heavy chain variable domains H1 through H52. Consensus sequences for groups of related CDR sequences are also provided.

FIG. 10 provides the amino acid sequence of a human IGF-1R extracellular domain fused to a human IgG1 Fc region (underlined) with an intervening caspase-3 cleavage site (bold) (SEQ ID NO:231).

FIG. 11 provides the amino acid sequence of a human insulin receptor extracellular domain fused to a human IgG1 Fc region (underlined) (SEQ ID NO: 232).

FIG. 12 provides the protein sequence of a human IGF-1R extracellular domain (including signal peptide) fused at the C-terminus with chicken avidin (SEQ ID NO: 233). The initiating met in the IGF-1R ECD is designated position 1 in this figure.

FIG. 13 provides the polypeptide sequence of a human kappa light chain antibody constant region (SEQ ID NO: 209) and a human IgG1 heavy chain antibody constant region (SEQ ID NO: 211).

SUMMARY OF THE INVENTION

Figure 14:
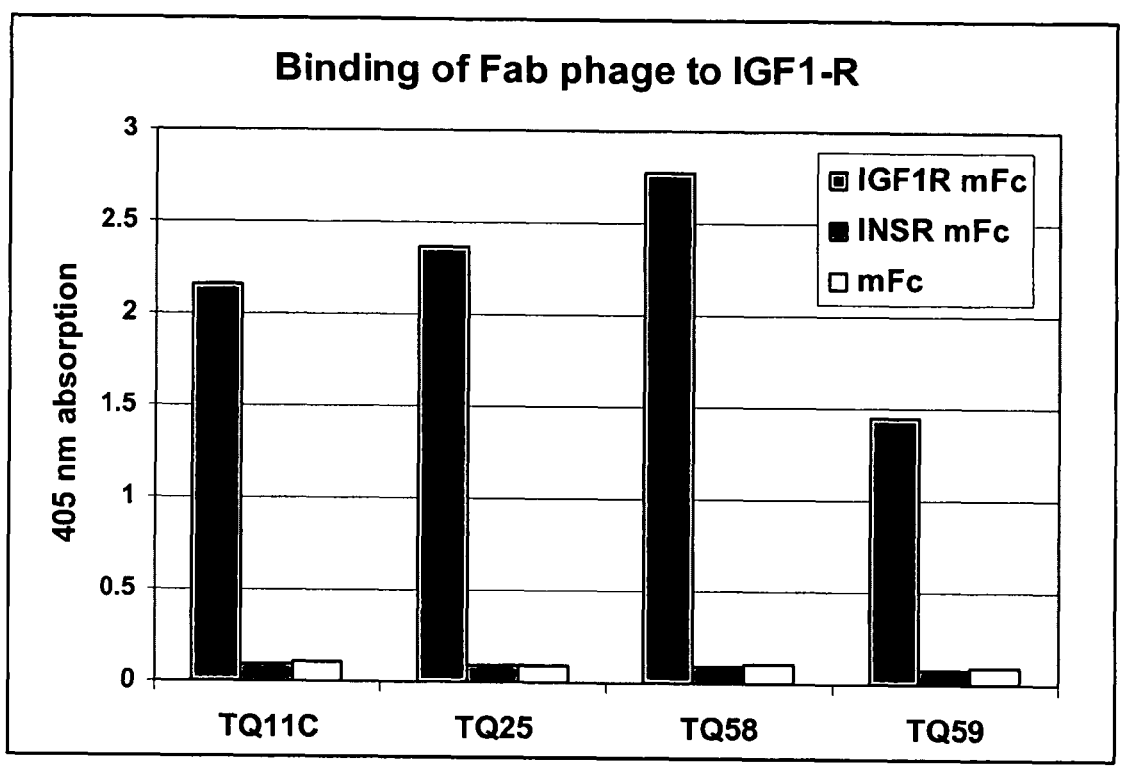
FIG. 14 provides a graph illustrating that four phage-displayed antibodies bind significantly better to an IGF-1R-Fc molecule than they bind to an insulin-receptor-Fc or a murine Fc.

In one aspect, the present invention provides an isolated antigen binding protein comprising either: a. a light chain CDR3 comprising a sequence selected from the group consisting of: i. a light chain CDR3 sequence that differs by no more than a total of two amino acid additions, substitutions, and/or deletions from a CDR3 sequence selected from the group consisting of the light chain CDR3 sequences of L1-L52 as shown in FIG. 6; ii. M $X_1 X_2 X_3 X_4 X_5$ P $X_6 X_7$; iii. Q Q $X_8 X_9 X_{10} X_{11}$ P $X_{12}$ T; and iv. Q S Y $X_{13} X_{14} X_{15}$ N $X_{16} X_{17} X_{18}$; b. a heavy chain CDR3 comprising a sequence selected from the group consisting of: i. a heavy chain CDR3 sequence that differs by no more than a total of three amino acid additions, substitutions, and/or deletions from a CDR3 sequence selected from the group consisting of the heavy chain CDR3 sequences of H1-H52 as shown in FIG. 9; ii. $X_{19} X_{20} X_{21} X_{22} X_{23} X_{24} X_{25} X_{26} X_{27}$ F D I; iii. $X_{28} X_{29} X_{30} X_{31} X_{32} X_{33} X_{34} X_{35} X_{36} X_{37} X_{38}$ M D V; iv. D S S $X_{39}$; or c. the light chain CDR3 sequence of (a) and the heavy chain CDR3 sequence of (b); wherein $X_1$ is a glutamine residue or a glutamate residue, $X_2$ is an alanine residue, a glycine residue, a threonine residue, or a serine residue, $X_3$ is a leucine residue, a phenylalanine residue, or a threonine residue, $X_4$ is glutamine residue, a glutamate residue, or a histidine residue, $X_5$ is a threonine residue, a methionine residue, a tryptophan residue, or a valine residue, $X_6$ is a glycine residue, an alanine residue, a valine residue, a leucine residue, an isoleucine residue, a proline residue, a phenylalanine residue, a methionine residue, a tryptophan residue, or a cysteine residue, $X_7$ is a threonine residue, an alanine residue, or a serine residue, $X_8$ is an arginine residue, a serine residue, a leucine residue, or an alanine residue, $X_9$ is an asparagine residue, a serine residue, or a histidine residue, $X_{10}$ is an asparagine residue or a serine residue, $X_{11}$ is a tryptophan residue, a valine residue, a tyrosine residue, a proline residue, or a phenylalanine residue, $X_{12}$ is a leucine residue, a tyrosine residue, or an isoleucine residue, $X_{13}$ is an aspartate residue or a glutamine residue, $X_{14}$ is a serine residue or a proline residue, $X_{15}$ is a serine residue, a tyrosine residue, an aspartate residue, or an alanine residue, $X_{16}$ is a glutamine residue, an arginine residue, a valine residue, or a tryptophan residue, $X_{17}$ is an arginine residue, a valine residue, an isoleucine residue, or no residue, $X_{18}$ is a valine residue or no residue, $X_{19}$ is a glutamate residue or no residue, $X_{20}$ is a tyrosine residue, a glycine residue, a serine residue, or no residue, $X_{21}$ is a serine residue, an asparagine residue, a tryptophan residue, a glutamate residue, as aspartate residue, or no residue, $X_{22}$ is a serine residue, an aspartate residue, a tryptophan residue, an alanine residue, an arginine residue, a threonine residue, a glutamine residue, a leucine residue, a glutamate residue, or no residue, $X_{23}$ is a serine residue, a glycine residue, an asparagine residue, a threonine residue, a tryptophan residue, a valine residue, an alanine residue, or an isoleucine residue, $X_{24}$ is an arginine residue, a glutamine residue, a tyrosine residue, a valine residue, an alanine residue, a glycine residue, a serine residue, a phenylalanine residue, or a tryptophan residue, $X_{25}$ is an asparagine residue, a leucine residue, an aspartate residue, a threonine residue, a tryptophan residue, a tyrosine residue, a valine residue, an alanine residue, or a histidine residue, $X_{26}$ is an aspartate residue, a serine residue, an asparagine residue, or a glutamine residue, $X_{27}$ is an alanine residue or a proline residue, $X_{28}$ is an alanine residue or no residue, $X_{29}$ is a glutamate residue, a tyrosine residue, a glycine residue, or no residue, $X_{30}$ is an arginine residue, a serine residue, or no residue, $X_{31}$ is a glycine residue, an aspartate residue, a valine residue, a serine residue, or no residue, $X_{32}$ is a serine residue, an aspartate residue, a glycine residue, or no residue, $X_{33}$ is a phenylalanine residue, an aspartate residue, a tyrosine residue, a glycine residue, a serine residue, a histidine residue, a tryptophan residue, or no residue, $X_{34}$ is a tryptophan residue, an aspartate residue, a tyrosine residue, a serine residue, or no residue, $X_{35}$ is an aspartate residue, a glutamate residue, an arginine residue, a serine residue, a glycine residue, a tyrosine residue, or a tryptophan residue, $X_{36}$ is a tyrosine residue, a lysine residue, an isoleucine residue, a leucine residue or a phenylalanine residue, $X_{37}$ is a tyrosine residue, a serine residue, a phenylalanine residue, an aspartate residue, or a glycine residue, $X_{38}$ is a glycine residue, an asparagine residue, or a tyrosine residue, $X_{39}$ is a valine residue, a glycine residue, or a serine residue, and said antigen binding protein binds specifically to human IGF-1R. In one embodiment, the isolated antigen binding protein comprises an amino acid sequence selected from the group consisting of: a. a light chain CDR1 sequence that differs by no more than a total of six amino acid additions, substitutions, and/or deletions from a CDR1 sequence of L1-L52 as shown in FIG. 4; b. a light chain CDR2 sequence that differs by no more than a total of two amino acid additions, substitutions, and/or deletions from a CDR2 sequence of L1-L52 as shown in FIG. 5; c. a light chain CDR3 sequence that differs by no more than a total of three amino acid additions, substitutions, and/or deletions from a CDR3 sequence of L1-L52 as shown in FIG. 6; d. a heavy chain CDR1 sequence that differs by no more than a total of two amino acid additions, substitutions, and/or deletions from a CDR1 sequence of H1-H52 as shown in FIG. 7; e. a heavy chain CDR2 sequence that differs by no more than a total of five amino acid additions, substitutions, and/or deletions from a CDR2 sequence of H1-H52 as shown in FIG. 8; and f. a heavy chain CDR3 sequence that differs by no more than a total of four amino acid additions, substitutions, and/or deletions from a CDR3 sequence of H1-H52 as shown in FIG. 9. In another embodiment, the isolated antigen binding protein comprises an amino acid sequence selected from the group consisting of: a. a light chain CDR1 sequence that differs by no more than a total of five amino acid additions, substitutions, and/or deletions from a CDR1 sequence of L1-L52 as shown in FIG. 4; b. a light chain CDR2 sequence that differs by no more than a total of one amino acid addition, substitution, or deletion from a CDR2 sequence of L1-L52 as shown in FIG. 5; c. a light chain CDR3 sequence that differs by no more than a total of two amino acid additions, substitutions, and/or deletions from a CDR3 sequence of L1-L52 as shown in FIG. 6; d. a heavy chain CDR1 sequence that differs by no more than a total of one amino acid addition, substitution, or deletion from a CDR1 sequence of H1-H52 as shown in FIG. 7; e. a heavy chain CDR2 sequence that differs by no more than a total of four amino acid additions, substitutions, and/or deletions from a CDR2 sequence of H1-H52 as shown in FIG. 8; and f. a heavy chain CDR3 sequence that differs by no more than a total of three amino acid additions, substitutions, and/or deletions from a CDR3 sequence of H1-H52 as shown in FIG. 9. In another embodiment, the isolated antigen binding protein comprises an amino acid sequence selected from the group consisting of: a. a light chain CDR1 sequence that differs by no more than a total of four amino acid additions, substitutions, and/or deletions from a CDR1 sequence of L1-L52 as shown in FIG. 4; b. a light chain CDR2 sequence of L1-L52 as shown in FIG. 5; c. a light chain CDR3 sequence that differs by no more than a total of one amino acid addition, substitution, or deletion from a CDR3 sequence of L1-L52 as shown in FIG. 6; d. a heavy chain CDR1 sequence of H1-H52 as shown in FIG. 7; e. a heavy chain CDR2 sequence that differs by no more than a total of three amino acid additions, substitutions, and/or deletions from a CDR2 sequence of H1-H52 as shown in FIG. 8; and f. a heavy chain CDR3 sequence that differs by no more than a total of two amino acid additions, substitutions, and/or deletions from a CDR3 sequence of H1-H52 as shown in FIG. 9. In another embodiment, the isolated antigen binding protein comprises an amino acid sequence selected from the group consisting of: a. a light chain CDR1 sequence that differs by no more than a total of three amino acid additions, substitutions, and/or deletions from a CDR1 sequence of L1-L52 as shown in FIG. 4; b. a light chain CDR3 sequence of L1-L52 as shown in FIG. 6; c. a heavy chain CDR2 sequence that differs by no more than a total of two amino acid additions, substitutions, and/or deletions from a CDR2 sequence of H1-H52 as shown in FIG. 8; and d. a heavy chain CDR3 sequence that differs by no more than a total of one amino acid addition, substitution, or deletion from a CDR3 sequence of H1-H52 as shown in FIG. 9. In another embodiment, the isolated antigen binding protein comprises an amino acid sequence selected from the group consisting of: a. a light chain CDR1 sequence that differs by no more than a total of two amino acid additions, substitutions, and/or deletions from a CDR1 sequence of L1-L52 as shown in FIG. 4; b. a heavy chain CDR2 sequence that differs by no more than a total of one amino acid addition, substitution, or deletion from a CDR2 sequence of H1-H52 as shown in FIG. 8; and c. a heavy chain CDR3 sequence of H1-H52 as shown in FIG. 9. In another embodiment, the isolated antigen binding protein comprises an amino acid sequence selected from the group consisting of: a. a light chain CDR1 sequence that differs by no more than a total of one amino acid addition, substitution, or deletion from a CDR1 sequence of L1-L52 as shown in FIG. 4; and b. a heavy chain CDR2 sequence of H1-H52 as shown in FIG. 8. In another embodiment, the isolated antigen binding protein comprises a CDR1 sequence of L1-L52 as shown in FIG. 4. In another embodiment, the isolated antigen binding protein comprises a sequence selected from the group consisting of: a. a light chain CDR1 sequence selected from the group consisting of: i. RSSQSLLHSNGYNYLD; ii. RASQ(G/S)(I/V)(G/S)X(Y/F)L(A/N); and iii. RSSQS(L/I)XXXXX; b. a light chain CDR2 sequence selected from the group consisting of: i. LGSNRAS; ii. AASTLQS; and iii. EDNXRPS; c. a heavy chain CDR1 sequence selected from the group consisting of: i. SSNWWS; ii. XYYWS; and iii. SYAM(S/H); and d. a heavy chain CDR2 sequence selected from the group consisting of: i. (E/I)(I/V)(Y/N)(H/Y)SGST(N/Y)YNPSLKS; and ii. XIS(G/S)SG(G/S)STYYADSVKG; wherein amino acid residue symbols enclosed in parentheses identify alternative residues for the same position in a sequence, each X is independently any amino acid residue, and each Z is independently a glycine residue, an alanine residue, a valine residue, a leucine residue, an isoleucine residue, a proline residue, a phenylalanine residue, a methionine residue, a tryptophan residue, or a cysteine residue. In another embodiment, the isolated antigen binding protein comprises a heavy chain CDR3 sequence that differs by no more than a total of two amino acid additions, substitutions, and/or deletions from a CDR3 sequence of H1-H52 as shown in FIG. 9. In another embodiment, the isolated antigen binding protein comprises a heavy chain CDR3 sequence that differs by no more than a total of one amino acid addition, substitution, or deletion from a CDR3 sequence of H1-H52 as shown in FIG. 9. In another embodiment, the isolated antigen binding protein comprises a heavy chain CDR3 sequence of H1-H52 as shown in FIG. 9. In another embodiment, the isolated antigen binding protein comprises two amino acid sequences selected from the group consisting of: a. a light chain CDR1 sequence that differs by no more than a total of six amino acid additions, substitutions, and/or deletions from a CDR1 sequence of L1-L52 as shown in FIG. 4; b. a light chain CDR2 sequence that differs by no more than a total of two amino acid additions, substitutions, and/or deletions from a CDR2 sequence of L1-L52 as shown in FIG. 5; c. a light chain CDR3 sequence that differs by no more than a total of three amino acid additions, substitutions, and/or deletions from a CDR3 sequence of L1-L52 as shown in FIG. 6; d. a heavy chain CDR1 sequence that differs by no more than a total of two amino acid additions, substitutions, and/or deletions from a CDR1 sequence of H1-H52 as shown in FIG. 7; e. a heavy chain CDR2 sequence that differs by no more than a total of five amino acid additions, substitutions, and/or deletions from a CDR2 sequence of H1-H52 as shown in FIG. 8; and f. a heavy chain CDR3 sequence that differs by no more than a total of four amino acid additions, substitutions, and/or deletions from a CDR3 sequence of H1-H52 as shown in FIG. 9. In another embodiment, the isolated antigen binding protein comprises three amino acid sequences selected from the group consisting of: a. a light chain CDR1 sequence that differs by no more than a total of six amino acid additions, substitutions, and/or deletions from a CDR1 sequence of L1-L52 as shown in FIG. 4; b. a light chain CDR2 sequence that differs by no more than a total of two amino acid additions, substitutions, and/or deletions from a CDR2 sequence of L1-L52 as shown in FIG. 5; c. a light chain CDR3 sequence that differs by no more than a total of three amino acid additions, substitutions, and/or deletions from a CDR3 sequence of L1-L52 as shown in FIG. 6; d. a heavy chain CDR1 sequence that differs by no more than a total of two amino acid additions, substitutions, and/or deletions from a CDR1 sequence of H1-H52 as shown in FIG. 7; e. a heavy chain CDR2 sequence that differs by no more than a total of five amino acid additions, substitutions, and/or deletions from a CDR2 sequence of H1-H52 as shown in FIG. 8; and f. a heavy chain CDR3 sequence that differs by no more than a total of four amino acid additions, substitutions, and/or deletions from a CDR3 sequence of H1-H52 as shown in FIG. 9. In another embodiment, the isolated antigen binding protein comprises four amino acid sequences selected from the group consisting of: a. a light chain CDR1 sequence that differs by no more than a total of six amino acid additions, substitutions, and/or deletions from a CDR1 sequence of L1-L52 as shown in FIG. 4; b. a light chain CDR2 sequence that differs by no more than a total of two amino acid additions, substitutions, and/or deletions from a CDR2 sequence of L1-L52 as shown in FIG. 5; c. a light chain CDR3 sequence that differs by no more than a total of three amino acid additions, substitutions, and/or deletions from a CDR3 sequence of L1-L52 as shown in FIG. 6; d. a heavy chain CDR1 sequence that differs by no more than a total of two amino acid additions, substitutions, and/or deletions from a CDR1 sequence of H1-H52 as shown in FIG. 7; e. a heavy chain CDR2 sequence that differs by no more than a total of five amino acid additions, substitutions, and/or deletions from a CDR2 sequence of H1-H52 as shown in FIG. 8; and f. a heavy chain CDR3 sequence that differs by no more than a total of four amino acid additions, substitutions, and/or deletions from a CDR3 sequence of H1-H52 as shown in FIG. 9. In another embodiment, the isolated antigen binding protein comprises five amino acid sequences selected from the group consisting of: a. a light chain CDR1 sequence that differs by no more than a total of six amino acid additions, substitutions, and/or deletions from a CDR1 sequence of L1-L52 as shown in FIG. 4; b. a light chain CDR2 sequence that differs by no more than a total of two amino acid additions, substitutions, and/or deletions from a CDR2 sequence of L1-L52 as shown in FIG. 5; c. a light chain CDR3 sequence that differs by no more than a total of three amino acid additions, substitutions, and/or deletions from a CDR3 sequence of L1-L52 as shown in FIG. 6; d. a heavy chain CDR1 sequence that differs by no more than a total of two amino acid additions, substitutions, and/or deletions from a CDR1 sequence of H1-H52 as shown in FIG. 7; e. a heavy chain CDR2 sequence that differs by no more than a total of five amino acid additions, substitutions, and/or deletions from a CDR2 sequence of H1-H52 as shown in FIG. 8; and f. a heavy chain CDR3 sequence that differs by no more than a total of four amino acid additions, substitutions, and/or deletions from a CDR3 sequence of H1-H52 as shown in FIG. 9. In another embodiment, the isolated antigen binding protein comprises: a. a light chain CDR1 sequence that differs by no more than a total of six amino acid additions, substitutions, and/or deletions from a CDR1 sequence of L1-L52 as shown in FIG. 4; b. a light chain CDR2 sequence that differs by no more than a total of two amino acid additions, substitutions, and/or deletions from a CDR2 sequence of L1-L52 as shown in FIG. 5; c. a light chain CDR3 sequence that differs by no more than a total of three amino acid additions, substitutions, and/or deletions from a CDR3 sequence of L1-L52 as shown in FIG. 6; d. a heavy chain CDR1 sequence that differs by no more than a total of two amino acid additions, substitutions, and/or deletions from a CDR1 sequence of H1-H52 as shown in FIG. 7; e. a heavy chain CDR2 sequence that differs by no more than a total of five amino acid additions, substitutions, and/or deletions from a CDR2 sequence of H1-H52 as shown in FIG. 8; and f. a heavy chain CDR3 sequence that differs by no more than a total of four amino acid additions, substitutions, and/or deletions from a CDR3 sequence of H1-H52 as shown in FIG. 9. In another embodiment, the isolated antigen binding protein comprises either: a. a light chain variable domain comprising: i. a light chain CDR1 sequence shown in FIG. 4; ii. a light chain CDR2 sequence shown in FIG. 5; and iii. a light chain CDR3 sequence shown in FIG. 6; b. a heavy chain variable domain comprising: i. a heavy chain CDR1 sequence shown in FIG. 7; ii. a heavy chain CDR2 sequence shown in FIG. 8; and iii. a heavy chain CDR3 sequence shown in FIG. 9; or c. the light chain variable domain of (a) and the heavy chain variable domain of (b). In another embodiment, the isolated antigen binding protein comprises either: a. light chain CDR1, CDR2, and CDR3 sequences that each is identical to the CDR1, CDR2, and CDR3 sequences, respectively, of the same light chain variable domain sequence selected from the group consisting of L1-L52; b. heavy chain CDR1, CDR2, and CDR3 sequences that each is identical to the CDR1, CDR2, and CDR3 sequences, respectively, of the same heavy chain variable domain sequence selected from the group consisting of H1-H52; or c. the light chain CDR1, CDR2, and CDR3 sequences of (a) and the heavy chain CDR1, CDR2, and CDR3 sequences of (b).

Figure 2B:
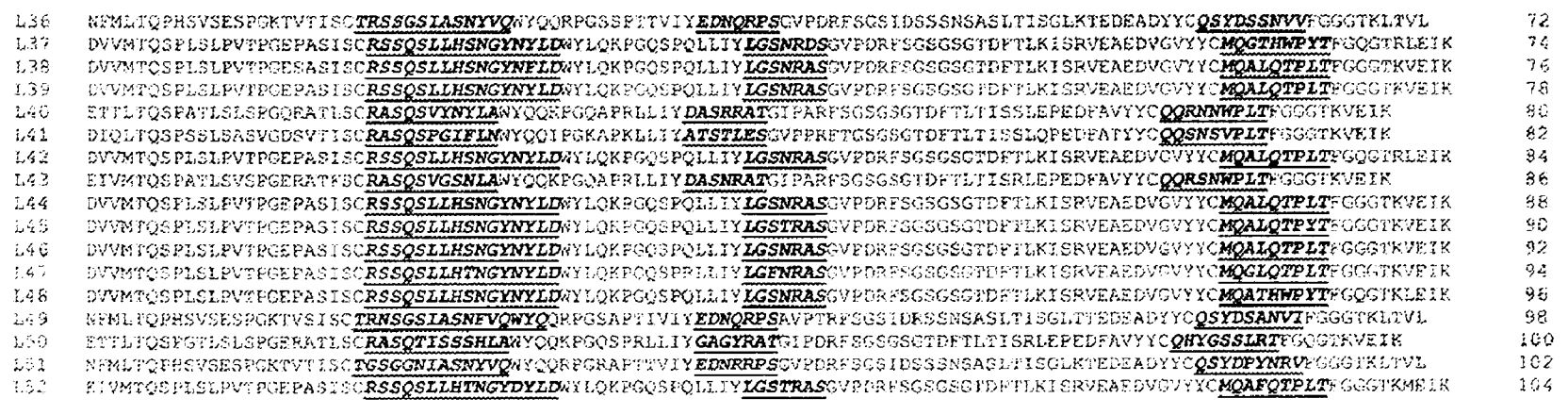
Figure 3A:
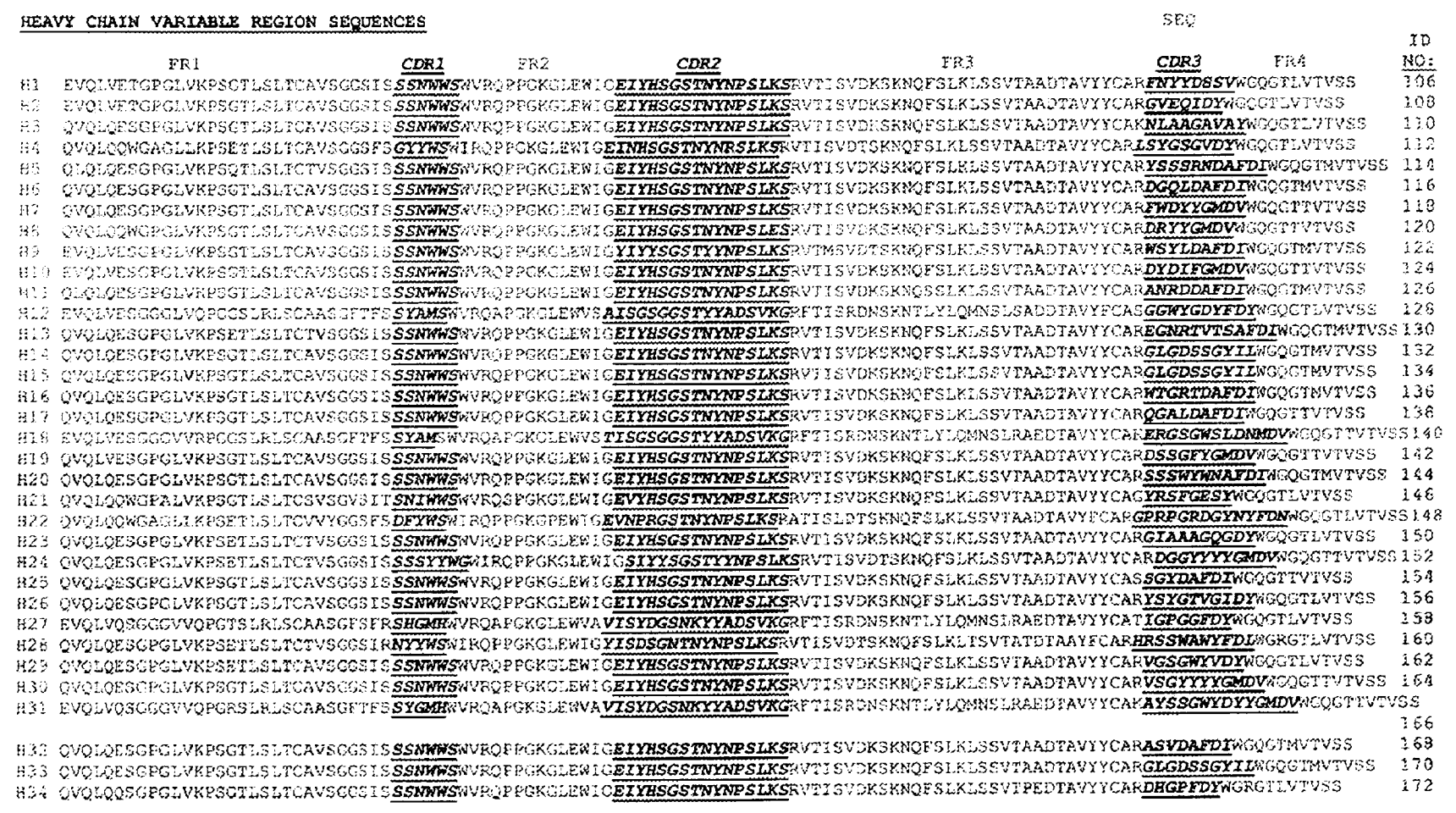
Figure 3B:
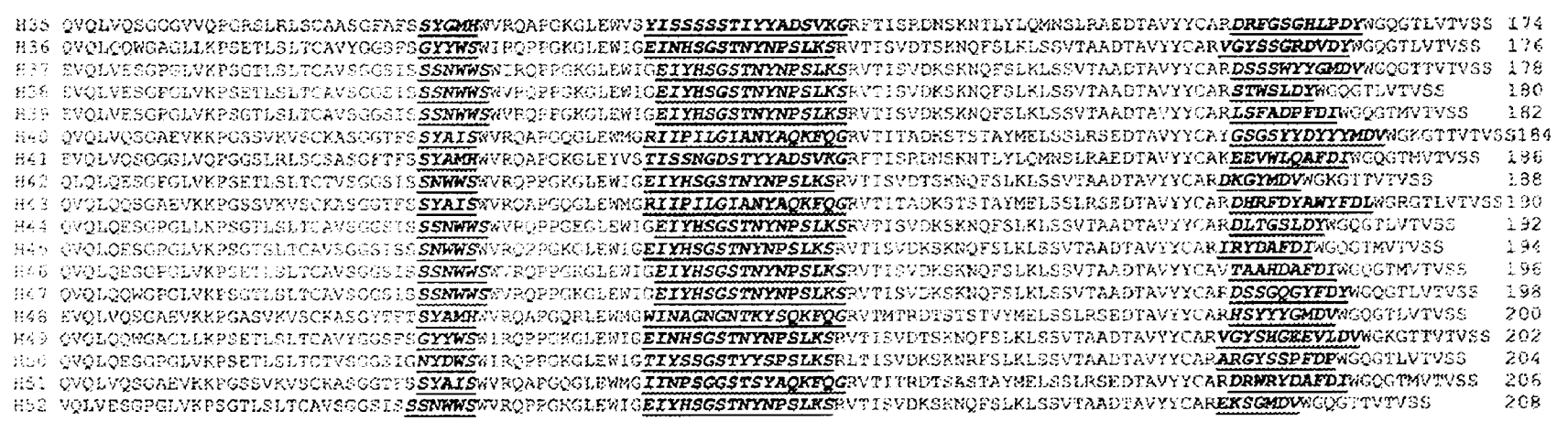

In another aspect, the present invention provides an isolated antigen binding protein comprising either: a. a light chain variable domain sequence selected from the group consisting of: i. a sequence of amino acids at least 80% identical to a light chain variable domain sequence of L1-L52 as shown in FIG. 2; ii. a sequence of amino acids comprising at least 15 contiguous amino acid residues of a light chain variable domain sequence of L1-L52 as shown in FIG. 2; iii. a sequence of amino acids encoded by a polynucleotide sequence that is at least 80% identical to a polynucleotide sequence encoding a light chain variable domain sequence of L1-L52 as shown in FIG. 1; and iv. a sequence of amino acids encoded by a polynucleotide sequence that hybridizes under moderately stringent conditions to the complement of a polynucleotide consisting of a light chain variable domain sequence of L1-L52 as shown in FIG. 1; b. a heavy chain variable domain sequence selected from the group consisting of: i. a sequence of amino acids at least 80% identical to a heavy chain variable domain sequence of H1-H52 as shown in FIG. 2; ii. a sequence of amino acids comprising at least 15 contiguous amino acid residues of a heavy chain variable domain sequence of H1-H52 as shown in FIG. 2; iii. a sequence of amino acids encoded by a polynucleotide sequence that is at least 80% identical to a polynucleotide sequence encoding a heavy chain variable domain sequence of H1-H52 as shown in FIG. 1; and iv. a sequence of amino acids encoded by a polynucleotide sequence that hybridizes under moderately stringent conditions to the complement of a polynucleotide consisting of a heavy chain variable domain sequence of H1-H52 as shown in FIG. 1; or c. the light chain variable domain of (a) and the heavy chain variable domain of (b); wherein said antigen binding protein binds to human IGF-1R. In one embodiment, the isolated antigen binding protein comprises either: a. a light chain variable domain sequence selected from the group consisting of: i. a sequence of amino acids at least 85% identical to a light chain variable domain sequence of L1-L52 as shown in FIG. 2; ii. a sequence of amino acids comprising at least 25 contiguous amino acid residues of a light chain variable domain sequence of L1-L52 as shown in FIG. 2; iii. a sequence of amino acids encoded by a polynucleotide sequence that is at least 85% identical to a polynucleotide sequence encoding a light chain variable domain sequence of L1-L52 as shown in FIG. 1; and iv. a sequence of amino acids encoded by a polynucleotide sequence that hybridizes under highly stringent conditions to the complement of a polynucleotide consisting of a light chain variable domain sequence of L1-L52 as shown in FIG. 1; b. a heavy chain variable domain sequence selected from the group consisting of: i. a sequence of amino acids at least 85% identical to a heavy chain variable domain sequence of H1-H52 as shown in FIG. 2; ii. a sequence of amino acids comprising at least 25 contiguous amino acid residues of a heavy chain variable domain sequence of H1-H52 as shown in FIG. 2; iii. a sequence of amino acids encoded by a polynucleotide sequence that is at least 85% identical to a polynucleotide sequence encoding a heavy chain variable domain sequence of H1-H52 as shown in FIG. 1; and iv. a sequence of amino acids encoded by a polynucleotide sequence that hybridizes under highly stringent conditions to the complement of a polynucleotide consisting of a heavy chain variable domain sequence of H1-H52 as shown in FIG. 1; or c) the light chain variable domain of (a) and the heavy chain variable domain of (b). In another embodiment, the isolated antigen binding protein comprises either: a. a light chain variable domain sequence selected from the group consisting of: i. a sequence of amino acids at least 90% identical to a light chain variable domain sequence of L1-L52 as shown in FIG. 2; ii. a sequence of amino acids comprising at least 35 contiguous amino acid residues of a light chain variable domain sequence of L1-L52 as shown in FIG. 2; and iii. a sequence of amino acids encoded by a polynucleotide sequence that is at least 90% identical to a polynucleotide sequence encoding a light chain variable domain sequence of L1-L52 as shown in FIG. 1; and b. a heavy chain variable domain sequence selected from the group consisting of: i. a sequence of amino acids at least 90% identical to a heavy chain variable domain sequence of H1-H52 as shown in FIG. 2; ii. a sequence of amino acids comprising at least 35 contiguous amino acid residues of a heavy chain variable domain sequence of H1-H52 as shown in FIG. 2; and iii. a sequence of amino acids encoded by a polynucleotide sequence that is at least 90% identical to a polynucleotide sequence encoding a heavy chain variable domain sequence of H1-H52 as shown in FIG. 1; or c) the light chain variable domain of (a) and the heavy chain variable domain of (b). In another embodiment, the isolated antigen binding protein comprises either: a. a light chain variable domain sequence selected from the group consisting of: i. a sequence of amino acids at least 95% identical to a light chain variable domain sequence of L1-L52 as shown in FIG. 2; ii. a sequence of amino acids comprising at least 50 contiguous amino acid residues of a light chain variable domain sequence of L1-L52 as shown in FIG. 2; and iii. a sequence of amino acids encoded by a polynucleotide sequence that is at least 95% identical to a polynucleotide sequence encoding a light chain variable domain sequence of L1-L52 as shown in FIG. 1; and b. a heavy chain variable domain sequence selected from the group consisting of: i. a sequence of amino acids at least 95% identical to a heavy chain variable domain sequence of H1-H52 as shown in FIG. 2; ii. a sequence of amino acids comprising at least 50 contiguous amino acid residues of a heavy chain variable domain sequence of H1-H52 as shown in FIG. 2; and iii. a sequence of amino acids encoded by a polynucleotide sequence that is at least 95% identical to a polynucleotide sequence encoding a heavy chain variable domain sequence of H1-H52 as shown in FIG. 1; or c) the light chain variable domain of (a) and the heavy chain variable domain of (b). In another embodiment, the isolated antigen binding protein comprises either: a. a light chain variable domain sequence selected from the group consisting of: i. a sequence of amino acids at least 97% identical to a light chain variable domain sequence of L1-L52 as shown in FIG. 2; ii. a sequence of amino acids comprising at least 75 contiguous amino acid residues of a light chain variable domain sequence of L1-L52 as shown in FIG. 2; and iii. a sequence of amino acids encoded by a polynucleotide sequence that is at least 97% identical to a polynucleotide sequence encoding a light chain variable domain sequence of L1-L52 as shown in FIG. 1; and b. a heavy chain variable domain sequence selected from the group consisting of: i. a sequence of amino acids at least 97% identical to a heavy chain variable domain sequence of H1-H52 as shown in FIG. 2; ii. a sequence of amino acids comprising at least 75 contiguous amino acid residues of a heavy chain variable domain sequence of H1-H52 as shown in FIG. 2; and iii. a sequence of amino acids encoded by a polynucleotide sequence that is at least 97% identical to a polynucleotide sequence encoding a heavy chain variable domain sequence of H1-H52 as shown in FIG. 1; or c) the light chain variable domain of (a) and the heavy chain variable domain of (b). In another embodiment, the isolated antigen binding protein comprises either: a. a light chain variable domain sequence selected from the group consisting of: i. a sequence of amino acids at least 99% identical to a light chain variable domain sequence of L1-L52 as shown in FIG. 2; ii. a sequence of amino acids comprising at least 90 contiguous amino acid residues of a light chain variable domain sequence of L1-L52 as shown in FIG. 2; and iii. a sequence of amino acids encoded by a polynucleotide sequence that is at least 99% identical to a polynucleotide sequence encoding a light chain variable domain sequence of L1-L52 as shown in FIG. 1; and b. a heavy chain variable domain sequence selected from the group consisting of: i. a sequence of amino acids at least 99% identical to a heavy chain variable domain sequence of H1-H52 as shown in FIG. 2; ii. a sequence of amino acids comprising at least 90 contiguous amino acid residues of a heavy chain variable domain sequence of H1-H52 as shown in FIG. 2; and iii. a sequence of amino acids encoded by a polynucleotide sequence that is at least 99% identical to a polynucleotide sequence encoding a heavy chain variable domain sequence of H1-H52 as shown in FIG. 1; or c. the light chain variable domain of (a) and the heavy chain variable domain of (b). In another embodiment, the isolated antigen binding protein comprises either: a. a light chain variable domain sequence selected from the group consisting of L1-L52 as shown in FIG. 2; b. a heavy chain variable domain sequence selected from the group consisting of H1-H52 as shown in FIG. 3; or c. the light chain variable domain of (a) and the heavy chain variable domain of (b). In another embodiment, the isolated antigen binding protein comprises a combination of a light chain variable domain and a heavy chain variable domain selected from the group of combinations consisting of: L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20, H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52. In another embodiment, the isolated antigen binding protein further comprises: a. the kappa light chain constant sequence of FIG. 13, b. the IgG1 heavy chain constant sequence of FIG. 13, or c. the kappa light chain constant sequence of FIG. 13 and the IgG1 heavy chain constant sequence of FIG. 13. In another embodiment, the isolated antigen binding protein, when bound to IGF-1R: a. inhibits IGF-1R; b. activates IGF-1R; c. cross-competes with a reference antibody for binding to IGF-1R; d. binds to the same epitope of IGF-1R as said reference antibody; e. binds to IGF-1R with substantially the same Kd as said reference antibody; or f. binds to IGF-1R with substantially the same off rate as said reference antibody; wherein said reference antibody comprises a combination of light chain and heavy chain variable domain sequences selected from the group of combinations consisting of L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20, H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52. In another embodiment, the isolated antigen binding protein, when bound to a human IGF-1R, inhibits binding of IGF-1 and/or IGF-2 to said human IGF-1R. In another embodiment, the isolated antigen binding protein inhibits the growth of a cancer cell by greater than about 80% in the presence of a growth stimulant selected from the group consisting of serum, IGF-1, and IGF-2. In another embodiment, said cancer cell is an MCF-7 human breast cancer cell. In another embodiment, the isolated antigen binding protein binds to human IGF-1R with a selectivity that is at least fifty times greater than its selectivity for human insulin receptor. In another embodiment, the isolated antigen binding protein inhibits tumor growth in vivo. In another embodiment, the isolated antigen binding protein inhibits IGF-1R mediated tyrosine phosphorylation. In another embodiment, the isolated antigen binding protein specifically binds to the IGF-1R of a non-human primate, a cynomologous monkey, a chimpanzee, a non-primate mammal, a rodent, a mouse, a rat, a hamster, a guinea pig, a cat, or a dog. In another embodiment, the isolated antigen binding protein comprises: a. a human antibody; b. a humanized antibody; c. a chimeric antibody; d. a monoclonal antibody; e. a polyclonal antibody; f a recombinant antibody; g. an antigen-binding antibody fragment; h. a single chain antibody; i. a diabody; j. a triabody; k. a tetrabody; l. a Fab fragment; m. a F(ab')$_2$ fragment; n. a domain antibody; o. an IgD antibody; p. an IgE antibody; q. an IgM antibody; r. an IgG1 antibody; s. an IgG2 antibody; t. an IgG3 antibody; u. an IgG4 antibody; or v. an IgG4 antibody having at least one mutation in a hinge region that alleviates a tendency to form intra-H chain disulfide bond.

In another aspect, the present invention provides an isolated polynucleotide comprising a sequence that encodes the light chain, the heavy chain, or both of said antigen binding protein. In one embodiment, said polynucleotide comprises a light chain variable domain nucleic acid sequence of FIG. 1 and/or a heavy chain variable domain nucleic acid sequence of FIG. 1. In another embodiment, a plasmid comprises said isolated polynucleotide. In another embodiment, said plasmid is an expression vector. In another embodiment, an isolated cell comprises said polynucleotide. In another embodiment, a chromosome of said cell comprises said polynucleotide. In another embodiment, said cell is a hybridoma. In another embodiment, an expression vector comprises said polynucleotide. In another embodiment, said cell is a CHO cell. In another embodiment, the present invention provides a method of making an antigen binding protein that binds human IGF-1R, comprising incubating said isolated cell under conditions that allow it to express said antigen binding protein.

In another aspect, the present invention provides a pharmaceutical composition comprising the antigen binding protein. In one embodiment, the present invention provides a method of treating a condition in a subject comprising administering to said subject said pharmaceutical composition, wherein said condition is treatable by reducing the activity of IGF-1R in said subject. In another embodiment, said subject is a human being. In another embodiment, said condition is multiple myeloma, a liquid tumor, liver cancer, a thymus disorder, a T-cell mediated autoimmune disease, an endocrinological disorder, ischemia, or a neurodegenerative disorder. In another embodiment, said liquid tumor is selected from the group consisting of acute lymphocytic leukemia (ALL) and chronic myelogenous leukemia (CML); wherein said liver cancer is selected from the group consisting of hepatoma, hepatocellular carcinoma, cholangiocarcinoma, angiosarcomas, hemangiosarcomas, hepatoblastoma; wherein said thymus disorder is selected from the group consisting of thymoma and thyroiditis, wherein said T-cell mediated autoimmune disease is selected from the group consisting of Multiple Sclerosis, Rheumatoid Arthritis, Systemic Lupus Erythematosus (SLE), Grave's Disease, Hashimoto's Thyroiditis, Myasthenia Gravis, Auto-Immune Thyroiditis, Bechet's Disease, wherein said endocrinological disorder is selected from the group consisting of Type II Diabetes, hyperthyroidism, hypothyroidism, thyroiditis, hyperadrenocorticism, and hypoadrenocorticism; wherein said ischemia is post cardiac infarct ischemia, or wherein said neurodegenerative disorder is Alzheimer's Disease. In another embodiment, said condition is selected from the group consisting of acromegaly, bladder cancer, Wilm's tumor, ovarian cancer, pancreatic cancer, benign prostatic hyperplasia, breast cancer, prostate cancer, bone cancer, lung cancer, colorectal cancer, cervical cancer, synovial sarcoma, diarrhea associated with metastatic carcinoid, vasoactive intestinal peptide secreting tumors, gigantism, psoriasis, atherosclerosis, smooth muscle restenosis of blood vessels, inappropriate microvascular proliferation, glioblastoma, medulloblastoma, head and neck squamous cell cancer, oral cancer, oral leukoplakia, prostate intraepithelial neoplasia, anal cancer, esophageal cancer, gastric cancer, bone cancer, metastatic cancer, polycythemia rubra vera, a benign condition related to oxidative stress, retinopathy of prematurity, Acute Respiratory Distress Syndrome, an overdose of acetaminophen, bronchopulmonary dysplasia, cystic fibrosis, lung fibrosis, and diabetic retinopathy. In another embodiment, the method further comprising administering to said subject a second treatment. In another embodiment, said second treatment is administered to said subject before and/or simultaneously with and/or after said pharmaceutical composition is administered to said subject. In another embodiment, said second treatment comprises radiation treatment, surgery, or a second pharmaceutical composition. In another embodiment, said second pharmaceutical composition comprises an agent selected from the group consisting of a corticosteroid, an anti-emetic, ondansetron hydrochloride, granisetron hydrochloride, metroclopramide, domperidone, haloperidol, cyclizine, lorazepam, prochlorperazine, dexamethasone, levomepromazine, tropisetron, a cancer vaccine, a GM-CSF inhibiting agent, a GM-CSF DNA vaccine, a cell-based vaccine, a dendritic cell vaccine, a recombinant viral vaccine, a heat shock protein (HSP) vaccine, an allogeneic tumor vaccine, an autologous tumor vaccine, an analgesic, ibuprofen, naproxen, choline magnesium trisalicylate, an oxycodone hydrochloride, an anti-angiogenic agent, an anti-vascular agent, bevacizumab, an anti-VEGF antibody, an anti-VEGF receptor antibody, a soluble VEGF receptor fragment, an anti-TWEAK antibody, an anti-TWEAK receptor antibody, a soluble TWEAK receptor fragment, AMG 706, AMG 386, an anti-proliferative agent, a farnesyl protein transferase inhibitor, an $\alpha v\beta 3$ inhibitor, an $\alpha v\beta 5$ inhibitor, a p53 inhibitor, a Kit receptor inhibitor, a ret receptor inhibitor, a PDGFR inhibitor, a growth hormone secretion inhibitor, an angiopoietin inhibitor, a tumor infiltrating macrophage-inhibiting agent, a c-fms inhibiting agent, an anti-c-fms antibody, an CSF-1 inhibiting agent, an anti-CSF-1 antibody, a soluble c-fms fragment, pegvisomant, gemcitabine, panitumumab, irinothecan, and SN-38. In another embodiment, said method comprises administering to said subject a third treatment. In another embodiment, said condition is a cancer, said second treatment comprises administering panitumumab, and said third treatment comprises administering gemcitabine. In another embodiment, said condition is selected from the group consisting of acromegaly, bladder cancer, Wilm's tumor, ovarian cancer, pancreatic cancer, benign prostatic hyperplasia, breast cancer, prostate cancer, bone cancer, lung cancer, colorectal cancer, cervical cancer, synovial sarcoma, diarrhea associated with metastatic carcinoid, vasoactive intestinal peptide secreting tumors, gigantism, psoriasis, atherosclerosis, smooth muscle restenosis of blood vessels, inappropriate microvascular proliferation, glioblastoma, medulloblastoma, head and neck squamous cell cancer, oral cancer, oral leukoplakia, prostate intraepithelial neoplasia, anal cancer, esophageal cancer, gastric cancer, bone cancer, metastatic cancer, polycythemia rubra vera, a benign condition related to oxidative stress, retinopathy of prematurity, Acute Respiratory Distress Syndrome, an overdose of acetaminophen, bronchopulmonary dysplasia, cystic fibrosis, lung fibrosis, and diabetic retinopathy.

In another aspect, the present invention provides a method of increasing the longevity of a subject comprising administering to said subject said pharmaceutical composition.

In another aspect, the present invention provides a method of decreasing IGF-1R activity in a subject in need thereof comprising administering to said subject said pharmaceutical composition.

In another aspect, the present invention provides a method of decreasing IGF-1R signaling in a subject in need thereof comprising administering to said subject said pharmaceutical composition.

In another aspect, the present invention provides a method of inhibiting the binding of IGF-1 and/or IGF-2 to IGF-1R in a subject in need thereof comprising administering to said subject said pharmaceutical composition.

DETAILED DESCRIPTION OF THE INVENTION

The present invention provides compositions, kits, and methods relating to molecules that bind to the Insulin-Like Growth Factor Receptor ("IGF-1R"), including molecules that agonize or antagonize IGF-1R, such as anti-IGF-1R antibodies, antibody fragments, and antibody derivatives, e.g., antagonistic anti-IGF-1R antibodies, antibody fragments, or antibody derivatives. Also provided are nucleic acids, and derivatives and fragments thereof, comprising a sequence of nucleotides that encodes all or a portion of a polypeptide that binds to IGF-1R, e.g., a nucleic acid encoding all or part of an anti-IGF-1R antibody, antibody fragment, or antibody derivative, plasmids and vectors comprising such nucleic acids, and cells or cell lines comprising such nucleic acids and/or vectors and plasmids. The provided methods include, for example, methods of making, identifying, or isolating molecules that bind to IGF-1R, such as anti-IGF-1R antibodies, methods of determining whether a molecule binds to IGF-1R, methods of determining whether a molecule agonizes or antagonizes IGF-1R, methods of making compositions, such as pharmaceutical compositions, comprising a molecule that binds to IGF-1R, and methods for administering a molecule that binds IGF-1R to a subject, for example, methods for treating a condition mediated by IGF-1R, and for agonizing or antagonizing a biological activity of IGF-1R, IGF-1, and/or IGF-2 in vivo or in vitro.

Polynucleotide and polypeptide sequences are indicated using standard one- or three-letter abbreviations. Unless otherwise indicated, polypeptide sequences have their amino termini at the left and their carboxy termini at the right and single-stranded nucleic acid sequences, and the top strand of double-stranded nucleic acid sequences, have their 5' termini at the left and their 3' termini at the right. A particular polypeptide or polynucleotide sequence also can be described by explaining how it differs from a reference sequence.

Polynucleotide and polypeptide sequences of particular light and heavy chain variable domains are shown in FIGS. 1, 2 and 3, where they are labeled, for example, L1 ("light chain variable domain 1"), H1 ("heavy chain variable domain 1"), etc. Antibodies comprising a light chain and heavy chain from FIGS. 2 and 3 are indicated by combining the name of the light chain and the name of the heavy chain variable domains. For example, "L4H7," indicates an antibody comprising the light chain variable domain of L4 and the heavy chain variable domain of H7.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "IGF-1R inhibitor" and "IGF-1R antagonist" are used interchangeably. Each is a molecule that detectably inhibits at least one function of IGF-1R. Conversely, an "IGF-1R agonist" is a molecule that detectably increases at least one function of IGF-1R. The inhibition caused by an IGF-1R inhibitor need not be complete so long as it is detectable using an assay. Any assay of a function of IGF-1R can be used, examples of which are provided herein. Examples of functions of IGF-1R that can be inhibited by an IGF-1R inhibitor, or increased by an IGF-1R agonist, include binding to IGF-1, IGF-12, and/or another IGF-1R-activating molecule, kinase activity, downstream signaling, and so on. Examples of types of IGF-1R inhibitors and IGF-1R agonists include, but are not limited to, IGF-1R binding polypeptides such as antigen binding proteins (e.g., IGF-1R inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts. A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

The present invention also provides non-peptide analogs of IGF-1R binding polypeptides. Non-peptide analogs are commonly used in the pharmaceutical industry as drugs with properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al. J. Med. Chem. 30:1229 (1987), which are incorporated herein by reference. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference), for example, by adding internal cysteine residues capable of forming intramolecular disulfide bridges which cyclize the peptide.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest*, 5 h Ed., US Dept. of Health and Human Services, PHS, NIH, NIH Publication no. 91-3242, 1991.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App.

Pub. No. 05/0202512, 04/0202995, 04/0038291, 04/0009507, 03/0039958, Ward et al., Nature 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886, 152 and 5,877,293.

The term "chimeric antibody" refers to an antibody that contains one or more regions from one antibody and one or more regions from one or more other antibodies. In one embodiment, one or more of the CDRs are derived from a human anti-IGF-1R antibody. In another embodiment, all of the CDRs are derived from a human anti-IGF-1R antibody. In another embodiment, the CDRs from more than one human anti-IGF-1R antibodies are mixed and matched in a chimeric antibody. For instance, a chimeric antibody may comprise a CDR1 from the light chain of a first human anti-IGF-1R antibody, a CDR2 and a CDR3 from the light chain of a second human anti-IGF-1R antibody, and the CDRs from the heavy chain from a third anti-IGF-1R antibody. Further, the framework regions may be derived from one of the same anti-IGF-1R antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody(-ies) from another species or belonging to another antibody class or subclass. Also included are fragments of such antibodies that exhibit the desired biological activity (i.e., the ability to specifically bind IGF-1R). See, e.g., U.S. Pat. No. 4,816,567 and Morrison, 1985, Science 229:1202-07.

A "neutralizing antibody" or "an inhibitory antibody" is an antibody that inhibits the binding of IGF-1R to IGF-1 and/or IGF-2 when an excess of the anti-IGF-1R antibody reduces the amount of IGF-1 and/or IGF-2 bound to IGF-1R by at least about 20% using the assay described in Example 9. In various embodiments, the antibody reduces the amount of IGF-1 and/or IGF-2 bound to IGF-1R by at least 30%, 40%, 50%, 60%, 70%, 75%, 80%, 85%, 90%, 95%, 97%, 99%, and 99.9%.

An "activating antibody" is an antibody that activates IGF-1R by at least about 20% when added to a cell, tissue or organism expressing IGF-1R, where "100% activation" is the level of activation achieved under physiological conditions by the same molar amount of IGF-1 and/or IGF-2. In various embodiments, the antibody activates IGF-1R activity by at least 30%, 40%, 50%, 60%, 70%, 80%, 90%, 100%, 125%, 150%, 175%, 200%, 250%, 300%, 350%, 400%, 450%, 500%, 750%, or 1000%.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human IGF-1R) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

IGF-1R

IGF-1R is a transmembrane receptor tyrosine kinase (Blume-Jensen et al., 2001, Nature 411:355-65). The human IGF-1R is synthesized as a 1367 amino acid precursor polypeptide that includes a 30 amino acid signal peptide removed during translocation into the endoplasmic reticulum (Swiss-Prot: P08069). The IGF-1R proreceptor is glycosylated and cleaved by a protease at positions 708-711 (counting from the first amino acid following the signal peptide sequence) during maturation in the ER-golgi resulting in the formation of an α-chain (1-707) and a β-chain (712-1337) that remain linked by disulfide bonds (Bhaumick et al., 1981, Proc Natl Acad Sci USA 78:4279-83, Chernausek et al., 1981, Biochemistry 20:7345-50, Jacobs et al., 1983, Proc Natl Acad Sci USA 80:1228-31, LeBon et al., 1986, J Biol Chem 261:7685-89, Elleman, et al., 2000, Biochem J 347: 771-79). The predominant form of the IGF-1R (and INSR) that exists on the cell-surface is a proteolytically processed and glycosylated $(\alpha\beta)_2$ dimer joined covalently by one or more disulfide bonds.

The extracellular portion of the IGF-1R consists of the α-chain and 191 amino acids of the β-chain (712-905). The receptor contains a single transmembrane spanning sequence (906-929) and a 408-residue cytoplasmic domain that includes a functional tyrosine kinase (Rubin et al., 1983, Nature 305:438-440). Comparative sequence analysis has revealed that the IGF-1R is composed of 11 distinct structural motifs (reviewed by Adams et al., 2000, Cell Mol Life Sci 57:1050-93, Marino-Buslje et al., 1998, FEBS Ltrs 441:331-36, Ward et al., 2001, BMC Bioinformatics 2:4). The N-terminal half of the extracellular domain contains two homologous domains referred to as L1 (1-151) and L2 (299-461) (Ward et al., 2001, supra) separated by a cysteine-rich (CR) region (152-298) consisting of several structural modules with disulfide linkages that align with repeating units present in the TNF receptor and laminin (Ward et al., 1995, Proteins 22:141-53). The crystal structure of the L1-CR-L2 domain has been solved (Garrett et al., 1998, Nature 394:395-99). The L2 domain is followed by three fibronectin type III domains (Marino-Buslje et al., 1998, supra, Mulhern et al., 1998, Trends Biochem Sci 23:465-66, Ward et al., 1999, Growth Factors 16:315-22). The first FnIII domain (FnIII-1, 461-579) is 118 amino acids in length. The second FnIII domain (FnIII-2, 580-798) is disrupted by a major insert sequence (ID) of about 120 amino acids in length. The ID domain includes a furin protease cleavage site that separates the α and β chains of the mature receptor. The third FnIII domain (FnIII-3) is located entirely in the β-chain (799-901) terminating several residues before the transmembrane sequence. The catalytic domain of the IGF-1R tyrosine kinase is located between amino acids positions 973-1229, and its structure has been solved (Favelyukis et al., 2001, Nature Structural Biol 8:1058-63, Pautsch et al., 2001, Structure 9:955-65). The kinase is flanked by two regulatory regions, the juxtamembrane region (930-972) and a 108 amino acid C-terminal tail (1220-1337) (Surmacz et al., 1995, Experimental Cell Res 218:370-80, Hongo et al., 1996, Oncogene 12:1231-38). The two regulatory regions contain tyrosine residues that serve as docking sites for signal transducing proteins when phosphorylated by the activated IGF-1R tyrosine kinase (reviewed by Baserga (ed.), 1998 *The IGF-1 Receptor in Normal and Abnormal Growth*, Hormones and Growth Factors in Development and Neoplasia, Wiley-Liss, Inc., Adams et al., 2000, Cell Mol Life Sci 57:1050-93).

The IGF-1R amino acid sequence is about 70% identical to the insulin receptor (INSR; Swiss-Prot: P06213). The highest homology between the receptors is located in the tyrosine kinase domain (84%); the lowest identity is in the CR region and the C-terminus. The IGF-1R is also highly related (~55% identical) to the insulin related receptor (IRR; Swiss-Prot: P14616).

Human IGF-1R can be activated by the insulin-like growth factors, IGF-1 and IGF-2 and insulin (INS) (Hill et al., 1985, Pediatric Research 19:879-86). IGF-1 and IGF-2 are encoded nonallelic genes (Brissenden et al., 1984, Nature 310: 781-8, Bell et al., 1985, Proceedings of the National Academy of Sciences of the United States of America 82: 6450-54), and both genes express alternative proteins related by differential RNA splicing and protein processing. The most common and well-studied mature forms of IGF-1 and IGF-2 are respectively 70 and 67 amino acids in length (Jansen et al., 1983, Nature 306:609-11, Dull et al., 1984, Nature 310: 777-81). These proteins (and their isoforms) are identical at 11/21 positions to the insulin A-peptide, and identical at 12/30 positions with the insulin B-peptide.

IGF-1R is expressed in all cells types in the normal adult animal except for liver hepatocytes and mature B-cells. Human blood plasma contains high concentrations of IGF-1 and IGF-2, and IGF-1 can be detected in most tissues. The receptor is an integral component of the physiological mechanism controlling organ size and homeostasis. Without being bound to a particular theory, the "Somatomedin Hypothesis" states that Growth Hormone (GH) mediated somatic growth that occurs during childhood and adolescence is dependent on the endocrine form of IGF-1 that is mainly produced and secreted by the liver (Daughaday, 2000, Pediatric Nephrology 14: 537-40). The synthesis of hepatic IGF-1 is stimulated by GH release in the pituitary in response to hypothalamic GHRH (GH releasing hormone). The serum concentration of IGF-1 increases over 100 fold between ages 5-15 in humans. The bioavailability of IGF-1 is regulated by IGF binding protein 3 (IGFBP3) with approximately 99% of the growth factor compartmentalized in the bound state. Primary IGF-1 deficiency arising form partial gene deletions, and secondary IGF-1 deficiency resulting from defects in GH production or signaling are not lethal (Woods, 1999, IGF Deficiency in Contemporary Endocrinology The IGF System, R. a. R. Rosenfeld, C. Jr. Totowa, ed.s, Humana Press, NJ: 651-74). The affected individuals exhibit growth retardation at birth, grow slowly and can face certain CNS abnormalities.

IGF-1R signaling promotes cell growth and survival through the IRS adapter protein-dependent activation of the PI3Kinase/Akt pathway. IGF-1R transmits a signal to its major substrates, IRS-1 through IRS-4 and the Shc proteins (Blakesley et al., 1999, *IGF-1 receptor function: transducing the IGF-1 signal into intracellular events* in The IGF System, R. G. a. R. Rosenfeld, Jr. C. T. Totowa, ed.s, Humana Press, NJ: 143-63). This results in activation of the Ras/Raf/MAP kinase and PI3 Kinase/Akt signaling pathways. However, induction of Akt-mediated cell survival via IRS is the dominant pathway response upon IGF stimulation of most cells. See FIG. 10.

Antigen Binding Proteins

In one aspect, the present invention provides antigen binding proteins (e.g., antibodies, antibody fragments, antibody derivatives, antibody muteins, and antibody variants), that bind to IGF-1R, e.g., human IGF-1R.

Antigen binding proteins in accordance with the present invention include antigen binding proteins that inhibit a biological activity of IGF-1R. Examples of such biological activities include binding a signaling molecule (e.g., IGF-1 and/or IGF-2), and transducing a signal in response to binding a signaling molecule.

Different antigen binding proteins may bind to different domains or epitopes of IGF-1R or act by different mechanisms of action. Examples include but are not limited to antigen binding proteins that interfere with binding of IGF-1 and/or IGF-2 to IGF-1R or that inhibit signal transduction. The site of action may be, for example, intracellular (e.g., by interfering with an intracellular signaling cascade) or extracellular. An antigen binding protein need not completely inhibit an IGF-1 and/or IGF-2 induced activity to find use in the present invention; rather, antigen binding proteins that reduce a particular activity of IGF-1 and/or IGF-2 are contemplated for use as well. (Discussions herein of particular mechanisms of action for IGF-1R-binding antigen binding proteins in treating particular diseases are illustrative only, and the methods presented herein are not bound thereby.)

It has been observed that IGF-1 and IGF-2 each exhibits biphasic binding to IGF-1R. High affinity binding has been reported to have a $K_D$ in the range of 0.2 nM; high affinity binding, about ten fold higher. Thus, in one embodiment, the present invention provides an IGF-1R inhibitor that inhibits both the high and low affinity binding of IGF-1 and/or IGF-2 to IGF-R. It has been suggested that the high affinity binding, rather than the low affinity binding, of IGF-1 and/or IGF-2 to IGF-1R is required for the conformation change that activates the tyrosine kinase activity of IGF-1R. Thus, in another embodiment, the IGF-1R inhibitor preferentially inhibits the high affinity binding of IGF-1 and/or IGF-2 to IGF-1R as compared to the low affinity binding.

In another aspect, the present invention provides antigen binding proteins that comprise a light chain variable region selected from the group consisting of L1 through L52 and/or a heavy chain variable region selected from the group consisting of H1 through H52, and fragments, derivatives, muteins, and variants thereof (see FIGS. 2 and 3). Such an antigen binding protein can be denoted using the nomenclature "LxHy", wherein "x" corresponds to the number of the light chain variable region and "y" corresponds to the number of the heavy chain variable region as they are labeled in FIGS. 2 and 3. For example, L2H1 refers to an antigen binding protein with a light chain variable region comprising the amino acid sequence of L2 and a heavy chain variable region comprising the amino acid sequence of H1, as shown in FIGS. 2 and 3. FIGS. 2 and 3 also indicate the location of the CDR and framework regions of each of these variable domain sequences. The CDR regions of each light and heavy chain also are grouped by type and by sequence similarity in FIGS. 4 through 9. Antigen binding proteins of the invention include, for example, antigen binding proteins having a combination of light chain and heavy chain variable domains selected from the group of combinations consisting of L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52.

In one embodiment, the present invention provides an antigen binding protein comprising a light chain variable domain comprising a sequence of amino acids that differs from the sequence of a light chain variable domain selected from the group consisting of L1 through L52 only at 15, 14, 13, 12, 11, 10, 9, 8, 7, 6, 5, 4, 3, 2, or 1 residues, wherein each such sequence difference is independently either a deletion, insertion, or substitution of one amino acid residue. In another embodiment, the light-chain variable domain comprises a sequence of amino acids that is at least 70%, 75%, 80%, 85%, 90%, 95%, 97%, or 99% identical to the sequence of a light chain variable domain selected from the group consisting of L1 through L52. In another embodiment, the light chain variable domain comprises a sequence of amino acids that is encoded by a nucleotide sequence that is at least 70%, 75%, 80%, 85%, 90%, 95%, 97%, or 99% identical to a nucleotide sequence that encodes a light chain variable domain selected from the group consisting of L1 through L52. In another embodiment, the light chain variable domain comprises a sequence of amino acids that is encoded by a polynucleotide that hybridizes under moderately stringent conditions to the complement of a polynucleotide that encodes a light chain variable domain selected from the group consisting of L1 through L52. In another embodiment, the light chain variable domain comprises a sequence of amino acids that is encoded by a polynucleotide that hybridizes under moderately stringent conditions to the complement of a polynucleotide that encodes a light chain variable domain selected from the group consisting of L1 through L52. In another embodiment, the light chain variable domain comprises a sequence of amino acids that is encoded by a polynucleotide that hybridizes under moderately stringent conditions to a complement of a light chain polynucleotide selected from FIG. 1.

In another embodiment, the present invention provides an antigen binding protein comprising a heavy chain variable domain comprising a sequence of amino acids that differs from the sequence of a heavy chain variable domain selected from the group consisting of H1 through H52 only at 15, 14, 13, 12, 11, 10, 9, 8, 7, 6, 5, 4, 3, 2, or 1 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of a heavy chain variable domain selected from the group consisting of H1 through H52. In another embodiment, the heavy chain variable domain comprises a sequence of amino acids that is encoded by a nucleotide sequence that is at least 70%, 75%, 80%, 85%, 90%, 95%, 97%, or 99% identical to a nucleotide sequence that encodes a heavy chain variable domain selected from the group consisting of H1 through H52. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of H1 through H52. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of H1 through H52. In another embodiment, the heavy chain variable domain comprises a sequence of amino acids that is encoded by a polynucleotide that hybridizes under moderately stringent conditions to a complement of a heavy chain polynucleotide selected from FIG. 1.

Particular embodiments of antigen binding proteins of the present invention comprise one or more amino acid sequences that are identical to the amino acid sequences of one or more of the CDRs and/or FRs illustrated in FIGS. 2 through 9. In one embodiment, the antigen binding protein comprises a light chain CDR1 sequence illustrated in FIG. 4. In another embodiment, the antigen binding protein comprises a light chain CDR2 sequence illustrated in FIG. 5. In another embodiment, the antigen binding protein comprises a light chain CDR3 sequence illustrated in FIG. 6. In another embodiment, the antigen binding protein comprises a heavy chain CDR1 sequence illustrated in FIG. 7. In another embodiment, the antigen binding protein comprises a heavy chain CDR2 sequence illustrated in FIG. 8. In another embodiment, the antigen binding protein comprises a heavy chain CDR3 sequence illustrated in FIG. 9. In another embodiment, the antigen binding protein comprises a light chain FR1 sequence illustrated in FIG. 2. In another embodiment, the antigen binding protein comprises a light chain FR2 sequence illustrated in FIG. 2. In another embodiment, the antigen binding protein comprises a light chain FR3 sequence illustrated in FIG. 2. In another embodiment, the antigen binding protein comprises a light chain FR4 sequence illustrated in FIG. 2. In another embodiment, the antigen binding protein comprises a heavy chain FR1 sequence illustrated in FIG. 3. In another embodiment, the antigen binding protein comprises a heavy chain FR2 sequence illustrated in FIG. 3. In another embodiment, the antigen binding protein comprises a heavy chain FR3 sequence illustrated in FIG. 3. In another embodiment, the antigen binding protein comprises a heavy chain FR4 sequence illustrated in FIG. 3.

In one embodiment, the present invention provides an antigen binding protein that comprises one or more CDR sequences that differ from a CDR sequence shown in FIGS. 2 through 9 by no more than 5, 4, 3, 2, or 1 amino acid residues.

In one embodiment, the present invention provides an antigen binding protein that comprises at least one CDR from L1-L52 and/or H1-H52, as shown in FIGS. 2 through 9, and at least one CDR sequence from an anti-IGF-1R antibody described in US Pat. App. Pub. Nos. 03/0235582, 04/0228859, 04/0265307, 04/0886503, 05/0008642, 05/0084906, 05/0186203, 05/0244408, PCT Pub. Nos. WO 03/059951, WO 03/100008, WO 04/071529A2, WO 04/083248, WO 04/087756, WO 05/016967, WO 05/016970, or WO 05/058967 (each of which is incorporated herein by reference in its entirety for all purposes) wherein the antigen binding protein binds to IGF-1 receptor. In another embodiment, the antigen binding protein comprises 2, 3, 4, or 5 CDR sequences from L1-L52 and/or H1-H52, as shown in FIGS. 2 through 9. In another embodiment, the antigen binding protein comprises 2, 3, 4, or 5 CDR sequences from an anti-IGF-1R antibody described in US Pat. App. Pub. Nos. 03/0235582, 04/0228859, 04/0265307, 04/0886503, 05/0008642, 05/0084906, 05/0186203, 05/0244408, PCT Pub. Nos. WO 03/059951, WO 03/100008, WO 04/071529A2, WO 04/083248, WO 04/087756, WO 05/016967, WO 05/016970, or WO 05/058967. In another embodiment, at least one of the antigen binding protein's CDR3 sequences is a CDR3 sequence from L1-L52 and/or H1-H52, as shown in FIGS. 2, 3, 6, and 9. In another embodiment, the antigen binding protein's light chain CDR3 sequence is a light chain CDR3 sequence from L1-L52 as shown in FIGS. 2 and 6 and the antigen binding protein's heavy chain CDR3 sequence is a heavy chain sequence from H1-H52 as shown in FIGS. 3 and 9. In another embodiment, the antigen binding protein comprises 1, 2, 3, 4, or 5 CDR sequences that each independently differs by 6, 5, 4, 3, 2, 1, or 0 single amino acid additions, substitutions, and/or deletions from a CDR sequence of L1-L52 and/or H1-H52, and the antigen binding protein further comprises 1, 2, 3, 4, or 5 CDR sequences that each independently differs by 6, 5, 4, 3, 2, 1, or 0 single amino acid additions, substitutions, and/or deletions from a CDR sequence of US Pat. App. Pub. Nos. 03/0235582, 04/0228859, 04/0265307, 04/0886503, 05/0008642, 05/0084906, 05/0186203, 05/0244408, PCT Pub. Nos. WO 03/059951, WO 03/100008, WO 04/071529A2, WO 04/083248, WO 04/087756, WO 05/016967, WO 05/016970, or WO 05/058967. In another embodiment, the CDR sequence(s) from US Pat. App. Pub. Nos. 03/0235582, 04/0228859, 04/0265307, 04/0886503, 05/0008642, 05/0084906, 05/0186203, 05/0244408, PCT Pub. Nos. WO 03/059951, WO 03/100008, WO 04/071529A2, WO 04/083248, WO 04/087756, WO 05/016967, WO 05/016970, or WO 05/058967. In another embodiment, the CDR sequence(s) are from (an) antibody(-ies) that bind(s) to the L2 portion of the extracellular domain of IGF-1 receptor. In another embodiment, the antigen binding protein does not comprise a light chain CDR3 sequence and/or a heavy chain CDR3 sequence from an anti-IGF-1R antibody from US Pat. App. Pub. Nos. 03/0235582, 04/0228859, 04/0265307, 04/0886503, 05/0008642, 05/0084906, 05/0186203, 05/0244408, PCT Pub. Nos. WO 03/059951, WO 03/100008, WO 04/071529A2, WO 04/083248, WO 04/087756, WO 05/016967, WO 05/016970, or WO 05/058967.

In one embodiment, the present invention provides an antigen binding protein that comprises a light chain CDR1 comprising the sequence RSSQSLLHX$_1$X$_2$GYNX$_3$LX$_4$ (SEQ ID NO:236), wherein X$_1$ is a serine or a threonine residue, X$_2$ is an asparagine, serine, or histidine residue, X$_3$ is a tyrosine or a phenylalanine residue, and X$_4$ is an aspartate or an asparagine residue. In another embodiment, the light chain CDR1 comprises the sequence TRSSGX$_1$X$_2$X$_3$NYVQ (SEQ ID NO:237), wherein X$_1$ is a serine or an aspartate residue, X$_2$ is an alanine or an aspartate residue, and X$_3$ is a serine or an asparagine residue. In another embodiment, the light chain CDR1 comprises the sequence RASQX$_1$X$_2$X$_3$X$_4$X$_5$LX$_6$ (SEQ ID NO:238), wherein X$_1$ is a glycine or a serine residue, X$_2$ is an isoleucine, valine, or proline residue, and X$_3$ is a serine, glycine, or tyrosine residue, X$_4$ is any amino acid residue, X$_5$ is a phenylalanine, tyrosine, asparagine, or tryptophan residue, and X$_6$ is an alanine or an asparagine residue. In another embodiment, X$_2$ is an isoleucine or valine residue, X$_3$ is a glycine or serine residue, X$_4$ is an arginine, serine, asparagine, serine, tyrosine, or isoleucine residue, and X$_5$ is a phenylalanine or a tyrosine residue.

In one embodiment, the present invention provides an antigen binding protein that comprises a light chain CDR2 comprising the sequence LX$_1$X$_2$X$_3$RX$_4$S (SEQ ID NO:239), wherein X$_1$ is a glycine or a valine residue, X$_2$ is a serine or a phenylalanine residue, X$_3$ is an asparagine, tyrosine, or threonine residue, and X$_4$ is an alanine or an aspartate residue. In another embodiment, the CDR comprises the sequence AX$_1$SX$_2$LX$_3$S (SEQ ID NO:240), wherein X$_1$ is an alanine or a threonine residue, X$_2$ is a threonine or a glycine residue, and X$_3$ is a glutamine or a glutamate residue. In another embodiment, the CDR2 comprises the sequence X$_1$X$_2$NX$_3$RPS (SEQ ID NO:241), wherein X$_1$ is a glutamate, glutamine, or glycine residue, X$_2$ is an aspartate or lysine residue, and X$_3$ is any amino acid residue.

In one embodiment, the present invention provides an antigen binding protein that comprises a light chain CDR3 comprising the sequence MX$_1$X$_2$X$_3$X$_4$X$_5$PX$_6$X$_7$ (SEQ ID NO:242), wherein X$_1$ is a glutamine or glutamate residue, X$_2$ is an alanine, glycine, serine, or threonine residue, X$_3$ is a leucine or threonine residue, X$_4$ is a glutamine, glutamate, or histidine residue, X$_5$ is a threonine, tryptophan, methionine, or valine residue, X$_6$ is a nonpolar side chain residue, and X$_7$ is a threonine, serine, or alanine residue. In another embodiment, the CDR3 comprises the sequence QQX$_1$X$_2$X$_3$X$_4$PX$_5$T (SEQ ID NO:243), wherein X$_1$ is an arginine, serine, leucine, or alanine residue, X$_2$ is an asparagine, serine, or histidine residue, X$_3$ is a serine or an asparagine residue, X$_4$ is a nonpolar side chain residue, and X$_5$ is a leucine, isoleucine, tyrosine, or tryptophan residue. In another embodiment, the CDR3 comprises the sequence QSYX$_1$SX$_2$NX$_3$X$_4$V (SEQ ID NO:244), wherein X$_1$ is an aspartate or a glutamine residue, $X_2$ is a serine or an aspartate residue, $X_3$ is a glutamine, valine, or tryptophan residue, and $X_4$ is an arginine residue or no residue.

In one embodiment, the present invention provides an antigen binding protein that comprises a heavy chain CDR1 comprising the sequence $X_1X_2X_3WWS$ (SEQ ID NO:245), wherein $X_1$ is a serine residue or no residue, $X_2$ is a serine or asparagine residue, and $X_3$ is an asparagine residue and an isoleucine residue. In another embodiment, the heavy chain CDR1 comprises the sequence $X_1X_2YWS$ (SEQ ID NO:246), wherein $X_1$ is a glycine, asparagine, or aspartate residue, and $X_2$ is a tyrosine or phenylalanine residue. In another embodiment, the heavy chain CDR1 comprises the sequence $SYX_1X_2X_3$ (SEQ ID NO:247), wherein $X_1$ is an alanine or glycine residue, $X_2$ is a methionine or isoleucine residue, and $X_3$ is a serine or histidine residue.

In one embodiment, the present invention provides an antigen binding protein that comprises a heavy chain CDR2 comprising the sequence $X_1X_2X_3X_4X_5GX_6TX_7YNPSLX_8S$ (SEQ ID NO:248), wherein $X_1$ is a glutamate, tyrosine, or serine residue, $X_2$ is a isoleucine or valine residue, $X_3$ is a tyrosine, asparagine, or serine residue, $X_4$ is a histidine, tyrosine, aspartate, or proline residue, $X_5$ is a serine or arginine residue, $X_6$ is a serine or asparagine residue, $X_7$ is an asparagine or tyrosine residue, and $X_8$ is a lysine or glutamate residue. In another embodiment, the heavy chain CDR2 comprises the sequence $X_1ISX_2X_3X_4X_5X_6X_7YYADSVKG$ (SEQ ID NO:249), wherein $X_1$ is a threonine, alanine, valine, or tyrosine residue, $X_2$ is a glycine, serine, or tyrosine residue, $X_3$ is a serine, asparagine, or aspartate residue, $X_4$ is a glycine or serine residue, $X_5$ is a glycine, serine, or aspartate residue, $X_6$ is a serine, threonine, or asparagine residue, and $X_7$ is a threonine, lysine, or isoleucine residue.

In one embodiment, the present invention provides an antigen binding protein that comprises a heavy chain CDR3 comprising the sequence $X_1X_2X_3X_4X_5X_6X_7X_8X_9FDI$ (SEQ ID NO:250), wherein $X_1$ is a glutamate residue or no residue, $X_2$ is tyrosine, glycine, or serine residue or no residue, $X_3$ is a serine, asparagine, tryptophan, or glutamate residue, or no residue, $X_4$ is a serine, aspartate, tryptophan, alanine, arginine, threonine, glycine, leucine, or glutamate residue, or no residue, $X_5$ is a serine, glycine, aspartate, threonine, tryptophan, alanine, valine, or isoleucine residue, $X_6$ is an arginine, glutamine, tyrosine, valine, alanine, glycine, serine, phenylalanine, or tryptophan residue, $X_7$ is a leucine, asparagine, aspartate, threonine, tryptophan, tyrosine, valine, alanine, or histidine residue, $X_8$ is an aspartate, serine, asparagine, or glutamine residue, and $X_9$ is an alanine or a proline residue. In another embodiment, the heavy chain CDR3 comprises the sequence $X_1X_2X_3X_4X_5X_6X_7X_8X_9X_{10}X_{11}MDV$ (SEQ ID NO:251), wherein $X_1$ is an alanine residue, or no residue, $X_2$ is a glutamate, tyrosine, or glycine residue, or no residue, $X_3$ is a serine or arginine residue, or no residue, $X_4$ is an aspartate, glycine, serine, or valine residue, or no residue, $X_5$ is a serine, glycine, or aspartate residue, or no residue, $X_6$ is a glycine, phenylalanine, aspartate, serine, tryptophan, or tyrosine residue, or no residue, $X_7$ is a tyrosine, tryptophan, serine, or aspartate residue, or no residue, $X_8$ is an aspartate, arginine, serine, glycine, tyrosine, or tryptophan residue, $X_9$ is a tyrosine, isoleucine, leucine, phenylalanine, or lysine residue, $X_{10}$ is a tyrosine, phenylalanine, aspartate, or glycine residue, and $X_{11}$ is a glycine, tyrosine, or asparagine residue. In another embodiment, the heavy chain CDR3 comprises the sequence $X_1X_2X_3X_4X_5X_6X_7X_8X_9X_{10}Y$ (SEQ ID NO:252), wherein $X_1$ is an aspartate or valine residue, or no residue, $X_2$ is a glycine, tyrosine, arginine, or aspartate residue, or no residue, $X_3$ is an asparagine, leucine, glycine, isoleucine, serine, valine, phenylalanine, or tyrosine residue, or no residue, $X_4$ is a leucine, serine, tryptophan, alanine, tyrosine, isoleucine, glycine, or aspartate residue, or no residue, $X_5$ is a glycine, alanine, tyrosine, serine, aspartate, or leucine residue, $X_6$ is a valine, alanine, glycine, threonine, proline, histidine, or glutamine residue, $X_7$ is a glutamate, glycine, serine, aspartate, glycine, valine, tryptophan, histidine, or arginine residue, $X_8$ is a glutamine, alanine, glycine, tyrosine, proline, leucine, aspartate, or serine residue, $X_9$ is a nonpolar side chain residue, and $X_{10}$ is an aspartate or alanine residue. In another embodiment, the heavy chain CDR3 comprises the sequence $X_1X_2X_3X_4X_5X_6X_7X_8X_9X_{10}YFDX_{11}$ (SEQ ID NO:253), wherein $X_1$ is a glycine residue, or no residue, $X_2$ is a proline residue, or no residue, $X_3$ is an arginine or aspartate residue, or no residue, $X_4$ is a histidine or proline residue, $X_5$ is an arginine or glycine residue, $X_6$ is an arginine, serine, or phenylalanine residue, $X_7$ is an aspartate or serine residue, $X_8$ is a glycine, tryptophan, or tyrosine residue, $X_9$ is a tyrosine or alanine residue, $X_{10}$ is an asparagine or tryptophan residue, and $X_{11}$ is an asparagine or leucine residue. In another embodiment, the heavy chain CDR3 comprises the sequence $X_1X_2X_3X_4DSSX_5X_6X_7X_8X_9X_{10}X_{11}X_{12}$ (SEQ ID NO:254), wherein $X_1$ is a phenylalanine residue, or no residue, $X_2$ is an asparagine or glycine residue, or no residue, $X_3$ is a tyrosine or a leucine residue, or no residue, $X_4$ is a tyrosine or glycine residue, or no residue, $X_5$ is a glycine, serine, or valine residue, $X_6$ is a tyrosine, phenylalanine, tryptophan, or glutamine residue, or no residue, $X_7$ is a tyrosine, glycine, or isoleucine residue, or no residue, $X_8$ is a tyrosine, leucine, or glycine residue, or no residue, $X_9$ is a methionine, glycine, or phenylalanine residue, or no residue, $X_{10}$ is an aspartate or methionine residue, or no residue, $X_{11}$ is a valine, aspartate, or tyrosine residue, or no residue, and $X_{12}$ is a valine residue, or no residue.

In one embodiment, the present invention provides an isolated antigen binding protein, comprising either: a. a light chain CDR3 comprising a sequence selected from the group consisting of: i. a light chain CDR3 sequence selected from the group consisting of the light chain CDR3 sequences of L1-L52 as shown in FIG. 6; ii. MQALQTPZT; iii. QQ(R/S)(N/S)(S/N)ZPLT; and iv. QSYDSSNXJV; b. a heavy chain CDR3 comprising a sequence selected from the group consisting of: i. a heavy chain CDR3 sequence that differs by no more than a total of three amino acid additions, substitutions, or deletions from a CDR3 sequence selected from the group consisting of the heavy chain CDR3 sequences of H1-H52 as shown in FIG. 9; ii. SRLDAFDI; iii. SXYDYYGMDV; iv. HRXDXAWYFDL; and v. DSSG; or c. the light chain CDR3 sequence of (a) and the heavy chain CDR3 sequence of (b); wherein amino acid residue symbols enclosed in parentheses identify alternative residues for the same position in a sequence, each X is independently any amino acid residue, each Z is independently a glycine residue, an alanine residue, a valine residue, a leucine residue, an isoleucine residue, a proline residue, a phenylalanine residue, a methionine residue, a tryptophan residue, or a cysteine residue, each J is independently a glutamine residue, an arginine residue, a valine residue, or a tryptophan residue, and the antigen binding protein binds to human IGF-1R.

The nucleotide sequences of FIG. 1, or the amino acid sequences of FIGS. 2 through 9, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al. 1985, Gene 37:73; Craik, BioTechniques, January 1985, 12-19; Smith et al., 1981, *Genetic Engineering: Principles and Methods*, Plenum Press; and U.S. Pat. Nos. 4,518,584 and 4,737,462. These and other methods can be used to make, for example, derivatives of anti-IGF-1R antibodies that have a desired property, for example, increased affinity, avidity, or specificity for IGF-1R, increased activity or stability in vivo or in vitro, or reduced in vivo side-effects as compared to the underivatized antibody.

Other derivatives of anti-IGF-1R antibodies within the scope of this invention include covalent or aggregative conjugates of anti-IGF-1R antibodies, or fragments thereof, with other proteins or polypeptides, such as by expression of recombinant fusion proteins comprising heterologous polypeptides fused to the N-terminus or C-terminus of an anti-IGF-1R antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG peptide Asp-Tyr-Lys-Asp-Asp-Asp-Asp-Lys (DYKDDDDK) (SEQ ID NO:255) as described in Hopp et al., *Bio/Technology* 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more antigen binding proteins may be employed as IGF-1R antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have IGF-1R binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in *Current Protocols in Immunology*, Suppl. 4, pages 10.19.1-10.19.11.

One embodiment of the present invention is directed to a dimer comprising two fusion proteins created by fusing an IGF-1R binding fragment of an anti-IGF-1R antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-IGF-1R antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-IGF-1R antibody fragment or derivative fused to a leucine zipper peptide are expressed in suitable host cells, and the soluble oligomeric anti-IGF-1R antibody fragments or derivatives that form are recovered from the culture supernatant.

In one aspect, the present invention provides antigen binding proteins that interfere with the binding of IGF-1 and/or IGF-2 to an IGF-1R. Such antigen binding proteins can be made against IGF-1R, or a fragment, variant or derivative thereof, and screened in conventional assays for the ability to interfere with binding of IGF-1 and/or IGF-2 to IGF-1R. Examples of suitable assays are assays that test the antigen binding proteins for the ability to inhibit binding of IGF-1 and/or IGF-2 to cells expressing IGF-1R, or that test antigen binding proteins for the ability to reduce a biological or cellular response that results from the binding of IGF-1 and/or IGF-2 to cell surface IGF-1R receptors.

In another aspect, the present invention provides an antigen binding protein that blocks the binding of IGF-1 and/or IGF-2 to IGF-1R but does not significantly block the binding of insulin to insulin receptor (INS-R). In one embodiment, the antigen binding protein does not bind to INS-R. In another embodiment, the antigen binding protein binds to the INS-R with such a low affinity that it does not effectively block the binding of insulin to INS-R. In another embodiment, the antigen binding protein binds to INS-R, but antigen binding protein-bound INS-R can still bind to insulin. In another embodiment, the antigen binding protein's selectivity for IGF-1R is at least 50 times greater than its selectivity for insulin receptor. In another embodiment, the selectivity of the antigen binding protein is more than 100 times greater than its selectivity for insulin receptor.

In another aspect, the present invention provides an antigen binding protein that demonstrates species selectivity. In one embodiment, the antigen binding protein binds to one or more mammalian IGF-1R, for example, to human IGF-1R and one or more of mouse, rat, guinea pig, hamster, gerbil, cat, rabbit, dog, goat, sheep, cow, horse, camel, and non-human primate IGF-1R. In another embodiment, the antigen binding protein binds to one or more primate IGF-1R, for example, to human IGF-1R and one or more of cynomologous, marmoset, rhesus, and chimpanzee IGF-1R. In another embodiment, the antigen binding protein binds specifically to human, cynomologous, marmoset, rhesus, or chimpanzee IGF-1R. In another embodiment, the antigen binding protein does not bind to one or more of mouse, rat, guinea pig, hamster, gerbil, cat, rabbit, dog, goat, sheep, cow, horse, camel, and non-human primate IGF-1R. In another embodiment, the antigen binding protein does not bind to a New World monkey species such as a marmoset. In another embodiment, the antigen binding protein does not exhibit specific binding to any naturally occurring protein other than IGF-1R. In another embodiment, the antigen binding protein does not exhibit specific binding to any naturally occurring protein other than mammalian IGF-1R. In another embodiment, the antigen binding protein does not exhibit specific binding to any naturally occurring protein other than primate IGF-1R. In another embodiment, the antigen binding protein does not exhibit specific binding to any naturally occurring protein other than human IGF-1R. In another embodiment, the antigen binding protein specifically binds to mouse, rat, cynomolgus monkey, and human IGF-1R. In another embodiment, the antigen binding protein specifically binds to mouse, rat, cynomolgus monkey, and human IGF-1R with a similar binding affinity. In another embodiment, the antigen binding protein blocks binding of human IGF-1 and IGF-2 with mouse, rat, cynomolgus monkey, and human IGF-1R. In another embodiment, the antigen binding protein blocks binding of human IGF-1 and IGF-2 with mouse, rat, cynomolgus monkey, and human IGF-1R with similar $K_i$. In another embodiment, the antigen binding protein blocks binding of human IGF-1 and IGF-2 with mouse, rat, cynomolgus monkey, and human IGF-1R with a $K_i$ of between about 0.57 and about 0.61 nM.

One may determine the selectivity of an antigen binding protein for an IGF-1R using methods well known in the art and following the teachings of the specification. For example, one may determine the selectivity using Western blot, FACS, ELISA or RIA.

In another aspect, the present invention provides an IGF-1R binding antigen binding protein (for example, an anti-IGF-1R antibody), that has one or more of the following characteristics: binds to both human and murine IGF-1R, inhibits the binding of both IGF-1 and IGF-2 to human IGF-1R, inhibits the binding of both IGF-1 and IGF-2 to murine IGF-1R, preferentially inhibits the high affinity binding of IGF-1 and/or of IGF-2 to IGF-1R, binds to the L2 domain of IGF-1R, causes relatively little down-regulation of cell-surface expressed IGF-1R after 17 hours of exposure (as compared to MAB391 (R&D systems, Minneapolis, Minn.); e.g., amount of IGF-1R is reduced by less than 20%), causes a level of down-regulation of cell-surface expressed IGF-1R on Colo-205 or MiaPaCa-2 xenograft tumor cells in mice as MA1391 after four weeks of once weekly doses of 200 micrograms.

Antigen-binding fragments of antigen binding proteins of the invention may be produced by conventional techniques. Examples of such fragments include, but are not limited to, Fab and F(ab')$_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. patent application Ser. No. 10/194,975 (published Feb. 27, 2003), U.S. Pat. Nos. 5,869,619, 5,225, 539, 5,821,337, 5,859,205, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with an IGF-1R polypeptide, such that antibodies directed against the IGF-1R polypeptide are generated in the animal. One example of a suitable immunogen is a soluble human IGF-1R, such as a polypeptide comprising the extracellular domain of the protein of FIG. 10, or other immunogenic fragment of the protein of FIG. 10. Examples of techniques for production and use of transgenic animals for the production of human or partially human antibodies are described in U.S. Pat. Nos. 5,814,318, 5,569,825, and 5,545, 806, Davis et al., 2003, *Production of human antibodies from transgenic mice* in Lo, ed. Antibody Engineering: Methods and Protocols, Humana Press, NJ: 191-200, Kellermann et al., 2002, Curr Opin Biotechnol. 13:593-97, Russel et al., 2000, Infect Immun. 68:1820-26, Gallo et al., 2000, Eur J Immun. 30:534-40, Davis et al., 1999, Cancer Metastasis Rev. 18:421-25, Green, 1999, J Immunol Methods. 231:11-23, Jakobovits, 1998, Advanced Drug Delivery Reviews 31:33-42, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat Genet. 15:146-56, Jakobovits, 1994, Curr Biol. 4:761-63, Arbones et al., 1994, Immunity. 1:247-60, Green et al., 1994, Nat Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar. "Immunoglobulin gene rearrangement in B cell deficient mice generated by targeted deletion of the JH locus." International Immunology 5 (1993): 647-656, Choi et al., 1993, Nature Genetics 4: 117-23, Fishwild et al., 1996, Nature Biotechnology 14: 845-51, Harding et al., 1995, Annals of the New York Academy of Sciences, Lonberg et al., 1994, Nature 368: 856-59, Lonberg, 1994, *Transgenic Approaches to Human Monoclonal Antibodies* in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Research 20: 6287-95, Taylor et al., 1994, International Immunology 6: 579-91, Tomizuka et al., 1997, Nature Genetics 16: 133-43, Tomizuka et al., 2000, Proceedings of the National Academy of Sciences USA 97: 722-27, Tuaillon et al., 1993, Proceedings of the National Academy of Sciences USA 90: 3720-24, and Tuaillon et al., 1994, Journal of Immunology 152: 2912-20.

In another aspect, the present invention provides monoclonal antibodies that bind to IGF-1R. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 41, Sp210-Ag14, FO, NSO/U, MPC-11, MPC11-X45-GTG 1.7 and S194/5XX0 Bu1; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In one embodiment, a hybridoma cell line is produced by immunizing an animal (e.g., a transgenic animal having human immunoglobulin sequences) with an IGF-1R immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds an IGF-1R polypeptide. Such hybridoma cell lines, and anti-IGF-1R monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as the ability to block an IGF-1 and/or IGF-2 induced activity. Examples of such screens are provided in the examples below.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to IGF-1R.

Antigen binding proteins directed against an IGF-1R can be used, for example, in assays to detect the presence of IGF-1R polypeptides, either in vitro or in vivo. The antigen binding proteins also may be employed in purifying IGF-1R proteins by immunoaffinity chromatography. Those antigen binding proteins that additionally can block binding of IGF-1 and/or IGF-2 to IGF-1R may be used to inhibit a biological activity that results from such binding. Blocking antigen binding proteins can be used in the methods of the present invention. Such antigen binding proteins that function as IGF-1 and/or IGF-2 antagonists may be employed in treating any IGF-1 and/or IGF-2-induced condition, including but not limited to cancer. In one embodiment, a human anti-IGF-1R monoclonal antibody generated by procedures involving immunization of transgenic mice is employed in treating such conditions.

Antigen binding proteins may be employed in an in vitro procedure, or administered in vivo to inhibit an IGF-1 and/or IGF-2-induced biological activity. Disorders caused or exacerbated (directly or indirectly) by the interaction of IGF-1 and/or IGF-2 with cell surface IGF-1R, examples of which are provided above, thus may be treated. In one embodiment, the present invention provides a therapeutic method comprising in vivo administration of an IGF-1 and/or IGF-2 blocking antigen binding protein to a mammal in need thereof in an amount effective for reducing an IGF-1 and/or IGF-2-induced biological activity.

Antigen binding proteins of the invention include partially human and fully human monoclonal antibodies that inhibit a biological activity of IGF-1 and also inhibit a biological activity of IGF-2. One embodiment is directed to a human monoclonal antibody that at least partially blocks binding of IGF-1 and of IGF-2 to a cell that expresses human IGF-1R. In one embodiment, the antibodies are generated by immunizing a transgenic mouse with an IGF-1R immunogen. In another embodiment, the immunogen is a human IGF-1R polypeptide (e.g., a soluble fragment comprising all or part of the IGF-1R extracellular domain). Hybridoma cell lines derived from such immunized mice, wherein the hybridoma secretes a monoclonal antibody that binds IGF-1R, also are provided herein.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject.

In another embodiment, the non-human antibody is from the same species as the non-human subject, e.g., a mouse antibody of the invention is administered to a mouse. An antibody from a particular species can be made by, for example, immunizing an animal of that species with the desired immunogen (e.g., a soluble IGF-1R polypeptide) or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, New York, 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of IGF-1R bound thereto. Polypeptides contemplated for use herein include substantially homogeneous recombinant mammalian anti-IGF-1R antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-IGF-1R antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

In one aspect, the present invention provides antigen-binding fragments of an anti-IGF-1R antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:3140). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein include, but are not limited to, scFvs comprising the variable domain combinations L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52) are encompassed by the present invention.

Antigen binding proteins (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16.

In one embodiment, an antigen binding protein of the invention comprises the IgG1 heavy chain domain of FIG. 13 or a fragment of the IgG1 heavy chain domain of FIG. 13. In another embodiment, an antigen binding protein of the invention comprises the kappa light chain constant chain region of FIG. 13 or a fragment of the kappa light chain constant region of FIG. 13. In another embodiment, an antigen binding protein of the invention comprises both the IgG1 heavy chain domain, or a fragment thereof, of FIG. 13 and the kappa light chain domain, or a fragment thereof, of FIG. 13.

Accordingly, the antigen binding proteins of the present invention include those comprising, for example, the variable domain combinations L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52, having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation (CPSCP→CPPCP) in the hinge region as described in Bloom et al., 1997, Protein Science 6:407, incorporated by reference herein) to alleviate a tendency to form intra-H chain disulfide bonds that can lead to heterogeneity in the IgG4 antibodies.

Moreover, techniques for deriving antigen binding proteins having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

In particular embodiments, antigen binding proteins of the present invention have a binding affinity ($K_a$) for IGF-1R of at least $10^6$, measured as described in the Examples. In other embodiments, the antigen binding proteins exhibit a $K_a$ of at least $10^7$, at least $10^8$, at least $10^9$, or at least $10^{10}$.

In another embodiment, the present invention provides an antigen binding protein that has a low dissociation rate from IGF-1R. In one embodiment, the antigen binding protein has a $K_{off}$ of $1\times10^{-4}$ s$^{-1}$ or lower. In another embodiment, the $K_{off}$ is $5\times10^{-5}$ s$^{-1}$ or lower. In another embodiment, the $K_{off}$ is substantially the same as an antibody having a combination of light chain and heavy chain variable domain sequences selected from the group of combinations consisting of L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52. In another embodiment, the antigen binding protein binds to IGF-1R with substantially the same $K_{off}$ as an antibody that comprises one or more CDRs from an antibody having a combination of light chain and heavy chain variable domain sequences selected from the group of combinations consisting of L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52. In another embodiment, the antigen binding protein binds to IGF-1R with substantially the same $K_{off}$ as an antibody that comprises one of the amino acid sequences illustrated in FIGS. 2 through 9. In another embodiment, the antigen binding protein binds to IGF-1R with substantially the same $K_{off}$ as an antibody that comprises one or more CDRs from an antibody that comprises one of the amino acid sequences illustrated in FIGS. 2 through 9.

In another aspect, the present invention provides an antigen binding protein that binds to the L2 domain of human IGF-1R. Antigen binding proteins that bind to the L2 domain can be made using any technique known in the art. For example, such antigen binding proteins can be isolated using the full-length IGF-1R polypeptide (e.g., in a membrane-bound preparation), a soluble extracellular domain fragment of IGF-1R (an example of which is provided in Example 1), or a smaller fragment of the IGF-1R extracellular domain comprising or consisting of the L2 domain (examples of which are provided in Example 10). Antigen binding proteins so isolated can be screened to determine their binding specificity using any method known in the art (an example of which is provided in Example 10).

In another aspect, the present invention provides an antigen binding protein that binds to human IGF-1R expressed on the surface of a cell and, when so bound, inhibits IGF-1R signaling activity in the cell without causing a significant reduction in the amount of IGF-1R on the surface of the cell. Any method for determining or estimating the amount of IGF-1R on the surface and/or in the interior of the cell can be used. In one embodiment, the present invention provides an antigen binding protein that binds to the L2 domain of a human IGF-1R expressed on the surface of a cell and, when so bound, inhibits IGF-1R signaling activity in the cell without significantly increasing the rate of internalization of the IGF-1R from the surface of the cell. In other embodiments, binding of the antigen binding protein to the IGF-1R-expressing cell causes less than about 75%, 50%, 40%, 30%, 20%, 15%, 10%, 5%, 1%, or 0.1% of the cell-surface IGF-1R to be internalized. In another aspect, binding of the antigen binding protein to the IGF-1R-expressing cell causes a gradual reduction in the amount of IGF-1R on the cell surface such that within a few hours of contacting the cell with the antigen binding protein, little or no decrease in cell surface IGF-1R is detected, but, after several days or weeks of exposure of the cell to the antigen binding protein, a marked decrease in cell surface IGF-1R is detected.

In another aspect, the present invention provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO 00/09560, published Feb. 24, 2000, incorporated by reference.

The present invention further provides multi-specific antigen binding proteins, for example, bispecific antigen binding protein, e.g., antigen binding protein that bind to two different epitopes of IGF-1R, or to an epitope of IGF-1R and an epitope of another molecule, via two different antigen binding sites or regions. Moreover, bispecific antigen binding protein as disclosed herein can comprise an IGF-1R binding site from one of the herein-described antibodies and a second IGF-1R binding region from another of the herein-described antibodies, including those described herein by reference to other publications. Alternatively, a bispecific antigen binding protein may comprise an antigen binding site from one of the herein described antibodies and a second antigen binding site from another IGF-1R antibody that is known in the art, or from an antibody that is prepared by known methods or the methods described herein.

Numerous methods of preparing bispecific antibodies are known in the art, and discussed in U.S. patent application Ser. No. 09/839,632, filed Apr. 20, 2001 (incorporated by reference herein). Such methods include the use of hybrid-hybridomas as described by Milstein et al., 1983, Nature 305:537, and others (U.S. Pat. No. 4,474,893, U.S. Pat. No. 6,106,833), and chemical coupling of antibody fragments (Brennan et al., 1985, Science 229:81; Glennie et al., 1987, J. Immunol. 139: 2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582, 996. Additional useful techniques include those described in Kortt et al., 1997, supra; U.S. Pat. No. 5,959,083; and U.S. Pat. No. 5,807,706.

In another aspect, the antigen binding protein of the present invention comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols. US Pat. App. No. 20030195154.

In another aspect, the present invention provides methods of screening for a molecule that binds to IGF-1R using the antigen binding proteins of the present invention. Any suitable screening technique can be used. In one embodiment, an IGF-1R molecule, or a fragment thereof to which an antigen binding protein of the present invention binds, is contacted with the antigen binding protein of the invention and with another molecule, wherein the other molecule binds to IGF-1R if it reduces the binding of the antigen binding protein to IGF-1R. Binding of the antigen binding protein can be detected using any suitable method, e.g., an ELISA. Detection of binding of the antigen binding protein to IGF-1R can be simplified by detectably labeling the antigen binding protein, as discussed above. In another embodiment, the IGF-1R-binding molecule is further analyzed to determine whether it inhibits IGF-1R, IGF-1, and/or IGF-2-mediated signaling.

Nucleic Acids

In one aspect, the present invention provides isolated nucleic acid molecules. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with IGF-1R. The nucleic acid may be isolated by conventional procedures such as polymerase chain reaction (PCR).

FIG. 1 provides nucleic acid sequences encoding the variable regions of the heavy and light chain variable regions shown in FIGS. 2 and 3. The skilled artisan will appreciate that, due to the degeneracy of the genetic code, each of the polypeptide sequences in FIGS. 2 through 9 also is encoded by a large number of other nucleic acid sequences. The present invention provides each degenerate nucleotide sequence encoding each antigen binding protein of the invention.

The invention further provides nucleic acids that hybridize to other nucleic acids (e.g., nucleic acids comprising a nucleotide sequence of FIG. 1) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property (e.g., binding to IGF-1R or blocking the binding of IGF-1 and/or IGF-2 to IGF-1R).

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence provided in FIG. 1, or a desired fragment, variant, or derivative thereof, is mutated such that it encodes an amino acid sequence comprising one or more deletions or substitutions of amino acid residues that are shown in FIGS. 2 through 9 to be residues where two or more sequences differ. In another embodiment, the mutagenesis inserts an amino acid adjacent to one or more amino acid residues shown in FIGS. 2 through 9 to be residues where two or more sequences differ. Alternatively, one or more mutations can be introduced into a nucleic acid that selectively change the biological activity (e.g., binding of IGF-1R, inhibiting IGF-1 and/or IGF-2, etc.) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., an IGF-1R binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, E. coli) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Indications

In one aspect, the present invention provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated in accordance with the present invention are conditions characterized by inappropriate expression or activity of IGF-1, IGF-2, and/or IGF-1R. In some such conditions, the expression or activity level is too high, and the treatment comprises administering an IGF-1R antagonist as described herein. In other such conditions, the expression or activity level is too low, and the treatment comprises administering an IGF-1R agonist as described herein.

One example of a type of condition that can be treated using the methods and compositions of the present invention is a condition that involves cell growth, for example, a cancerous condition. Thus, in one embodiment, the present invention provides compositions and methods for treating a cancerous condition. The cancerous condition can be any cancerous condition that can be treated using the compositions comprised herein, for example, IGF-1R antagonizing antigen binding proteins such as anti-IGF-1R antibodies, antibody fragments, or antibody derivatives. Examples of cancerous conditions include, for example, Acute Lymphoblastic Leukemia, Adrenocortical Carcinoma, AIDS-Related Cancers, AIDS-Related Lymphoma, Anal Cancer, Childhood Cerebellar Astrocytoma, Childhood Cerebral Astrocytoma, Basal Cell Carcinoma, Extrahepatic Bile Duct Cancer, Bladder Cancer, Osteosarcoma/Malignant Fibrous Histiocytoma Bone Cancer, Brain Tumors (e.g., Brain Stem Glioma, Cerebellar Astrocytoma, Cerebral Astrocytoma/Malignant Glioma, Ependymoma, Medulloblastoma, Supratentorial Primitive Neuroectodermal Tumors, Visual Pathway and Hypothalamic Glioma), Breast Cancer, Bronchial Adenomas/Carcinoids, Burkitt's Lymphoma, Carcinoid Tumor, Gastrointestinal Carcinoid Tumor, Carcinoma of Unknown Primary, Primary Central Nervous System, Cerebellar Astrocytoma, Cerebral Astrocytoma/Malignant Glioma, Cervical Cancer, Childhood Cancers, Chronic Lymphocytic Leukemia, Chronic Myelogenous Leukemia, Chronic Myeloproliferative Disorders, Colon Cancer, Colorectal Cancer, Cutaneous T-Cell Lymphoma, Endometrial Cancer, Ependymoma, Esophageal Cancer, Ewing's Family of Tumors, Extracranial Germ Cell Tumor, Extragonadal Germ Cell Tumor, Extrahepatic Bile Duct Cancer, Intraocular Melanoma Eye Cancer, Retinoblastoma Eye Cancer, Gallbladder Cancer, Gastric (Stomach) Cancer, Gastrointestinal Carcinoid Tumor, Germ Cell Tumors (e.g., Extracranial, Extragonadal, and Ovarian), Gestational Trophoblastic Tumor, Glioma (e.g., Adult, Childhood Brain Stem, Childhood Cerebral Astrocytoma, Childhood Visual Pathway and Hypothalamic), Hairy Cell Leukemia, Head and Neck Cancer, Hepatocellular (Liver) Cancer, Hodgkin's Lymphoma, Hypopharyngeal Cancer, Hypothalamic and Visual Pathway Glioma, Intraocular Melanoma, Islet Cell Carcinoma (Endocrine Pancreas), Kaposi's Sarcoma, Kidney (Renal Cell) Cancer, Laryngeal Cancer, Leukemia (e.g., Acute Lymphoblastic, Acute Myeloid, Chronic Lymphocytic, Chronic Myelogenous, and Hairy Cell), Lip and Oral Cavity Cancer, Liver Cancer, Non-Small Cell Lung Cancer, Small Cell Lung Cancer, Lymphoma (e.g., AIDS-Related, Burkitt's, Cutaneous T-Cell, Hodgkin's, Non-Hodgkin's, and Primary Central Nervous System), Waldenström's Macroglobulinemia, Malignant Fibrous Histiocytoma of Bone/Osteosarcoma, Medulloblastoma, Melanoma, Intraocular (Eye) Melanoma, Merkel Cell Carcinoma, Mesothelioma, Metastatic Squamous Neck Cancer with Occult Primary, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Chronic Myeloid Leukemia, Multiple Myeloma, Chronic Myeloproliferative Disorders, Nasal Cavity and Paranasal Sinus Cancer, Nasopharyngeal Cancer, Neuroblastoma, Oral Cancer, Oropharyngeal Cancer, Osteosarcoma/Malignant Fibrous Histiocytoma of Bone, Ovarian Cancer, Ovarian Epithelial Cancer, Ovarian Germ Cell Tumor, Ovarian Low Malignant Potential Tumor, Pancreatic Cancer, Islet Cell Pancreatic Cancer, Paranasal Sinus and Nasal Cavity Cancer, Parathyroid Cancer, Penile Cancer, Pheochromocytoma, Pineoblastoma, Pituitary Tumor, Plasma Cell Neoplasm/Multiple Myeloma, Pleuropulmonary Blastoma, Primary Central Nervous System Lymphoma, Prostate Cancer, Rectal Cancer, Renal Cell (Kidney) Cancer, Renal Pelvis and Ureter Transitional Cell Cancer, Retinoblastoma, Rhabdomyosarcoma, Salivary Gland Cancer, Soft Tissue Sarcoma, Uterine Sarcoma, Sezary Syndrome, non-Melanoma Skin Cancer, Merkel Cell Skin Cancer, Small Intestine Cancer, Soft Tissue Sarcoma, Squamous Cell Carcinoma, Cutaneous T-Cell Lymphoma, Testicular Cancer, Thymoma, Thymic Carcinoma, Thyroid Cancer, Gestational Trophoblastic Tumor, Carcinoma of Unknown Primary Site, Cancer of Unknown Primary Site, Urethral Cancer, Endometrial Uterine Cancer, Uterine Sarcoma, Vaginal Cancer, Visual Pathway and Hypothalamic Glioma, Vulvar Cancer, Waldenström's Macroglobulinemia, and Wilms' Tumor.

Four different groups have studied a total of 425 breast cancers, mostly ductal in origin, and 48 normal tissues or benign specimens by radioimmunoassay ("RIA") or immunohistochemistry ("IHC") (Papa et al., 1993, Cancer Research 53: 3736-40, Happerfield et al., 1997, Journal of Pathology 183: 412-17; Ellis et al., 1998, Breast Cancer Research & Treatment 52: 175-84, Lee et al., 1998, Breast Cancer Research & Treatment 47: 295-302, Schnarr et al., 2000, International Journal of Cancer 89: 506-13). These studies suggest that elevated IGF-1R expression, on the order of 5-10 fold, is associated with favorable prognosis and biomarkers (ER+PR+), suggesting that estrogen and IGF cooperate in the maintenance or progression of well differentiated tumor. Similarly, estrogen has been shown to be essential for the growth and survival of the ER+MCF-7 breast cancer cell line, and in this context IGF-1R is up-regulated by estrogen treatment (reviewed in Ellis et al., 1998, Breast Cancer Research & Treatment 52: 175-84). Thus, in one embodiment, the present invention provides a method of treating breast cancer in a subject in need of such treatment, comprising administering to the subject an effective amount of an IGF-1R antagonist as described herein. In another embodiment, the method further comprises administering a hormone inhibitor, e.g., an estrogen inhibitor.

A retrospective IGF-1R IHC analysis has been reported for a collection of 12 colonic adenomas, 36 primary colorectal adenocarcinomas and 27 corresponding metastases, and 34 adjacent normal tissues (Hakam et al., 1999, Human Pathology. 30: 1128-33). The frequency of moderate to strong IHC staining appeared to dramatically increase with higher stage and tumor grade (0% normal vs. 93% metastases). The results are consistent with RNA analysis by RNAse protection assay ("RPA") (Freier et al., 1999, Gut 44: 704-08). Thus, in one embodiment, the present invention provides a method of treating colon cancer in a subject in need of such treatment, comprising administering to the subject an effective amount of an IGF-1R antagonist as described herein.

High plasma IGF-1 and reduced IGFbp3 in men 40-80 years old is associated with increased prostate cancer risk (Chan et al., 1998, Science 279: 563-6). High IGF-1 is associated with a risk of other cancers including breast (Hankinson et al., 1998, Lancet 351: 1393-96), colon (Ma et al., 1999, Journal of the National Cancer Institute 91: 620-25) and lung (Yu et al., 1999, Journal of the National Cancer Institute 91: 151-56). In transgenic mouse models, tumor incidence is increased by IGF-1 overexpression in diverse locations (Bol et al., 1997, Oncogene 14: 1725-34; DiGiovanni et al., 2000, Cancer Research 60: 1561-70; DiGiovanni et al., 2000, Proceedings of the National Academy of Sciences of the United States of America 97: 3455-60, Hadsell et al., 2000, Oncogene 19: 889-98). These mouse studies point to a role for both serum and stromal produced IGF-1. Thus, in one embodiment, the present invention provides a method of treating a subject in need of such treatment, comprising administering to the subject an effective amount of an antagonist of IGF-1R as described herein, wherein the antagonist inhibits the activation of IGF-1R by IGF-1. In another embodiment, the subject has cancer. In another embodiment, the subject has a tumor. In another embodiment, the cancer is prostate, breast, colon or lung cancer.

It has been observed that bone is the major source of IGF-1 in the body. Thus, in one aspect, the present invention provides compositions and methods for inhibiting IGF-1R in a bone of a subject. In one embodiment, an IGF-1R inhibitor of the present invention is administered to a subject that has, or is at risk for developing, a tumor in a bone. The tumor can be, for example, a primary tumor or a metastatic tumor. The treatment optionally further comprises administering to the subject one or more additional therapeutic and/or palliative treatments, for example, an anti-tumor treatment (e.g., chemotherapy, radiation therapy, or anti-hormone therapy) or a treatment that inhibits bone turnover (e.g., denosumab (Amgen Inc., Thousand Oaks, Calif.)).

IGF-2 is overexpressed in a variety of tumors and stromal tissues. IGF-2 levels appear especially high (as much as 40 fold) in primary liver cancers (Cariani et al., 1988, Cancer Research 48: 6844-49) and adenocarcinoma of the colon (Freier et al., 1999, Gut 44: 704-08). Many of the overgrowth disorders are associated with an increased incidence of childhood tumors. Five to ten percent of individuals with either the prenatal growth disorder Beckwith-Weidmann Syndrome (BWS) or hemihyperplasia develop tumors such as nephroblastoma, adrenal carcinoma, and neuroblastoma (reviewed by Morison et al., 1998, Molecular Medicine Today 4: 110-05). The tumor-predisposing factor in these children appears to be the mosaic loss of maternal IGF-2 gene imprinting, or duplication of the paternal chromosomal arm (11p) that carries IGF-2. Both alterations would increase the level of IGF-2 expression. IGF-2 overexpression as a result of mosaic uniparental disomy or loss of IGF-2 imprinting has also been detected in Wilms tumors. Growth disorders are not observed in these children even though the IGF-2 gene alterations also occur in some normal tissues, perhaps reflecting the tissue distribution of the affected cells. Imprinting of the maternal IGF-2 gene also occurs in mice, and the effects of IGF-2 overexpression are consistent with the human situation (Cariani et al., 1991, Journal of Hepatology 13: 220-26, Schirmacher et al., 1992, Cancer Research 52: 2549-56; Harris et al., 1998, Oncogene 16: 203-09). The incidence of tumors and organomegaly increases in mice that transgenically express excess IGF-2 (Christofori et al., 1994, Nature 369: 414-18, Ward et al., 1994, Proceedings of the National Academy of Sciences of the United States of America 91: 10365-9, Wolf et al., 1994, Endocrinology 135: 1877-86, Bates et al., 1995, British Journal of Cancer 72: 1189-93, Hassan et al., 2000, Cancer Research 60: 1070-76). Local IGF-2 overexpression increases the spontaneous appearance of prostate, mammary, intestinal, liver and epidermal tumors. Plasma specific expression using liver promoters elevate hepatocellular carcinomas and lymphoma. Thus, in one embodiment, the present invention provides a method of treating a subject in need of such treatment, comprising administering to the subject an effective amount of an antagonist of IGF-1R as described herein, wherein the antagonist inhibits the activation of IGF-1R by IGF-2. In another embodiment, the subject has cancer. In another embodiment, the subject has a tumor. In another embodiment, the subject has liver cancer, adenocarcinoma of the colon, Beckwith-Weidmann Syndrome, hemihyperplasia, nephroblastoma, adrenal carcinoma, neuroblastoma, mosaic loss of maternal IGF-2 gene imprinting, duplication of the paternal chromosomal arm (11p), increased IGF-2 expression, a tumor (e.g., a prostate, mammary, intestinal, liver, epidermal, or Wilms tumor), organomegaly, hepatocellular carcinoma, or lymphoma.

In another aspect, the invention provides methods of preventing or inhibiting a cancer from spreading to another part of the body, or of treating a cancer that has spread to another part of the body. In one embodiment, the cancer has spread to a regional lymph node. In another embodiment, the cancer is metastatic. The primary tumor can be any kind of tumor, for example, an adenocarcinoma tumor (e.g., a prostate adenocarcinoma tumor, a breast carcinoma tumor, or a renal cell carcinoma tumor), a non-small cell or small cell lung cancer tumor, a thyroid cancer tumor, etc. The site of the metastatic tumor can be anywhere in the body. It can be, for example, in bone, the lymph system, lung, brain, eye, skin, pancrease, or liver. In one particular embodiment, a subject having a tumor disease is treated with an effective amount of an IGF-1R inhibiting composition of the present invention such that the primary tumor is prevented from metastasizing. In another particular embodiment, a subject having a primary tumor is treated with an effective amount of an IGF-1R inhibiting composition of the present invention such that the primary tumor is inhibited from metastasizing. In another particular embodiment, a subject having a metastatic tumor is treated with an effective amount of an IGF-1R inhibiting composition of the present invention such that growth or spreading of the secondary tumor is inhibited. In another particular embodiment, a subject having a metastatic tumor is treated with an effective amount of an IGF-1R inhibiting composition of the present invention such that the secondary tumor is reduced in size. In a more particular embodiment, the primary tumor is an adenocarcinoma tumor, a non-small cell lung tumor, a small cell lung tumor, or a thyroid cancer. In another more particular embodiment, the metastatic tumor is in a bone. In another more particular embodiment, a metastatic tumor is prevented or inhibited from forming in a bone. In another more particularly defined embodiment, the method comprises treating the subject with an IGF-1R inhibiting composition of the present invention and one or more other treatments (e.g., a treatment that kills or inhibits the growth of cancer cells, such as radiation, hormonal therapy, or chemotherapy, or a treatment that inhibits the turnover of bone, such as denosumab), non-limiting examples of which are provided herein. The one or more other treatments can include, for example the standard of care for the subject's particular condition and/or palliative care.

Without being bound to any particular theory, tumor cells appear to depend on the PI3 Kinase/Akt signaling pathway to resist the apoptosis-inducing activity of chemotherapeutics, radiation, and anti-hormone therapy. Thus, in one embodiment, the present invention provides methods of treating a subject in need of such treatment comprising administering to the subject an IGF-1R antagonist of the present invention and a chemotherapeutic, radiation, and/or an anti-hormone therapy. This concept has been validated experimentally in cell culture models and rodent tumor models by antisense and dominant negative mutations (reviewed by Baserga et al., 1997, Biochimica et Biophysica Acta 1332: F105-26, Baserga, 2000, Oncogene 19: 5574-81). In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

One example of a chemotherapeutic agent that can be administered in combination with an IGF-1 receptor inhibitor of the invention is CPT-11. CPT-11 (Irinotecan hydrochloride trihydrate) is a semi synthetic, water soluble derivative of camptothecin, a plant alkaloid. CPT-11 and an associated metabolite called SN38 inhibit topoisomerase 1 (TOPO1). This enzyme introduces reversible single-strand breaks in DNA that allow unwinding and permit DNA replication to proceed. Inhibition of TOPO1 prevents religation of single-strand breaks after DNA replication resulting in greatly increased chromosomal fragmentation. This DNA damage promotes cell death by apoptosis through the action of p53 and other systems that monitor genome integrity. The cytotoxic effect of CPT-11 is generally limited to cells that are replicating DNA (S-Phase). Quiescent cells are largely unaffected.

In another embodiment, the present invention provides treating a subject in need thereof with an effective amount of an IGF-1R antagonist of the present invention and with an effective amount of an apoptosis-inducing agent.

In another embodiment, an anti-angiogenesis agent, such as an MMP-2 (matrix-metalloproteinase 2) inhibitor, an MMP-9 (matrix-metalloproteinase 9) inhibitor, and/or a COX-II (cyclooxygenase II) inhibitor, is used in conjunction with a compound of the invention. Examples of useful COX-II inhibitors include CELEBREX™ (alecoxib), BEXTRA™ (valdecoxib), and VIOXX™ (rofecoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. In one embodiment, the MMP inhibitor is one that does not demonstrate arthralgia. In another embodiment, the MMP inhibitor selectively inhibits MMP-2 and/or MMP-9 relative to other matrix-metalloproteinases (i.e., MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, RS 13-0830, and the compounds recited in the following list: 3-[[4-(4-fluoro-phenoxy)-benzene-sulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfon-yl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-icyclo[3.2.1]octane-3-carboxylic acid hydroxyamide; 3-endo-3-[4-(4-fluoro-phenoxy)-benzenesulfonylamino]-8-oxa-icyclo [3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts, solvates, derivatives, and other preparations of the compounds.

Sporadic mutations that inactivate the PETN gene product occur relatively frequently in most human cancers (Yamada et al., 2001, J Cell Sci 114:2375-82, Hill et al., 2002, Pharmacol Therapeut 93:243-51). Loss of PTEN causes the Akt phosphorylated state to persist through loss of the ability to downregulate stimulatory signals originating from IGF-1R and other sources. The status of the p53 tumor suppressor also influences the activity of the IGF-1R signaling system. In the ground state, the basal or constitutive transcription of IGF-1R is repressed by p53 via an indirect mechanism. Activation of Akt promotes the phosphorylation of mdm2, which then binds the p53 tumor suppressor and promotes its degradation (Mayo et al., 2002, TIBS 27:462-67), resulting in increased IGF-1R expression. A similar outcome is observed when p53 is inactivated by mutation. When transiently expressed in Saos-2 (a human osteosarcoma cell line) and RD (a rhabdomyosarcoma cell line), wild-type p53 is able to suppress the activity of a cotransfected IGF-1R promoter construct, whereas tumor-derived, mutant versions of p53 have no effect. It has been proposed that the increased level of IGF-1R promotes the resistance to apoptosis associated with p53 loss in malignant cells (Werner et al., 2000, Cell Mol Life Sci 57:93242). Thus, in one embodiment, the present invention provides a method of treating a cancerous condition in a subject in need of such treatment comprising administering to the subject an effective amount of an IGF-1R antagonist as described herein, wherein the cancerous condition is characterized by cells that have a reduced expression or activity of p53.

The WT1 (Wilms kidney tumor suppressor 1 protein) also has been shown to bind and repress the IGF-1R promoter. Thus, in one embodiment, the present invention provides a method of treating a cancerous condition in a subject in need of such treatment comprising administering to the subject an effective amount of an IGF-1R antagonist as described herein wherein the cancerous condition is characterized by a reduced expression or activity of WT1.

The proliferation of normal fibroblasts has been shown to require, under defined culture conditions, the combined action of IGF and a stromal growth factor (e.g. PDGF, EGF) to ramp-up Ras/Raf/Map Kinase and promote cell cycle entry (the G0 to G1 transition). Fibroblasts derived from IGF-1R (−/−) mice do not respond to growth factor alone, or most oncogenes (e.g. oncogenic Ras) that activate the Ras/Raf/Map Kinase pathway. Thus, in one embodiment, the present invention provides a method of treating a subject in need of such treatment comprising administering to the subject an IGF-1R antagonist as described herein and an agent that targets a growth factor and/or a growth factor receptor, such as a growth factor receptor tyrosine kinase, e.g., the EGFR, HER-2, bcr-abl, VEGFR, Kit, raf, mTOR, CDK1/2, VEGFR2, PKCp, Mek, and/or KDR. Examples of molecules that target such growth factors and/or receptors include panitumumab (Abgenix, Fremont, Calif./Amgen, Thousand Oaks, Calif.), HERCEPTIN™ (Genentech, South San Francisco, Calif.), GLEEVEC™ (Novartis, East Hanover, N.J.), IRESSA™ (AstraZeneca, Wilmington, Del.), ERBITUX™, (ImClone, New York, N.Y.), AVASTIN™, (Genentech), PTK787 (Novartis), SU11248 (Pfizer, New York, N.Y.), TARCEVA™ (OSI Pharmaceuticals, Melville, N.Y.), 43-9006 (Bayer, West Haven, Conn.), CCI-779 (Wyeth, Madison, N.J.), RAD001 (Novartis), BMS-387032 (Bristol-Myers Squibb, New York, N.Y.), IMC-1C11 (ImClone), LY333531 (Eli Lilly, Indianapolis, Ind.), PD 184352 (Pfizer), 2C4 (Genentech), and GW2016 (GlaxoSmithKline, Research Triangle Park, N.C.).

The role of IGF-1R in hematological malignancies has been reviewed by (Novak et al., 2003, *Insulin-Like Growth Factors and Hematological Malignancies* in Insulin-Like Growth Factors, LeRoith et al., ed.s, Landes Bioscience). A functional role for the IGF-1R in hematopoietic malignancies is demonstrated by, for example, the ability of IGF-1R monoclonal antibodies to block transformed cell growth in culture. IGF-1 has been found to enhance growth of freshly isolated human acute myelogenous leukemia and acute lymphoblastic leukemia blasts. With respect to T cell malignancies, IGF-1 has been shown to influence the growth of murine lymphoma cells bearing a pre-T cell phenotype and, immature and mature primary human T lineage acute lymphoblastic leukemia cells were found to express high numbers of IGF-1R. Thus, in one embodiment, the present invention provides methods of treating a hematological malignancy in a subject in need thereof comprising administering to the subject an antagonist of IGF-1R as described herein. In another embodiment, the malignancy is an acute myelogenous leukemia, an acute lymphoblastic leukemia, or a T cell malignancy.

In another aspect, the present invention provides methods of identifying subjects who are more likely to benefit from treatment using the compositions and/or methods of treatment of the present invention. Such methods can enable a caregiver to better tailor a therapeutic regimen to a particular subject's needs and reduce the likelihood of an ineffective or counterproductive course of treatment. In one embodiment, the present invention provides a method of determining whether a subject is a candidate for treatment using a composition or method as described herein comprising determining whether a target cell type in the subject expresses IGF-1R, wherein if the target cell type expresses IGF-1R, then the subject is a candidate for treatment. In another embodiment, the method comprises determining the approximate average number of IGF-1R molecules per target cell, wherein $10^2$, $10^3$, $10^4$, $10^5$, or $10^6$ IGF-1R per cell indicates that the subject is a candidate for treatment. The approximate average number of IGF-1R molecules per target cell can be determined using any technique known in the art, for example, by staining a sample comprising cells of the target cell type with an IGF-1R binding molecule, and detecting the amount of IGF-1R binding molecule bound to the sample, where the amount of IGF-1R binding molecule detected is proportional to the average number of IGF-1R molecules in the sample. In another embodiment, the method comprises comparing the approximate average number of IGF-1R molecules per target cell to a reference standard, wherein if the approximate average number of IGF-1R molecules per target cell is greater than the reference standard, then the subject is more likely to benefit from treatment using the compositions and/or methods of treatment of the present invention. In another embodiment, the target cell type is a cancerous cell type. In another embodiment, the target cell type is a colon cancer cell type, a breast cancer cell type, an NSCLC cell type, or a leukemic cell type.

In another embodiment, a subject who is a candidate for treatment is identified by detecting IGF-1 and/or IGF-2 in the target cell type, or in the stratum of the target cell type. In another embodiment, the target cell type is a cancerous cell type. In another embodiment, the target cell type is a colon cancer cell type, a breast cancer cell type, an NSCLC cell type, or a leukemic cell type.

In another embodiment, a subject who is a candidate for treatment is identified by detecting activity of IGF-1R-mediated signaling in the target cell type, wherein IGF-1R-mediated signaling in the target cell type indicates that the subject is a candidate for treatment. Examples of molecules that can be monitored for IGF-1R-dependent changes are shown in FIG. 10, such as molecules in the PI3/Akt pathway, e.g., IGF-1R, IRS adapters, Akt, etc. Such molecules can be monitored for, for example, a change in phosphorylation status, e.g., an increase in phosphorylation. Phosphospecific antibodies that recognize the activated forms of these protein markers are highly developed, and these reagents have proven to be reliable for immunoblot detection in experimental systems.

The compositions and/or methods of the present invention also can be used, for example, in cosmetic treatments, in veterinary treatments, to increase longevity, to treat reproductive defects, and to treat a variety of growth related disorders.

Therapeutic Methods and Administration of Antigen Binding Proteins

Certain methods provided herein comprise administering an IGF-1R binding antigen binding protein to a subject, thereby reducing an IGF-1-induced biological response that plays a role in a particular condition. In particular embodiments, methods of the invention involve contacting endogenous IGF-1R with an IGF-1R binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an IGF-1R antagonist in an amount and for a time sufficient to induce a sustained improvement over baseline of an indicator that reflects the severity of the particular disorder.

As is understood in the pertinent field, pharmaceutical compositions comprising the molecules of the invention are administered to a subject in a manner appropriate to the indication. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds IGF-1R ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second IGF-1 receptor-inhibiting substance, an anti-angiogenic substance, a chemotherapeutic substance, an analgesic substance, etc., non-exclusive examples of which are provided herein. In various particular embodiments, the composition comprises one, two, three, four, five, or six physiologically active agents in addition to an IGF-1R binding antigen binding protein In one embodiment, the pharmaceutical composition comprise an antigen binding protein of the invention together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, $16^{th}$ Ed. (1980) and $20^{th}$ Ed. (2000), Mack Publishing Company, Easton, Pa.

Kits for use by medical practitioners include an IGF-1 receptor-inhibiting substance of the invention and a label or other instructions for use in treating any of the conditions discussed herein. In one embodiment, the kit includes a sterile preparation of one or more IGF-1R binding antigen binding proteins, which may be in the form of a composition as disclosed above, and may be in one or more vials.

Dosages and the frequency of administration may vary according to such factors as the route of administration, the particular antigen binding proteins employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

An IGF-1 receptor inhibiting substance of the invention may be administered, for example, once or more than once, e.g., at regular intervals over a period of time. In particular embodiments, an antigen binding protein is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antigen binding protein is administered until the patient manifests a medically relevant degree of improvement over baseline for the chosen indicator or indicators.

Particular embodiments of the present invention involve administering an antigen binding protein at a dosage of from about 1 ng of antigen binding protein per kg of subject's weight per day ("1 ng/kg/day") to about 10 mg/kg/day, more preferably from about 500 ng/kg/day to about 5 mg/kg/day, and most preferably from about 5 µg/kg/day to about 2 mg/kg/day, to a subject. In additional embodiments, an antigen binding protein is administered to adults one time per week, two times per week, or three or more times per week, to treat an IGF-1 and/or IGF-2 mediated disease, condition or disorder, e.g., a medical disorder disclosed herein. If injected, the effective amount of antigen binding protein per adult dose may range from 1-20 $mg/m^2$, and preferably is about 5-12 $mg/m^2$. Alternatively, a flat dose may be administered; the amount may range from 5-100 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of antigen binding protein to one to three times per week over a period of at least three weeks, though treatment for longer periods may be necessary to induce the desired degree of improvement. For pediatric subjects (age 4-17), one exemplary suitable regimen involves the subcutaneous injection of 0.4 mg/kg, up to a maximum dose of 25 mg of antigen binding protein administered two or three times per week.

Particular embodiments of the methods provided herein involve subcutaneous injection of from 0.5 mg to 10 mg, preferably from 3 to 5 mg, of an antigen binding protein, once or twice per week. Another embodiment is directed to pulmonary administration (e.g., by nebulizer) of 3 or more mg of antigen binding protein once a week.

Examples of therapeutic regimens provided herein comprise subcutaneous injection of an antigen binding protein once a week, at a dose of 1.5 to 3 mg, to treat a condition in which IGF-1R signaling plays a role. Examples of such conditions are provided herein and include, for example, cancer, acromegaly and other overgrowth disorders, diabetes, obesity, macular degeneration, and aging. Weekly administration of antigen binding protein is continued until a desired result is achieved, e.g., the subject's symptoms subside. Treatment may resume as needed, or, alternatively, maintenance doses may be administered.

Other examples of therapeutic regimens provided herein comprise subcutaneous or intravenous administration of a dose of 1, 3, 5, 6, 7, 8, 9, 10, 11, 12, 15, or 20 milligrams of an IGF-1R inhibitor of the present invention per kilogram body mass of the subject (mg/kg). The dose can be administered once to the subject, or more than once at a certain interval, for example, once a day, three times a week, twice a week, once a week, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

In another embodiment, an antigen binding protein is administered to the subject in an amount and for a time sufficient to induce an improvement; preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionnaires that are administered to the subject, such as quality-of-life questionnaires developed for a given disease.

Elevated levels of IGF-1 and/or IGF-2 are associated with a number of disorders, including, for example, cancer (e.g., lung, prostate, breast and colon cancers), and acromegaly and other overgrowth disorders (e.g., constitutionally tall children). Subjects with a given disorder may be screened, to identify those individuals who have elevated IGF-1 and/or IGF-2 levels, thereby identifying the subjects who may benefit most from treatment with an IGF-1R binding antigen binding protein. Thus, treatment methods provided herein optionally comprise a first step of measuring a subject's IGF-1 and/or IGF-2 levels. An antigen binding protein may be administered to a subject in whom IGF-1 and/or IGF-2 levels are elevated above normal. In one embodiment, the present invention provides a method of treating an overgrowth disorder (e.g., acromegaly) comprising administering to a subject in need thereof an antigen binding protein of the present invention and pegvisomant.

A subject's levels of IGF-1 and/or IGF-2 may be monitored before, during and/or after treatment with an antigen binding protein, to detect changes, if any, in their levels. For some disorders, the incidence of elevated IGF-1 and/or IGF-2 levels may vary according to such factors as the stage of the disease or the particular form of the disease. Known techniques may be employed for measuring IGF-1 and/or IGF-2 levels, e.g., in a subject's serum. IGF-1 and/or IGF-2 levels in blood samples may be measured using any suitable technique, for example, ELISA.

Particular embodiments of methods and compositions of the invention involve the use of an antigen binding protein and one or more additional IGF-1R antagonists, for example, two or more antigen binding proteins of the invention, or an antigen binding protein of the invention and one or more other IGF-1R antagonists. In further embodiments, antigen binding protein are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antigen binding protein is administered at least once during a course of treatment that involves administering at least one other therapeutic agent to the patient.

Examples of other agents that may be co-administered with an antigen binding protein are other antigen binding proteins or therapeutic polypeptides that are chosen according to the particular condition to be treated. Alternatively, non-proteinaceous drugs that are useful in treating one of the particular conditions discussed above may be co-administered with an IGF-1R antagonist.

Combination Therapy

In another aspect, the present invention provides a method of treating a subject with an IGF-1R inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue (e.g., within a tumor). For example, an IGF-1R inhibitor of the present invention can be combined with a treatment that inhibits IGF-1, promotes apoptosis, inhibits angiogenesis, or inhibits macrophage. In another embodiment, a targeted agent, that, when used by itself, fails to elicit a therapeutically desired effect, could be used to, for example, sensitize cancer cells or augment treatment effect of other agents. In another embodiment, an IGF-1R inhibitor according to the invention is used in combination with a cytotoxic drug or other targeted agent that induces apoptosis. In another embodiment, an IGF-1R inhibitor is used in combination with one or more agents that inhibit different targets that are involved in cell survival (e.g., PKB, mTOR), different receptor tyrosine kinases (e.g., ErbB1, ErbB2, c-Met, c-kit), or different cell types (e.g., KDR inhibitors, c-fms). In another embodiment, an IGF-1R inhibitor of the invention is added to the existing standard of care for a particular condition. Examples of therapeutic agents include, but are not limited to, gemcitabine, taxol, taxotere, and CPT-11.

In another embodiment, a combination therapy method comprises administering to the subject two, three, four, five, six, or more of the IGF-1R agonists or antagonists described herein. In another embodiment, the method comprises administering to the subject two or more treatments that together inhibit or activate (directly or indirectly) IGF-1R-mediated signal transduction. Examples of such methods include using combinations of two or more IGF-1R inhibiting antigen binding proteins, of an IGF-1R inhibiting antigen binding protein and one or more other IGF-1, IGF-2, and/or IGF-1R agonists or antagonists (e.g., IGF-1 and/or IGF-2 binding polypeptides, IGF-1R binding polypeptides, IGF-1 and/or IGF-2 derivatives, anti-IGF-1 and/or IGF-2 antibodies, anti-sense nucleic acids against IGF-1, IGF-2, and/or IGF-1R, or other molecules that bind to IGF-1, IGF-2, and/or IGF-1R polypeptides or nucleic acids), or of an IGF-1R inhibiting antigen binding protein and one or more other treatments (e.g., surgery, ultrasound, radiotherapy, chemotherapy, or treatment with another anti-cancer agent), as described, for example, in U.S. Pat. Nos. 5,473,054 (issued Dec. 5, 1995), 6,051,593 (issued Apr. 18, 2000), 6,084,085 (issued Jul. 4, 2000), 6,506,763 (issued Jan. 14, 2003), US Pat. App. Pub. Nos. 03/0092631 (published May 15, 2003), 03/0165502 (published Sep. 4, 2003), 03/0235582 (published Dec. 25, 2003), 04/0886503 (published May 6, 2004), 05/0272637 (published Dec. 8, 2005), PCT Pub. Ser. Nos. WO 99/60023 (published Nov. 25, 1999), WO 02/053596 (published Jul. 11, 2002), WO 02/072780 (published Sep. 19, 2002), WO 03/027246 (published Mar. 3, 2003), WO 03/020698 (published Mar. 13, 2003), WO 03/059951 (published Jul. 24, 2003), WO 03/100008 (published Dec. 4, 2003), WO 03/106621 (published Dec. 24, 2003), WO 04/071529 (published Aug. 26, 2004), WO 04/083248 (published Sep. 30, 2004), WO 04/087756 (published Oct. 14, 2004), WO 05/112969 (published Dec. 1, 2005), Kull et al., 1983, J Biol Chem 258:6561-66, Flier et al., 1986, Proc Natl Acad Sci USA 83:664-668, Conover et al., 1987, J Cell Physiol 133:

560-66, Rohlik et al., 1987, Biochem Biophys Res Comm 149:276-81, Arteaga et al., 1989, J Clinical Investigation 84:1418-23, Arteaga et al., 1989, Cancer Res 49:623741, Gansler et al., 1989, American J Pathol 135:961-66, Gustafson et al., 1990, J Biol Chem 265:18663-67, Steele-Perkins et al., 1990, Biochem Biophys Res Comm 171:1244-51, Cullen et al, 1992, Mol Endocrinol 6:91-100, Soos et al., 1992, J Biol Chem 267:12955-63, Xiong et al., 1992, Proc Natl Acad Sci USA 89:5356-60, Brunner et al., 1993, Euro J Cancer 29A:562-69, Furlanetto et al., 1993, Cancer Res 53:2522-26, Li et al., 1993, Biochem Biophys Res Comm 196:92-98, Kalebic et al., 1994, Cancer Res 54:5531-34, Lahm et al., 1994, Intl J Cancer 58:452-59, Zia et al., 1996, J Cell Biochem Supp 24:269-75, Jansson et al., 1997, J Biol Chem 272:8189-97, Scotlandi et al., 1998, Cancer Res 58:4127-31, Logie et al., 1999, Li et al., 2000, Cancer Immunol Immunotherapy 49:243-52, J Mol Endocrinol 23:23-32, De Meyts et al., 2002, Nature Reviews 1:769-83, Hailey et al., 2002, Mol Cancer Therapeutics 1: 1349-53, Maloney et al., 2003, Cancer Research 63:5073-83, Burtrum et al., 2003, Cancer Research 63:8912-21, and Karavitaki et al., 2004, Hormones 3:27-36, (each incorporated herein by reference in its entirety) may be employed in methods and compositions of the present invention. Furthermore, one or more anti-IGF-1R antibodies or antibody derivatives can be used in combination with one or more molecules or other treatments, wherein the other molecule(s) and/or treatment(s) do not directly bind to or affect IGF-1R, IGF-1, or IGF-2, but which combination is effective for treating or preventing a condition, such as cancer or an overgrowth disorder (e.g., acromegaly). In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the IGF-1R antagonists described herein and one or more other treatments (e.g., a therapeutic or palliative treatment), for example, anti-cancer treatments (such as surgery, ultrasound, radiotherapy, chemotherapy, or treatment with another anti-cancer agent). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen. Examples of agents that can be administered in combination with the IGF-1R antagonists described herein include, but are not limited to, neutrophil-boosting agents, irinothecan, SN-38, gemcitabine, herstatin, or an IGF-1R-binding herstatin derivative (as described, for example, in US Pat. App. No. 05/0272637), AVASTIN® (Genentech, South San Francisco, Calif.), HERCEPTIN® (Genentech), RITUXAN® (Genentech), ARIMIDEX® (AstraZeneca, Wilmington, Del.), IRESSA® (AstraZeneca), BEXXAR® (Corixa, Seattle, Wash.), ZEVALIN® (Biogen Idec, Cambridge, Mass.), ERBITUX® (Imclone Systems Inc., New York, N.Y.), GEMZAR® (Eli Lilly and Co., Indianapolis, Ind.), CAMPTOSAR® (Pfizer, New York, N.Y.), GLEEVEC® (Novartis), SU-11248 (Pfizer), BMS-354825 (Bristol-Myers Squibb), panitumumab (Abgenix, Fremont, Calif./Amgen Inc., Thousand Oaks, Calif.), and denosumab (Amgen Inc., Thousand Oaks, Calif.).

The following examples, both actual and prophetic, are provided for the purpose of illustrating specific embodiments or features of the instant invention and do not limit its scope.

EXAMPLE 1

Preparation of Antibodies

This example demonstrates a method of preparing antibodies recognizing the IGF-1 receptor. IGF-1 receptor polypeptides may be employed as immunogens in generating monoclonal antibodies by conventional techniques. It is recognized that polypeptides in various forms may be employed as immunogens, e.g., full length proteins, fragments thereof, fusion proteins thereof such as Fc fusions, cells expressing the recombinant protein on the cell surface, etc.

To summarize an example of such a procedure, an IGF-1R immunogen emulsified in complete Freund's adjuvant is injected subcutaneously into Lewis rats, in amounts ranging from 10-100 µl. Three weeks later, the immunized animals are boosted with additional immunogen emulsified in incomplete Freund's adjuvant and boosted every three weeks thereafter. Serum samples are periodically taken by retro-orbital bleeding or tail-tip excision for testing by dot-blot assay, ELISA (enzyme-linked immunosorbent assay), or inhibition of binding of $^{125}$I-IGF-1 or $^{125}$I-IGF-2 to extracts of IGF-1R-expressing cells. Following detection of an appropriate antibody titer, positive animals are given a final intravenous injection of antigen in saline. Three to four days later, the animals are sacrificed, splenocytes harvested, and fused to the murine myeloma cell line AG8653. The resulting hybridoma cell lines are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated are screened for reactivity with IGF-1R. Initial screening of hybridoma supernatants utilizes an antibody capture and binding of partially purified $^{125}$I-IGF-1 receptor. Hybridomas that are positive in this screening method are tested by a modified antibody capture to detect hybridoma cells lines that are producing blocking antibody. Hybridomas that secrete a monoclonal antibody capable of inhibiting $^{125}$I-IGF-1 binding to cells expressing IGF-1R are thus detected. Such hybridomas then are injected into the peritoneal cavities of nude mice to produce ascites containing high concentrations (>1 mg/ml) of anti-IGF-1R monoclonal antibody. The resulting monoclonal antibodies may be purified by ammonium sulfate precipitation followed by gel exclusion chromatography, and/or affinity chromatography based on binding of antibody to Protein G.

Similar methods can be used to generate human antibodies in transgenic mice. See, e.g., Chen et al., 1993, Internat. Immunol. 5: 647-56; Chen et al., 1993, EMBO J. 12: 821-30; Choi et al., 1993, Nature Genetics 4: 117-23; Fishwild et al., 1996, Nature Biotech. 14: 845-51; Harding et al., 1995, Annals New York Acad. Sci.; Lonberg et al., 1994, Nature 368: 856-59; Lonberg, 1994, Handbook Exper.1 Pharmacol. 113: 49-101; Lonberg et al., 1995, Internal Rev. Immunol. 13:

65-93; Morrison, 1994, Nature 368: 812-13; Neuberger, 1996, Nature Biotech. 14: 826; Taylor et al., 1992, Nuc. Acids Res. 20: 6287-95; Taylor et al., 1994, Internat. Immunol. 6: 579-91; Tomizuka et al., 1997, Nature Genetics 16: 133-43; Tomizuka et al., 2000, Proc. Nat. Acad. Sci. USA 97: 722-27; Tuaillon et al., 1993, Proc. Nat. Acad. Sci. USA 90: 3720-24; Tuaillon et al., 1994, J. Immunol. 152: 2912-20; Russel et al., 2000, Infection and Immunity April 2000: 1820-26; Gallo et al., 2000, Eur. J. Immunol. 30: 534-40; Davis et al., 1999, Cancer Metastasis Rev. 18:421-25; Green, 1999, J. Immunol. Methods 231:11-23; Jakobovits, 1998, Advanced Drug Delivery Rev. 31:33-42; Green et al., 1998, J. Exp. Med. 188: 483-95; Jakobovits, 1998, Exp. Opin. Invest. Drugs 7: 607-14; Tsuda et al., 1997, Genomics 42: 413-21; Mendez et al., 1997, Nature Genetics 15: 146-56; Jakobovits, 1996, Weir's Handbook of Experimental Immunology, The Integrated Immune System Vol. IV, 194.1-194.7; Mendez et al., 1995, Genomics 26: 294-307; Jakobovits, 1994, Current Biol. 4: 761-63; Arbones, 1994, Immunity 1: 247-60; Green et al., 1994, Nature Genetics 7: 13-21; Jakobovits et al., 1993, Nature 362: 255-58; Jakobovits et al., 1993, Proc. Nat. Acad. Sci. USA 90: 2551-55.

EXAMPLE 2

Isolation of Human IGF-1R(ECD)-C3-muIgG1

This example provides a method of making a soluble fragment of IGF-1R useful for raising antibodies.

Cloning of pDSRα:huIGF-1R(ECD)-C3-muIgG1Fc

```
Primers 2830-36:
                                       SEQ ID NO: 256)
5' AGCAAGCTTCCACCATGAAGTCTGGCTCCGGAGGAGG 3'
and 2830-38:
                                       SEQ ID NO: 257)
5' ATTTGTCGACTTCGTCCAGATGGATGAAGTTTTCAT 3',
``` were used to amplify the human IGF-1R extracellular domain (1-906) cDNA sequence. The primers included a Kozak translation initiation sequence (underlined above) preceding the start codon, restriction sites for subsequent subcloning, and a caspase-3 site, which is inserted next to the extracellular domain C-terminus. PCR was performed on a PerkinElmer 2400 (PerkinElmer, Torrance, Calif.) under the following conditions: 1 cycle at 95° C. for 2 min, 23 cycles at 95° C. for 30 sec, 58.5° C. for 30 sec, and 72° C. for 3 min, and 1 cycle at 72° C. for 10 min. Final reaction conditions were 1×pfu TURBO® buffer (Stratagene, La Jolla, Calif.), 200 μM dNTPs, 2 μM each primer, 5 U pfu TURBO® (Stratagene) and 1 ng template DNA. The PCR product was purified using a Clontech Nucleospin Column (Clontech, Palo Alto, Calif.) according to the manufacturers instructions, digested with Hind III and Sal I (Roche, Indianapolis, Ind.) and gel purified. The human IGF-1R insert was ligated into Hind III/Sal I digested pDSRα-muIgG1. Integrity of the insert was confirmed by DNA sequencing. The sequence of the protein encoded by the resulting open reading frame (IGF-1R-C3-muFc) is shown in FIG. 10. The final expression vector, pDSRα:huIGF1R(ECD)-C3-muIgG1 Fc, is described in Table 1.

TABLE 1

| pDSRα: huIGF1R(ECD)-C3-muIgG1Fc Plasmid Base Pair Number: | |
|---|---|
| 11-3496 | HuIGF1R (Caspase 3 site)-muIgG1Fc |
| | atgaagtctggctccggaggagggtccccgacctcgc |
| | tgtgggggctcctgtttctctccgccgcgctctcgct |
| | ctggccgacgagtggagaaatctgcgggccaggcatc |
| | gacatccgcaacgactatcagcagctgaagcgcctgg |
| | agaactgcacggtgatcgagggctacctccacatcct |
| | gctcatctccaaggccgaggactaccgcagctaccgc |
| | ttccccaagctcacggtcattaccgagtacttgctgc |
| | tgttccgagtggctggcctcgagagcctcggagacct |
| | cttccccaacctcacggtcatccgcggctggaaactc |
| | ttctacaactacgccctggtcatcttcgagatgacca |
| | atctcaaggatattgggctttacaacctgaggaacat |
| | tactcgggggccatcaggattgagaaaaatgctgac |
| | ctctgttacctctccactgtggactggtccctgatcc |
| | tggatgcggtgtccaataactacattgtggggaataa |
| | gccccaaaggaatgtggggacctgtgtccagggacc |
| | atggaggagaagccgatgtgtgagaagaccaccatca |
| | acaatgagtacaactaccgctgctggaccacaaaccg |
| | ctgccagaaaatgtgcccaagcacgtgtgggaagcgg |
| | gcgtgcaccgagaacaatgagtgctgccaccccgagt |
| | gcctgggcagctgcagcgcgcctgacaacgacacggc |
| | ctgtgtagcttgccgccactactactatgccggtgtc |
| | tgtgtgcctgcctgcccgcccaacacctacaggtttg |
| | agggctggcgctgtgtggaccgtgacttctgcgccaa |
| | catcctcagcgccgagagcagcgactccgaggggttt |
| | gtgatccacgacggcgagtgcatgcaggagtgcccct |
| | cgggcttcatccgcaacggcagccagagcatgtactg |
| | catcccttgtgaaggtcctttgcccgaaggtctgtgag |
| | gaagaaaagaaaacaaagaccattgattctgttactt |
| | ctgctcagatgctccaaggatgcaccatcttcaaggg |
| | caatttgctcattaacatccgacggggaataacatt |
| | gcttcagagctggagaacttcatggggctcatcgagg |
| | tggtgacggctacgtgaagatccgccattctcatgc |
| | cttggtctccttgtccttcctaaaaaaccttcgcctc |
| | atcctaggagaggagcagctagaagggaattactcct |
| | tctacgtcctcgacaaccagaacttgcagcaactgtg |
| | ggactgggaccaccgcaacctgaccatcaaagcaggg |
| | aaaatgtactttgctttcaatcccaaattatgtgttt |
| | ccgaaatttaccgcatggaggaagtgacggggactaa |
| | agggcgccaaagcaaaggggacataaacaccaggaac |
| | aacggggagagagcctcctgtgaaagtgacgtcctgc |
| | atttcacctccaccaccacgtcgaagaatcgcatcat |
| | cataacctggcaccggtaccggccccctgactacagg |
| | gatctcatcagcttcaccgttttactacaaggaagcac |
| | cctttaagaatgtcacagagtatgatgggcaggatgc |
| | ctgcggctccaacagctggaacatggtggacgtggac |
| | ctcccgcccaacaaggacgtggagcccggcatcttac |
| | tacatgggctgaagccctggactcagtacgccgttta |
| | cgtcaaggctgtgaccctcaccatggtggagaacgac |
| | catatccgtggggccaagagtgagatcttgtacattc |
| | gcaccaatgcttcagttccttccattcccttggacgt |
| | tctttcagcatcgaactcctcttctcagttaatcgtg |
| | aagtggaaccctccctctctgcccaacggcaacctga |
| | gttactacattgtgcgctggcagcggcagcctcagga |
| | cggctacctttaccggcacaattactgctccaaagac |
| | aaaatccccatcaggaagtatgccgacggcaccatcg |
| | acattgaggaggtcacagagaaccccaagactgaggt |
| | gtgtgggtggggagaaagggccttgctgcgcctgcccc |
| | aaaactgaagccgagaagcaggccgagaaggaggagg |
| | ctgaataccgcaaagtctttgagaatttcctgcacaa |
| | ctccatcttcgtgcccagacctgaaaggaagcggaga |
| | gatgtcatgcaagtggccaacaccaccatgtccagcc |
| | gaagcaggaacaccacggccgcagacacctacaacat |
| | cactgacccgaagagctggagacagagtaccccttc |
| | tttgagagcagagtggataacaaggagagaactgtca |
| | tttctaaccttcggccttcacattgtaccgcatcga |
| | tatccacagctgcaaccacgaggctgagaagctgggc |
| | tgcagcgcctccaacttcgtctttgcaaggactatgc |
| | ccgcagaaggagcagatgacattcctgggccagtgac |
| | ctgggagccaaggcctgaaaactccatcttttaaag |
| | tggccggaacctgagaatcccaatggattgattctaa |
| | tgtatgaaataaaatacggatcacaagttgaggatca |
| | gcgagaatgtgtgtccagacaggaatacaggaagtat |
| | ggaggggccaagctaaaccggctaaaccggggaact |
| | acacagcccggattcaggccacatctctctctgggaa |

TABLE 1-continued pDSRα: huIGF1R(ECD)-C3-muIgG1Fc Plasmid Base Pair Number:

|  |  |
|---|---|
|  | tgggtcgtggacagatcctgtgttcttctatgtccag<br>gccaaaacaggatatgaaaacttcatccatctggacg<br>aagtcgacggttgtaagccttgcatatgtacagtccc<br>agaagtatcatctgtcttcatcttcccccccaaagccc<br>aaggatgtgctcaccattactctgactcctaaggtca<br>cgtgtgttgtggtagacatcagcaaggatgatcccga<br>ggtccagttcagctggtttgtagatgatgtggaggtg<br>cacacagctcagacgcaaccccgggaggagcagttca<br>acagcactttccgctcagtcagtgaacttcccatcat<br>gcaccaggactggctcaatggcaaggagttcaaatgc<br>agggtaaacagtgcagctttccctgcccccatcgaga<br>aaaccatctccaaaaccaaaggcagaccgaaggctcc<br>acaggtgtacaccattccacctcccaaggagcagatg<br>gccaaggataaagtcagtctgacctgcatgataacag<br>acttcttccctgaagacattactgtggagtggcagtg<br>gaatgggcagccagcggagaactacaagaacactcag<br>cccatcatggacacagatggctcttacttcgtctaca<br>gcaagctcaatgtgcagaagagcaactgggaggcagg<br>aaatactttcacctgctctgtgttacatgagggcctg<br>cacaaccaccatactgagaagagcctctcccactctc<br>ctggtaaa (SEQ ID NO: 258) |
| 3507 to 4391 | A transcription termination/poly-adenylation signal from the α-subunit of the bovine pituitary glycoprotein hormone (α-FSH) (Goodwin et at., 1983, Nucleic Acids Res. 11: 6873-82; Genbank Accession Number X00004) |
| 4600 to 5163 | A mouse dihydrofolate reductase (DHFR) minigene containing the endogenous mouse DHFR promoter, the cDNA coding sequences, and the DHFR transcription termination/polyadenylation signals (Gasser et at., 1982, Proc. Natl. Acad. Sci. U.S.A. 79: 6522-6; Nunberg et at., 1980 Cell 19: 355-64; Setzer et al., 1982, J. Biol. Chem. 257: 5143-7; McGrogan et al., 1985, J. Biol. Chem. 260: 2307-14) |
| 6389 to 7246 | pBR322 sequences containing the ampicillin resistance marker gene and the origin for replication of the plasmid in E. coli (Genbank Accession Number J01749) |
| 7459 to 7802 | An SV40 early promoter, enhancer and origin of replication (Takebe et al., 1988, Mol. Cell Biol. 8: 466-72; Genbank Accession Number J02400) |
| 7809 to 8065 | A translational enhancer element from the HTLV-1 LTR domain (Seiki et al., 1983, Proc. Natl. Acad. Sci. U.S.A. 80: 3618-22, Genbank Accession Number J02029) |
| 8109 to 8205 | An intron from the SV40 16S, 19S splice donor/acceptor signals (Okayama and Berg, 1983. Mol. Cell Biol. 3: 280-9, Genbank Accession Number J02400) |

Expression of hu IGF-1R(ECD)-C3-muIgG1Fc

Fifteen micrograms of linearized expression vector pDSRα:huIGF1R(ECD)-C3-muIgG1Fc was transfected into AM-1/D CHOd-cells using LT1 lipofection reagent (PanVera Corp., Madison, Wis.), and cells cultured under conditions to allow expression and secretion of protein into the cell media. Twenty-four colonies were selected after 10-14 days on DHFR selection medium (Dulbecco's Modified Eagles Medium (Invitrogen) supplemented with 10% dialyzed fetal bovine serum, 1× penicillin-streptomycin (Invitrogen)) and expression levels evaluated by western blot. To perform this assay, 0.5 ml of serum free medium was added to a single well confluent cells cultured in a 24 well plate (Falcon). The conditioned medium was recovered after 48 hr. Samples for western blotting were run in 10% Tris-glycine gel (Novex), and blotted on 0.45 μm Nitrocellulose membrane (Invitrogen), using the Mini Trans-Blot cell (Biorad). The blotted membranes were incubated with rabbit anti-mouse IgG Fc antibody, conjugated with Horseradish Peroxidase (Pierce). The clone expressing the highest level of IGF-1R(ECD)-C3-muIgG1Fc was expanded in DHFR selection medium and $2 \times 10^7$ cells were inoculated into 50 roller bottles each (Corning) in 250 ml of high-glucose DMEM (Invitrogen), 10% dialyzed FBS (Invitrogen), 1× glutamine (Invitrogen), 1× Non essential amino acids (Invitrogen), 1× sodium pyruvate (Invitrogen). Medium was gassed with 10% $CO_2$/balance air for 5 seconds before capping the roller bottle. Roller bottles were kept at 37° C. on roller racks spinning at 0.75 rpm.

When cells reached approximately 85-90% confluency (after approximately 5-6 days in culture), growth medium was discarded, cells washed with 100 ml PBS and 200 ml production medium was added (50% DMEM (Invitrogen)/50% F12 (Invitrogen), 1× glutamine (Invitrogen), 1× non-essential amino acids (Invitrogen), 1× sodium pyruvate (Invitrogen), 1.5% DMSO (Sigma)). The conditioned medium was harvested and replaced at one week intervals. The resulting 30 liters of conditioned medium were filtered through a 0.45 μm cellulose acetate filter (Corning, Acton, Mass.).

Purification of hu IGF-1R(ECD)-C3-muIgG1Fc

The resulting filtrate from the conditioned medium was concentrated 20-fold using a spiral-wound cartridge (molecular weight cut-off 10 kDa), then diluted 1:1 with 3 M KCl, 1 M glycine, pH 9.0 to bring the final salt concentration to 1.5 M KCl, 0.5 M glycine, pH 9.0. This sample was applied to a rProtein A-Sepharose column (Amersham Pharmacia Biotech, Uppsala, Sweden) which had been equilibrated in 1.5 M KCl, 0.5 M glycine, pH 9.0. The column was washed with 40 column volumes of the same buffer, then eluted with 20 column volumes of 0.1 M glycine-HCl, pH 2.8. Five-mL fractions were collected and immediately neutralized with 1 mL of 1 M Tris-HCl, pH 7.5. Fractions containing huIGF1R(ECD)-C3-muIgGFc were identified by SDS-PAGE, pooled, and dialyzed against phosphate-buffered saline. The yield was 2.4 mg/L of conditioned medium. The major protein species detected were the mature α and β chains and murine Fc, each of which appeared to be properly glycosylated based on their elevated and heterogeneous molecular weights. Unprocessed IGF-1R(ECD), as well as glycosylated but not proteolytically cleaved IGF-1R(CED), was also present in the preparation. The shift in bands to higher molecular weights under non-reducing conditions indicates that disulfide linkages joined the α and β chains. Amino-terminal sequencing of the final product indicated that 60% of the protein was correctly processed between the α- and β-chains of IGF-1R (ECD), while 40% remained unprocessed.

EXAMPLE 3

Isolation of Human INSR(ECD)-muIgG1

This example presents a method of cloning and expressing a soluble fragment of the human insulin receptor.

Cloning of pDSRα:huINSR(ECD)-muIgG1Fc

Primers 2830-40:
SEQ ID NO: 259
5' AGC<u>AAGCTT</u>CCACCATGGGCACCGGGGCCGG 3'

(Hind III site underlined)
and 2830-41:
SEQ ID NO: 260
5' ATTT<u>GTCGAC</u>TTTTGCAATATTTGACGGGACGTCTAA 3'

(Sal I site underlined) were used to amplify the human INSR extracellular domain (1-929) from and INSR parental plasmid encoding the B form of the INSR splice variant (Ullrich et al., 1985, Nature 313:756-61; Ebina et al., 1985, Cell 40:747-58). The primers included a Kozak translation initiation sequence preceding the start codon and restriction sites for subsequent sub-cloning. PCR was performed on a Perkin Elmer 2400 under the following conditions: 1 cycle at 95° C. for 2 min, 32 cycles at 95° C. for 30 sec, 58.5° C. for 30 sec, and 72° C. for 3 min, and 1 cycle at 72° C. for 10 min. Final reaction conditions were 1×pfu TURBO® buffer, 200 μM dNTPs, 2 μM each primer, 5 U pfu TURBO® (Stratagene) and 10 ng template DNA. The PCR product was purified using a NUCLEOSPIN® Column (BD Biosciences Clontech, Palo Alto, Calif.) according to the manufacturer's instructions, digested with Hind III and Sal I (Roche), and gel purified prior to ligation into Hind III/Sal I digested pDSRα-muIgG1. The integrity of the insert was confirmed by DNA sequencing. The protein sequence of the INSR-muFc is shown in FIG. 11. The final expression vector is described in Table 2.

TABLE 2

| Plasmid Base Pair Number: | |
|---|---|
| 11-3550 | HuINSR-muIgG1Fc<br>atgggcaccggggccggcgggggcggcggccgcgc<br>cgctgctggtggcggtggccgcgctgctactgggcgc<br>cgcgggccacctgtaccccggagaggtgtgtccggc<br>atggatatccggaacaacctcactaggttgcatgagc<br>tggagaattgctctgtcatcgaaggacacttgcagat<br>actcttgatgttcaaaacgaggcccgaagatttccga<br>gacctcagtttccccaaactcatcatgatcactgatt<br>actttgctgctcttccgggtctatgggctcgagagcct<br>gaaggacctgttcccaacctcacggtcatccgggga<br>tcacgactgttctttaactacgcgctggtcatcttcg<br>agatggttcacctcaaggaactcggcctctacaacct<br>gatgaacatcacccggggttctgtccgcatcgagaag<br>aacaatgagctctgttacttggccactatcgactggt<br>cccgtatcctggattccgtggaggataatcacatcgt<br>gttgaacaaagatgacaacgaggagtgtggagacatc<br>tgtccgggtaccgcgaagggcaagaccaactgccccg<br>ccaccgtcatcaacgggcagtttgtcgaacgatgttg<br>gactcatagtcactgccagaaagtttgcccgaccatc<br>tgtaagtcacacggctgcaccgccgaaggcctctgtt<br>gccacagcgagtgcctgggcaactgttctcagcccga<br>cgaccccaccaagtgcgtggcctgccgcaacttctac<br>ctggacggcaggtgtgtggagacctgcccgcccccgt<br>actaccacttccaggactggcgctgtgtgaacttcag<br>cttctgccaggacctgcaccacaaatgcaagaactcg<br>cggaggcagggctgccaccagtacgtcattcacaaca<br>acaagtgcatccctgagtgtccctccgggtacacgat<br>gaattccagcaacttgctgtgcacccccatgcctgggt<br>ccctgtcccaaggtgtgccacctcctagaaggcgaga<br>agaccatcgactcggtgacgtctgcccaggagctccg<br>aggatgcaccgtcatcaacgggagtctgatcatcaac<br>attcgaggaggcaacaatctggcagctgagctagaag<br>ccaacctcggcctcattgaagaaatttcagggtatct<br>aaaaatcgccgatcctacgctctggtgtcactttcc<br>ttcttccggaagttacgtctgattcgaggagagacct<br>tggaaattgggaactactccttctatgccttggacaa<br>ccagaacctaaggcagctctgggactggagcaaacac<br>aacctcaccaccactcaggggaaactcttcttccact<br>ataaccccaaactctgcttgtcagaaatccacaagat<br>ggaagaagtttcaggaaccaaggggcgccaggagaga<br>aacgacattgccctgaagaccaatggggacaaggcat<br>cctgtgaaaatgagttacttaaattttcttacattcg<br>gacatctttgacaagatcttgctgagatgggagccg<br>tactggcccccccgacttccgagacctcttggggttca<br>tgctgttctacaaagaggcccctatcagaatgtgac<br>ggagttcgatgggcaggatgcgtgtggttccaacagt<br>tggacggtggtagacattgacccaccccctgaggtcca<br>acgaccccaaatcacagaacccaccccagggtggctgat<br>gcggggtctcaagccctggacccagtatgccatcttt<br>gtgaagacctggtcaccttttcggatgaacgccgga<br>cctatggggccaagagtgacatcatttatgtccagac<br>agatgccaccaaccccctctgtgcccctggatccaatc<br>tcagtgtctaactcatcatcccagattattctgaagt<br>ggaaaccaccctccgaccccaatggcaacatcaccca<br>ctacctggttttctgggagaggcaggcggaagacagt<br>gagctgttcgagctggattattgcctcaaagggctga<br>agctgccctcgaggacctggtctccaccattcgagtc<br>tgaagattctcagaagcacaaccagagtgagtatgag<br>gattcggccggcgaatgctgctcctgtccaaagacag<br>actctcagatcctgaaggagctggaggagttcctcgtt<br>taggaagacgtttgaggattacctgcacaacgtggtt<br>ttcgtccccagaaaaacctcttcaggcactggtgccg<br>aggaccctaggccatctcggaaacgcaggtcccttgg<br>cgatgttgggaatgtgacggtggccgtgcccacggtg<br>gcagctttccccaacacttcctcgaccagcgtgccca<br>cgagtccggaggagcacaggcctttgagaaggtggt<br>gaacaaggagtcgctggtcatctccggcttgcgacac<br>ttcacgggctatcgcatcgagctgcaggcttgcaacc<br>aggacacccctgaggaacggtgcagtgtggcagccta<br>cgtcagtgcgaggaccatgcctgaagccaaggctgat<br>gacattgttggccctgtgacgcatgaaatctttgaga<br>acaacgtcgtccacttgatgtggcaggagccgaagga<br>gcccaatggtctgatcgtgctgtatgaagtgagttat<br>cggcgatatggtgatgaggagctgcatctctgcgtct<br>cccgcaagcacttcgctctggaacggggctgcaggct<br>gcgtgggctgtcaccggggaactacagcgtgcgaatc<br>cgggccacctccccttgcgggcaacggctcttggacgg<br>aacccacctattcctacgtgacagactatttagacgt<br>cccgtcaaatattgcaaaagtcgacggttgtaagcct<br>tgcatatgtacagtcccagaagtatcatctgtcttca<br>tcttcccccccaaagcccaaggatgtgcttcaccattac<br>tctgactcctaaggtcacgtgtgttgtggtagacatc<br>agcaaggatgatcccgaggtccagttcagctggttg<br>tagatgatgtggaggtgcacacagctcagacgcaacc<br>ccgggaggagcagtttcaacagcagtttccgctcagtc<br>agtgaacttcccatcatgcaccaggactggctcaatg<br>gcaaggagttcaaatgcagggtaaacagtgcagcttt<br>ccctgccccatcgagaaaaccatctccaaaaccaaa<br>ggcagaccgaaggctccacaggtgtacaccattccac<br>ctcccaaggagcagatggccaaggataaagtcagtct<br>gacctgcatgataacagacttcttccctgaagacatt<br>actgtggagtggcagtggaatgggcagccagcggaga<br>actacaagaacactcagcccatcatggacacagatgg<br>ctcttacttcgtctacagcaagctcaatgtgcagaag<br>agcaactgggaggcaggaaatactttcacctgctctg<br>tgttacatgagggcctgcacaaccaccatactgagaa<br>gagcctctcccactctcctggtaaa (SEQ ID NO: 261) |
| 3557 to 4441 | A transcription termination/poly-adenylation signal from the α-subunit of the bovine pituitary glycoprotein hormone (α-FSH) (Goodwin et al., 1983, Nucleic Acids Res. 11: 6873-82; Genbank Accession Number X00004) |
| 4446 to 5586 | A mouse dihydrofolate reductase (DHFR) minigene containing the endogenous mouse DHFR promoter, the cDNA coding sequences, and the DHFR |

TABLE 2-continued

| Plasmid Base Pair Number: | |
|---|---|
| | transcription termination/polyadenylation signals (Gasser et al., 1982, Proc. Natl. Acad. Sci. U.S.A. 79: 6522-6; Nunberg et al., 1980 Cell 19: 355-64; Setzer et al., 1982, J. Biol. Chem. 257: 5143-7; McGrogan et al., 1985, J. Biol. Chem. 260: 2307-14) |
| 5594 to 6241 | pBR322 sequences containing the ampicillin resistance marker gene and the origin for replication of the plasmid in E. coli (Genbank Accession Number J01749) |
| 7513 to 7856 | An SV40 early promoter, enhancer and origin of replication (Takebe et al., 1988, Mol. Cell Biol. 8: 466-72, Genbank Accession Number J02400) |
| 7863 to 8119 | A translational enhancer element from the HTLV-1 LTR domain (Seiki et al., 1983, Proc. Natl. Acad. Sci. U.S.A. 80: 3618-22, Genbank Accession Number J02029) |
| 8163 to 8259 | An intron from the SV40 16S, 19S splice donor/acceptor signals (Okayama and Berg, 1983. Mol. Cell Biol. 3: 280-9, Genbank Accession Number J02400) |

Expression of hu INSR(ECD)-C3-muIgG1Fc

AM-1/D CHOd-cells were transfected with 15 µm of linearized expression vector pDSRα:huINSR(ECD)-muIgG1 Fc using FUGENE™ 6 lipofection reagent (Roche Diagnostics Corp., Indianapolis, Ind.), then cultured under conditions to allow expression and secretion of protein into the cell medium. Colonies were selected and analyzed as described above.

Purification of hu INSR(ECD)-C3-muIgG1Fc

The filtered conditioned medium containing huINSR (ECD)-muIgGFc was concentrated 17-fold using a spiral-wound cartridge (molecular weight cut-off=10 kDa), then diluted 1:1 with 3 M KCl, 1 M glycine, pH 9.0 to bring the final salt concentration to 1.5 M KCl, 0.5 M glycine, pH 9.0. This sample was applied to a rProtein A-Sepharose column (Pharmacia) which had been equilibrated in 1.5 M KCl, 0.5 M glycine, pH 9.0. The column was washed with 40 column volumes of the same buffer, then eluted with 20 column volumes of 0.1 M glycine-HCl, pH 2.8. Five-mL fractions were collected and immediately neutralized with 1-mL of 1 M Tris-HCl, pH 7.5. Fractions containing huINSR(ECD)-muIgGFc were identified by SDS-PAGE, pooled, and dialyzed against phosphate-buffered saline. The yield was 0.9 mg/L of conditioned medium. The major protein species were the mature α and β chains and murine Fc. Each of these species appeared to be properly glycosylated based on its elevated and heterogeneous molecular weight. Unprocessed INSR (ECD) as well as glycosylated but not proteolytically cleaved INSR (CED) also was present in the preparation. The shift in bands to higher molecular weights under non-reducing conditions indicated that disulfide linkages joined the α and β chains. Amino-terminal sequencing of the final product indicated that 87% of the protein was correctly processed between the α- and β-chains of INSR(ECD), while 13% remained unprocessed.

EXAMPLE 3

Initial Screen for Anti-IGF-1R Phage Fab

This example provides a method of identifying anti-IGF-1R antibodies.

A Target Quest Q Fab library ("the TQ library"; Target Quest, Maastricht, the Netherlands), which was constructed using peripheral blood lymphocytes from four healthy donors and splenic lymphocytes from one patient with gastric carcinoma, was obtained. The library diversity was $3.7 \times 10^{10}$ clones, containing $3 \times 10^9$ heavy chains. The source, screening methods, and characterization of the library have been published (de Haard et al, 1999, J Biol Chem 274:18218-30). Dynabeads (200 µl) M-450 Uncoated (catalog #140.02, Dynal, Lake Success, N.Y.) were washed 3 times with PBS, resuspended in 200 µl of IGF1R(ECD)-C3-mFc to a concentration of 0.5 µM in PBS, and incubated at 4° C. on a rotator overnight. The IGF-1R(ECD)-C3-mFc coated beads were washed 3× with 1 ml of 2% non-fat dry milk (M) in PBS (2% MPBS), and then blocked with 1 ml of 2% MPBS at room temperature for 1 hour. In parallel, 750 µl of the TQ library ($4 \times 10^{12}$ pfu) was preblocked by mixing with 250 µl 8% MPBS at room temperature for 30 minutes to 1 hour. 500 µl of blocked beads were transferred into another microfuge tube and separated from the blocking solution on a magnetic separator. The preblocked phage mixture was added to the blocked beads and incubated for 90 minutes on a rotator at room temperature. Bead-bound phage were separated from the unbound phage, and then washed 6× with 1 ml 2% MPBS/ 0.1% Tween 20, 6× with 1 ml PBS/0.1% Tween 20, 2× with PBS with a change of tubes between different wash solutions. Bound phage was eluted with 1 ml of 0.1M TEA (pH11) for 10 minutes, then immediately separated from the beads and neutralized with 0.5 ml of 1 M Tris.HCl. The eluted phage pool was mixed with 4 ml 2×YT broth (10 g yeast extract, 16 g bacto-tryptone, 5 g NaCl per liter of water) and 5 ml of TG1 bacterial culture (O.D. 590 about 0.5) in a 50-ml conical tube. The infection mixture was incubate at 37° C. in an incubator for 30 min., then centrifuged at 3500 rpm for 20 min. The cell pellet was resuspended in 1500 µl 2×YT-CG broth and 300 µl were spread on each of five 2×YT-CG (2×YT broth containing 100 µg/ml carbenicillin and 2% glucose) plates. After 20 hours of incubation at 30° C., 4 ml of 2×YT-AG were added to each plate and the cells were recovered with cell scraper from the plates. This step was repeated three times. A small portion of the recovered cells was used for phage rescue (see below). The remaining cell suspension was centrifuged at 3500 rpm for 20 min. The cell pellet was suspended into an amount of 50% glycerol roughly half the volume of the pellet size and stored at −80° C.

In order to rescue phage, the plated-amplified cell suspension was used to inoculate 40 ml of 2×YT-CG to an $OD_{590}$ of about 0.05. The culture was incubated at 37° C. on a shaker to $OD_{590}$ 0.5. The log phase culture was infected with M13KO7 helper phage (GIBCO BRL, Gaithersburg, Md., catalog #18311-019, $1.1 \times 10^{11}$ pfu/ml) at M.O.I. 20 followed by incubation at 37° C. for 30 min. The infected cells were centrifuged at 4000 rpm for 20 min. The cell pellet was re-suspended in 200 ml of 2×YT-CK (100 µg/ml carbenicillin and 40 µg/ml kanamycin) and transferred to two 250-ml flasks and incubated at 30° C. with shaking at 270 rpm for 20 hours. The over-night culture was centrifuged at 4000 rpm for 20 min to removal cell debris. The centrifugation was repeated to ensure the removal of cell debris. About ⅕ volume of PEG solution (20% PEG 8000, 2.5 M NaCl) was added to the supernatant to precipitate the phage particles. The mixture was incubated on ice for at least 1 hour, followed by centrifugation at 4000 rpm for 20 min to collect the precipitated phage particles. The phage pellet was re-suspended into 1 ml of PBS and transferred to a microfuge tube. The phage suspension was left on ice for 1 hour to allow complete suspension of phage particles, and clarified by centrifugation at 14,000 rpm for 2 min to remove the residual cell debris. Phage precipitation step was repeated. The final phage pellet was suspended into PBS after clarification. The rescued phage suspension was used in the next round of selection.

Four rounds of selection were performed that included alterations of various standard binding parameters. The second round of selection was identical to the first round of selection. Variations in input phage number and elution reagent were introduced in rounds three and four. For the round three selection, $5 \times 10^{11}$ pfu of phages were selected and bound phages were eluted either with 1 µM IGF-1 (catalog #13769, Sigma, St. Louis, Mo.) or with a 1 µM concentration of a chimeric αIR3-huFc antibody to yield two round-three pools, TQ4-3IS and TQ4-3CA. Round four selection was carried out on rescued phage pools from both round three pools. Two rounds of negative selection with mouse IgG Fc-coated DYNABEADS® (Dynal Biotech, Oslo, Norway) were included to remove mouse Fc binders prior to actual IGF-1R selection. The incubation time for negative selection was 30 minutes each. $3.78 \times 10^{11}$ pfu of TQ4-3IS pool and $3.75 \times 10^{12}$ pfu of TQ4-3CA pool were selected separately. Bound phage were eluted with 1 µM IGF-2 (catalog #12526, Sigma, St. Louis, Mo.) to yield two round-4 pools, TQ4-4ISI2 and TQ4-4CAI2. The sequence of about 96-192 phage DNA inserts was determined at each elution step.

In some cases, a secondary screen was done. Phagemid DNA mixtures of the total TQ library, and the selected phage amplified after several rounds of selection against IGF-1R, were prepared using a DNA Maxiprep kit according to the manufacturer's instructions (Qiagen, Valencia, Calif.). All four DNA preparations were digested with Asc I and EcoR I (New England Biolab, Beverly, Mass.). The resulting two Asc I/EcoR I fragments were separated on preparative 0.5% agarose gels. The 2.1 kb fragments containing heavy chains were gel purified from the IGF-1R selected phage. The 3.9 kb fragments containing the light chains and pCES1 vector portion were gel purified from the total TQ library DNA. The 2.1 kb fragments were ligated to the 3.9 kb fragments from the DNA sample of TQ library in 3:1 ratio. The ligated DNA was precipitated and used to transform TG1 cells by electroporation. The library size of the resulted light chain shuffled secondary library was $8.8 \times 10^8$. After sequencing 96 randomly picked clones, 76 unique light chain sequences were obtained, indicating that the attempt to shuffle light chains was successful.

The binding, washing and elution condition for screening the light chain shuffle library were essentially the same as described for the initial screen. However, several variations were included to increase selection pressure for amplification of IGF-1R binders with higher affinities, especially those with significantly slower off-rates. These parameters were: higher number of input phage ($2$-$2.7 \times 10^{13}$ pfu), smaller bead volume (100 µl for round one, 50 µl for round two, and 25 µl for round three), and extended specific elution time up to 20 hours. Elution buffers were 0.1 M TEA for round one (RD1), 1 µM IGF-1 in 0.4% MPBS for RD2 and 1 µM IGF-1 or IGF-2 in 0.4% MPBS for RD3. In RD2 and RD3, binders that were eluted in 15 min or 2 hours were discarded. Elution was continued and eluted phages were collected after 8-10 hours and again after 20 hours.

Phage Fab ELISA Screen

In 96-well 2-ml deep-well blocks, 480 µl/well 2×YT-CG broth was inoculated with 20 µl of overnight cultures of the individual clones, then incubated at 37° C., 300 rpm for 3 hours. To each well, 50 µl of 1:3 diluted M13KO7 helper phage were added to infect the cells. The block was incubated at 37° C. without shaking for 30 minutes, and then shaken gently for another 30 minutes at 150 rpm. The block was centrifuged at 3600 rpm for 20 minutes to pellet the infected cells. The cell pellet in each well was suspended into 480 µl of 2×YT-CK (2×YT broth containing 100 µg/ml carbenicillin and 40 µg/ml kanamycin), and incubated at 30° C. overnight for about 20 hours. The cell debris was separated by centrifugation at 3600 rpm for 20 minutes. The rescued phage supernatant was used in the phage ELISA to check for IGF-1R-specific, INSR-cross reactive, or mouse Fc binding of individual clones.

Three sets of Nunc MaxiSorb Immunoplates were coated with 100 µl/well of IGF-1R-C3-mFc at 5 µg/ml, INSR-mFc at 5 µg/ml, or mouse IgG1 (catalog #010-0103, Rockland, Gilbertsville, Pa.) at 2 µg/ml in PBS, respectively, at 4° C. overnight. The coated plates were washed 3× with 300 µl/well of PBS. The washed plates were blocked with 300 µl/well 2% MPBS at room temperature for one hour. Meanwhile, rescued phages of individual clones were pre-blocked by mixing 170 µl of rescued phage with 170 µl of 4% MPBS. The blocked plates were washed 5× with 300 µl/well TBST (TBS: 10 mM Tris-HCl, pH 7.5, 1 mM EDTA, 150 mM NaCl; Tween-20. 0.1%). 100 µl/well of pre-blocked phage dilutions were distributed to each set of coated plate, which were incubated at room temperature on a rocker for 90 minutes. The plates were washed 5× with 300 µl/well TBST. 100 µl/well of anti-M13-HRP in 2% MPBS (1:3000 dilution, catalog number 27-9421-01, Amersham Pharmacia Biotech) were distributed, and plates were incubated at room temperature on rocker for one hour. The plates were washed 5× with 300 µl/well TBST. 100 µl/well of the substrate 1-Step™ ABTS (Pierce Biotechnology, Rockford, Ill., catalog number 37615) were added. Plates were incubated for one hour. $OD_{405}$ was measured for signal detection.

The phage displayed antibodies exhibited essentially no crossreactivity with the insulin receptor and murine Fc domain. The signal observed in the IGF-1R ELISA is therefore specific for the IGF-1R extracellular domain. Results from similar assays for four of the phage-displayed antibodies are shown in FIG. 14.

The DNA inserts of IGF-1R positive, INSR and mu IgG1 negative, clones were sequenced. Fifty-two unique Fab sequences were identified, having the following combinations of light chain and heavy chain variable domain sequences: L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20, H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52, wherein "Lx" indicates light chain variable domain number "x" and "Hx" indicates heavy chain variable domain number "x." FIG. 1 presents the polynucleotide sequences of each of these light and heavy variable domains. FIGS. 2 and 3 present the corresponding amino acid sequences.

EXAMPLE 4

Subcloning of $V_H$ and $V_L$ into IgG1 Expression Vectors

This example presents a method of subcloning the previously identified variable domain sequences into an IgG1 expression vector.

Construction of pDSRα20 and pDSRα20:hIgG1C$_H$

The pDSRα20:hIgG1C$_H$ expression vector (WO 90/14363) was a derivative of pDSR19:hIgG1C$_H$ (see U.S.

Provisional Patent Application No. 60/370,407, filed Apr. 5, 2002, "Human Anti-OPGL Neutralizing Antibodies As Selective OPGL Pathway Inhibitors," incorporated herein by reference in its entirety). The pDSRα19:hIgG1C$_H$ plasmid encoded a rat variable region/human constant region IgG1 (rVh/hCh1). The plasmid was constructed by the three-piece ligation of Xba I and BsmB I terminated rat antibody variable region PCR product, the human IgG1 constant region (C$_{H1}$, hinge, C$_{H2}$ and C$_{H3}$ domains) derived by Sal I cleavage and gel isolation of the BsmB I and Sal I fragment from the linear plasmid pDSRα19:hIgG1 C$_H$ (Hind III and BsmB I ends) and a linearized pDSRα19 with Xba I and Sal I ends. pDSRα20 was produced by changing nucleotide 2563 in pDSRα19 from a guanosine to an adenosine by site directed mutagenesis. The heavy chain expression vector, pDSRα20:hIgG1C$_H$ rat variable region/human constant region IgG1 (rVh/hCh1), is 6163 base pairs and contains the 7 functional regions described in Table 3.

TABLE 3

| Plasmid Base Pair Number: | |
|---|---|
| 2 to 881 | A transcription termination/polyadenylation signal from the α-subunit of the bovine pituitary glycoprotein hormone (α-FSH) (Goodwin et al., 1983, Nucleic Acids Res. 11: 6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al., 1982, Proc. Natl. Acad. Sci. U.S.A. 79: 6522-6; Nunberg et al., 1980, Cell 19: 355-64; Setzer et al., 1982, J. Biol. Chem. 257: 5143-7; McGrogan et al., 1985, J. Biol. Chem. 260: 2307-14) |
| 2031 to 3947 | pBR322 sequences containing the ampicillin resistance marker gene and the origin for replication of the plasmid in E. coli (Genbank Accession Number J01749) |
| 3949 to 4292 | An SV40 early promoter, enhancer and origin of replication (Takebe et al., 1988, Mol. Cell Biol. 8: 466-72, Genbank Accession Number J02400) |
| 4299 to 4565 | A translational enhancer element from the HTLV-1 LTR domain (Seiki et al,, 1983, Proc. Natl. Acad. Sci. U.S.A. 80: 36 18-22, Genbank Accession Number J02029) |
| 4574 to 4730 | An intron from the SV40 16S, 19S splice donor/acceptor signals (Okayama and Berg, 1983. Mol. Cell Biol. 3: 280-9, Genbank Accession Number J02400) |
| 4755 to 6158 | The rVh/hCh1 heavy chain cDNA between the XbaI and SafI sites. This heavy chain fragment sequence is shown below (SEQ ID NO: 262) with the sequences of the restriction sites underlined: |

```
       XbaI
   TCTAG ACCACCATGG ACATCAGGCT CAGCTTAGTT
TTCCTTGTCC TTTTCATAAA AGGTGTCCAG
TGTGAGGTAG AACTGGTGGA GTCTGGGGGC
GGCTTAGTAC AACCTGGAAG GTCCATGACA
CTCTCCTGTG CAGCCTCGGG ATTCACTTTC
AGAACCTATG GCATGGCCTG GGTCCGCCAG
GCCCCAACGA AGGGTGTGGA GTGGGTCTCA
TCAATTACTG CTAGTGGTGG TACCACCTAC
TATCGAGACT CCGTGAAGGG CCGCTTCACT
ATTTTTAGGG ATAATGCAAA AAGTACCCTA
```

TABLE 3-continued

| Plasmid Base Pair Number: |
|---|
| TACCTGCAGA TGGACAGTCC GAGGTCTGAG |
| GACACGGCCA CTTATTTCTG TACATGAATT |
| TCGGAATACT GGGGCCACGG AGTCATGGTG |
|   BsmB1 |
| ACCGTCTCTA GTGCCTCCAC CAAGGGCCCA |
| TCGGTCTTCC CCCTGGCACC CTCCTCCAAG |
| AGCACCTCTG GGGGCACAGC GGCCCTGGGC |
| TGCCTGGTCA AGGACTACTT CCCCGAACCG |
| GTGACGGTGT CGTGGAACTC AGGCGGCCTG |
| ACCAGCGGCG TGCACACCTT CCCGGCTGTC |
| CTACAGTCCT GAGGACTCTA CTCCCTCAGC |
| AGCGTGGTGA CGGTGCCCTC CAGCAGCTTG |
| GGCACCCAGA CCTACATCTG CAACGTGAAT |
| CACAAGCCCA GCAACACCAA GGTGGACAAG |
| AAAGTTGAGC CCAAATCTTG TGACAAAACT |
| CACACATGCC CACCGTGCCC AGCACCTGAA |
| CTCCTGGGGG GACCGTCAGT CTTCCTCTTC |
| CCCCCAAAAC CCAAGGACAC CCTCATGATC |
| TCCCGGACCC CTGAGGTCAC ATGCGTGGTG |
| GTGGACGTGA GCCACGAAGA CCCTGAGGTC |
| AAGTTCAACT GGTACGTGGA CGGCGTGGAG |
| GTGCATAATG CCAAGACAAA GCCGCGGGAG |
| GAGCAGTACA ACAGCACGTA CCGTGTGGTC |
| AGCGTCCTCA CCGTCCTGCA CCAGGACTGG |
| CTGAATGGCA AGGAGTACAA GTGCAAGGTC |
| TCCAACAAAG CCCTCCCAGC CCCCATCGAG |
| AAAACCATCT CCAAAGCCAA AGGGCAGCCC |
| CGAGAACCAC AGGTGTACAC CCTGCCCCCA |
| TCCCGGGATG AGCTGACCAA GAACCAGGTC |
| AGCCTGACCT GCCTGGTCAA AGGCTTCTAT |
| CCCAGCGACA TCGCCGTGGA GTGGGAGAGC |
| AATGGGCAGC CGGAGAACAA CTACAAGACC |
| ACGCCTCCCG TGCTGGACTC CGACGGCTCC |
| TTCTTCCTCT ATAGCAAGCT CACCGTGGAC |
| AAGAGCAGGT GGCAGCAGGG GAACGTCTTC |
| TCATGCTCCG TGATGCATGA GGGTCTGCAC |
| AACCACTACA CGCAGAAGAG CCTCTCCCTG |
| TCTCCGGGTA |
|   SalI |
| AATGATAAGT CGAC |

The linear plasmid pDSRα20:hIgG1 C$_H$ was prepared by digesting the pDSR20: rat variable region/human constant region IgG1 plasmid with the restriction enzymes Xba I and BsmB I to remove the rat variable region and purified using a QIAquick Gel Extraction kit. The linear plasmid pDSRα20:hIgG1C$_H$ containing the 1.0 kbp human IgG1 constant region domain was used to accept anti-IGF-1R variable heavy chain coding sequences.

Construction of the Anti-IGF-1R IgG1 Heavy Chain Expression Clones

The sequence coding for the anti-IGF-1R variable region of the heavy chains was amplified from phagemid DNA with complementary oligonucleotide primers. Primers for polymerase chain reaction (PCR) were designed to incorporate a Hind III site, Xba I site, Kozak sequence (CCACC) and signal sequence (translated peptide is MDMRVPAQLLGLLLLWL-RGARC; SEQ ID NO:263) onto the 5' end of the variable region, while a BsmB I site was added onto the 3' end of the PCR product. The PCR products were digested with Xba I and BsmB I, and then cloned into the Xba I-BsmB I linear pDSRα20:hIgG1 C$_H$ expression vector containing the human IgG1 constant region (FIG. 13). The final expression vectors contained the seven functional regions described in Table 4.

TABLE 4

| Plasmid Base Pair Number: | |
|---|---|
| 2 to 881 | A transcription termination/polyadenylation signal from the α-subunit of the bovine pituitary glycoprotein hormone (α-FSH) (Goodwin et al., 1983, Nucleic Acids Res. 11: 6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al., 1982, Proc. Natl. Acad. Sci. U.S.A. 79: 6522-6; Nunberg et al., 1980, Cell 19: 355-64; Setzer et al., 1982, J. Biol. Chem. 257: 5143-7; McGrogan et al., 1985, J. Biol. Chem. 260: 2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, Mol. Cell Biol. 8: 466-72, Genbank Accession Number J02400) |
| 4299 to 4565 | A translational enhancer element from the HTLV-1 LTR domain (Seiki et al., 1983, Proc. Natl. Acad. Sci. U.S.A. 80: 3618-22, Genbank Accession Number J02029) |
| 4574 to 4730 | An intron from the SV40 16S, 19S splice donor/acceptor signals (Okayama and Berg, 1983. Mol. Cell Biol. 3: 280-9, Genbank Accession Number J02400) |
| 4755 to 6185 | The heavy chain IgG1 cDNA between the XbaI and SalI sites |

Construction of the Anti-IGF-1R IgG1 Variable Chain Expression Clones.

The light chains encoded in anti-IGF-1R phage were either kappa or lambda class. They were cloned using one of two approaches. Complementary primers were designed to add a Hind III site, an Xba I site, Kozak sequence (CCACC) and signal sequence (translated peptide is MDMRV-PAQLLGLLLLWLRGARC, SEQ ID NO:264) were added to the 5' end of the coding region. Those chains that had error-free coding regions were cloned as full-length products. The full-length light chains were cloned as Xba I and Sal I fragments into the expression vector pDSRα20. The final expression vectors contained the seven functional regions described in Table 5.

EXAMPLE 5

Transient Expression of Antibodies

This example provides a method of transiently expressing anti-IGF-1R antibodies.

The antibodies were expressed transiently in serum-free suspension adapted 293T cells. All transfections were performed as 250 mL cultures. Briefly, $1.25 \times 10^8$ cells ($5.0 \times 10^5$ cells/mL×250 mL) were centrifuged at 2,500 RPM for 10 minutes at 4° C. to remove the conditioned medium. The cells were resuspended in serum-free DMEM and centrifuged again at 2,500 RPM for 10 minutes at 4° C. After aspirating the wash solution, the cells were resuspended in growth

TABLE 5

| Plasmid Base Pair Number: | |
|---|---|
| 2 to 881 | A transcription termination/polyadenylation signal from the α-subunit of the bovine pituitary glycoprotein hormone (α-FSH) (Goodwin et al., 1983, Nucleic Acids Res. 11: 6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al, 1982, Proc. Natl. Acad. Sci. U.S.A. 79: 6522-6; Nunberg et al., 1980, Cell 19: 355-64; Setzer et al., 1982, J. Biol. Chem. 257: 5143-7; McGrogan et al., 1985, J. Biol. Chem. 260: 2307-14) |
| 2031 to 3947 | pBR322 sequences containing the ampicillin resistance marker gene and the origin for replication of the plasmid in *E. coli* (Genbank Accession Number J01749) |
| 3949 to 4292 | An SV40 early promoter, enhancer and origin of replication (Takebe et al., 1988, Mol. Cell Biol. 8: 466-72, Genbank Accession Number J02400) |
| 4299 to 4565 | A translational enhancer element from the HTLV-1 LTR domain (Seiki et al., 1983, Proc. Natl Acad. Sci. U.S.A. 80: 3618-22, Genbank Accession Number J02029) |
| 4574 to 4730 | An intron from the SV40 16S, 19S splice donor/acceptor signals (Okayama and Berg, 1983, Mol Cell Biol. 3: 280-9, Genbank Accession Number J02400) |
| 4755 to 5485 | The kappa light chain cDNA between the XbaI and SalI sites |

Some kappa clones had errors in their constant regions when compared to natural human constant region sequence. To eliminate these discrepancies, the kappa variable region was amplified with a primer that would introduce an Xba I site into the 5' end and a BsmB I site into the 3' end. This fragment was then ligated along with a human kappa constant region (FIG. 13) with a compatible BsmB I on the 5' end and a 3'Sal I ends into pDSRα20 with Xba I and Sal I ends.

medium [DMEM/F12 (3:1)+1× Insulin-Transferrin-Selenium Supplement+1× Pen Strep Glut+2 mM L-Glutamine+20 mM HEPES+0.01% Pluronic F68] in a 500 mL spinner flask culture. The spinner flask culture was maintained on magnetic stir plate at 125 RPM which was placed in a humidified incubator maintained at 37° C. and 5% $CO_2$. The plasmid DNA was incubated with the transfection reagent in a 50 mL conical tube. The DNA-transfection reagent complex was prepared in 5% of the final culture volume in serum-free DMEM. One microgram of plasmid DNA per milliliter of culture was first added to serum-free DMEM, followed by 1 µl X-TremeGene RO-1539/mL culture. The complexes were incubated at room temperature for approximately 30 minutes and then added to the cells in the spinner flask. The transfection/expression was performed for 7 days, after which the conditioned medium was harvested by centrifugation at 4,000 RPM for 60 minutes at 4° C.

If the initial transfection failed to yield the required 100 µg purified antibody, those clones were re-expressed in roller bottles. These transfections used 293T adherent cells grown and maintained in DMEM supplemented with 5% FBS+1× Non-Essential Amino Acids+1× Pen Strep Glut+1× Sodium Pyruvate. Approximately, $4-5 \times 10^7$ 293T cells were seeded in a 850 cm² roller bottles overnight. The previously seeded cells were then transfected the following day using FUGENE™ 6 transfection reagent. The DNA-transfection reagent mixture was prepared in approximately in 6.75 mL serum-free DMEM. 675 µl FUGENE™ 6 transfection reagent was first added, followed by 112.5 µg plasmid DNA. The complex was incubated at room temperature for 30 minutes. The entire mixture was then added to a roller bottle. The roller bottle was infused with a 5% $CO_2$ gas mixture, capped tightly and placed in a 37° C. incubator on a roller rack rotating at 0.35 RPM. The transfection was performed for 24 hours after which the medium was replaced with 100 mL DMEM+1× Insulin-Transferrin-Selenium Supplement+1× Pen Strep Glu+1× Non-Essential Amino Acids+1× Sodium Pyruvate. Typically, 2-3 harvests (100 ml) were obtained from each roller bottle at a 48 hr interval. The harvested serum-free conditioned medium was pooled together and centrifuged at 4,000 RPM for 30 minutes at 4° C.

EXAMPLE 6

Anti-IGF-1R Antibody Small-Scale Purification

This example provides a method of purifying anti-IGF-1R antibodies on a small scale.

Conditioned medium was filtered through a 0.45 µm cellulose acetate filter and concentrated approximately 8-fold using a Vivaflow 200 50 K tangential flow membrane (Vivascience, Goettingen, Germany). rProtein A SEPHAROSE™ Fast Flow resin (Amersham Biosciences, Piscataway, N.J.) was washed with phosphate buffered saline (2.7 mM potassium chloride, 138 mM sodium chloride, 1.5 mM potassium phosphate, and 8.1 mM sodium phosphate, pH 7.4) (PBS) four times then directly applied to the concentrated media. The amount of resin used was based on antibody concentration determined by ELISA where 1 µl of resin was used per 5 µg antibody. The medium was incubated overnight at 4° C. with gentle agitation. The resin was centrifuged at 500 g for 10 min. at 4° C. The supernatant was decanted as the unbound fraction. The resin was washed with PBS four times for one minute at room temperature with gentle agitation, each time collecting the resin by centrifugation at 500 g for 10 min. at 4° C. The antibody was eluted by incubating the resin with 1.5 volumes of 0.1 M glycine pH 3.0 for 10 min. at room temperature. The resin was centrifuged at 500 g for 10 min. at 4° C. and the supernatant decanted as eluted antibody. The elution step described above was repeated for a total of three elutions; each time the eluted material was neutralized with 0.04 volumes of 1.0 M tris-HCl, pH 9.2. The sample was filtered through a 0.2 µm cellulose acetate filter. Protein concentration was determined by the Bradford method using the Bio-Rad Protein Assay (Bio-Rad Laboratories, Hercules, Calif.) as per the supplied instructions using Human IgG (Sigma-Aldrich, St. Louis, Mo.) as a standard. The sample was compared to a Human IgG1, K standard (Sigma-Aldrich, St. Louis, Mo.) using a 4-20% tris-glycine SDS polyacrylamide gel (SDS-PAGE) gel stained with Coomassie brilliant blue dye. No contaminating protein was visible in these preparations.

EXAMPLE 7

Isolation of Stable CHO Clones Expressing Antibodies

This example provides a method for isolating stable CHO cell lines expressing anti-IGF-1R antibodies.

Stable expression of TQ11C, TQ25, TQ 58 and TQ59 IgG1 was achieved by co-transfection of AM1-D CHO cells (U.S. Pat. No. 6,210,924, incorporated herein by reference in its entirety) with pDSRα20 heavy and light chain IgG1 expression constructs. The plasmid transfections were performed using LF2000 (Invitrogen, Carlsbad, Calif.) according to the manufacturer's instructions. Briefly, 4×10⁶ AM1-D CHO cells were plated 24 hours prior to transfection, in 100 mm diameter FALCONS plastic petri dishes (BD Falcon, Franklin Lakes, N.J.) in 10 ml of Dulbecco's Modified Eagles Medium (Invitrogen) supplemented with 5% fetal bovine serum, 1× penicillin-streptomycin and glutamine (Invitrogen), non-essential amino acids (Invitrogen), sodium pyruvate, and HT (0.1 mM sodiumhypoxanthine, 16 nM thymidine; Invitrogen). Approximately 15 mg of each pDSRα21-light chain and heavy chain plasmid DNA were linearized using Pvu I (New England Biolabs) and diluted in 2 ml of OPTI-MEM® (Invitrogen). The diluted plasmids were mixed with 75 µl of LIPOFECTAMINE™ 2000 (LF2000; GIBCO/BRL) diluted in 2 ml of OPTI-MEM® and the mixture was incubated for 20 min at room temperature. The following day fresh growth medium was added. The cells were cultured in complete growth medium for 48 hours, then plated in HT-selection medium in 1:20 and 1:50 dilutions. Approximately 2 weeks after transfection, 12-24 visible colonies were picked into 24-well plates, using the sterile cloning discs (RPI). The clones expressing the highest level of TQ11C, TQ25, TQ58 and TQ59 IgG1 were identified by western immunoblot analysis. To perform this assay, 0.5 ml of serum free medium was added to a single-well confluent cells cultured in a 24 well plate (BD Falcon). The conditioned medium was recovered after 24 hr, and 10 µl of CM was mixed with an equal volume of loading buffer to run a 10% Tris-Glycine polyacrylamide protein gel (Invitrogen). The gel was transferred to a 0.45 µm pore size nitrocellulose membrane (Invitrogen), and western blot analysis was done using 1:1000 dilution of goat anti-human IgG Fc ImmunoPure antibody (Pierce Biotechnology, Inc., Rockford, Ill.) and ECL as detection agent.

EXAMPLE 8

Mid-Scale Expression of Antibodies

This example provides a method of expressing anti IGF-1R antibodies expressed by stable CHO cell lines.

The CHO cell lines made according to Example 7 were expanded to T-175 tissue culture flasks (Falcon) for scale-up expression. A confluent T175 flask (approximately $2-3 \times 10^7$ cells) was used to seed 3-850 cm2 roller bottles (Corning Life Sciences, Acton, Mass.), and three confluent roller bottles (approximately $1-2 \times 10^8$ cells per roller bottle) were used to seed 30 rollers in 250 ml of high-glucose DMEM (Invitrogen), 10% dialyzed FBS (Invitrogen), 1× glutamine (Invitrogen), 1× non-essential amino acids (Invitrogen), 1× sodium pyruvate (Invitrogen). Medium was infused with 10% $CO_2$/balance air for 5 seconds before capping the roller bottle. Roller bottles were incubated at 37° C. on roller racks spinning at 0.75 rpm.

When cells reached approximately 85-90% confluency (approximately 5-6 days in culture), the growth medium was discarded, the cells were washed with 100 ml PBS, and 200 ml production medium was added (50% DMEM (Invitrogen)/50% F12 (Invitrogen), 1× glutamine (Invitrogen), 1× non-essential amino acids (Invitrogen), 1× sodium pyruvate (Invitrogen), 1.5% DMSO (Sigma). Conditioned medium was harvested every seven days for a total of four harvests.

Conditioned medium was filtered through a 0.45 μm cellulose acetate filter and concentrated approximately 10-fold using a Sartorius Sartocon Slice Disposable 30 K tangential flow membrane (Sartorius AG, Goettingen, Germany). The concentrated material was applied to a 10 ml rProtein A Sepharose column at 4° C. and the flowthrough was collected as the unbound fraction. The column was washed with four column volumes of PBS. The bound sample was eluted with approximately four column volumes of 0.1 M glycine pH 3.0. The eluate peak was collected and neutralized with 0.04 volumes of 1.0 M tris-HCl, pH 9.2. The eluate was dialyzed against 150 volumes of PBS overnight at 4° C. The sample was filtered through a 0.2 μm cellulose acetate filter and protein concentration was measured by determining the absorbance at 280 nm using an extinction coefficient of 14,000 M-1. The sample was compared to a Human IgG1, K standard (Sigma-Aldrich, St. Louis, Mo., USA) using a 4-20% tris-glycine SDS-PAGE gel stained with Coomassie brilliant blue stain. Endotoxin levels in each antibody preparation was determined using the Pyrotell Limulus Amebocyte Lysate Assay (Associates of Cape Cod, Inc., Falmouth, Ma) as per the supplied instructions.

EXAMPLE 9

ORIGEN® Dose Response Competition Assays

This example provides methods for testing the ability of an antibody to block ligand binding to IGF-1R.

An ORIGEN® binding assay was used to determine whether TQ11C, TQ25, TQ 58 and TQ59 IgG1 antibodies could block ligand binding to IGF-1R using procedures provided by the manufacturer (Igen, Inc., Gaithersburg, Md.). To label IGF-1 and IGF-2 with ruthenium, lyophilized proteins were dissolved into PBS to give a 1.0 mg/ml solution. Label (ORI-TAG-NHS ester from Igen, Cat # 110034) was added to the protein at a molar ratio of 5:1 (label:protein) from a label stock of 5 mg/ml in DMSO. The mixture was incubated at room temperature (20-22° C.) for 1 hr in the dark then treated with 20 μl 2M glycine for 10 min at room temperature. The labeled protein was separated from the free label by application to an Amersham Biosciences NAP-5 column (Amersham Biosciences, Piscataway, N.J.) equilibrated in PBS and 0.33 ml fractions collected. The protein concentration of the fractions was determined by Micro BCA Protein Assay (Pierce Biotechnology, Inc., Rockford, Ill.). Fractions two and three contained significant protein and were combined. The amount of incorporated ruthenium label was assessed using the following formula: ruthenium tris-bipyridyl compound $(Ru(bpy)_3^{2+})$ labeling of IGF-1 and IGF-2.

Figure 15A:
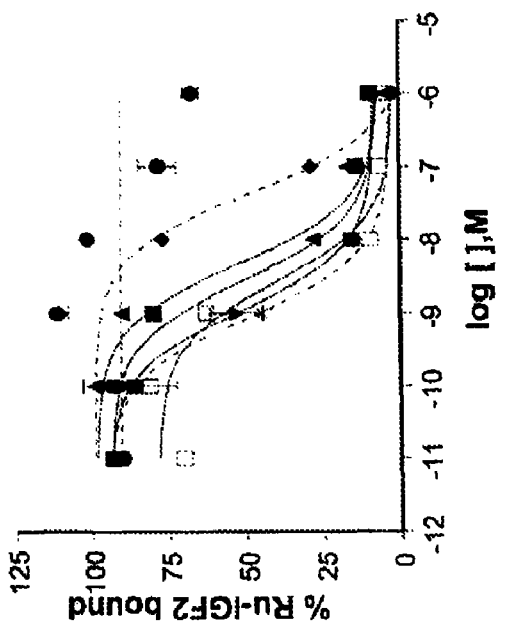
FIG. 15 provides graphs illustrating the ability of certain antibodies to compete for binding to IGF-1R with IGF-1 and IGF-2.
Figure 15B:
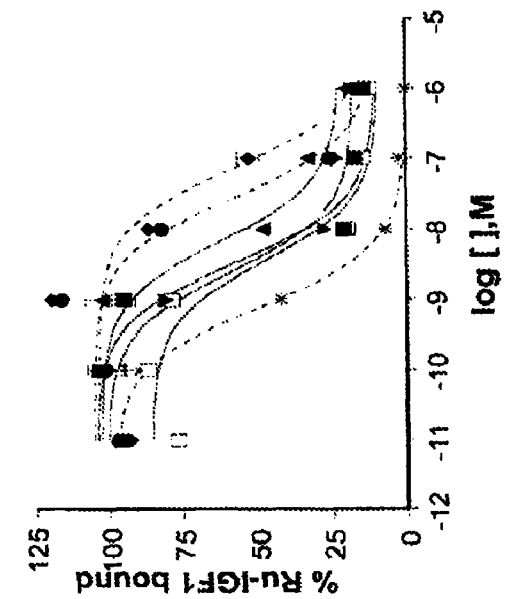
Figure 16A:
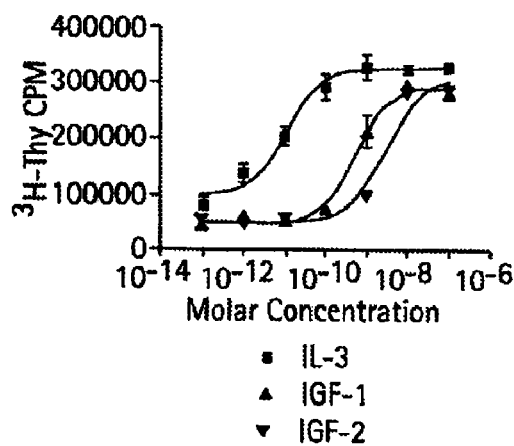
FIG. 16 provides graphs illustrating the ability of certain antibodies to inhibit the growth of 32D hu IGF-1R+IRS-1 cells.
Figure 16B:
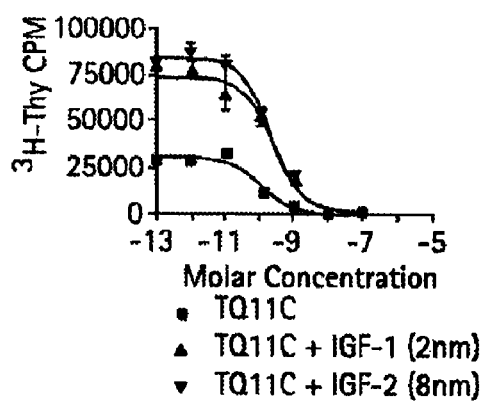
Figure 16C:
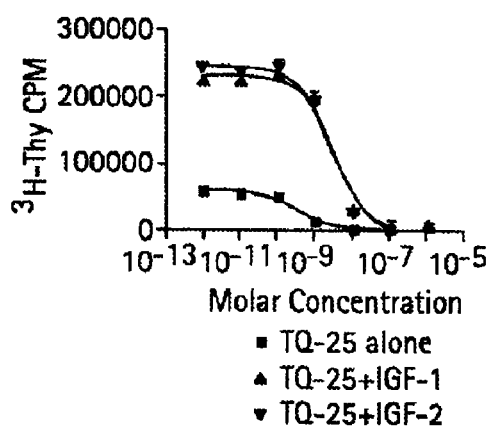
Figure 16D:
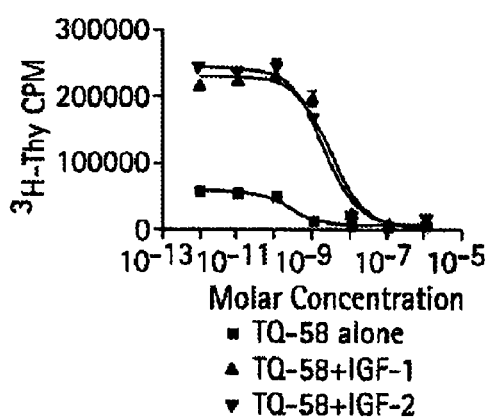
Figure 16E:
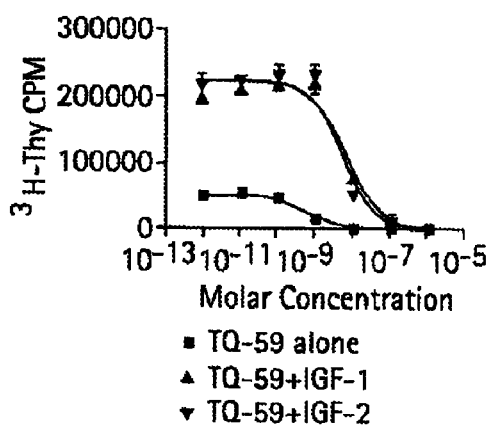
Figure 16F:
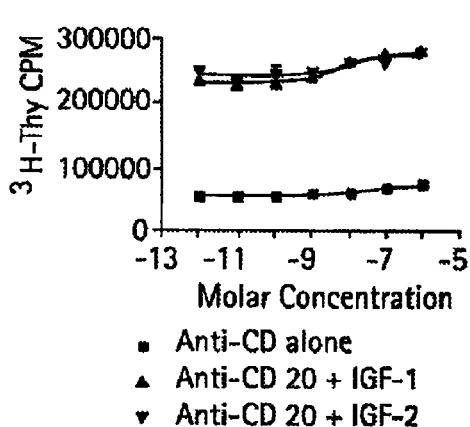
Figure 17A:
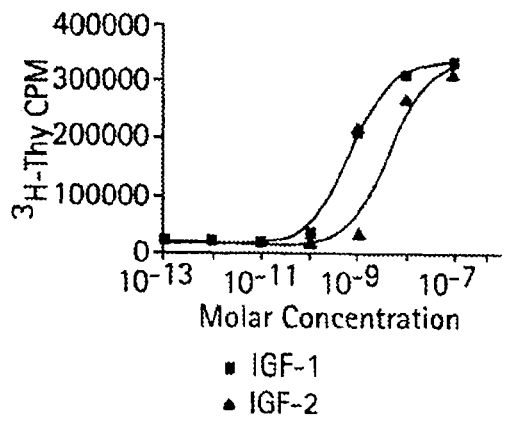
FIG. 17 provides graphs illustrating the ability of certain antibodies to inhibit the growth of Balb/C 3T3 hu IGF-1R cells.
Figure 17B:
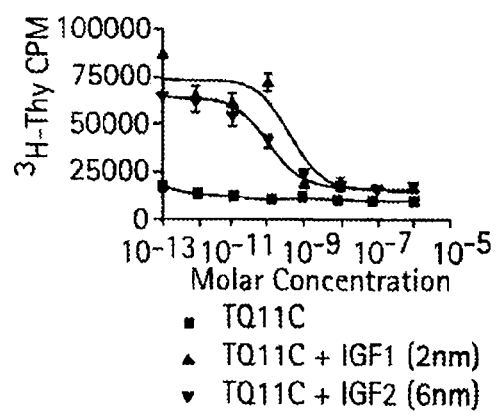
Figure 17C:
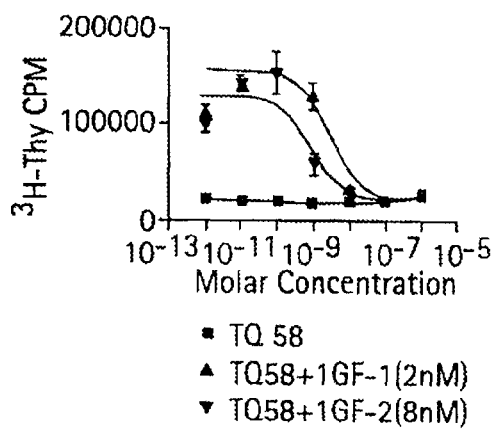
Figure 17D:
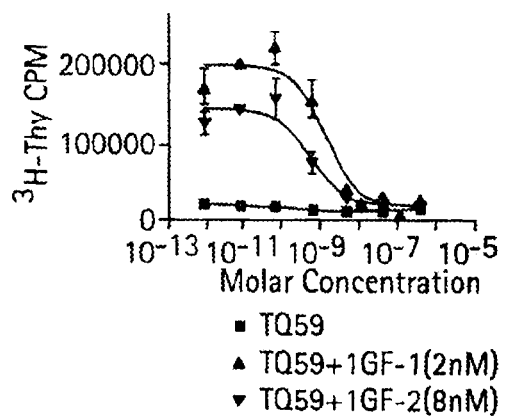
Figure 17E:
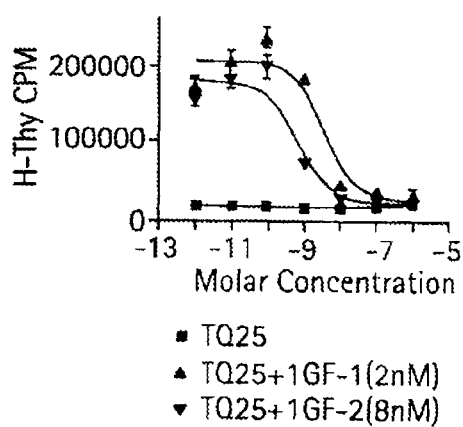
Figure 17F:
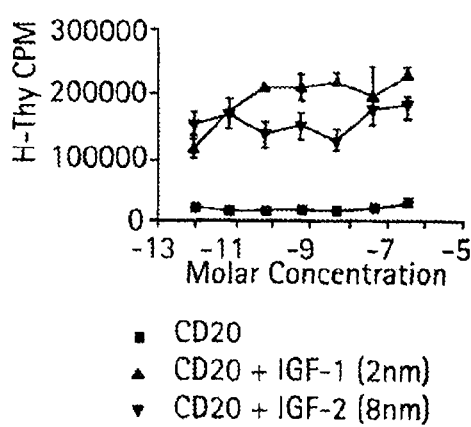

Dynal M450 paramagnetic beads coated with sheep anti-mouse IgG was used as the solid support phase for the IGF-1R(ECD)-C3-muFc. The M450 beads were prepared for receptor loading by washing three times with assay buffer containing 1×PBS, 0.05% TWEEN™ 20 (ICI Americas, Inc., Wilmington Del.) 0.1% BSA, 0.01% sodium azide. The IGF-1R(ECD)-C3-muFc was bound for 1 hr at a ratio of 50 ng receptor per 1×10⁶ M450 beads in a volume of 25 μl assay buffer. To generate dose response data, the antibodies or unlabeled IGF-1 and IGF-2 factors were added at increasing concentrations ($10^{-11}$M to $10^{-6}$M) simultaneously with 1 nM Ru-IGF-1 or 2 nM Ru-IGF-2. The final reaction volume was 100 μl. After incubation at room temperature in the dark for 2 hr, an M8 Analyzer (Igen) was used to remove free ruthenium labeled ligand and determine the amount of ligand bound to receptor. The data were expressed as the percent of total ligand bound minus background remaining after competition with excess unlabeled growth IGF1 or IGF-2. Competition curves were generated with GraphPad Prism software (GraphPad Software, San Diego, Calif.) using a single component equilibrium model. Essentially all (>98%) binding was competed with excess unlabeled growth factors. The positive control antibodies in the binding analysis were the murine anti-IGF-1R antibodies αIR3 (Calbiochem, San Diego, Calif.) or MAB391 (R&D systems, Minneapolis, Minn.), 24-57 (Biocarta, San Diego, Calif.) and 1H7 (Santa Cruz Biotechnology, Inc., Santa Cruz, Calif.). The negative control antibody was an anti-CD20 antibody. Ligand competition data are shown in FIG. 15. The Ki and maximum inhibition values observed for IGF-1 and IGF-2 binding reactions are listed in Table 6.

TABLE 6

| Antibody | IGF-1 | | IGF-2 | |
|---|---|---|---|---|
| | Ki (nM)[1] | Max (%)[2] | Ki (nM)[1] | Max (%)[2] |
| TQ11C | 0.6 | 84 | 0.3 | 91 |
| TQ25 | 0.8 | 88 | 0.8 | 94 |
| TQ58 | 0.8 | 91 | 0.8 | 91 |
| TQ59 | 1.5 | 79 | 1.4 | 91 |
| 1H7 | 16.0 | 89 | 13.1 | 99 |
| αIR3 | 5.3 | 91 | No Inhibition | |

[1]Ki of inhibition.
[2]Maximum level of inhibition at 1 μM antibody concentration.

EXAMPLE 10

SPA Dose Response Competition Assay

This example presents a scintillation proximity assay (SPA) for assessing the effect of antibodies on the interaction of insulin (INS) with the insulin receptor (INSR) and of IGF-1 and IGF-2 to IGF-1R.

IGF-1R binding reactions for TQ11C, TQ25, TQ 58 and TQ59 IgG1 antibodies contained 1×PBS, 0.05% TWEEN® 20 (Mallinkrodt), 0.1% BSA (EM Science, Gibbstown, N.J.), 50 ng IGF-1R(ECD)-C3-muFc, 500 ug SPA PVT anti-mouse IgG fluoromicrospheres (Amersham) and $^{125}$I-labeled IGF-1 or IGF-2 obtained from Amersham at a final concentration of 0.64 nM. The total reaction volume was 100 μl. The INSR binding reactions were identical except they contained 50 ng INSR(ECD)-muFc and 0.64 nM $^{125}$I-INS (Amersham). Receptor was loaded onto SPA PVT microspheres for 1 h at room temperature prior to assembly of the binding reactions. To generate dose response data, antibodies or unlabeled growth factors were added at increasing concentrations ($10^{-11}$ M to $10^{-6}$ M) simultaneously with $^{125}$I-labeled growth factors. Essentially all binding was competed with excess unlabeled growth factors. The receptor-independent background, caused by random γ stimulation of the SPT PVT microspheres, was less than 0.5% of the input $^{125}$I cpm. The data were expressed as the percent of total ligand bound minus background remaining after competition with excess unlabeled growth IGF1 or IGF-2. Competition curves were generated with GraphPad Prism software using a single component equilibrium model.

EXAMPLE 11

Antibody Binding to IGF-1R

This example provides a method of detecting the binding of an anti-IGF-1R antibody to IGF-1R.

BIACORE® 2000, sensor chip CM5, surfactant P20, HBS-EP (10 mM HEPES, 0.15M NaCl, 3.4 mM EDTA, 0.005% P20, pH 7.4), amine coupling kit, 10 mM acetate pH 4.5 and 10 mM glycine pH 1.5 all were purchased from BIACore, Inc. (Piscataway, N.J.). Phosphate-buffered saline (PBS, 1×, no calcium chloride, no magnesium chloride) was from Gibco. Bovine serum albumin (BSA, fraction V, IgG free) was from Sigma. Recombinant Protein G ("rProtein G") was from Pierce Biotechnology.

Immobilization of rProtein G and IGF-1R-C3-muFc to the sensor chip surface was performed according to manufacturer's instructions, using a continuous flow of 10 mM HEPES, 0.15M NaCl, 3.4 mM EDTA, 0.005% P20, pH 7.4 (HBS-EP buffer). Briefly, carboxyl groups on the sensor chips's surfaces were activated by injecting 60 μl of a mixture containing 0.2 M N-ethyl-N'-(dimethylaminopropyl)carbodimide (EDC) and 0.05 M N-hydroxysuccinimide (NHS). Specific surfaces were obtained by injecting rProtein A (Pierce) or IGF-1R-C3-mFc diluted in 10 mM acetate, pH 4.5 at concentrations between 20 and 50 μg/ml. Excess reactive groups on the surfaces were deactivated by injecting 60 μl of 1 M ethanolamine. Final immobilized levels were 5,000-6,000 resonance units (RU) for the Protein G surfaces, and ~7,800 RU for the IGF-1R-mFc surfaces. A blank, mock-coupled reference surface was also prepared on the IGF-1R-mFc sensor chip.

The kinetic analysis of the interaction between IGF-1R-mFc and antibodies was performed as follows. Antibodies as well as a positive control antibody (anti-IR3-CDR-human-mouse chimera) were diluted in PBS+0.005% P20+0.1 mg/ml BSA and injected over the Protein G surfaces to capture the antibodies. IGF-1R-mFc was diluted in PBS+0.005% P20+0.1 mg/ml BSA from 500 nM to 3.9 nM, and each concentration was injected over the captured antibody surfaces, as well as over a blank Protein G surface for background subtraction. After a 10 minute dissociation, each surface was regenerated by injecting 10 mM glycine, pH 1.5. Kinetic analysis of the resulting sensorgrams was performed using BIAEvaluation, v. 3.2 (BIACore, Inc.).

A solution affinity analysis was done by incubating two different concentrations (0.2 nM and 1 nM) of antibody with varying concentrations (0.01 nM to 50 nM) of IGF-1R-mFc in PBS+0.005% P-20+0.1 mg/ml BSA. Incubations were done at room temperature for at least five hours to allow samples to reach equilibrium. Samples were then injected over the immobilized IGF-1R-mFc surface. After the sample injection, the surfaces were regenerated by injecting 25 μl 8 mM glycine, pH 1.5. The binding signal obtained is proportional to the free antibody in solution at equilibrium. The dissociation equilibrium constant ($K_D$) was obtained from nonlinear regression analysis of the competition curves using a dual-curve one-site homogeneous binding model (KinExA software v. 2.3, Sapidyne Instruments Inc., Boise Id.). The data are shown in Table 7

TABLE 7

| Antibody | $k_{on}$ (1/MS) | $K_d$ (1/s) | Kd ($k_d/k_a$) Kinetic Method | Kd Equilibrium Method |
|---|---|---|---|---|
| TQ11C | $6.0 \times 10^4$ | $6.7 \times 10^{-5}$ | 1.1 nM | 0.3 nM |
| TQ25 | $4.4 \times 10^4$ | $<<5 \times 10^{-5}$ | | 0.10 nM |
| TQ58 | $1.1 \times 10^5$ | $2.8 \times 10^{-5}$ | 0.25 nM | 0.25 nM |
| TQ59 | $6.9 \times 10^4$ | $2.1 \times 10^{-4}$ | 3.0 nM | 0.30 nM |

EXAMPLE 12

Epitope Mapping Avidin-Fusion Proteins

This example provides a method of determining the epitope of IGF-1R bound by an anti-IGF-1R antibody.

The subdomains of IGF-1R bound by antibodies TQ11C, TQ25, TQ58, and TQ59 were determined using avidin-IGF-1R fusion proteins. To express each protein the coding DNA sequences of the complete IGF-1R(ECD) was cloned into the expression vector pCep-4-avidin-C such that chicken avidin sequence is joined to the C-terminus of the expressed IGF-1R protein. The ECD coding sequence (1-932) was PCR amplified from a parental IGF-1R plasmid using PCR primers 2804-25:

```
                                          SEQ ID NO: 265
5' GCAAGCTTGGGAGAAATCTGCGGGCCAG 3'
and 2826-68:
                                          SEQ ID NO: 266
5' ATTGCGGCCGCTTCATATCCTGTTTTGGCCTG 3'
```

The primers include a 5' Hind III site and a 3' Not I site for cloning into pCep4avidin-C. The amino acid sequence of the avidin-human IGF-1R(ECD) fusion protein is shown in FIG. 12. The IGF-1R subdomains constructs used for epitope mapping included: L1 (1-151), CR (152-298), L2 (299-461), FnIII-1 (461-579), FnIII-2/ID (580-798), FnIII-3 (799-901), L1+CR+L2 (1461), and L1+CR (1-298). The amino acid coordinates of the IGF-1R subdomain represented in each expression plasmid are given in parenthesis. The coding sequence of each domain was PCR amplified from a parental IGF1R cDNA clone using the following primer pairs:

```
L1:
2804-25:
                                          (SEQ ID NO: 265)

2804-19:
                                          SEQ ID NO: 267
5' ATTGCGGCCGCCCCACATTCCTTTGGGGGC 3'

CR:
2804-38:
                                          SEQ ID NO: 268
5' AGCAAGCTTGGACCTGTGTCCAGGGACC 3'

2804-20:
                                          SEQ ID NO: 269
5' ATTGCGGCCGCGCAAGGACCTTCACAAGGC 3'

L2:
2804-39:
```

-continued 2804-22:
SEQ ID NO: 270
5' AGCAAGCTTGCCGAAGGTCTGTGAGGAAG 3'

2804-23:
SEQ ID NO: 271
5' ATTGCGGCCGCACTTTCACAGGAGGCTCTC 3'

FnIII-1:
2808-08:
SEQ ID NO: 272
5' AGCAAGCTTGGACGTCCTGCATTTCACCTC 3'

2804-52:
SEQ ID NO: 273
5' ATTGCGGCCGCGGTGCGAATGTACAAGATCTC 3'

FnIII-2 + ID:
2804-41:
SEQ ID NO: 274
5' AGCAAGCTTGAATGCTTCAGTTCCTTCCATTC 3'

2804-51:
SEQ ID NO: 275
5' ATTGCGGCCGCAGTCCTTGCAAAGACGAAGTTG 3'

FnIII-3:
2804-42:
SEQ ID NO: 276
5' AGCAAGCTTGATGCCCGCAGAAGGAGCAG 3'

2804-50:
SEQ ID NO: 277
5' ATTGCGGCCGCTTTAATGGCCACTCTGGTTTC 3'

L1 + CR + L2:
2804-25:
SEQ ID NO: 278
5' AGCAAGCTTGGGAGAAATCTGCGGGCCAG 3'

(SEQ ID NO: 272)
2804-23

L1 + CR:
2804-25:
(SEQ ID NO: 279)
AGC AAG CTT GGG AGA AAT CTG CGG GCC AG (SEQ ID NO: 270)
2804-20

The primers included Hind III and Not I site for cloning as described for the IGF-1R (ECD). The IGF-1R subdomains were cloned into the expression vector pCep4avidin-N such that chicken avidin sequence (with endogenous signal sequence) is joined to the N-terminus of the expressed IGF-1R proteins. Expression of each avidin-fusion protein was achieved by transient transfection of human 293-EBNA cells (Invitrogen) in roller bottles cultures. The cells were grown and maintained in DMEM supplemented with 5% FBS+1× Non-Essential Amino Acids+1× Pen Strep Glut+1× Sodium Pyruvate. Approximately 4-5×10$^7$ 293-EBNA cells were seeded in 850 cm$^2$ roller bottles overnight. The previously seeded cells were then transfected with pCep-4-avidin plasmid DNA the following day using FUGENE™ 6 transfection reagent. The DNA-transfection reagent mixture was prepared in approximately in 6.75 mL serum-free DMEM. 675 µl FUGENE™ 6 transfection reagent was first added, followed by 112.5 µg plasmid DNA. The complex was incubated at room temperature for 30 minutes. The entire mixture was then added to a roller bottle. The roller bottle was gassed with a 5% CO$_2$ gas mixture, capped tightly and placed in a 37° C. incubator on a roller rack rotating at 0.35 RPM. The transfection was performed for 24 hours after which the medium was replaced with 100 mL DMEM+1× Insulin-Transferrin-Selenium Supplement+1× Pen Strep Glu+1× Non-Essential Amino Acids+1× Sodium Pyruvate. Harvest of the condition medium and replacement with fresh medium occurred 48 hr intervals (2-3 cycles). The harvested serum-free conditioned medium was pooled together and clarified by centrifugation at 10,000×g for 30 minutes at 4° C.

The concentration of avidin-fusion in each conditioned medium was determined using a quantitative FACS based method. The avidin fusion protein in 200 µl of conditioned medium was captured by incubation for 2 hr at room temperature with 5 µl (~3.5×10$^5$) of biotin coated polystyrene beads (Spherotech, Inc., Libertyville, Ill.). The conditioned medium was removed by three cycles of centrifugation and resuspension of the avidin-coated beads in PBS containing 0.5% BSA (BPBS). The avidin-beads were stained with 1 µg/ml of goat FITC-labeled anti-avidin antibody (Vector Lab Burlingame, Calif.) in 1 ml BPBS. After 0.5 hr incubation antibody-beads complexes were collected by centrifugation at 1800 rpm for 5 min and the pellet was washed three times. The FITC fluorescence was detected with a FACSCAN (Beckton Dickson Bioscience, Franklin Lakes, N.J.). The signal was converted to protein mass using a standard curve derived with recombinant avidin. For epitope mapping the biotin-beads were loaded with 50-100 ng avidin-fusion protein per ~3.5×10$^5$ beads of beads by incubation with the appropriate amount (1-20 ml) of conditioned medium. The loaded beads were washed extensively and resuspended in 1 ml BPBS. For all experiment the biotin-beads were blocked with 10% BSA in PBS prior to loading fusion protein.

Method 1, One Color Assay: Biotin-coated polystyrene beads loaded with IGF-1R (ECD) and IGF-1R subdomain fusion proteins were mixed with 1 µg of anti-IGF-1R antibody in 1 ml of BPBS. After incubation for 1 hr at room temperature, 4 ml washing buffer was added and the antibody-beads complexes were collected by centrifugation for 5 min at 750 g. The pellet was washed 3 times by resuspension in 4 ml of BPBS. The antibody bound to avidin-bead complexes was detected by treatment with 0.5 µg/ml Phycoerythrin-(PE) labeled goat anti-human F(ab')2 (Southern Biotech Associates, Inc., Birmingham, Ala.) in 1 ml BPBS. Tested antibodies were found to bind to the avidin-fusion protein containing the complete IGF-1R ECD and the L2 domain. Binding to L1, CR or FnIII-1 was not detected in this experiment. A relatively weak reaction was also observed with the L1 domain.

Method 2, Two color assay: To simultaneously monitor the amounts of anti-IGF-1R monoclonal antibody and avidin-fusion bound to biotin-beads, FITC-labeled anti-avidin antibody was included (1 µg/ml) was included in the binding reaction in combination with 0.5 µg/ml PE-labeled goat anti-human IgG1. The beads were prepared for FACSCAN analysis as described for the one color assay.

Method 3, Antibody Competition: To prepare for labeling with fluorescein the antibodies were dialyzed or resuspended at a concentration of 1 mg/ml in PBS (pH 8.5). Label ([6-fluorescein-5- (and -6)-carboxamido]hexanoic acid, succinimidyl ester 5(6)-SFX] mixed isomers from Molecular Probes (Eugene, Oreg., Cat. No. F2181) was added to the protein at a molar ratio 9.5:1 (label:protein) from a label stock of 5 mg/ml in DMSO. The mixture was incubated at 4° C. overnight in the dark. The labeled antibody was separated from the free label by dialysis in PBS. The FITC/antibody ratios obtained ranged from 3 to 8. For each competition experiment, a binding reaction was assembled that contained a 50 fold excess (10-50 µg/ml) of unlabeled competitor antibody, 3.5×10$^5$ biotin beads coated with avidin fusion protein in BPBS. The FITC-labeled antibody (1 µg/ml) was added after a 30 min preincubation. The process followed the one color method from this point forward.

Each of the four tested antibodies binds to the IGF-1R L2 domain, as shown in Table 8. However, the precise amino acid contacts of each antibody in the IGF-1R L2 domain may differ.

TABLE 8

| Antibody | L1[1] | CR[1] | L2[1] | FnIII-1[1] | ECD[1,2] |
|---|---|---|---|---|---|
| TQ11C | No | No | Yes | No | Yes |
| TQ25 | No | No | Yes | No | Yes |
| TQ58 | Yes | No | Yes | No | Yes |
| TQ59 | No | No | Yes | No | Yes |

[1]Epitope mapping was performed with avidin-IGF-1R fusion proteins containing the indicated human IGF-1R regions.
[2]The ECD fusion contains L1 + CR + L2 + FnIII-1 + FnIII-2 + ID + FnIII-3.

EXAMPLE 13

Antibody Binding to Cell-Surface IGF-1R

This example provides a method for detecting the binding of an anti-IGF-1R antibody to cell-surface expressed IGF-1R.

The ability of antibodies TQ11C, TQ25, TQ58, and TQ59 to bind to human IGF-1R displayed on the cell surface was evaluated using Balb/C 3T3 fibroblasts and MCF-7 human breast cancer cells engineered to overexpress the human IGF-1R receptor at a level of ~3-4×10$^5$ molecules per cell. A Balb/C 3T3 cell line that stably overexpresses the human IGF-1R (~3×10$^5$ receptors per cell) was derived using with a retroviral vector essentially as described by Pietrzkowski et al., 1992, Cell Growth Differentiation 3:199-205. MCF-7 breast cancer cells that overproduce huIGF-1R were transfected with a pcDNA3.1 expression vector (Invitrogen Corp.). Zeocin resistant cells that express a high level of hu IGF-1R (~4×10$^5$ receptors per cell) were expanded after selection by FACS using anti-IGF-1R monoclonal antibody αIR3 and an PE-labeled goat anti murine IgG antibody (Caltag Laboratories, Burlingame, Calif.). The process of selection and expansion was repeated four times.

IGF-1R Receptor antibody staining and receptor expression was monitored by FACS as follows: the cells were released from T175 flasks (Corning) by washing 2 times with excess PBS (Ca/Mg free) followed by treatment with 5 ml of Cell Dissociation Buffer (Sigma) for 10 min at room temperature. The cells were collected by centrifugation and washed two times by resuspending them in PBS and centrifugation. For primary antibody staining, 1 µg of antibody was added to 10$^6$ cells resuspended in 100 µl PBS plus 0.5% BSA (BPBS) and the cells were incubated at 4° C. for 1.5 hr. The cells were collected by centrifugation and washed twice with BPBS to remove unbound primary antibody. The cells were resuspended in 100 µl of BPBS and incubated with 1 µg of FITC-labeled goat anti-human F(ab')2 (Southern Biotechnology Associates, Inc., Birmingham, Ala.) at 4° C. for 30 minutes. After washing to remove unbound FITC secondary antibody, the cells were resuspended in 1 ml of PBS+0.5% BSA and FITC cell fluorescence was detected with a FACSCAN (Beckton Dickson Bioscience, Franklin Lakes, N.J.). The fluorescence levels were converted to absolute receptor levels using Quantum microbead (Bangs Laboratories, Inc., Fishers, Ind.) with predetermined IgG1 binding capacity to generate a standard curve. Data reduction was performed with QuickCal v2.1 software (Verity Software House, Topsham, Me.) provided by the manufacturer.

The peak fluorescent intensity of anti-IGF-1R antibody labeling of the IGF-1R overexpressors was increased 10-20 fold relative to parental Balb/C 3T3 and MCF-7 cells for each of the tested antibodies. This is the result predicted for an antibody that specifically binds IGF-1R. Background fluorescence of cells treated with no antibodies or FITC-labeled secondary alone were insignificant.

EXAMPLE 14

Inhibition of IGF-1R

This example presents methods of detecting inhibition of IGF-1R by anti-IGF-1R antibodies.

32D hu IGF-1R+IRS-1 Cell Inhibition

Murine 32D cells that coexpress the human IGF-1R receptor (20K per cell) and human IRS-1 have proven to be a effective system to examine the molecular components IGF-1R signaling Valentinis et al., 1999, J Biol Chem 274:12423-30. Normal 32D cells express relatively low levels of the murine orthologs of these two gene products. 32D cell normally required IL3 for growth and survival. IGF-1 or IGF-2 can replace IL3 in 32D huIGF-1R+IRS-1 cells as shown in FIG. 16, panel A. The $EC_{50}$ to the IGF-1 dose response curve was about 0.5 nM, whereas the IGF-2 $EC_{50}$ (2.8 nM) is about six fold higher reflecting weaker affinity of IGF-2 for IGF-1R. To assess the ability of the antibodies TQ11C, TQ25, TQ58, and TQ59 to block IGF-1 or IGF-2 stimulation, 96-well microtitre plates were seeded with 30,000 32D hu IGF-1R+ IRS-1 cells per well in a volume of 200 µl of RPMI (Gibco/BRL) containing 5% fetal bovine serum (Gibco/BRL) and 1× penicillin, streptomycin, glutamine (Gibco/BRL) and increasing concentrations of antibody ($10^{-12}$M to $10^{-6}$M) or no antibody. IGF-1 (2 nM), IGF-2 (8 nM) or nothing was added after 1 hr preincubation with antibody. $^3$H-thymidine (1 µCi per well) was added at 27 hr post-antibody addition. The cells were harvested 21 hr later, and incorporation of $^3$H-thymidine into DNA was determined for each sample. The assays were performed in triplicate. An anti-CD20 antibody was used as a negative control. Each of antibodies TQ11C, TQ25, TQ58, and TQ59 was able to completely block the IGF-1 and IGF-2 mediated stimulation of the 32D cells. The reduction of background proliferation in the absence of added IGF-1 and IGF-2 is due to the inhibition of serum IGF-1 and IGF-2. The binding data were analyzed using GraphPad PRIZM™ software. The data are shown in FIG. 16.

Balb/C 3T3 hu IGF-1R Cell Inhibition

IGF-1 greatly stimulates the incorporation of $^3$H-thymidine by serum-starved cultures of mouse embryonic fibroblasts (Balb/C 3T3 or NIH 3T3) that overexpress IGF-1R (~1×10$^6$ IGF1R per cell). Kato et al., 1993, J Biol Chem 268:2655-61; Pietrzkowski et al., 1992, Cell Growth Differentiation 3:199-205. This phenomenon is recapitulated with both IGF-1 and IGF-2 in a Balb/C 3T3 cell line hu IGF-1R overexpressor. Both growth factors stimulated $^3$H-thymidine incorporation by about 20-fold. The $EC_{50}$ of the IGF-1 dose response curve was about 0.7 nM, whereas the IGF-2 $EC_{50}$ (4.4 nM) is sevenfold higher, indicating a weaker affinity of IGF-2 for IGF-1R. To assess the ability of a given antibody to block IGF-1 or IGF-2 stimulation, 96-well microtitre plates were seeded with 10,000 cells per well in a volume of 200 µl of DMEM (Gibco/BRL) containing 10% calf serum (Gibco/BRL) and 1× penicillin, streptomycin, glutamine (Gibco/BRL). After overnight incubation when the cells were about 80% confluent the growth medium was replaced with 100 µl DMEM containing 0.1% BSA after washing once with 200 µl PBS. Antibodies at increasing concentrations ($10^{-12}$ M to $10^{-6}$ M), or no antibody, were added at 24 hr post-serum starvation. IGF-1 (2 nM), IGF-2 (8 nM) and $^3$H-thymidine (1 µCi per well) were added after a 1 hr preincubation with antibody. The cells were harvested 24 hr later, and incorporation of $^3$H-thymidine into DNA was determined for each sample. The assays were performed in triplicate. Each tested antibody was able to completely block the IGF-1 and IGF-2 mediated stimulation of Balb/C 3T3 cells, as shown in FIG. 17. An anti-CD20 antibody was used as a negative control ("CD20" in FIG. 17).

Each reference cited herein is incorporated by reference in its entirety for all that it teaches and for all purposes.

What is claimed is:

1. An isolated anti-IGF-1R antibody, or an isolated antigen-binding fragment thereof, wherein said antibody or fragment comprises a light chain variable region and a heavy chain variable region, and wherein:
   a. said light chain variable region comprises the amino acid sequence of SEQ ID NO:32; and
   said heavy chain variable region comprises the amino acid sequence of SEQ ID NO:136; or
   b. said light chain variable region comprises:
      i. the CDR 1 sequence of residues 24 through 39 of SEQ ID NO:32; and
      ii. the CDR 2 sequence of residues 55 through 61 of SEQ ID NO:32; and
      iii. the CDR 3 sequence of residues 94 through 102 of SEQ ID NO:32;
      and said heavy chain variable region comprises:
      i. the CDR 1 sequence of residues 31 through 36 of SEQ ID NO:136; and
      ii. the CDR 2 sequence of residues 51 through 66 of SEQ ID NO:136; and
      iii. the CDR 3 sequence of residues 99 through 108 of SEQ ID NO:136; or
   c. said light chain variable region is at least 90 percent identical to SEQ ID NO:32 and said heavy chain variable region is at least 90 percent identical to SEQ ID NO:136.

2. The antibody or antigen-binding fragment thereof of claim 1 further comprising:
   a. the kappa light chain constant sequence of SEQ ID NO:234,
   b. the IgG1 heavy chain constant sequence of SEQ ID NO:235, or
   c. the kappa light chain constant sequence of SEQ ID NO:234 and the IgG1 heavy chain constant sequence of SEQ ID NO:235.

3. The antibody or antigen-binding fragment thereof of claim 1, that
   a. cross-competes with a reference antibody for binding to IGF-1R; or
   b. binds to the same epitope of IGF-1R as said reference antibody;
wherein said reference antibody is L16H16 comprises the light chain and heavy chain variable domain sequences of SEQ ID NO: 32 and SEQ ID NO: 136, respectively.

4. The antibody or antigen-binding fragment thereof of claim 1, that, when bound to a human IGF-1R, inhibits binding of IGF-1 and IGF-2 to said human IGF-1R.

5. The antibody or antigen-binding fragment thereof of claim 1, that inhibits the growth of a cancer cell by greater than about 80% in the presence of a growth stimulant selected from the group consisting of serum, IGF-1, and IGF-2.

6. The antibody or antigen-binding fragment thereof of claim 5, wherein said cancer cell is an MCF-7 human breast cancer cell.

7. The antibody or antigen-binding fragment thereof of claim 1, that binds to human IGF-1R with a selectivity that is at least fifty times greater than its selectivity for human insulin receptor.

8. The antibody or antigen-binding fragment thereof of claim 1, that inhibits tumor growth in vivo.

9. The antibody or antigen-binding fragment thereof of claim 1, that inhibits IGF-1R mediated tyrosine phosphorylation.

10. The antibody or antigen-binding fragment thereof of claim 1, wherein said antibody is:
   a. a human antibody;
   b. a humanized antibody;
   c. a chimeric antibody;
   d. a monoclonal antibody;
   e. a polyclonal antibody;
   f. a recombinant antibody;
   g. an antigen-binding antibody fragment;
   h. a single chain antibody;
   i. a diabody;
   j. a triabody;
   k. a tetrabody;
   l. a Fab fragment;
   m. a $F(ab')_2$ fragment;
   n. a domain antibody;
   o. an IgD antibody;
   p. an IgE antibody;
   q. an IgM antibody;
   r. an IgG1 antibody;
   s. an IgG2 antibody;
   t. an IgG3 antibody;
   u. an IgG4 antibody; or
   v. an IgG4 antibody having at least one mutation in a hinge region that alleviates a tendency to form intra-H chain disulfide bond.

11. A composition comprising the antibody or antigen-binding fragment thereof of claim 1 and a pharmaceutically acceptable carrier, diluent, or excipient.

12. The antibody or antigen-binding fragment thereof of claim 1, wherein:
   said light chain variable region that is at least 95 percent identical to SEQ ID NO:32; and
   said heavy chain variable region that is at least 95 percent identical to SEQ ID NO:136.

13. The antibody or antigen-binding fragment thereof of claim 1, wherein:
   said light chain variable region that is at least 97 percent identical to SEQ ID NO:32; and
   said heavy chain variable region that is at least 97 percent identical to SEQ ID NO:136.

14. The antibody or antigen-binding fragment thereof of claim 1, wherein:
   said light chain variable region that is at least 99 percent identical to SEQ ID NO:32; and
   said heavy chain variable region that is at least 99 percent identical to SEQ ID NO:136.

15. The antibody or antigen-binding fragment thereof of claim 1, wherein:
   said light chain variable region has the sequence of SEQ ID NO:32; and
   said heavy chain variable region has the sequence of SEQ ID NO:136.

16. An isolated antibody that specifically binds to human IGF-1R, wherein the light chain of said isolated antibody comprises the variable region of SEQ ID NO:32 and the kappa light chain constant sequence of SEQ ID NO:234, and the heavy chain of said isolated antibody comprises the heavy chain variable region of SEQ ID NO:136 and the IgG1 heavy chain constant sequence of SEQ ID NO:235.

* * * * *

```
                        SEQUENCE LISTING

<160> NUMBER OF SEQ ID NOS: 279

<210> SEQ ID NO 1
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 1 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 agt gga tac aac tat ttg gat tgg tac ctg cag aag cca ggg cag tct     144
Ser Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccg atc acc ttc ggc caa ggg aca cga ctg gag att aaa     336
Leu Gln Thr Pro Ile Thr Phe Gly Gln Gly Thr Arg Leu Glu Ile Lys
            100                 105                 110

<210> SEQ ID NO 2
<211> LENGTH: 112
<212> TYPE: PRT
<213> ORGANISM: Artificial Sequence
<220> FEATURE:
<223> OTHER INFORMATION: light chain variable region

<400> SEQUENCE: 2

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Ser Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
            85                  90                  95

Leu Gln Thr Pro Ile Thr Phe Gly Gln Gly Thr Arg Leu Glu Ile Lys
            100                 105                 110

<210> SEQ ID NO 3
<211> LENGTH: 327
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(327)

<400> SEQUENCE: 3 atg act cag tct cca ctc tcc ctg ccc gtc acc cct gga gag ccg gcc      48
Met Thr Gln Ser Pro Leu Ser Leu Pro Val Thr Pro Gly Glu Pro Ala
1               5                   10                  15 tcc atc tcc tgc agg tct agt cag agc ctc ctg cat agt aat gga tac      96
Ser Ile Ser Cys Arg Ser Ser Gln Ser Leu Leu His Ser Asn Gly Tyr
            20                  25                  30 aac tat ttg gat tgg tac ctg cag aag cca ggg cag tct cca cag ctc     144
Asn Tyr Leu Asp Trp Tyr Leu Gln Lys Pro Gly Gln Ser Pro Gln Leu
        35                  40                  45 ctg atc tat ttg ggt tct aat cgg gcc tcc ggg gtc cct gac agg ttc     192
Leu Ile Tyr Leu Gly Ser Asn Arg Ala Ser Gly Val Pro Asp Arg Phe
    50                  55                  60 agt ggc agt gga tca ggc aca gat ttt aca ctg aaa atc agc aga gtg     240
Ser Gly Ser Gly Ser Gly Thr Asp Phe Thr Leu Lys Ile Ser Arg Val
65                  70                  75                  80 gag gct gag gat gtt ggg gtt tat tac tgc atg caa gct cta caa act     288
Glu Ala Glu Asp Val Gly Val Tyr Tyr Cys Met Gln Ala Leu Gln Thr
                85                  90                  95 ccg atc acc ttc ggc caa ggg aca cga ctg gag att aaa                 327
Pro Ile Thr Phe Gly Gln Gly Thr Arg Leu Glu Ile Lys
            100                 105

<210> SEQ ID NO 4
<211> LENGTH: 109
<212> TYPE: PRT
<213> ORGANISM: Artificial Sequence
<220> FEATURE:
<223> OTHER INFORMATION: light chain variable region

<400> SEQUENCE: 4

Met Thr Gln Ser Pro Leu Ser Leu Pro Val Thr Pro Gly Glu Pro Ala
1               5                   10                  15

Ser Ile Ser Cys Arg Ser Ser Gln Ser Leu Leu His Ser Asn Gly Tyr
            20                  25                  30

Asn Tyr Leu Asp Trp Tyr Leu Gln Lys Pro Gly Gln Ser Pro Gln Leu
        35                  40                  45

Leu Ile Tyr Leu Gly Ser Asn Arg Ala Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Val Gly Val Tyr Tyr Cys Met Gln Ala Leu Gln Thr
                85                  90                  95

Pro Ile Thr Phe Gly Gln Gly Thr Arg Leu Glu Ile Lys
            100                 105
```

<210> SEQ ID NO 5
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 5

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cca ctc act ttc ggc ggc ggg acc aag gtg gag atc aaa     336
Leu Gln Thr Pro Leu Thr Phe Gly Gly Gly Thr Lys Val Glu Ile Lys
            100                 105                 110
```

<210> SEQ ID NO 6
<211> LENGTH: 112
<212> TYPE: PRT
<213> ORGANISM: Artificial Sequence
<220> FEATURE:
<223> OTHER INFORMATION: light chain variable region

<400> SEQUENCE: 6

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 7
<211> LENGTH: 336
<212> TYPE: DNA
<213> ORGANISM: Artificial Sequence
<220> FEATURE:
<223> OTHER INFORMATION: light chain variable region

```
<220> FEATURE:
<221> NAME/KEY: CDS
<222> LOCATION: (1)..(336)

<400> SEQUENCE: 7 gaa att gtg atg acg cag tct cca ctc tcc ctg ccc gtc acc cct gga      48
Glu Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct cac act ttc ggc gga ggg acc aag gtg gag atc aaa     336
Leu Gln Thr Pro His Thr Phe Gly Gly Gly Thr Lys Val Glu Ile Lys
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: light chain variable region

<400> SEQUENCE: 8

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro His Thr Phe Gly Gly Gly Thr Lys Val Glu Ile Lys
            100                 105                 110

<210> SEQ ID NO 9
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 9 gaa att gtg ctg act cag tct cca ctc tcc ctg ccc gtc acc cct gga      48
```

```
                Glu Ile Val Leu Thr Gln Ser Pro Leu Ser Leu Pro Val Thr Pro Gly
                1               5                   10                  15 gag ccg gcc tcc atc tcc tgc agg tct agt cag agc ctc ctg cat agt            96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct           144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct           192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca ctg aaa atc           240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct           288
Ser Arg Val Glu Ala Glu Asp Val Gly Val Tyr Tyr Cys Met Gln Ala
                85                  90                  95 cta caa acc cct ctc act ttc ggc cct ggg acc aaa gtg gat atc aaa           336
Leu Gln Thr Pro Leu Thr Phe Gly Pro Gly Thr Lys Val Asp Ile Lys
            100                 105                 110

<210> SEQ ID NO 10
<211> LENGTH: 112
<212> TYPE: PRT
<213> ORGANISM: Artificial Sequence
<220> FEATURE:
<223> OTHER INFORMATION: light chain variable region

<400> SEQUENCE: 10

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Pro Gly Thr Lys Val Asp Ile Lys
            100                 105                 110

<210> SEQ ID NO 11
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 11 gat gtt gtg atg act cag tct cca ctc tcc ctg gcc gtc acc cct gga            48
Asp Val Val Met Thr Gln Ser Pro Leu Ser Leu Ala Val Thr Pro Gly
1               5                   10                  15 gag ccg gcc tcc atc tcc tgc agg tct agt cag agc ctc ctg cat agt            96
Glu Pro Ala Ser Ile Ser Cys Arg Ser Ser Gln Ser Leu Leu His Ser
                20                  25                  30
```

```
aat gga tac aac tat ttg gat tgg tac ctg cag aag cca ggg cag tct        144
Asn Gly Tyr Asn Tyr Leu Asp Trp Tyr Leu Gln Lys Pro Gly Gln Ser
         35                  40                  45 cca cag ctc ctg atc tat ttg ggt tct aat cgg gcc tcc ggg gtc cct        192
Pro Gln Leu Leu Ile Tyr Leu Gly Ser Asn Arg Ala Ser Gly Val Pro
 50                  55                  60 gac agg ttc agt ggc agt gga tca ggc aca gat ttt aca ctg aaa atc        240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct        288
Ser Arg Val Glu Ala Glu Asp Val Gly Val Tyr Tyr Cys Met Gln Ala
                 85                  90                  95 cta caa act ccg ctc act ttc ggc gga ggg acc aag gtg gag atc aaa        336
Leu Gln Thr Pro Leu Thr Phe Gly Gly Gly Thr Lys Val Glu Ile Lys
            100                 105                 110
```

<210> SEQ ID NO 12
<211> LENGTH: 112
<212> TYPE: PRT
<213> ORGANISM: Artificial Sequence
<220> FEATURE:
<223> OTHER INFORMATION: light chain variable region

<400> SEQUENCE: 12

```
Asp Val Val Met Thr Gln Ser Pro Leu Ser Leu Ala Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
```

<210> SEQ ID NO 13
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 13

```
gat gtt gtg atg act cag tct cca ctc tcc ctg ccc gtc acc cct gga         48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt         96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct        144
Asn Gly Tyr Asn Tyr Leu Asp Trp Tyr Leu Gln Lys Pro Gly Gln Ser
         35                  40                  45 cca cag ctc ctg atc tat ttg ggt tct aat cgg gcc tcc ggg gtc cct        192
Pro Gln Leu Leu Ile Tyr Leu Gly Ser Asn Arg Ala Ser Gly Val Pro
 50                  55                  60
```

```
gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                 85                  90                  95 cta caa act cct ctc act ttc ggc gga ggg acc aag gtg gag atc aaa       336
Leu Gln Thr Pro Leu Thr Phe Gly Gly Gly Thr Lys Val Glu Ile Lys
            100                 105                 110
```

<210> SEQ ID NO 14
<211> LENGTH: 112
<212> TYPE: PRT
<213> ORGANISM: Artificial Sequence
<220> FEATURE:
<223> OTHER INFORMATION: light chain variable region

<400> SEQUENCE: 14

```
Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110
```

<210> SEQ ID NO 15
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 15

```
gat gtt gtg atg act cag tct cca ctc tcc ctg ccc gtc acc cct gga        48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
 65                  70                  75                  80 agc aga gtg gag gct gaa gat gtt ggg gtt tat tac tgt atg caa gct       288
Ser Arg Val Glu Ala Glu Asp Val Gly Val Tyr Tyr Cys Met Gln Ala
```

```
                    85                  90                  95
cta caa acc ccc ctc act ttc ggc gga ggg acc aag gtg gag atc aaa        336
Leu Gln Thr Pro Leu Thr Phe Gly Gly Gly Thr Lys Val Glu Ile Lys
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: light chain variable region

<400> SEQUENCE: 16

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 17
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 17 gat gtt gtg atg act cag tct cca ctc tcc ctg ccc gtc acc cct gga        48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct        144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct        192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc        240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct        288
Ser Arg Val Glu Ala Glu Asp Val Gly Val Tyr Tyr Cys Met Gln Ala
                85                  90                  95 cta caa act ccg ttc acc ttc ggc caa ggg aca cga ctg gag att aaa        336
Leu Gln Thr Pro Phe Thr Phe Gly Gln Gly Thr Arg Leu Glu Ile Lys
            100                 105                 110
```

<210> SEQ ID NO 18
<211> LENGTH: 112
<212> TYPE: PRT
<213> ORGANISM: Artificial Sequence
<220> FEATURE:
<223> OTHER INFORMATION: light chain variable region

<400> SEQUENCE: 18

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Gln Gly Thr Arg Leu Glu Ile Lys
            100                 105                 110
```

<210> SEQ ID NO 19
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 19

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct ctg gcg ttc ggc caa ggg acc aag gtg gaa atc aaa     336
Leu Gln Thr Pro Leu Ala Phe Gly Gln Gly Thr Lys Val Glu Ile Lys
            100                 105                 110
```

<210> SEQ ID NO 20
<211> LENGTH: 112
<212> TYPE: PRT
<213> ORGANISM: Artificial Sequence
<220> FEATURE:
<223> OTHER INFORMATION: light chain variable region

<400> SEQUENCE: 20

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ala Phe Gly Gln Gly Thr Lys Val Glu Ile Lys
            100                 105                 110
```

<210> SEQ ID NO 21
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 21

```
gaa att gtg ctg act cag tct cca ctc tcc ctg ccc gtc acc cct gga      48
Glu Ile Val Leu Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg aat tgg tac ctg cag aag cca ggg cag tct     144
Asn Gly Tyr Asn Tyr Leu Asn Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt gcc agt gga tca ggc aca gat ttt aca ctg aaa atc     240
Asp Arg Phe Ser Ala Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct atc acc ttc ggc caa ggg aca cga ctg gag att aaa     336
Leu Gln Thr Pro Ile Thr Phe Gly Gln Gly Thr Arg Leu Glu Ile Lys
            100                 105                 110
```

<210> SEQ ID NO 22
<211> LENGTH: 112
<212> TYPE: PRT
<213> ORGANISM: Artificial Sequence
<220> FEATURE:
<223> OTHER INFORMATION: light chain variable region

<400> SEQUENCE: 22

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asn Trp Tyr Leu Gln Lys Pro Gly Gln Ser
            35                  40                  45

Pro Gln Leu Leu Ile Tyr Leu Gly Ser Asn Arg Ala Ser Gly Val Pro
         50                  55                  60

Asp Arg Phe Ser Ala Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Ile Thr Phe Gly Gln Gly Thr Arg Leu Glu Ile Lys
            100                 105                 110

<210> SEQ ID NO 23
<211> LENGTH: 333
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(333)

<400> SEQUENCE: 23 aat ttt atg ctg act cag ccc cac tct gtg tcg gag tct ccg ggg aag      48
Asn Phe Met Leu Thr Gln Pro His Ser Val Ser Glu Ser Pro Gly Lys
 1               5                  10                  15 acg gta acc atc tcc tgc acc cgc agc agt ggc agc att gcc agc aac      96
Thr Val Thr Ile Ser Cys Thr Arg Ser Ser Gly Ser Ile Ala Ser Asn
             20                  25                  30 tat gtg cag tgg tac cag cag cgc ccg ggc agt tcc ccc acc act gtg     144
Tyr Val Gln Trp Tyr Gln Gln Arg Pro Gly Ser Ser Pro Thr Thr Val
         35                  40                  45 atc tat gag gat aac caa aga ccc tct ggg gtc cct gat cgg ttc tct     192
Ile Tyr Glu Asp Asn Gln Arg Pro Ser Gly Val Pro Asp Arg Phe Ser
     50                  55                  60 ggc tcc atc gac agc tcc tcc aac tct gcc tcc ctc acc atc tct gga     240
Gly Ser Ile Asp Ser Ser Ser Asn Ser Ala Ser Leu Thr Ile Ser Gly
 65                  70                  75                  80 ctg aag act gag gac gag gct gac tac tac tgt cag tct tat gat agc     288
Leu Lys Thr Glu Asp Glu Ala Asp Tyr Tyr Cys Gln Ser Tyr Asp Ser
                 85                  90                  95 agc aat cag aga gtg ttc ggc gga ggg acc aag ctg acc gtc cta         333
Ser Asn Gln Arg Val Phe Gly Gly Gly Thr Lys Leu Thr Val Leu
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: light chain variable region

<400> SEQUENCE: 24

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
             20                  25                  30

Tyr Val Gln Trp Tyr Gln Gln Arg Pro Gly Ser Ser Pro Thr Thr Val
         35                  40                  45

Ile Tyr Glu Asp Asn Gln Arg Pro Ser Gly Val Pro Asp Arg Phe Ser
     50                  55                  60
```

```
Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn Gln Arg Val Phe Gly Gly Gly Thr Lys Leu Thr Val Leu
            100                 105                 110

<210> SEQ ID NO 25
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 25 gat gtt gtg atg act cag tct cca ctc tcc ctg ccc gtc acc cct gga      48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt     96
Glu Pro Ala Ser Ile Ser Cys Arg Ser Ser Gln Ser Leu Leu His Ser
             20                  25                  30 aat gga tac aac tat ttg gat tgg tac ctg cag aag cca ggg cag tct    144
Asn Gly Tyr Asn Tyr Leu Asp Trp Tyr Leu Gln Lys Pro Gly Gln Ser
         35                  40                  45 cca cag ctc ctg atc tat ttg ggt tct aat cgg gcc tcc ggg gtc cct    192
Pro Gln Leu Leu Ile Tyr Leu Gly Ser Asn Arg Ala Ser Gly Val Pro
     50                  55                  60 gac agg ttc agt ggc agt gga tca ggc aca gat ttt aca ctg aaa atc    240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct    288
Ser Arg Val Glu Ala Glu Asp Val Gly Val Tyr Tyr Cys Met Gln Ala
                 85                  90                  95 cta caa acc ccg ctc act ttc ggc gga ggg acc aag gtg gag atc aaa    336
Leu Gln Thr Pro Leu Thr Phe Gly Gly Gly Thr Lys Val Glu Ile Lys
            100                 105                 110

<210> SEQ ID NO 26
<211> LENGTH: 112
<212> TYPE: PRT
<213> ORGANISM: Artificial Sequence
<220> FEATURE:
<223> OTHER INFORMATION: light chain variable region

<400> SEQUENCE: 26

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
```

<210> SEQ ID NO 27
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 27

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct ctt act ttc ggc gga ggg acc aag gtg gag atc aaa     336
Leu Gln Thr Pro Leu Thr Phe Gly Gly Gly Thr Lys Val Glu Ile Lys
            100                 105                 110
```

<210> SEQ ID NO 28
<211> LENGTH: 112
<212> TYPE: PRT
<213> ORGANISM: Artificial Sequence
<220> FEATURE:
<223> OTHER INFORMATION: light chain variable region

<400> SEQUENCE: 28

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 29
<211> LENGTH: 336
<212> TYPE: DNA
<213> ORGANISM: Artificial Sequence -continued

```
<220> FEATURE:
<223> OTHER INFORMATION: light chain variable region
<220> FEATURE:
<221> NAME/KEY: CDS
<222> LOCATION: (1)..(336)

<400> SEQUENCE: 29 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg caa aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct tat cgg gcc tcc ggg gtc cct     192
Pro Gln Leu Leu Ile Tyr Leu Gly Ser Tyr Arg Ala Ser Gly Val Pro
    50                  55                  60 gac agg ttc agt gcc agt gga tca ggc aca gat ttt aca ctg aaa atc     240
Asp Arg Phe Ser Ala Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccg atc acc ttc ggc caa ggg aca cga ctg gag att aaa     336
Leu Gln Thr Pro Ile Thr Phe Gly Gln Gly Thr Arg Leu Glu Ile Lys
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: light chain variable region

<400> SEQUENCE: 30

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Tyr Arg Ala Ser Gly Val Pro
    50                  55                  60

Asp Arg Phe Ser Ala Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 31
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 31
```

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65              70                  75                  80 agc agg gtg gag gct gag gat gtt ggg gtt tat tac tgc atg caa ggt     288
Ser Arg Val Glu Ala Glu Asp Val Gly Val Tyr Tyr Cys Met Gln Gly
                85                  90                  95 aca cac tgg cct ctg acg ttc ggc caa ggg acc aag gtg gag atc aaa     336
Thr His Trp Pro Leu Thr Phe Gly Gln Gly Thr Lys Val Glu Ile Lys
            100                 105                 110
```

<210> SEQ ID NO 32
<211> LENGTH: 112
<212> TYPE: PRT
<213> ORGANISM: Artificial Sequence
<220> FEATURE:
<223> OTHER INFORMATION: light chain variable region

<400> SEQUENCE: 32

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110
```

<210> SEQ ID NO 33
<211> LENGTH: 335
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(333)

<400> SEQUENCE: 33

```
gaa att gtg atg acg cag tct cca ctc tcc ctg ccc gtc acc cct gga      48
Glu Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
```

```
                    20                  25                  30
aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
             35                  40                  45 cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
     50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct      288
Ser Arg Val Glu Ala Glu Asp Val Gly Val Tyr Tyr Cys Met Gln Ala
                 85                  90                  95 cta caa act cct ctc act ttc ggc gga ggg acc aag gtg gag atc aa       335
Leu Gln Thr Pro Leu Thr Phe Gly Gly Gly Thr Lys Val Glu Ile
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: light chain variable region

<400> SEQUENCE: 34

Glu Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                      40                  45

Pro Gln Leu Leu Ile Tyr Leu Gly Ser Asn Arg Ala Ser Gly Val Pro
     50                  55                      60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile
            100                 105                 110

<210> SEQ ID NO 35
<211> LENGTH: 321
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(321)

<400> SEQUENCE: 35 gac atc cag ttg acc cag tct cca tct tcc gtg tct gcg tct gtc gga     48
Asp Ile Gln Leu Thr Gln Ser Pro Ser Ser Val Ser Ala Ser Val Gly
 1               5                  10                  15 gac aga gtc acc atc act tgt cgg gcg agt cag ggt att agc agg tgg     96
Asp Arg Val Thr Ile Thr Cys Arg Ala Ser Gln Gly Ile Ser Arg Trp
             20                  25                  30 tta gcc tgg tat caa cag aaa cca ggg aaa gcc cct aga ctc ctg atc    144
Leu Ala Trp Tyr Gln Gln Lys Pro Gly Lys Ala Pro Arg Leu Leu Ile
         35                  40                  45 tat gct gcg tcc ggt tta caa agt ggg gtc cca tca agg ttc agc ggc    192
```

```
Tyr Ala Ala Ser Gly Leu Gln Ser Gly Val Pro Ser Arg Phe Ser Gly
         50                  55                  60 agt gga tct ggg aca gat ttc act ctc acc atc agc aac ctg cag cct      240
Ser Gly Ser Gly Thr Asp Phe Thr Leu Thr Ile Ser Asn Leu Gln Pro
 65              70                  75                  80 gaa gat ttt gca act tac tat tgt caa cag gct agc agt ttt cca atc      288
Glu Asp Phe Ala Thr Tyr Tyr Cys Gln Gln Ala Ser Ser Phe Pro Ile
                 85                  90                  95 acc ttc ggc caa ggg aca cga ctg gag act aaa                          321
Thr Phe Gly Gln Gly Thr Arg Leu Glu Thr Lys
                100                 105

<210> SEQ ID NO 36
<211> LENGTH: 107
<212> TYPE: PRT
<213> ORGANISM: Artificial Sequence
<220> FEATURE:
<223> OTHER INFORMATION: light chain variable region

<400> SEQUENCE: 36

Asp Ile Gln Leu Thr Gln Ser Pro Ser Ser Val Ser Ala Ser Val Gly
 1               5                  10                  15

Asp Arg Val Thr Ile Thr Cys Arg Ala Ser Gln Gly Ile Ser Arg Trp
                 20                  25                  30

Leu Ala Trp Tyr Gln Gln Lys Pro Gly Lys Ala Pro Arg Leu Leu Ile
             35                  40                  45

Tyr Ala Ala Ser Gly Leu Gln Ser Gly Val Pro Ser Arg Phe Ser Gly
         50                  55                  60

Ser Gly Ser Gly Thr Asp Phe Thr Leu Thr Ile Ser Asn Leu Gln Pro
 65              70                  75                  80

Glu Asp Phe Ala Thr Tyr Tyr Cys Gln Gln Ala Ser Ser Phe Pro Ile
                 85                  90                  95

Thr Phe Gly Gln Gly Thr Arg Leu Glu Thr Lys
                100                 105

<210> SEQ ID NO 37
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 37 gat gtt gtg atg act cag tct cca ctc tcc ctg ccc gtc acc cct gga       48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
                 20                  25                  30 aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
             35                  40                  45 cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
         50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
 65              70                  75                  80
```

-continued

```
agc aga gtg gag gct gag gat gtt gga gtt tat tac tgc atg caa gct    288
Ser Arg Val Glu Ala Glu Asp Val Gly Val Tyr Tyr Cys Met Gln Ala
                85                  90                  95 cta caa act ccg tac act ttt ggc cag ggg acc aag ctg gag atc aaa    336
Leu Gln Thr Pro Tyr Thr Phe Gly Gln Gly Thr Lys Leu Glu Ile Lys
            100                 105                 110
```

<210> SEQ ID NO 38
<211> LENGTH: 112
<212> TYPE: PRT
<213> ORGANISM: Artificial Sequence
<220> FEATURE:
<223> OTHER INFORMATION: light chain variable region

<400> SEQUENCE: 38

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 39
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 39

```
gat gtt gtg atg act cag tct cca ctc tcc ctg ccc gtc acc cct gga     48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt     96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct    144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct    192
Pro Gln Leu Leu Ile Tyr Leu Gly Ser Asn Arg Ala Ser Gly Val Pro
    50                  55                  60 aac agg ttc agt ggc agt gga tca ggc aca gat ttt aca ctg aaa atc    240
Asn Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct    288
Ser Arg Val Glu Ala Glu Asp Val Gly Val Tyr Tyr Cys Met Gln Ala
                85                  90                  95 cta caa act cca ttc act ttc ggc cct ggg acc aaa gtg gat atc aaa    336
Leu Gln Thr Pro Phe Thr Phe Gly Pro Gly Thr Lys Val Asp Ile Lys
            100                 105                 110
```

-continued

<210> SEQ ID NO 40
<211> LENGTH: 112
<212> TYPE: PRT
<213> ORGANISM: Artificial Sequence
<220> FEATURE:
<223> OTHER INFORMATION: light chain variable region

<400> SEQUENCE: 40

```
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asn Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Phe Thr Phe Gly Pro Gly Thr Lys Val Asp Ile Lys
            100                 105                 110
```

<210> SEQ ID NO 41
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 41

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 cat gga tac aac tat ttg gat tgg tac ctg cag aag cca ggg cag tct     144
His Gly Tyr Asn Tyr Leu Asp Trp Tyr Leu Gln Lys Pro Gly Gln Ser
        35                  40                  45 cca caa ctt ctg atc tat ttg ggt tct tat cgg gcc tcc ggg gtc cct     192
Pro Gln Leu Leu Ile Tyr Leu Gly Ser Tyr Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa tct     288
Ser Arg Val Glu Ala Glu Asp Val Gly Val Tyr Tyr Cys Met Gln Ser
                85                  90                  95 cta gaa gtt ccg ttc act ttt ggc cag ggg acc aag ctg gag atc aaa     336
Leu Glu Val Pro Phe Thr Phe Gly Gln Gly Thr Lys Leu Glu Ile Lys
            100                 105                 110
```

<210> SEQ ID NO 42
<211> LENGTH: 112
<212> TYPE: PRT
<213> ORGANISM: Artificial Sequence
<220> FEATURE:

-continued

<223> OTHER INFORMATION: light chain variable region

<400> SEQUENCE: 42

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Val Pro Phe Thr Phe Gly Gln Gly Thr Lys Leu Glu Ile Lys
            100                 105                 110

<210> SEQ ID NO 43
<211> LENGTH: 321
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(321)

<400> SEQUENCE: 43 tct tct gag ctg act cag gac cct gct gtg tct gtg gcc ttg gga cag      48
Ser Ser Glu Leu Thr Gln Asp Pro Ala Val Ser Val Ala Leu Gly Gln
1               5                   10                  15 aca gtc agg atc aca tgc caa gga gac agc ctc aga att tat tat aca      96
Thr Val Arg Ile Thr Cys Gln Gly Asp Ser Leu Arg Ile Tyr Tyr Thr
            20                  25                  30 ggc tgg tac caa cag aag cca gga cag gcc cct gtg ctt gtc ctc ttt     144
Gly Trp Tyr Gln Gln Lys Pro Gly Gln Ala Pro Val Leu Val Leu Phe
        35                  40                  45 ggt aag aac aat cgg ccc tca ggg atc cca gac cga ttc tct ggc tcc     192
Gly Lys Asn Asn Arg Pro Ser Gly Ile Pro Asp Arg Phe Ser Gly Ser
    50                  55                  60 cac tca ggg aac aca gct tcc ttg acc atc act ggg gct caa gcg gaa     240
His Ser Gly Asn Thr Ala Ser Leu Thr Ile Thr Gly Ala Gln Ala Glu
65                  70                  75                  80 gat gag gct gac tat tac tgt aac tcc cgg gac atc act ggt gtc cat     288
Asp Glu Ala Asp Tyr Tyr Cys Asn Ser Arg Asp Ile Thr Gly Val His
                85                  90                  95 cga ttc ggc gga ggg acc aag ctg acc gtc cta                         321
Arg Phe Gly Gly Gly Thr Lys Leu Thr Val Leu
            100                 105

<210> SEQ ID NO 44
<211> LENGTH: 107
<212> TYPE: PRT
<213> ORGANISM: Artificial Sequence
<220> FEATURE:
<223> OTHER INFORMATION: light chain variable region

<400> SEQUENCE: 44

Ser Ser Glu Leu Thr Gln Asp Pro Ala Val Ser Val Ala Leu Gly Gln
1               5                   10                  15

-continued

```
Thr Val Arg Ile Thr Cys Gln Gly Asp Ser Leu Arg Ile Tyr Tyr Thr
            20                  25                  30

Gly Trp Tyr Gln Gln Lys Pro Gly Gln Ala Pro Val Leu Val Leu Phe
        35                  40                  45

Gly Lys Asn Asn Arg Pro Ser Gly Ile Pro Asp Arg Phe Ser Gly Ser
    50                  55                  60

His Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Thr Gly Val His
                85                  90                  95

Arg Phe Gly Gly Gly Thr Lys Leu Thr Val Leu
            100                 105
```

<210> SEQ ID NO 45
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 45

```
gaa att gtg ctg act cag tct cca ctc tcc ctg ccc gtc acc cct gga       48
Glu Ile Val Leu Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct ctc act ttc ggc gga ggg acc aag gtg gag atc aaa     336
Leu Gln Thr Pro Leu Thr Phe Gly Gly Gly Thr Lys Val Glu Ile Lys
            100                 105                 110
```

<210> SEQ ID NO 46
<211> LENGTH: 112
<212> TYPE: PRT
<213> ORGANISM: Artificial Sequence
<220> FEATURE:
<223> OTHER INFORMATION: light chain variable region

<400> SEQUENCE: 46

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Leu Thr Phe Gly Gly Gly Thr Lys Val Glu Ile Lys
                100                 105                 110

<210> SEQ ID NO 47
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 47 gat gtt gtg atg act cag tct cca ctc tcc ctg ccc gtc acc cct gga      48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
                 20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
             35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
         50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                 85                  90                  95 cta caa act cct aac act ttc ggc gga ggg acc aag gtg gag atc aaa     336
Leu Gln Thr Pro Asn Thr Phe Gly Gly Gly Thr Lys Val Glu Ile Lys
            100                 105                 110

<210> SEQ ID NO 48
<211> LENGTH: 112
<212> TYPE: PRT
<213> ORGANISM: Artificial Sequence
<220> FEATURE:
<223> OTHER INFORMATION: light chain variable region

<400> SEQUENCE: 48

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95
```

```
Leu Gln Thr Pro Asn Thr Phe Gly Gly Gly Thr Lys Val Glu Ile Lys
            100                 105                 110

<210> SEQ ID NO 49
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 49 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cca atc act ttc ggc cct ggg acc aaa gtg gat atc aaa     336
Leu Gln Thr Pro Ile Thr Phe Gly Pro Gly Thr Lys Val Asp Ile Lys
            100                 105                 110

<210> SEQ ID NO 50
<211> LENGTH: 112
<212> TYPE: PRT
<213> ORGANISM: Artificial Sequence
<220> FEATURE:
<223> OTHER INFORMATION: light chain variable region

<400> SEQUENCE: 50

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Pro Gly Thr Lys Val Asp Ile Lys
            100                 105                 110

<210> SEQ ID NO 51
<211> LENGTH: 336
```

```
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 51 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
                20                  25                  30 aat gga tac acc tat ttg gat tgg tac ctg cag aag cca ggg cag tct     144
Asn Gly Tyr Thr Tyr Leu Asp Trp Tyr Leu Gln Lys Pro Gly Gln Ser
            35                  40                  45 cca caa ctc ctg atc tat ttg ggt tct aat cgg gcc tcc ggg gtc cct     192
Pro Gln Leu Leu Ile Tyr Leu Gly Ser Asn Arg Ala Ser Gly Val Pro
        50                  55                  60 gac agg ttc agc ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag cct gag gat gtt ggg gtc tat tac tgc atg caa gct     288
Ser Arg Val Glu Pro Glu Asp Val Gly Val Tyr Tyr Cys Met Gln Ala
                85                  90                  95 cta gaa atg ccc ctc act ttc ggc gga ggg acc aag gtg gag atc aaa     336
Leu Glu Met Pro Leu Thr Phe Gly Gly Gly Thr Lys Val Glu Ile Lys
            100                 105                 110

<210> SEQ ID NO 52
<211> LENGTH: 112
<212> TYPE: PRT
<213> ORGANISM: Artificial Sequence
<220> FEATURE:
<223> OTHER INFORMATION: light chain variable region

<400> SEQUENCE: 52

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Thr Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Pro Glu Asp Val Gly Val Tyr Tyr Cys Met Gln Ala
                85                  90                  95

Leu Glu Met Pro Leu Thr Phe Gly Gly Gly Thr Lys Val Glu Ile Lys
            100                 105                 110

<210> SEQ ID NO 53
<211> LENGTH: 321
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(321)
```

<400> SEQUENCE: 53

```
gac atc cag ttg acc cag tct cca tcc ttc ctg tct gca tct gta gga      48
Asp Ile Gln Leu Thr Gln Ser Pro Ser Phe Leu Ser Ala Ser Val Gly
1               5                   10                  15 gac aga gtc acc atc act tgc cgg gcc agt cag ggc att agc agt tat      96
Asp Arg Val Thr Ile Thr Cys Arg Ala Ser Gln Gly Ile Ser Ser Tyr
                20                  25                  30 tta gcc tgg tat cag caa aaa cca ggg aaa gcc cct aag ctc ctg atc     144
Leu Ala Trp Tyr Gln Gln Lys Pro Gly Lys Ala Pro Lys Leu Leu Ile
            35                  40                  45 tat gct gca tcc act ttg caa agt ggg gtc cca tca agg ttc agc ggc     192
Tyr Ala Ala Ser Thr Leu Gln Ser Gly Val Pro Ser Arg Phe Ser Gly
        50                  55                  60 agt gga tct ggg aca gaa ttc act ctc aca atc agc agc ctg cag cct     240
Ser Gly Ser Gly Thr Glu Phe Thr Leu Thr Ile Ser Ser Leu Gln Pro
65                  70                  75                  80 gaa gat ttt gca act tat tac tgt caa cag ctt aat agt tac ccc ctc     288
Glu Asp Phe Ala Thr Tyr Tyr Cys Gln Gln Leu Asn Ser Tyr Pro Leu
                85                  90                  95 act ttc ggc gga ggg acc aag gtg gag atc aaa                         321
Thr Phe Gly Gly Gly Thr Lys Val Glu Ile Lys
                100                 105
```

<210> SEQ ID NO 54
<211> LENGTH: 107
<212> TYPE: PRT
<213> ORGANISM: Artificial Sequence
<220> FEATURE:
<223> OTHER INFORMATION: light chain variable region

<400> SEQUENCE: 54

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
                100                 105
```

<210> SEQ ID NO 55
<211> LENGTH: 315
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(315)

<400> SEQUENCE: 55

```
tcc tat gtg ctg act cag cca ccc tca gtg tcc gtg tcc cca gga cag      48
Ser Tyr Val Leu Thr Gln Pro Pro Ser Val Ser Val Ser Pro Gly Gln
1               5                   10                  15
```

```
aca gcc agc atc acc tgc tct gga gat aaa ttg ggg gat aaa tat gtt    96
Thr Ala Ser Ile Thr Cys Ser Gly Asp Lys Leu Gly Asp Lys Tyr Val
         20                  25                  30 ggc tgg tat cag caa aag gca ggc caa gcc cct gtt ttg gtc atc tat   144
Gly Trp Tyr Gln Gln Lys Ala Gly Gln Ala Pro Val Leu Val Ile Tyr
             35                  40                  45 caa gac aac aag cga ccc tca ggg atc cct gag cga ttc tct ggc tcc   192
Gln Asp Asn Lys Arg Pro Ser Gly Ile Pro Glu Arg Phe Ser Gly Ser
 50                  55                  60 aac tct ggg aac aca gcc agt ctg acc atc agc ggg acc cag gct atg   240
Asn Ser Gly Asn Thr Ala Ser Leu Thr Ile Ser Gly Thr Gln Ala Met
 65                  70                  75                  80 gat gag gct gac tat tac tgt cag gcg tgg gac agc ggc acg gtg ttc   288
Asp Glu Ala Asp Tyr Tyr Cys Gln Ala Trp Asp Ser Gly Thr Val Phe
                 85                  90                  95 ggc gga ggg acc aag ctg acc gtc cta                               315
Gly Gly Gly Thr Lys Leu Thr Val Leu
            100                 105

<210> SEQ ID NO 56
<211> LENGTH: 105
<212> TYPE: PRT
<213> ORGANISM: Artificial Sequence
<220> FEATURE:
<223> OTHER INFORMATION: light chain variable region

<400> SEQUENCE: 56

Ser Tyr Val Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Val
             20                  25                  30

Gly Trp Tyr Gln Gln Lys Ala Gly Gln Ala Pro Val Leu Val Ile Tyr
         35                  40                  45

Gln Asp Asn Lys Arg Pro Ser Gly Ile Pro Glu Arg Phe Ser Gly Ser
     50                  55                  60

Asn Ser Gly Asn Thr Ala Ser Leu Thr Ile Ser Gly Thr Gln Ala Met
 65                  70                  75                  80

Asp Glu Ala Asp Tyr Tyr Cys Gln Ala Trp Asp Ser Gly Thr Val Phe
                 85                  90                  95

Gly Gly Gly Thr Lys Leu Thr Val Leu
            100                 105

<210> SEQ ID NO 57
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 57 gat gtt gtg atg act cag tct cca ctc tcc ctg ccc gtc acc cct gga    48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt    96
Glu Pro Ala Ser Ile Ser Cys Arg Ser Ser Gln Ser Leu Leu His Ser
             20                  25                  30 aat gga tac aac tat ttg gat tgg tac ctg cag aag cca ggg cag tct   144
Asn Gly Tyr Asn Tyr Leu Asp Trp Tyr Leu Gln Lys Pro Gly Gln Ser
         35                  40                  45
```

| | |
|---|---|
| cca cag ctc ctg atc tat ttg ggt tct aat cgg gcc tcc ggg gtc cct<br>Pro Gln Leu Leu Ile Tyr Leu Gly Ser Asn Arg Ala Ser Gly Val Pro<br>50 55 60 | 192 |
| gac agg ttc agt ggc agt gga tca ggc aca gat ttt aca ctg aaa atc<br>Asp Arg Phe Ser Gly Ser Gly Ser Gly Thr Asp Phe Thr Leu Lys Ile<br>65 70 75 80 | 240 |
| agc aga gtg gag gct gag gat gtt ggg gtt tat tac tgc atg caa gct<br>Ser Arg Val Glu Ala Glu Asp Val Gly Val Tyr Tyr Cys Met Gln Ala<br>85 90 95 | 288 |
| cta caa acc ccc ctc act ttc ggc gga ggg acc aag gtg gag atc aaa<br>Leu Gln Thr Pro Leu Thr Phe Gly Gly Gly Thr Lys Val Glu Ile Lys<br>100 105 110 | 336 |

<210> SEQ ID NO 58
<211> LENGTH: 112
<212> TYPE: PRT
<213> ORGANISM: Artificial Sequence
<220> FEATURE:
<223> OTHER INFORMATION: light chain variable region

<400> SEQUENCE: 58

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 59
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 59

| | |
|---|---|
| gat gtt gtg atg act cag tct cca ctc tcc ctg ccc gtc acc cct gga<br>Asp Val Val Met Thr Gln Ser Pro Leu Ser Leu Pro Val Thr Pro Gly<br>1 5 10 15 | 48 |
| gag ccg gcc tcc atc tcc tgc agg tct agt cag agc ctc ctg cat agt<br>Glu Pro Ala Ser Ile Ser Cys Arg Ser Ser Gln Ser Leu Leu His Ser<br>20 25 30 | 96 |
| aat gga tac aac tat ttg gat tgg tac ctg cag aag cca ggg cag tct<br>Asn Gly Tyr Asn Tyr Leu Asp Trp Tyr Leu Gln Lys Pro Gly Gln Ser<br>35 40 45 | 144 |
| cca cag ctc ctg atc tat ttg ggt tct aat cgg gcc tcc ggg gtc cct<br>Pro Gln Leu Leu Ile Tyr Leu Gly Ser Asn Arg Ala Ser Gly Val Pro<br>50 55 60 | 192 |
| gac agg ttc agt ggc agt gga tca ggc aca gat ttt aca ctg aaa atc<br>Asp Arg Phe Ser Gly Ser Gly Ser Gly Thr Asp Phe Thr Leu Lys Ile | 240 |

```
                  65                  70                  75                  80
agc aga gtg gag gct gag gat gtt ggg gtt tat tac tgc atg gaa gct        288
Ser Arg Val Glu Ala Glu Asp Val Gly Val Tyr Tyr Cys Met Glu Ala
                      85                  90                  95 cta caa act cca ttc act ttc ggc cct ggg acc aag gtg gaa atc aaa        336
Leu Gln Thr Pro Phe Thr Phe Gly Pro Gly Thr Lys Val Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: light chain variable region

<400> SEQUENCE: 60

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glu Ala
                85                  90                  95

Leu Gln Thr Pro Phe Thr Phe Gly Pro Gly Thr Lys Val Glu Ile Lys
            100                 105                 110

<210> SEQ ID NO 61
<211> LENGTH: 321
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(321)

<400> SEQUENCE: 61 gac atc cag ttg acc cag tct cca tcc tcc ctg tct gcg tct gtg gga        48
Asp Ile Gln Leu Thr Gln Ser Pro Ser Ser Leu Ser Ala Ser Val Gly
1               5                   10                  15 gac aga gtc acc atc act tgc cgg tca agt caa ggc att ggt tac ttc        96
Asp Arg Val Thr Ile Thr Cys Arg Ser Ser Gln Gly Ile Gly Tyr Phe
                20                  25                  30 tta aat tgg tat cag cag gaa cca ggg aaa gcc cca aag atc ctg atc       144
Leu Asn Trp Tyr Gln Gln Glu Pro Gly Lys Ala Pro Lys Ile Leu Ile
            35                  40                  45 tct gct gca tcc act ttg caa agt ggg gtc cca tca agg ttc agt ggc       192
Ser Ala Ala Ser Thr Leu Gln Ser Gly Val Pro Ser Arg Phe Ser Gly
        50                  55                  60 agt gga tct ggg aca gat ttc aca ctc tcc atc aac aat ctg caa ccc       240
Ser Gly Ser Gly Thr Asp Phe Thr Leu Ser Ile Asn Asn Leu Gln Pro
65                  70                  75                  80 gca gat ttt gcg aca tac tac tgt caa cag agt cac agt ccc ccg tac       288
Ala Asp Phe Ala Thr Tyr Tyr Cys Gln Gln Ser His Ser Pro Pro Tyr
                85                  90                  95 act ttc ggc cag ggg acc aag gtg gag atc aaa                            321
```

```
Thr Phe Gly Gln Gly Thr Lys Val Glu Ile Lys
            100                 105

<210> SEQ ID NO 62
<211> LENGTH: 107
<212> TYPE: PRT
<213> ORGANISM: Artificial Sequence
<220> FEATURE:
<223> OTHER INFORMATION: light chain variable region

<400> SEQUENCE: 62

Asp Ile Gln Leu Thr Gln Ser Pro Ser Leu Ser Ala Ser Val Gly
1               5                   10                  15

Asp Arg Val Thr Ile Thr Cys Arg Ser Ser Gln Gly Ile Gly Tyr Phe
                20                  25                  30

Leu Asn Trp Tyr Gln Gln Glu Pro Gly Lys Ala Pro Lys Ile Leu Ile
            35                  40                  45

Ser Ala Ala Ser Thr Leu Gln Ser Gly Val Pro Ser Arg Phe Ser Gly
50                  55                  60

Ser Gly Ser Gly Thr Asp Phe Thr Leu Ser Ile Asn Asn Leu Gln Pro
65                  70                  75                  80

Ala Asp Phe Ala Thr Tyr Tyr Cys Gln Gln Ser His Ser Pro Pro Tyr
                85                  90                  95

Thr Phe Gly Gln Gly Thr Lys Val Glu Ile Lys
            100                 105

<210> SEQ ID NO 63
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 63 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccg ctc act ttc ggc gga ggg acc aag gtg gag atc aaa     336
Leu Gln Thr Pro Leu Thr Phe Gly Gly Gly Thr Lys Val Glu Ile Lys
            100                 105                 110

<210> SEQ ID NO 64
<211> LENGTH: 112
<212> TYPE: PRT
```

```
<213> ORGANISM: Artificial Sequence
<220> FEATURE:
<223> OTHER INFORMATION: light chain variable region

<400> SEQUENCE: 64

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 65
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 65 gaa att gtg ctg act cag tct cca ctc tcc ctg ccc gtc acc cct gga      48
Glu Ile Val Leu Thr Gln Ser Pro Leu Ser Leu Pro Val Thr Pro Gly
1               5                   10                  15 gag ccg gcc tcc atc tcc tgc agg tct agt cag agc ctc ctg cat agt     96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct    144
Asn Gly Tyr Asn Tyr Leu Asp Trp Tyr Leu Gln Lys Pro Gly Gln Ser
        35                  40                  45 cca cag ctc ctg atg tat ttg gtt tct aat cgg gcc tcc ggg gtc cct    192
Pro Gln Leu Leu Met Tyr Leu Val Ser Asn Arg Ala Ser Gly Val Pro
    50                  55                  60 gag agg ttc agt ggc agt gga tca ggc aca gat ttt aca ctg aaa atc    240
Glu Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa act    288
Ser Arg Val Glu Ala Glu Asp Val Gly Val Tyr Tyr Cys Met Gln Thr
                85                  90                  95 cta caa act cct ctc agt ttt ggc cag ggg acc aag ctg gag atc aaa    336
Leu Gln Thr Pro Leu Ser Phe Gly Gln Gly Thr Lys Leu Glu Ile Lys
            100                 105                 110

<210> SEQ ID NO 66
<211> LENGTH: 112
<212> TYPE: PRT
<213> ORGANISM: Artificial Sequence
<220> FEATURE:
<223> OTHER INFORMATION: light chain variable region

<400> SEQUENCE: 66

Glu Ile Val Leu Thr Gln Ser Pro Leu Ser Leu Pro Val Thr Pro Gly
```

```
                    1               5                   10                  15
Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Met Tyr Leu Val Ser Asn Arg Ala Ser Gly Val Pro
        50                  55                  60

Glu Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Ser Phe Gly Gln Gly Thr Lys Leu Glu Ile Lys
            100                 105                 110

<210> SEQ ID NO 67
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 67 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccg ctc act ttc ggc gga ggg acc aag gtg gag atc aaa     336
Leu Gln Thr Pro Leu Thr Phe Gly Gly Gly Thr Lys Val Glu Ile Lys
            100                 105                 110

<210> SEQ ID NO 68
<211> LENGTH: 112
<212> TYPE: PRT
<213> ORGANISM: Artificial Sequence
<220> FEATURE:
<223> OTHER INFORMATION: light chain variable region

<400> SEQUENCE: 68

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45
```

```
Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 69
<211> LENGTH: 330
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(330)

<400> SEQUENCE: 69

```
aat ttt atg ctg act cag ccc cac tct gtg tcg gcg tct ccg ggg aag    48
Asn Phe Met Leu Thr Gln Pro His Ser Val Ser Ala Ser Pro Gly Lys
1               5                   10                  15 acg gtt acc atc tcc tgc acc cgc agc agt ggc gac att gac aac aac    96
Thr Val Thr Ile Ser Cys Thr Arg Ser Ser Gly Asp Ile Asp Asn Asn
            20                  25                  30 tat gtg cag tgg tac cag cag cgc ccg ggc aat tcc ccc acc aat gtg   144
Tyr Val Gln Trp Tyr Gln Gln Arg Pro Gly Asn Ser Pro Thr Asn Val
        35                  40                  45 att tat gag gat aac cga aga ccc tct ggg gtc ccg gat cgc ttc tct   192
Ile Tyr Glu Asp Asn Arg Arg Pro Ser Gly Val Pro Asp Arg Phe Ser
    50                  55                  60 ggc tcc atc gac agc tcc tcc aac tct gcc tcc ctc acc atc tct gga   240
Gly Ser Ile Asp Ser Ser Ser Asn Ser Ala Ser Leu Thr Ile Ser Gly
65                  70                  75                  80 ctg cag cct gag gac gag gct gac tac tat tgt cag tct tat caa agc   288
Leu Gln Pro Glu Asp Glu Ala Asp Tyr Tyr Cys Gln Ser Tyr Gln Ser
                85                  90                  95 gac aat tgg gtg ttc ggc gga ggg acc aag gtg acc gtc cta           330
Asp Asn Trp Val Phe Gly Gly Gly Thr Lys Val Thr Val Leu
            100                 105                 110
```

<210> SEQ ID NO 70
<211> LENGTH: 110
<212> TYPE: PRT
<213> ORGANISM: Artificial Sequence
<220> FEATURE:
<223> OTHER INFORMATION: light chain variable region

<400> SEQUENCE: 70

```
Asn Phe Met Leu Thr Gln Pro His Ser Val Ser Ala Ser Pro Gly Lys
1               5                   10                  15

Thr Val Thr Ile Ser Cys Thr Arg Ser Ser Gly Asp Ile Asp Asn Asn
            20                  25                  30

Tyr Val Gln Trp Tyr Gln Gln Arg Pro Gly Asn Ser Pro Thr Asn Val
        35                  40                  45

Ile Tyr Glu Asp Asn Arg Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80
```

```
Leu Gln Pro Glu Asp Glu Ala Asp Tyr Tyr Cys Gln Ser Tyr Gln Ser
                85                  90                  95

Asp Asn Trp Val Phe Gly Gly Gly Thr Lys Val Thr Val Leu
            100                 105                 110

<210> SEQ ID NO 71
<211> LENGTH: 330
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(330)

<400> SEQUENCE: 71 aat ttt atg ctg act cag ccc cac tct gtg tcg gag tct ccg ggg aag      48
Asn Phe Met Leu Thr Gln Pro His Ser Val Ser Glu Ser Pro Gly Lys
1               5                   10                  15 acg gta acc atc tcc tgc acc cgc agc agt ggc agc att gcc agc aac      96
Thr Val Thr Ile Ser Cys Thr Arg Ser Ser Gly Ser Ile Ala Ser Asn
            20                  25                  30 tat gtg cag tgg tac cag cag cgc ccg ggc agt tcc ccc acc act gtg     144
Tyr Val Gln Trp Tyr Gln Gln Arg Pro Gly Ser Ser Pro Thr Thr Val
        35                  40                  45 atc tat gag gat aac caa aga ccc tct ggg gtc cct gat cga ttc tct     192
Ile Tyr Glu Asp Asn Gln Arg Pro Ser Gly Val Pro Asp Arg Phe Ser
    50                  55                  60 ggc tcc atc gac agc tcc tcc aac tct gcc tcc ctc acc atc tct gga     240
Gly Ser Ile Asp Ser Ser Ser Asn Ser Ala Ser Leu Thr Ile Ser Gly
65                  70                  75                  80 ctg aag act gag gac gag gct gac tac tac tgt cag tct tat gat agc     288
Leu Lys Thr Glu Asp Glu Ala Asp Tyr Tyr Cys Gln Ser Tyr Asp Ser
                85                  90                  95 agc aat gtg gtg ttc ggc gga ggg acc aag ctg acc gtc cta              330
Ser Asn Val Val Phe Gly Gly Gly Thr Lys Leu Thr Val Leu
            100                 105                 110

<210> SEQ ID NO 72
<211> LENGTH: 110
<212> TYPE: PRT
<213> ORGANISM: Artificial Sequence
<220> FEATURE:
<223> OTHER INFORMATION: light chain variable region

<400> SEQUENCE: 72

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Val Phe Gly Gly Gly Thr Lys Leu Thr Val Leu
            100                 105                 110
```

```
<210> SEQ ID NO 73
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 73 gat gtt gtg atg act cag tct cca ctc tcc ctg ccc gtc acc cct ggg      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aac cgg gac tct ggg gtc cca     192
Pro Gln Leu Leu Ile Tyr Leu Gly Ser Asn Arg Asp Ser Gly Val Pro
    50                  55                  60 gac aga ttc agc ggc agt ggg tca ggc act gat ttc aca ctg aaa atc     240
Asp Arg Phe Ser Gly Ser Gly Ser Gly Thr Asp Phe Thr Leu Lys Ile
65                  70                  75                  80 agc agg gtg gag gct gag gat gtt ggg gtt tat tac tgc atg caa ggt     288
Ser Arg Val Glu Ala Glu Asp Val Gly Val Tyr Tyr Cys Met Gln Gly
                85                  90                  95 aca cac tgg ccg tac act ttt ggc cag ggg acc agg ctg gag atc aaa     336
Thr His Trp Pro Tyr Thr Phe Gly Gln Gly Thr Arg Leu Glu Ile Lys
            100                 105                 110

<210> SEQ ID NO 74
<211> LENGTH: 112
<212> TYPE: PRT
<213> ORGANISM: Artificial Sequence
<220> FEATURE:
<223> OTHER INFORMATION: light chain variable region

<400> SEQUENCE: 74

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Arg Leu Glu Ile Lys
            100                 105                 110

<210> SEQ ID NO 75
<211> LENGTH: 336
<212> TYPE: DNA
<213> ORGANISM: Artificial Sequence
<220> FEATURE:
<223> OTHER INFORMATION: light chain variable region
<220> FEATURE:
```

```
<221> NAME/KEY: CDS
<222> LOCATION: (1)..(336)

<400> SEQUENCE: 75 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag tcg gcc tcc atc tcc tgc agg tct agt cag agc ctc ctg cat agt      96
Glu Ser Ala Ser Ile Ser Cys Arg Ser Ser Gln Ser Leu Leu His Ser
            20                  25                  30 aat gga tac aac ttt ttg gat tgg tac ctg cag aag cca ggg cag tct     144
Asn Gly Tyr Asn Phe Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct ctc act ttc ggc gga ggg acc aag gtg gag atc aaa     336
Leu Gln Thr Pro Leu Thr Phe Gly Gly Gly Thr Lys Val Glu Ile Lys
            100                 105                 110

<210> SEQ ID NO 76
<211> LENGTH: 112
<212> TYPE: PRT
<213> ORGANISM: Artificial Sequence
<220> FEATURE:
<223> OTHER INFORMATION: light chain variable region

<400> SEQUENCE: 76

Asp Val Val Met Thr Gln Ser Pro Leu Ser Leu Pro Val Thr Pro Gly
1               5                   10                  15

Glu Ser Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 77
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 77 gat gtt gtg atg act cag tct cca ctc tcc ctg ccc gtc acc cct gga      48
Asp Val Val Met Thr Gln Ser Pro Leu Ser Leu Pro Val Thr Pro Gly
```

```
                 1               5                  10                 15
gag ccg gcc tcc atc tcc tgc agg tct agt cag agc ctc ctg cat agt         96
Glu Pro Ala Ser Ile Ser Cys Arg Ser Ser Gln Ser Leu Leu His Ser
                 20                  25                 30 aat gga tac aac tat ttg gat tgg tac ctg cag aag cca ggg cag tct        144
Asn Gly Tyr Asn Tyr Leu Asp Trp Tyr Leu Gln Lys Pro Gly Gln Ser
             35                  40                 45 cca cag ctc ctg atc tat ttg ggt tct aat cgg gcc tcc ggg gtc cct        192
Pro Gln Leu Leu Ile Tyr Leu Gly Ser Asn Arg Ala Ser Gly Val Pro
         50                  55                 60 gac agg ttc agt ggc agt gga tca ggc aca gat ttt aca ctg aaa atc        240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct        288
Ser Arg Val Glu Ala Glu Asp Val Gly Val Tyr Tyr Cys Met Gln Ala
                 85                  90                 95 cta caa acc ccc ctc act ttc ggc gga ggg acc aag gtg gag atc aaa        336
Leu Gln Thr Pro Leu Thr Phe Gly Gly Gly Thr Lys Val Glu Ile Lys
             100                 105                110
```

<210> SEQ ID NO 78
<211> LENGTH: 112
<212> TYPE: PRT
<213> ORGANISM: Artificial Sequence
<220> FEATURE:
<223> OTHER INFORMATION: light chain variable region

<400> SEQUENCE: 78

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 79
<211> LENGTH: 321
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(321)

<400> SEQUENCE: 79

```
gaa acg aca ctc acg cag tct cca gcc acc ctg tct ttg tct cca ggg         48
Glu Thr Thr Leu Thr Gln Ser Pro Ala Thr Leu Ser Leu Ser Pro Gly
1               5                   10                  15 caa aga gcc acc ctc tcc tgc agg gcc agt cag agt gtc tac aac tac         96
Gln Arg Ala Thr Leu Ser Cys Arg Ala Ser Gln Ser Val Tyr Asn Tyr
            20                  25                  30 tta gcc tgg tac caa cag aag cct ggc cag gct ccc agg ctc ctc atc        144
```

```
Leu Ala Trp Tyr Gln Gln Lys Pro Gly Gln Ala Pro Arg Leu Leu Ile
        35                  40                  45 tat gat gca tcc aga agg gca act ggc atc cca gcc agg ttc agt ggc      192
Tyr Asp Ala Ser Arg Arg Ala Thr Gly Ile Pro Ala Arg Phe Ser Gly
 50                  55                  60 agt ggg tct ggg aca gac ttc act ctc acc atc agc agc cta gag cct      240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt aac aac tgg ccg ctc      288
Glu Asp Phe Ala Val Tyr Tyr Cys Gln Gln Arg Asn Asn Trp Pro Leu
                 85                  90                  95 act ttc ggt gga ggg acc aag gtg gag atc aaa                          321
Thr Phe Gly Gly Gly Thr Lys Val Glu Ile Lys
        100                 105

<210> SEQ ID NO 80
<211> LENGTH: 107
<212> TYPE: PRT
<213> ORGANISM: Artificial Sequence
<220> FEATURE:
<223> OTHER INFORMATION: light chain variable region

<400> SEQUENCE: 80

Glu Thr Thr Leu Thr Gln Ser Pro Ala Thr Leu Ser Leu Ser Pro Gly
 1               5                  10                  15

Gln Arg Ala Thr Leu Ser Cys Arg Ala Ser Gln Ser Val Tyr Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Arg Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Asn Trp Pro Leu
                 85                  90                  95

Thr Phe Gly Gly Gly Thr Lys Val Glu Ile Lys
            100                 105

<210> SEQ ID NO 81
<211> LENGTH: 321
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(321)

<400> SEQUENCE: 81 gac atc cag ttg acc cag tct cca tcc tcc ctg tct gct tct gtt gga       48
Asp Ile Gln Leu Thr Gln Ser Pro Ser Ser Leu Ser Ala Ser Val Gly
 1               5                  10                  15 gac agc gtc acc atc tct tgc cgg gca agt cag agt cct ggc atc ttt       96
Asp Ser Val Thr Ile Ser Cys Arg Ala Ser Gln Ser Pro Gly Ile Phe
            20                  25                  30 tta aat tgg tat cag cag ata cca ggg aaa gcc cct aaa ctc ctg atc      144
Leu Asn Trp Tyr Gln Gln Ile Pro Gly Lys Ala Pro Lys Leu Leu Ile
        35                  40                  45 tac gct aca tcc act ctg gaa agt ggg gtc ccc ccc agg ttc acc ggc      192
Tyr Ala Thr Ser Thr Leu Glu Ser Gly Val Pro Pro Arg Phe Thr Gly
 50                  55                  60
```

```
agt gga tct ggg aca gat ttc act ctc acc atc agc agt ctg caa cct    240
Ser Gly Ser Gly Thr Asp Phe Thr Leu Thr Ile Ser Ser Leu Gln Pro
65                  70                  75                  80 gag gac ttt gca act tac tac tgt caa cag agt aac agt gtt ccg ctc    288
Glu Asp Phe Ala Thr Tyr Tyr Cys Gln Gln Ser Asn Ser Val Pro Leu
                85                  90                  95 act ttc ggc ggc ggg acc aag gtg gag atc aaa                        321
Thr Phe Gly Gly Gly Thr Lys Val Glu Ile Lys
                100                 105

<210> SEQ ID NO 82
<211> LENGTH: 107
<212> TYPE: PRT
<213> ORGANISM: Artificial Sequence
<220> FEATURE:
<223> OTHER INFORMATION: light chain variable region

<400> SEQUENCE: 82

Asp Ile Gln Leu Thr Gln Ser Pro Ser Ser Leu Ser Ala Ser Val Gly
1               5                   10                  15

Asp Ser Val Thr Ile Ser Cys Arg Ala Ser Gln Ser Pro Gly Ile Phe
                20                  25                  30

Leu Asn Trp Tyr Gln Gln Ile Pro Gly Lys Ala Pro Lys Leu Leu Ile
            35                  40                  45

Tyr Ala Thr Ser Thr Leu Glu Ser Gly Val Pro Pro Arg Phe Thr Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Val Pro Leu
                85                  90                  95

Thr Phe Gly Gly Gly Thr Lys Val Glu Ile Lys
                100                 105

<210> SEQ ID NO 83
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 83 gat gtt gtg atg act cag tct cca ctc tcc ctg ccc gtc acc cct gga     48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt     96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct    144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct    192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca cta aaa atc    240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct    288
Ser Arg Val Glu Ala Glu Asp Val Gly Val Tyr Tyr Cys Met Gln Ala
                85                  90                  95
```

```
cta caa act cct cta acc ttc ggc caa ggg aca cga ctg gag att aaa      336
Leu Gln Thr Pro Leu Thr Phe Gly Gln Gly Thr Arg Leu Glu Ile Lys
        100                 105                 110

<210> SEQ ID NO 84
<211> LENGTH: 112
<212> TYPE: PRT
<213> ORGANISM: Artificial Sequence
<220> FEATURE:
<223> OTHER INFORMATION: light chain variable region

<400> SEQUENCE: 84

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gln Gly Thr Arg Leu Glu Ile Lys
            100                 105                 110

<210> SEQ ID NO 85
<211> LENGTH: 321
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(321)

<400> SEQUENCE: 85 gaa att gtg atg acg cag tct cca gcc acc ctg tct gtg tct cca ggg       48
Glu Ile Val Met Thr Gln Ser Pro Ala Thr Leu Ser Val Ser Pro Gly
1               5                   10                  15 gaa aga gcc acc ttc tcc tgt agg gcc agt cag agt gtt ggc agc aac       96
Glu Arg Ala Thr Phe Ser Cys Arg Ala Ser Gln Ser Val Gly Ser Asn
            20                  25                  30 tta gcc tgg tac cag cag aaa cct ggc cag gct ccc agg ctc ctc atc      144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc      192
Tyr Asp Ala Ser Asn Arg Ala Thr Gly Ile Pro Ala Arg Phe Ser Gly
    50                  55                  60 agt ggg tct ggg aca gac ttc act ctc acc atc agc aga ctg gag cct      240
Ser Gly Ser Gly Thr Asp Phe Thr Leu Thr Ile Ser Arg Leu Glu Pro
65                  70                  75                  80 gaa gat ttt gca gtg tat tac tgt cag cag cgt agc aac tgg ccc ctc      288
Glu Asp Phe Ala Val Tyr Tyr Cys Gln Gln Arg Ser Asn Trp Pro Leu
                85                  90                  95 act ttc ggc gga ggg acc aag gtg gag atc aaa                          321
Thr Phe Gly Gly Gly Thr Lys Val Glu Ile Lys
            100                 105

<210> SEQ ID NO 86
```

```
<211> LENGTH: 107
<212> TYPE: PRT
<213> ORGANISM: Artificial Sequence
<220> FEATURE:
<223> OTHER INFORMATION: light chain variable region

<400> SEQUENCE: 86

Glu Ile Val Met Thr Gln Ser Pro Ala Thr Leu Ser Val Ser Pro Gly
1               5                   10                  15

Glu Arg Ala Thr Phe Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 87
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 87 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccg ctc act ttc ggc gga ggg acc aag gtg gag atc aaa     336
Leu Gln Thr Pro Leu Thr Phe Gly Gly Gly Thr Lys Val Glu Ile Lys
            100                 105                 110

<210> SEQ ID NO 88
<211> LENGTH: 112
<212> TYPE: PRT
<213> ORGANISM: Artificial Sequence
<220> FEATURE:
<223> OTHER INFORMATION: light chain variable region

<400> SEQUENCE: 88
```

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 89
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 89

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tac ttg ggt tct act cgg gcc tcc ggc gtc cct     192
Pro Gln Leu Leu Ile Tyr Leu Gly Ser Thr Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct tac act ttc ggc gga ggg acc aag gtg gag atc aaa     336
Leu Gln Thr Pro Tyr Thr Phe Gly Gly Gly Thr Lys Val Glu Ile Lys
            100                 105                 110
```

<210> SEQ ID NO 90
<211> LENGTH: 112
<212> TYPE: PRT
<213> ORGANISM: Artificial Sequence
<220> FEATURE:
<223> OTHER INFORMATION: light chain variable region

<400> SEQUENCE: 90

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Thr Arg Ala Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gly Gly Thr Lys Val Glu Ile Lys
            100                 105                 110

<210> SEQ ID NO 91
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 91 gat gtt gtg atg act cag tct cca ctc tcc ctg ccc gtc acc cct gga      48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
 65                 70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccc ctc act ttc ggc gga ggg acc aag gtg gag atc aaa     336
Leu Gln Thr Pro Leu Thr Phe Gly Gly Gly Thr Lys Val Glu Ile Lys
            100                 105                 110

<210> SEQ ID NO 92
<211> LENGTH: 112
<212> TYPE: PRT
<213> ORGANISM: Artificial Sequence
<220> FEATURE:
<223> OTHER INFORMATION: light chain variable region

<400> SEQUENCE: 92

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
```

```
                    65                  70                  75                  80
Ser Arg Val Glu Ala Glu Asp Val Gly Val Tyr Tyr Cys Met Gln Ala
                        85                  90                  95

Leu Gln Thr Pro Leu Thr Phe Gly Gly Gly Thr Lys Val Glu Ile Lys
                100                 105                 110

<210> SEQ ID NO 93
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 93 gat gtt gtg atg act cag tct cca ctc tcc ctg ccc gtc acc cct gga        48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat act        96
Glu Pro Ala Ser Ile Ser Cys Arg Ser Ser Gln Ser Leu Leu His Thr
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cgg ctc ctg atc tat ttg ggt ttt aat cgg gcc tcc ggg gtc cct       192
Pro Arg Leu Leu Ile Tyr Leu Gly Phe Asn Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgt atg caa ggt       288
Ser Arg Val Glu Ala Glu Asp Val Gly Val Tyr Tyr Cys Met Gln Gly
                85                  90                  95 cta caa act ccc ctc act ttc ggc gga ggg acc aag gtg gag atc aaa       336
Leu Gln Thr Pro Leu Thr Phe Gly Gly Gly Thr Lys Val Glu Ile Lys
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: light chain variable region

<400> SEQUENCE: 94

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Leu Gln Lys Pro Gly Gln Ser
        35                  40                  45

Pro Arg Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Leu Thr Phe Gly Gly Gly Thr Lys Val Glu Ile Lys
            100                 105                 110
```

<210> SEQ ID NO 95
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 95

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc agg gtg gag gct gag gat gtt ggg gtt tat tat tgc atg caa gct     288
Ser Arg Val Glu Ala Glu Asp Val Gly Val Tyr Tyr Cys Met Gln Ala
                85                  90                  95 aca cac tgg ccg tac act ttt ggc cag ggg acc aag ctg gag atc aaa     336
Thr His Trp Pro Tyr Thr Phe Gly Gln Gly Thr Lys Leu Glu Ile Lys
            100                 105                 110
```

<210> SEQ ID NO 96
<211> LENGTH: 112
<212> TYPE: PRT
<213> ORGANISM: Artificial Sequence
<220> FEATURE:
<223> OTHER INFORMATION: light chain variable region

<400> SEQUENCE: 96

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Tyr Thr Phe Gly Gln Gly Thr Lys Leu Glu Ile Lys
            100                 105                 110
```

<210> SEQ ID NO 97
<211> LENGTH: 330
<212> TYPE: DNA
<213> ORGANISM: Artificial Sequence
<220> FEATURE:

```
<223> OTHER INFORMATION: light chain variable region
<220> FEATURE:
<221> NAME/KEY: CDS
<222> LOCATION: (1)..(330)

<400> SEQUENCE: 97 aat ttt atg ctg act cag ccc cac tct gtg tcg gag tct ccg ggg aag        48
Asn Phe Met Leu Thr Gln Pro His Ser Val Ser Glu Ser Pro Gly Lys
1               5                   10                  15 acg gta agc atc tcc tgc acc cgc aac agt ggc agc att gcc agc aac        96
Thr Val Ser Ile Ser Cys Thr Arg Asn Ser Gly Ser Ile Ala Ser Asn
            20                  25                  30 ttt gtg cag tgg tac cag cag cgc ccg ggc agt gcc ccc acc att gta       144
Phe Val Gln Trp Tyr Gln Gln Arg Pro Gly Ser Ala Pro Thr Ile Val
        35                  40                  45 atc tat gag gat aac caa aga ccc tct gcg gtc cct act cgg ttc tct       192
Ile Tyr Glu Asp Asn Gln Arg Pro Ser Ala Val Pro Thr Arg Phe Ser
    50                  55                  60 ggc tcc atc gac agg tcc tcc aac tct gcc tcc ctc acc atc tct gga       240
Gly Ser Ile Asp Arg Ser Ser Asn Ser Ala Ser Leu Thr Ile Ser Gly
65                  70                  75                  80 ctg acg act gag gac gag gct gac tac tac tgt cag tct tat gat agc       288
Leu Thr Thr Glu Asp Glu Ala Asp Tyr Tyr Cys Gln Ser Tyr Asp Ser
                85                  90                  95 gcc aat gtc att ttc ggc ggg ggg acc aag ctg acc gtc cta               330
Ala Asn Val Ile Phe Gly Gly Gly Thr Lys Leu Thr Val Leu
            100                 105                 110

<210> SEQ ID NO 98
<211> LENGTH: 110
<212> TYPE: PRT
<213> ORGANISM: Artificial Sequence
<220> FEATURE:
<223> OTHER INFORMATION: light chain variable region

<400> SEQUENCE: 98

Asn Phe Met Leu Thr Gln Pro His Ser Val Ser Glu Ser Pro Gly Lys
1               5                   10                  15

Thr Val Ser Ile Ser Cys Thr Arg Asn Ser Gly Ser Ile Ala Ser Asn
            20                  25                  30

Phe Val Gln Trp Tyr Gln Gln Arg Pro Gly Ser Ala Pro Thr Ile Val
        35                  40                  45

Ile Tyr Glu Asp Asn Gln Arg Pro Ser Ala Val Pro Thr Arg Phe Ser
    50                  55                  60

Gly Ser Ile Asp Arg Ser Ser Asn Ser Ala Ser Leu Thr Ile Ser Gly
65                  70                  75                  80

Leu Thr Thr Glu Asp Glu Ala Asp Tyr Tyr Cys Gln Ser Tyr Asp Ser
                85                  90                  95

Ala Asn Val Ile Phe Gly Gly Gly Thr Lys Leu Thr Val Leu
            100                 105                 110

<210> SEQ ID NO 99
<211> LENGTH: 324
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(324)

<400> SEQUENCE: 99
```

```
gaa acg aca ctc acg cag tct cca ggc acc ctg tct ttg tct cca ggg      48
Glu Thr Thr Leu Thr Gln Ser Pro Gly Thr Leu Ser Leu Ser Pro Gly
1               5                   10                  15 gag aga gcc acc ctc tcc tgc agg gcc agt cag act atc agc agc agc      96
Glu Arg Ala Thr Leu Ser Cys Arg Ala Ser Gln Thr Ile Ser Ser Ser
            20                  25                  30 cac tta gcc tgg tac cag cag aaa cct ggc cag tct ccc agg ctc ctc     144
His Leu Ala Trp Tyr Gln Gln Lys Pro Gly Gln Ser Pro Arg Leu Leu
        35                  40                  45 atc tat ggt gcg ggc tac agg gcc acc ggc att cca gac agg ttc agt     192
Ile Tyr Gly Ala Gly Tyr Arg Ala Thr Gly Ile Pro Asp Arg Phe Ser
    50                  55                  60 ggc agt ggg tct ggc aca gac ttc act ctc acc atc agc aga ctg gag     240
Gly Ser Gly Ser Gly Thr Asp Phe Thr Leu Thr Ile Ser Arg Leu Glu
65              70                  75                  80 cct gaa gat ttt gca gtg tat tac tgt cag cac tat ggt agt tca ctc     288
Pro Glu Asp Phe Ala Val Tyr Tyr Cys Gln His Tyr Gly Ser Ser Leu
                85                  90                  95 cgg acg ttc ggc caa ggg acc aag gtg gaa atc aaa                     324
Arg Thr Phe Gly Gln Gly Thr Lys Val Glu Ile Lys
            100                 105

<210> SEQ ID NO 100
<211> LENGTH: 108
<212> TYPE: PRT
<213> ORGANISM: Artificial Sequence
<220> FEATURE:
<223> OTHER INFORMATION: light chain variable region

<400> SEQUENCE: 100

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Ser Ser Ser
            20                  25                  30

His Leu Ala Trp Tyr Gln Gln Lys Pro Gly Gln Ser Pro Arg Leu Leu
        35                  40                  45

Ile Tyr Gly Ala Gly Tyr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln His Tyr Gly Ser Ser Leu
                85                  90                  95

Arg Thr Phe Gly Gln Gly Thr Lys Val Glu Ile Lys
            100                 105

<210> SEQ ID NO 101
<211> LENGTH: 330
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(330)

<400> SEQUENCE: 101 aat ttt atg ctg act cag ccc cac tct gtg tcg gag tct ccg ggg aag      48
Asn Phe Met Leu Thr Gln Pro His Ser Val Ser Glu Ser Pro Gly Lys
1               5                   10                  15 acg gta acc atc tcc tgc acc ggc agc ggt ggc aac att gcc agc aat      96
Thr Val Thr Ile Ser Cys Thr Gly Ser Gly Gly Asn Ile Ala Ser Asn
            20                  25                  30
```

```
tat gtg cag tgg tac cag cag cgc ccg ggc agg gcc ccc acc act gtg      144
Tyr Val Gln Trp Tyr Gln Gln Arg Pro Gly Arg Ala Pro Thr Thr Val
         35                  40                  45 atc tat gag gat aat cga aga ccc tct ggg gtc cct gat cgg ttc tct      192
Ile Tyr Glu Asp Asn Arg Arg Pro Ser Gly Val Pro Asp Arg Phe Ser
 50                  55                  60 ggc tcc atc gac agc tcc tcc aac tct gcc tcc ctc acc atc tct gga      240
Gly Ser Ile Asp Ser Ser Ser Asn Ser Ala Ser Leu Thr Ile Ser Gly
 65                  70                  75                  80 ctg aag act gaa gac gag gct gac tac tac tgt cag tct tat gat ccc      288
Leu Lys Thr Glu Asp Glu Ala Asp Tyr Tyr Cys Gln Ser Tyr Asp Pro
                 85                  90                  95 tac aat cga gtg ttc ggc gga ggg acc aag ctg acc gtc cta              330
Tyr Asn Arg Val Phe Gly Gly Gly Thr Lys Leu Thr Val Leu
            100                 105                 110

<210> SEQ ID NO 102
<211> LENGTH: 110
<212> TYPE: PRT
<213> ORGANISM: Artificial Sequence
<220> FEATURE:
<223> OTHER INFORMATION: light chain variable region

<400> SEQUENCE: 102

Asn Phe Met Leu Thr Gln Pro His Ser Val Ser Glu Ser Pro Gly Lys
 1               5                  10                  15

Thr Val Thr Ile Ser Cys Thr Gly Ser Gly Gly Asn Ile Ala Ser Asn
            20                  25                  30

Tyr Val Gln Trp Tyr Gln Gln Arg Pro Gly Arg Ala Pro Thr Thr Val
         35                  40                  45

Ile Tyr Glu Asp Asn Arg Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Pro
                 85                  90                  95

Tyr Asn Arg Val Phe Gly Gly Gly Thr Lys Leu Thr Val Leu
            100                 105                 110

<210> SEQ ID NO 103
<211> LENGTH: 336
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)..(336)

<400> SEQUENCE: 103 gaa att gtg atg acg cag tct cca ctc tcc ctg ccc gtc acc cct gga       48
Glu Ile Val Met Thr Gln Ser Pro Leu Ser Leu Pro Val Thr Pro Gly
 1               5                  10                  15 gag ccg gcc tcc atc tcc tgc agg tct agt cag agc ctc ctg cat act       96
Glu Pro Ala Ser Ile Ser Cys Arg Ser Ser Gln Ser Leu Leu His Thr
            20                  25                  30 aat gga tac gac tat ttg gat tgg tac ctg cag aag cca ggg cag tct      144
Asn Gly Tyr Asp Tyr Leu Asp Trp Tyr Leu Gln Lys Pro Gly Gln Ser
         35                  40                  45 cca cag ctt ctg atc tat ttg ggt tct act cgg gcc tcc ggg gtc cct      192
Pro Gln Leu Leu Ile Tyr Leu Gly Ser Thr Arg Ala Ser Gly Val Pro
```

```
                50                  55                  60
gac agg ttc agt ggc agt gga tcg ggc aca gat ttt aca ctg aaa atc        240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct        288
Ser Arg Val Glu Ala Glu Asp Val Gly Val Tyr Tyr Cys Met Gln Ala
                 85                  90                  95 ttt caa act ccg ctc act ttc ggc gga ggg acc aag atg gag atc aaa        336
Phe Gln Thr Pro Leu Thr Phe Gly Gly Gly Thr Lys Met Glu Ile Lys
            100                 105                 110
```

<210> SEQ ID NO 104
<211> LENGTH: 112
<212> TYPE: PRT
<213> ORGANISM: Artificial Sequence
<220> FEATURE:
<223> OTHER INFORMATION: light chain variable region

<400> SEQUENCE: 104

```
Glu Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Thr
                20                  25                  30

Asn Gly Tyr Asp Tyr Leu Asp Trp Tyr Leu Gln Lys Pro Gly Gln Ser
            35                  40                  45

Pro Gln Leu Leu Ile Tyr Leu Gly Ser Thr Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Phe Gln Thr Pro Leu Thr Phe Gly Gly Gly Thr Lys Met Glu Ile Lys
            100                 105                 110
```

<210> SEQ ID NO 105
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)

<400> SEQUENCE: 105

```
gag gtg cag ctg gtg gag acc ggc cca gga ctg gtg aag cct tcg ggg         48
Glu Val Gln Leu Val Glu Thr Gly Pro Gly Leu Val Lys Pro Ser Gly
 1               5                  10                  15 acc ctg tcc ctc acc tgc gct gtc tct ggt ggc tcc atc agc agt agt         96
Thr Leu Ser Leu Thr Cys Ala Val Ser Gly Gly Ser Ile Ser Ser Ser
                20                  25                  30 aac tgg tgg agt tgg gtc cgc cag ccc cca ggg aag ggg ctg gag tgg        144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc        192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc        240
Lys Ser Arg Val Thr Ile Ser Val Asp Lys Ser Lys Asn Gln Phe Ser
 65                  70                  75                  80 ctg aag ctg agc tct gtg acc gcc gcg gac acg gcc gtg tat tac tgt        288
Leu Lys Leu Ser Ser Val Thr Ala Ala Asp Thr Ala Val Tyr Tyr Cys
```

```
Leu Lys Leu Ser Ser Val Thr Ala Ala Asp Thr Ala Val Tyr Tyr Cys
            85                  90                  95 gcg aga ttt aat tac tat gat agt agt gtc tgg ggc cag gga acc ctg      336
Ala Arg Phe Asn Tyr Tyr Asp Ser Ser Val Trp Gly Gln Gly Thr Leu
            100                 105                 110 gtc acc gtc tca agc                                                  351
Val Thr Val Ser Ser
        115

<210> SEQ ID NO 106
<211> LENGTH: 117
<212> TYPE: PRT
<213> ORGANISM: Artificial Sequence
<220> FEATURE:
<223> OTHER INFORMATION: heavy chain variable region

<400> SEQUENCE: 106

Glu Val Gln Leu Val Glu Thr Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Phe Asn Tyr Tyr Asp Ser Ser Val Trp Gly Gln Gly Thr Leu
            100                 105                 110

Val Thr Val Ser Ser
        115

<210> SEQ ID NO 107
<211> LENGTH: 348
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(348)

<400> SEQUENCE: 107 gag gtg cag ctg gtg gag acc ggc cca gga ctg gtg aag cct tcg ggg      48
Glu Val Gln Leu Val Glu Thr Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
```

```
Leu Lys Leu Ser Ser Val Thr Ala Ala Asp Thr Ala Val Tyr Tyr Cys
            85                  90                  95 gcg aga ggg gtt gag cag att gac tac tgg ggc cag gga acc ctg gtc      336
Ala Arg Gly Val Glu Gln Ile Asp Tyr Trp Gly Gln Gly Thr Leu Val
            100                 105                 110 acc gtc tca agc                                                      348
Thr Val Ser Ser
        115

<210> SEQ ID NO 108
<211> LENGTH: 116
<212> TYPE: PRT
<213> ORGANISM: Artificial Sequence
<220> FEATURE:
<223> OTHER INFORMATION: heavy chain variable region

<400> SEQUENCE: 108

Glu Val Gln Leu Val Glu Thr Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Val Glu Gln Ile Asp Tyr Trp Gly Gln Gly Thr Leu Val
            100                 105                 110

Thr Val Ser Ser
        115

<210> SEQ ID NO 109
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 109 cag gtg cag ctg cag gag tcg ggc cca gga ctg gtg aag cct tcg ggg       48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg act gcc gcg gac acg gcc gtg tat tac tgt      288
```

```
Leu Lys Leu Ser Ser Val Thr Ala Ala Asp Thr Ala Val Tyr Tyr Cys
                85                  90                  95 gcg aaa aat tta gca gca ggg gcg gtt gcc tac tgg ggc cag ggc acc    336
Ala Lys Asn Leu Ala Ala Gly Ala Val Ala Tyr Trp Gly Gln Gly Thr
            100                 105                 110 ctg gtc acc gtc tca agc                                            354
Leu Val Thr Val Ser Ser
        115

<210> SEQ ID NO 110
<211> LENGTH: 118
<212> TYPE: PRT
<213> ORGANISM: Artificial Sequence
<220> FEATURE:
<223> OTHER INFORMATION: heavy chain variable region

<400> SEQUENCE: 110

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Lys Asn Leu Ala Ala Gly Ala Val Ala Tyr Trp Gly Gln Gly Thr
            100                 105                 110

Leu Val Thr Val Ser Ser
        115

<210> SEQ ID NO 111
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)

<400> SEQUENCE: 111 cag gtg cag cta cag cag tgg ggc gca gga ctg ttg aag cct tcg gag    48
Gln Val Gln Leu Gln Gln Trp Gly Ala Gly Leu Leu Lys Pro Ser Glu
1               5                   10                  15 acc ctg tcc ctc acc tgc gct gtc tct ggt ggg tcc ttc agt ggt tac    96
Thr Leu Ser Leu Thr Cys Ala Val Ser Gly Gly Ser Phe Ser Gly Tyr
            20                  25                  30 tac tgg agc tgg atc cgt cag ccc cca ggg aag ggg ctg gag tgg att    144
Tyr Trp Ser Trp Ile Arg Gln Pro Pro Gly Lys Gly Leu Glu Trp Ile
        35                  40                  45 ggg gaa atc aat cat agt gga agt acc aac tac aac cgg tcc ctc aag    192
Gly Glu Ile Asn His Ser Gly Ser Thr Asn Tyr Asn Arg Ser Leu Lys
    50                  55                  60 agt cga gtc acc ata tca gta gac acg tcc aag aac cag ttc tcc ctg    240
Ser Arg Val Thr Ile Ser Val Asp Thr Ser Lys Asn Gln Phe Ser Leu
65                  70                  75                  80 aag ctg agc tct gtg acc gcc gcg gac acg gct gtg tat tac tgt gcg    288
```

```
Lys Leu Ser Ser Val Thr Ala Ala Asp Thr Ala Val Tyr Tyr Cys Ala
                85                  90                  95 aga ctt tca tat ggt tcg ggc gtt gac tac tgg ggc cag ggc acc ctg      336
Arg Leu Ser Tyr Gly Ser Gly Val Asp Tyr Trp Gly Gln Gly Thr Leu
            100                 105                 110 gtc acc gtc tca agc                                                  351
Val Thr Val Ser Ser
        115

<210> SEQ ID NO 112
<211> LENGTH: 117
<212> TYPE: PRT
<213> ORGANISM: Artificial Sequence
<220> FEATURE:
<223> OTHER INFORMATION: heavy chain variable region

<400> SEQUENCE: 112

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Arg Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Ser Tyr Gly Ser Gly Val Asp Tyr Trp Gly Gln Gly Thr Leu
            100                 105                 110

Val Thr Val Ser Ser
        115

<210> SEQ ID NO 113
<211> LENGTH: 360
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(360)

<400> SEQUENCE: 113 cag ctg cag ctg cag gag tcg ggc cca gga ctg gtg aag cct tca cag      48
Gln Leu Gln Leu Gln Glu Ser Gly Pro Gly Leu Val Lys Pro Ser Gln
1               5                   10                  15 acc ctg tcc ctc acc tgc act gtc tct ggt ggc tcc atc agc agt agt       96
Thr Leu Ser Leu Thr Cys Thr Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
```

```
Leu Lys Leu Ser Ser Val Thr Ala Ala Asp Thr Ala Val Tyr Tyr Cys
            85                  90                  95 gcg agg tat agc agc agc cgc aat gat gct ttt gat atc tgg ggc caa      336
Ala Arg Tyr Ser Ser Ser Arg Asn Asp Ala Phe Asp Ile Trp Gly Gln
            100                 105                 110 ggg aca atg gtc acc gtc tca agc                                       360
Gly Thr Met Val Thr Val Ser Ser
        115                 120

<210> SEQ ID NO 114
<211> LENGTH: 120
<212> TYPE: PRT
<213> ORGANISM: Artificial Sequence
<220> FEATURE:
<223> OTHER INFORMATION: heavy chain variable region

<400> SEQUENCE: 114

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Tyr Ser Ser Ser Arg Asn Asp Ala Phe Asp Ile Trp Gly Gln
            100                 105                 110

Gly Thr Met Val Thr Val Ser Ser
        115                 120

<210> SEQ ID NO 115
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 115 cag gtg cag ctg cag gag tcg ggc cca gga ctg gtg aag cct tcg ggg       48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
```

```
Leu Lys Leu Ser Ser Val Thr Ala Ala Asp Thr Ala Val Tyr Tyr Cys
                85                  90                  95 gcg aga gat ggg cag ctg gat gct ttt gat atc tgg ggc caa ggg aca      336
Ala Arg Asp Gly Gln Leu Asp Ala Phe Asp Ile Trp Gly Gln Gly Thr
            100                 105                 110 atg gtc acc gtc tca agc                                              354
Met Val Thr Val Ser Ser
        115

<210> SEQ ID NO 116
<211> LENGTH: 118
<212> TYPE: PRT
<213> ORGANISM: Artificial Sequence
<220> FEATURE:
<223> OTHER INFORMATION: heavy chain variable region

<400> SEQUENCE: 116

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Gln Leu Asp Ala Phe Asp Ile Trp Gly Gln Gly Thr
            100                 105                 110

Met Val Thr Val Ser Ser
        115

<210> SEQ ID NO 117
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 117 cag gtg cag ctg cag gag tcg ggc cca gga ctg gtg aag cct tcg ggg      48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
```

```
                                                          -continued

Leu Lys Leu Ser Ser Val Thr Ala Ala Asp Thr Ala Val Tyr Tyr Cys
                85                  90                  95 gcg aga ttt tgg gac tac tac ggt atg gac gtc tgg ggc caa ggg acc      336
Ala Arg Phe Trp Asp Tyr Tyr Gly Met Asp Val Trp Gly Gln Gly Thr
            100                 105                 110 acg gtc acc gtc tca agc                                              354
Thr Val Thr Val Ser Ser
        115

<210> SEQ ID NO 118
<211> LENGTH: 118
<212> TYPE: PRT
<213> ORGANISM: Artificial Sequence
<220> FEATURE:
<223> OTHER INFORMATION: heavy chain variable region

<400> SEQUENCE: 118

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Trp Asp Tyr Tyr Gly Met Asp Val Trp Gly Gln Gly Thr
            100                 105                 110

Thr Val Thr Val Ser Ser
        115

<210> SEQ ID NO 119
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)

<400> SEQUENCE: 119 cag gtg cag cta cag cag tgg ggc cca gga ctg gtg aag cct tcg ggg      48
Gln Val Gln Leu Gln Gln Trp Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 gag agt cga gtc acc ata tca gta gac aag tcc aag aac cag ttc tcc      240
Glu Ser Arg Val Thr Ile Ser Val Asp Lys Ser Lys Asn Gln Phe Ser
65                  70                  75                  80 ctg aag ctg agc tct gtg acc gcc gca gac acg gcc gtg tat tac tgt      288
```

```
                        Leu Lys Leu Ser Ser Val Thr Ala Ala Asp Thr Ala Val Tyr Tyr Cys
                                    85                  90                  95 gcg aga gat cgg tac tac ggt atg gac gtc tgg ggc caa ggg acc acg              336
Ala Arg Asp Arg Tyr Tyr Gly Met Asp Val Trp Gly Gln Gly Thr Thr
                100                 105                 110 gtc acc gtc tca agc                                                          351
Val Thr Val Ser Ser
        115

<210> SEQ ID NO 120
<211> LENGTH: 117
<212> TYPE: PRT
<213> ORGANISM: Artificial Sequence
<220> FEATURE:
<223> OTHER INFORMATION: heavy chain variable region

<400> SEQUENCE: 120

Gln Val Gln Leu Gln Gln Trp Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Glu Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Arg Tyr Tyr Gly Met Asp Val Trp Gly Gln Gly Thr Thr
                100                 105                 110

Val Thr Val Ser Ser
        115

<210> SEQ ID NO 121
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 121 gag gtg cag ctg gtc gag tct ggc cca gga ctg gtg aag cct tcg ggg              48
Glu Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt              96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg              144
Asn Trp Trp Ser Trp Val Arg Gln Pro Pro Gly Lys Gly Leu Glu Trp
        35                  40                  45 att ggg tac atc tat tat agt ggg agc acc tac tac aac ccg tcc ctc              192
Ile Gly Tyr Ile Tyr Tyr Ser Gly Ser Thr Tyr Tyr Asn Pro Ser Leu
    50                  55                  60 aag agt cga gtc acc atg tca gta gac acg tcc aag aac cag ttc tcc              240
Lys Ser Arg Val Thr Met Ser Val Asp Thr Ser Lys Asn Gln Phe Ser
65                  70                  75                  80 ctg aag ctg agc tct gtg acc gcc gca gac acg gcc gtg tat tac tgt              288
```

```
Leu Lys Leu Ser Ser Val Thr Ala Ala Asp Thr Ala Val Tyr Tyr Cys
            85                  90                  95 gcg aga tgg agc tac ttg gat gct ttt gat atc tgg ggc caa ggg aca     336
Ala Arg Trp Ser Tyr Leu Asp Ala Phe Asp Ile Trp Gly Gln Gly Thr
            100                 105                 110 atg gtc acc gtc tca agc                                              354
Met Val Thr Val Ser Ser
        115

<210> SEQ ID NO 122
<211> LENGTH: 118
<212> TYPE: PRT
<213> ORGANISM: Artificial Sequence
<220> FEATURE:
<223> OTHER INFORMATION: heavy chain variable region

<400> SEQUENCE: 122

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Trp Ser Tyr Leu Asp Ala Phe Asp Ile Trp Gly Gln Gly Thr
            100                 105                 110

Met Val Thr Val Ser Ser
        115

<210> SEQ ID NO 123
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 123 gag gtg cag ctg gtg gag tct ggc cca gga ctg gtg aag cct tcg ggg     48
Glu Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt     96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt    288
```

```
                Leu Lys Leu Ser Ser Val Thr Ala Ala Asp Thr Ala Val Tyr Tyr Cys
                                85                  90                  95 gcg aga gat tac gat att ttc ggt atg gac gtc tgg ggc caa ggg acc         336
Ala Arg Asp Tyr Asp Ile Phe Gly Met Asp Val Trp Gly Gln Gly Thr
            100                 105                 110 acg gtc acc gtc tca agc                                                  354
Thr Val Thr Val Ser Ser
        115

<210> SEQ ID NO 124
<211> LENGTH: 118
<212> TYPE: PRT
<213> ORGANISM: Artificial Sequence
<220> FEATURE:
<223> OTHER INFORMATION: heavy chain variable region

<400> SEQUENCE: 124

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Asp Ile Phe Gly Met Asp Val Trp Gly Gln Gly Thr
            100                 105                 110

Thr Val Thr Val Ser Ser
        115

<210> SEQ ID NO 125
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 125 cag ctg cag ctg cag gag tcg ggc cca gga ctg gtg aag cct tcg ggg         48
Gln Leu Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt         96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg        144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc        192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag tcc tcc        240
Lys Ser Arg Val Thr Ile Ser Val Asp Lys Ser Lys Asn Gln Ser Ser
65                  70                  75                  80 ctg aag ctg agc tct gtg acc gcc gcg gac acg gcc gtg tat tac tgt        288
```

```
Leu Lys Leu Ser Ser Val Thr Ala Ala Asp Thr Ala Val Tyr Tyr Cys
            85                  90                  95 gcg aga gcc aac aga gat gat gct ttt gat atc tgg ggc caa ggg aca      336
Ala Arg Ala Asn Arg Asp Asp Ala Phe Asp Ile Trp Gly Gln Gly Thr
            100                 105                 110 atg gtc acc gtc tca agc                                              354
Met Val Thr Val Ser Ser
            115

<210> SEQ ID NO 126
<211> LENGTH: 118
<212> TYPE: PRT
<213> ORGANISM: Artificial Sequence
<220> FEATURE:
<223> OTHER INFORMATION: heavy chain variable region

<400> SEQUENCE: 126

Gln Leu Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Ser Ser
65                  70                  75                  80

Leu Lys Leu Ser Ser Val Thr Ala Ala Asp Thr Ala Val Tyr Tyr Cys
            85                  90                  95

Ala Arg Ala Asn Arg Asp Asp Ala Phe Asp Ile Trp Gly Gln Gly Thr
            100                 105                 110

Met Val Thr Val Ser Ser
            115

<210> SEQ ID NO 127
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 127 gag gtg cag ctg gtg gag tct ggg gga ggc ttg gta cag ccg ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80 ctg caa atg aac agt ctg agc gcc gac gac acg gcc gta tat ttc tgt      288
```

```
Leu Gln Met Asn Ser Leu Ser Ala Asp Asp Thr Ala Val Tyr Phe Cys
            85                  90                  95 gcg tcg ggt ggc tgg tac ggg gac tac ttt gac tac tgg ggc cag gga      336
Ala Ser Gly Gly Trp Tyr Gly Asp Tyr Phe Asp Tyr Trp Gly Gln Gly
            100                 105                 110 acc ctg gtc acc gtc tca agc                                           357
Thr Leu Val Thr Val Ser Ser
        115

<210> SEQ ID NO 128
<211> LENGTH: 119
<212> TYPE: PRT
<213> ORGANISM: Artificial Sequence
<220> FEATURE:
<223> OTHER INFORMATION: heavy chain variable region

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Asp Asp Thr Ala Val Tyr Phe Cys
            85                  90                  95

Ala Ser Gly Gly Trp Tyr Gly Asp Tyr Phe Asp Tyr Trp Gly Gln Gly
            100                 105                 110

Thr Leu Val Thr Val Ser Ser
        115

<210> SEQ ID NO 129
<211> LENGTH: 363
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(363)

<400> SEQUENCE: 129 cag gtg cag ctg cag gag tcc ggc cca gga ctg gtg aag cct tcg gag       48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agc agt agt       96
Thr Leu Ser Leu Thr Cys Thr Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
Leu Lys Leu Ser Ser Val Thr Ala Ala Asp Thr Ala Val Tyr Tyr Cys
```

```
Leu Lys Leu Ser Ser Val Thr Ala Ala Asp Thr Ala Val Tyr Tyr Cys
            85                  90                  95 gcg aga gaa ggg aac cga acg gtg act agt gct ttt gat atc tgg ggc      336
Ala Arg Glu Gly Asn Arg Thr Val Thr Ser Ala Phe Asp Ile Trp Gly
            100                 105                 110 caa ggg aca atg gtc acc gtc tca agc                                  363
Gln Gly Thr Met Val Thr Val Ser Ser
            115                 120

<210> SEQ ID NO 130
<211> LENGTH: 121
<212> TYPE: PRT
<213> ORGANISM: Artificial Sequence
<220> FEATURE:
<223> OTHER INFORMATION: heavy chain variable region

<400> SEQUENCE: 130

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Glu Gly Asn Arg Thr Val Thr Ser Ala Phe Asp Ile Trp Gly
            100                 105                 110

Gln Gly Thr Met Val Thr Val Ser Ser
            115                 120

<210> SEQ ID NO 131
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 131 cag gtg cag ctg cag gag tcc ggc cca gga ctg gtg aag cct tcg ggg      48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gct gcg gac acg gcc gtg tac tac tgt     288
```

| | | | | | | | | | | | |
|---|---|---|---|---|---|---|---|---|---|---|---|
| Leu | Lys | Leu | Ser | Ser | Val | Thr | Ala | Ala | Asp | Thr | Ala | Val | Tyr | Tyr | Cys |
| | | | | 85 | | | | 90 | | | | | 95 | | |

| gcg | aga | ggg | ctg | ggg | gat | agt | agt | ggt | tat | atc | ctt | tgg | ggc | caa | ggg | 336 |
|---|---|---|---|---|---|---|---|---|---|---|---|---|---|---|---|---|
| Ala | Arg | Gly | Leu | Gly | Asp | Ser | Ser | Gly | Tyr | Ile | Leu | Trp | Gly | Gln | Gly | |
| | | | 100 | | | | | 105 | | | | | 110 | | | |

| aca | atg | gtc | acc | gtc | tca | agc | 357 |
|---|---|---|---|---|---|---|---|
| Thr | Met | Val | Thr | Val | Ser | Ser | |
| | | 115 | | | | | |

<210> SEQ ID NO 132
<211> LENGTH: 119
<212> TYPE: PRT
<213> ORGANISM: Artificial Sequence
<220> FEATURE:
<223> OTHER INFORMATION: heavy chain variable region

<400> SEQUENCE: 132

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Leu Gly Asp Ser Ser Gly Tyr Ile Leu Trp Gly Gln Gly
            100                 105                 110

Thr Met Val Thr Val Ser Ser
        115

<210> SEQ ID NO 133
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 133

| cag | gtg | cag | ctg | cag | gag | tcc | ggc | cca | gga | ctg | gtg | aag | cct | tcg | ggg | 48 |
|---|---|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Gly | |
| 1 | | | | 5 | | | | | 10 | | | | | 15 | | |

| acc | ctg | tcc | ctc | acc | tgc | gct | gtc | tct | ggt | ggc | tcc | atc | agc | agt | agt | 96 |
|---|---|---|---|---|---|---|---|---|---|---|---|---|---|---|---|---|
| Thr | Leu | Ser | Leu | Thr | Cys | Ala | Val | Ser | Gly | Gly | Ser | Ile | Ser | Ser | Ser | |
| | | | 20 | | | | | 25 | | | | | 30 | | | |

| aac | tgg | tgg | agt | tgg | gtc | cgc | cag | ccc | cca | ggg | aag | ggg | ctg | gag | tgg | 144 |
|---|---|---|---|---|---|---|---|---|---|---|---|---|---|---|---|---|
| Asn | Trp | Trp | Ser | Trp | Val | Arg | Gln | Pro | Pro | Gly | Lys | Gly | Leu | Glu | Trp | |
| | | 35 | | | | | 40 | | | | | 45 | | | | |

| att | ggg | gaa | atc | tat | cat | agt | ggg | agc | acc | aac | tac | aac | ccg | tcc | ctc | 192 |
|---|---|---|---|---|---|---|---|---|---|---|---|---|---|---|---|---|
| Ile | Gly | Glu | Ile | Tyr | His | Ser | Gly | Ser | Thr | Asn | Tyr | Asn | Pro | Ser | Leu | |
| | 50 | | | | | 55 | | | | | 60 | | | | | |

| aag | agt | cga | gtc | acc | ata | tca | gta | gac | aag | tcc | aag | aac | cag | ttc | tcc | 240 |
|---|---|---|---|---|---|---|---|---|---|---|---|---|---|---|---|---|
| Lys | Ser | Arg | Val | Thr | Ile | Ser | Val | Asp | Lys | Ser | Lys | Asn | Gln | Phe | Ser | |
| 65 | | | | 70 | | | | | 75 | | | | | 80 | | |

| ctg | aag | ctg | agc | tct | gtg | acc | gct | gcg | gac | acg | gcc | gtg | tac | tac | tgt | 288 |

```
Leu Lys Leu Ser Ser Val Thr Ala Ala Asp Thr Ala Val Tyr Tyr Cys
            85                  90                  95 gcg aga ggg ctg ggg gat agt agt ggt tat atc ctt tgg ggc caa ggg      336
Ala Arg Gly Leu Gly Asp Ser Ser Gly Tyr Ile Leu Trp Gly Gln Gly
            100                 105                 110 aca atg gtc acc gtc tca agc                                          357
Thr Met Val Thr Val Ser Ser
        115

<210> SEQ ID NO 134
<211> LENGTH: 119
<212> TYPE: PRT
<213> ORGANISM: Artificial Sequence
<220> FEATURE:
<223> OTHER INFORMATION: heavy chain variable region

<400> SEQUENCE: 134

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Leu Gly Asp Ser Ser Gly Tyr Ile Leu Trp Gly Gln Gly
            100                 105                 110

Thr Met Val Thr Val Ser Ser
        115

<210> SEQ ID NO 135
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 135 cag gtg cag ctg cag gag tcg ggc cca gga ctg gtg aag cct tcg ggg      48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
```

```
Leu Lys Leu Ser Ser Val Thr Ala Ala Asp Thr Ala Val Tyr Tyr Cys
            85                  90                  95 gcg aga tgg acc ggg cgt act gat gct ttt gat atc tgg ggc caa ggg        336
Ala Arg Trp Thr Gly Arg Thr Asp Ala Phe Asp Ile Trp Gly Gln Gly
            100                 105                 110 aca atg gtc acc gtc tca agc                                            357
Thr Met Val Thr Val Ser Ser
            115

<210> SEQ ID NO 136
<211> LENGTH: 119
<212> TYPE: PRT
<213> ORGANISM: Artificial Sequence
<220> FEATURE:
<223> OTHER INFORMATION: heavy chain variable region

<400> SEQUENCE: 136

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Trp Thr Gly Arg Thr Asp Ala Phe Asp Ile Trp Gly Gln Gly
            100                 105                 110

Thr Met Val Thr Val Ser Ser
            115

<210> SEQ ID NO 137
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 137 cag gtg cag ctg cag gag tcc ggc cca gga ctg gtg aag cct tcg ggg        48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt        96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg        144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc        192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc        240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt        288
```

```
                Leu Lys Leu Ser Ser Val Thr Ala Ala Asp Thr Ala Val Tyr Tyr Cys
                            85                  90                  95 gcg aga caa ggg gcg tta gat gct ttt gat atc tgg ggc caa ggg acc         336
Ala Arg Gln Gly Ala Leu Asp Ala Phe Asp Ile Trp Gly Gln Gly Thr
            100                 105                 110 acg gtc acc gtc tca agc                                                 354
Thr Val Thr Val Ser Ser
        115

<210> SEQ ID NO 138
<211> LENGTH: 118
<212> TYPE: PRT
<213> ORGANISM: Artificial Sequence
<220> FEATURE:
<223> OTHER INFORMATION: heavy chain variable region

<400> SEQUENCE: 138

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ala Leu Asp Ala Phe Asp Ile Trp Gly Gln Gly Thr
            100                 105                 110

Thr Val Thr Val Ser Ser
        115

<210> SEQ ID NO 139
<211> LENGTH: 366
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(366)

<400> SEQUENCE: 139 cag gtg cag ctg gtg gag tcc ggg gga ggc gtg gtc cga cct ggg ggg         48
Gln Val Gln Leu Val Glu Ser Gly Gly Gly Val Val Arg Pro Gly Gly
1               5                   10                  15 tcc ctg aga ctc tcc tgt gca gcg tct gga ttc acc ttt agc agc tat         96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc         144
Ala Met Ser Trp Val Arg Gln Ala Pro Gly Lys Gly Leu Glu Trp Val
        35                  40                  45 tca act att agt ggt agt ggt ggt agc aca tac tac gca gac tcc gtg         192
Ser Thr Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat         240
Lys Gly Arg Phe Thr Ile Ser Arg Asp Asn Ser Lys Asn Thr Leu Tyr
65                  70                  75                  80 ctg cag atg aac agc ctg aga gcc gag gac acg gcc gta tat tac tgt         288
```

```
Leu Gln Met Asn Ser Leu Arg Ala Glu Asp Thr Ala Val Tyr Tyr Cys
                85                  90                  95 gcg aaa gag cgt ggc agt ggc tgg tcc tta gac aat atg gac gtc tgg        336
Ala Lys Glu Arg Gly Ser Gly Trp Ser Leu Asp Asn Met Asp Val Trp
            100                 105                 110 ggc caa ggg acc acg gtc acc gtc tca agc                                366
Gly Gln Gly Thr Thr Val Thr Val Ser Ser
        115                 120

<210> SEQ ID NO 140
<211> LENGTH: 122
<212> TYPE: PRT
<213> ORGANISM: Artificial Sequence
<220> FEATURE:
<223> OTHER INFORMATION: heavy chain variable region

<400> SEQUENCE: 140

Gln Val Gln Leu Val Glu Ser Gly Gly Val Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Arg Gly Ser Gly Trp Ser Leu Asp Asn Met Asp Val Trp
            100                 105                 110

Gly Gln Gly Thr Thr Val Thr Val Ser Ser
        115                 120

<210> SEQ ID NO 141
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 141 cag gtg cag ctg gtg gag tct ggc cca gga ctg gtg aag cct tcg ggg        48
Gln Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt        96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg        144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc        192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc        240
Lys Ser Arg Val Thr Ile Ser Val Asp Lys Ser Lys Asn Gln Phe Ser
65                  70                  75                  80 ctg aag ctg agc tct gtg acc gct gcg gac acg gcc gtg tat tac tgt        288
```

```
Leu Lys Leu Ser Ser Val Thr Ala Ala Asp Thr Ala Val Tyr Tyr Cys
                85                  90                  95 gcg aga gat agc agt ggg ttc tac ggt atg gac gtc tgg ggc caa ggg       336
Ala Arg Asp Ser Ser Gly Phe Tyr Gly Met Asp Val Trp Gly Gln Gly
            100                 105                 110 acc acg gtc acc gtc tca agc                                           357
Thr Thr Val Thr Val Ser Ser
        115

<210> SEQ ID NO 142
<211> LENGTH: 119
<212> TYPE: PRT
<213> ORGANISM: Artificial Sequence
<220> FEATURE:
<223> OTHER INFORMATION: heavy chain variable region

<400> SEQUENCE: 142

Gln Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ser Ser Gly Phe Tyr Gly Met Asp Val Trp Gly Gln Gly
            100                 105                 110

Thr Thr Val Thr Val Ser Ser
        115

<210> SEQ ID NO 143
<211> LENGTH: 360
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(360)

<400> SEQUENCE: 143 cag gtg cag ctg cag gag tcg ggc cca gga ctg gtg aag cct tcg ggg       48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg act gcc gcg gac acg gcc gtg tat tac tgt      288
```

```
Leu Lys Leu Ser Ser Val Thr Ala Ala Asp Thr Ala Val Tyr Tyr Cys
            85                  90                  95 gcg aga agc agc agc tgg tac tgg aat gct ttt gat atc tgg ggc caa      336
Ala Arg Ser Ser Ser Trp Tyr Trp Asn Ala Phe Asp Ile Trp Gly Gln
            100                 105                 110 ggg aca atg gtc acc gtc tca agc                                      360
Gly Thr Met Val Thr Val Ser Ser
        115                 120

<210> SEQ ID NO 144
<211> LENGTH: 120
<212> TYPE: PRT
<213> ORGANISM: Artificial Sequence
<220> FEATURE:
<223> OTHER INFORMATION: heavy chain variable region

<400> SEQUENCE: 144

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Ser Ser Ser Trp Tyr Trp Asn Ala Phe Asp Ile Trp Gly Gln
            100                 105                 110

Gly Thr Met Val Thr Val Ser Ser
        115                 120

<210> SEQ ID NO 145
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)

<400> SEQUENCE: 145 cag gtg cag cta cag cag tgg ggc cca gca ctg gtg aag cct tcg ggg      48
Gln Val Gln Leu Gln Gln Trp Gly Pro Ala Leu Val Lys Pro Ser Gly
1               5                   10                  15 acc ctg tcc ctc acc tgc tct gtc tct ggt gtc tcc atc acc agt aat      96
Thr Leu Ser Leu Thr Cys Ser Val Ser Gly Val Ser Ile Thr Ser Asn
            20                  25                  30 atc tgg tgg agt tgg gtc cgc cag tcc cca ggg aag ggg ctg gag tgg      144
Ile Trp Trp Ser Trp Val Arg Gln Ser Pro Gly Lys Gly Leu Glu Trp
        35                  40                  45 att ggg gaa gtc tat cat agt ggg agc acc aac tac aac ccg tcc ctc      192
Ile Gly Glu Val Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gct gtg tat tac tgt      288
```

```
Leu Lys Leu Ser Ser Val Thr Ala Ala Asp Thr Ala Val Tyr Tyr Cys
            85                  90                  95 gcg ggg tac cgt agc ttc ggg gag tcc tac tgg ggc cag gga acc ctg        336
Ala Gly Tyr Arg Ser Phe Gly Glu Ser Tyr Trp Gly Gln Gly Thr Leu
            100                 105                 110 gtc acc gtc tca agc                                                    351
Val Thr Val Ser Ser
        115

<210> SEQ ID NO 146
<211> LENGTH: 117
<212> TYPE: PRT
<213> ORGANISM: Artificial Sequence
<220> FEATURE:
<223> OTHER INFORMATION: heavy chain variable region

<400> SEQUENCE: 146

Gln Val Gln Leu Gln Gln Trp Gly Pro Ala Leu Val Lys Pro Ser Gly
1               5                   10                  15

Thr Leu Ser Leu Thr Cys Ser Val Ser Gly Val Ser Ile Thr Ser Asn
            20                  25                  30

Ile Trp Trp Ser Trp Val Arg Gln Ser Pro Gly Lys Gly Leu Glu Trp
        35                  40                  45

Ile Gly Glu Val Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Gly Tyr Arg Ser Phe Gly Ser Tyr Trp Gly Gln Gly Thr Leu
            100                 105                 110

Val Thr Val Ser Ser
        115

<210> SEQ ID NO 147
<211> LENGTH: 366
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(366)

<400> SEQUENCE: 147 cag gtg cag cta cag cag tgg ggc gca ggg ctg ttg aag cct tcg gag        48
Gln Val Gln Leu Gln Gln Trp Gly Ala Gly Leu Leu Lys Pro Ser Glu
1               5                   10                  15 acc ctg tct ctc acc tgc gtt gtc tat ggt ggg tcc ttc agc gat ttc        96
Thr Leu Ser Leu Thr Cys Val Val Tyr Gly Gly Ser Phe Ser Asp Phe
            20                  25                  30 tac tgg agc tgg atc cgc cag ccc cca ggg aag ggg cca gag tgg att       144
Tyr Trp Ser Trp Ile Arg Gln Pro Pro Gly Lys Gly Pro Glu Trp Ile
        35                  40                  45 ggg gaa gtc aat cct aga gga agc acc aac tac aac ccg tcc ctc aag       192
Gly Glu Val Asn Pro Arg Gly Ser Thr Asn Tyr Asn Pro Ser Leu Lys
    50                  55                  60 agt cga gcc acc ata tca cta gac acg tcc aag aac cag ttc tcc ctg       240
Ser Arg Ala Thr Ile Ser Leu Asp Thr Ser Lys Asn Gln Phe Ser Leu
65                  70                  75                  80 aag ctg agt tct gtg acc gcc gcg gac acg gct gtg tat ttc tgt gcg       288
```

```
Lys Leu Ser Ser Val Thr Ala Ala Asp Thr Ala Val Tyr Phe Cys Ala
                85                  90                  95 aga ggt cct cgg ccc ggg aga gat ggc tac aat tac ttt gac aac tgg      336
Arg Gly Pro Arg Pro Gly Arg Asp Gly Tyr Asn Tyr Phe Asp Asn Trp
            100                 105                 110 ggc cag ggc acc ctg gtc acc gtc tca agc                              366
Gly Gln Gly Thr Leu Val Thr Val Ser Ser
        115                 120

<210> SEQ ID NO 148
<211> LENGTH: 122
<212> TYPE: PRT
<213> ORGANISM: Artificial Sequence
<220> FEATURE:
<223> OTHER INFORMATION: heavy chain variable region

<400> SEQUENCE: 148

Gln Val Gln Leu Gln Gln Trp Gly Ala Gly Leu Leu Lys Pro Ser Glu
1               5                   10                  15

Thr Leu Ser Leu Thr Cys Val Val Tyr Gly Gly Ser Phe Ser Asp Phe
            20                  25                  30

Tyr Trp Ser Trp Ile Arg Gln Pro Pro Gly Lys Gly Pro Glu Trp Ile
        35                  40                  45

Gly Glu Val Asn Pro Arg Gly Ser Thr Asn Tyr Asn Pro Ser Leu Lys
    50                  55                  60

Ser Arg Ala Thr Ile Ser Leu Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Gly Pro Arg Pro Gly Arg Asp Gly Tyr Asn Tyr Phe Asp Asn Trp
            100                 105                 110

Gly Gln Gly Thr Leu Val Thr Val Ser Ser
        115                 120

<210> SEQ ID NO 149
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 149 cag gtg cag ctg cag gag tcg ggc cca gga ctg gtg aag cct tcg gag       48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agc agt agt       96
Thr Leu Ser Leu Thr Cys Thr Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
Leu Lys Leu Ser Ser Val Thr Ala Ala Asp Thr Ala Val Tyr Tyr Cys
```

```
Leu Lys Leu Ser Ser Val Thr Ala Ala Asp Thr Ala Val Tyr Tyr Cys
            85                  90                  95 gcg aga ggt ata gca gca gct ggt caa ggt gac tac tgg ggc cag gga      336
Ala Arg Gly Ile Ala Ala Ala Gly Gln Gly Asp Tyr Trp Gly Gln Gly
            100                 105                 110 acc ctg gtc acc gtc tca agc                                          357
Thr Leu Val Thr Val Ser Ser
        115

<210> SEQ ID NO 150
<211> LENGTH: 119
<212> TYPE: PRT
<213> ORGANISM: Artificial Sequence
<220> FEATURE:
<223> OTHER INFORMATION: heavy chain variable region

<400> SEQUENCE: 150

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Ile Ala Ala Ala Gly Gln Gly Asp Tyr Trp Gly Gln Gly
            100                 105                 110

Thr Leu Val Thr Val Ser Ser
        115

<210> SEQ ID NO 151
<211> LENGTH: 363
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(363)

<400> SEQUENCE: 151 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agc agt agt      96
Thr Leu Ser Leu Thr Cys Thr Val Ser Gly Gly Ser Ile Ser Ser Ser
            20                  25                  30 agt tac tac tgg ggc tgg atc cgc cag ccc cca ggg aag ggg ctg gag     144
Ser Tyr Tyr Trp Gly Trp Ile Arg Gln Pro Pro Gly Lys Gly Leu Glu
            35                  40                  45 tgg att ggg agt atc tat tat agt ggg agc acc tac tac aac ccg tcc     192
Trp Ile Gly Ser Ile Tyr Tyr Ser Gly Ser Thr Tyr Tyr Asn Pro Ser
        50                  55                  60 ctc aag agt cga gtc acc ata tcc gta gac acg tcc aag aac cag ttc     240
Leu Lys Ser Arg Val Thr Ile Ser Val Asp Thr Ser Lys Asn Gln Phe
65                  70                  75                  80 tcc ctg aag ctg agc tct gtg acc gcc gcg gac acg gcc gtg tat tac     288
```

```
Ser Leu Lys Leu Ser Ser Val Thr Ala Ala Asp Thr Ala Val Tyr Tyr
            85                  90                  95 tgt gcg aga gat ggg gga tac tac tac ggt atg gac gtc tgg ggc         336
Cys Ala Arg Asp Gly Gly Tyr Tyr Tyr Gly Met Asp Val Trp Gly
            100                 105                 110 caa ggg acc acg gtc acc gtc tca agc                                 363
Gln Gly Thr Thr Val Thr Val Ser Ser
        115                 120

<210> SEQ ID NO 152
<211> LENGTH: 121
<212> TYPE: PRT
<213> ORGANISM: Artificial Sequence
<220> FEATURE:
<223> OTHER INFORMATION: heavy chain variable region

<400> SEQUENCE: 152

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Gly Gly Tyr Tyr Tyr Gly Met Asp Val Trp Gly
            100                 105                 110

Gln Gly Thr Thr Val Thr Val Ser Ser
        115                 120

<210> SEQ ID NO 153
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)

<400> SEQUENCE: 153 cag gtg cag ctg cag gag tcg ggc cca gga ctg gtg aag cct tcg ggg    48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt    96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg   144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc   192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc   240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt   288
```

```
Leu Lys Leu Ser Ser Val Thr Ala Ala Asp Thr Ala Val Tyr Tyr Cys
            85                  90                  95 gcg agt agt ggt tat gat gct ttt gat atc tgg ggc caa ggg acc acg      336
Ala Ser Ser Gly Tyr Asp Ala Phe Asp Ile Trp Gly Gln Gly Thr Thr
                100                 105                 110 gtc acc gtc tca agc                                                  351
Val Thr Val Ser Ser
        115

<210> SEQ ID NO 154
<211> LENGTH: 117
<212> TYPE: PRT
<213> ORGANISM: Artificial Sequence
<220> FEATURE:
<223> OTHER INFORMATION: heavy chain variable region

<400> SEQUENCE: 154

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Ser Ser Gly Tyr Asp Ala Phe Asp Ile Trp Gly Gln Gly Thr Thr
                100                 105                 110

Val Thr Val Ser Ser
        115

<210> SEQ ID NO 155
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 155 cag gtg cag ctg cag gag tcg ggc cca gga ctg gtg aag cct tcg ggg       48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30 aat tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
```

```
Leu Lys Leu Ser Ser Val Thr Ala Ala Asp Thr Ala Val Tyr Tyr Cys
            85                  90                  95 gca cga tac agc tat gga acg gta gga att gac tac tgg ggc cag gga    336
Ala Arg Tyr Ser Tyr Gly Thr Val Gly Ile Asp Tyr Trp Gly Gln Gly
            100                 105                 110 acc ctg gtc acc gtc tca agc                                        357
Thr Leu Val Thr Val Ser Ser
            115

<210> SEQ ID NO 156
<211> LENGTH: 119
<212> TYPE: PRT
<213> ORGANISM: Artificial Sequence
<220> FEATURE:
<223> OTHER INFORMATION: heavy chain variable region

<400> SEQUENCE: 156

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Tyr Ser Tyr Gly Thr Val Gly Ile Asp Tyr Trp Gly Gln Gly
            100                 105                 110

Thr Leu Val Thr Val Ser Ser
            115

<210> SEQ ID NO 157
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)
<223> OTHER INFORMATION: heavy chain variable region

<400> SEQUENCE: 157 gag gtg cag ctg gtg cag tct ggg gga ggc gtg gtc cag cct ggg acg    48
Glu Val Gln Leu Val Gln Ser Gly Gly Gly Val Val Gln Pro Gly Thr
1               5                   10                  15 tcc ctg aga ctc tcc tgt gca gcc tct gga ttc agc ttc aga agt cat    96
Ser Leu Arg Leu Ser Cys Ala Ala Ser Gly Phe Ser Phe Arg Ser His
            20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg    192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80
```

```
ctg caa atg aac agc ctg aga gct gag gac acg gct gtg tat tac tgt      288
Leu Gln Met Asn Ser Leu Arg Ala Glu Asp Thr Ala Val Tyr Tyr Cys
                85                  90                  95 gcg act ata ggg ccg ggg gga ttt gac tac tgg ggc cag ggc acc ctg      336
Ala Thr Ile Gly Pro Gly Gly Phe Asp Tyr Trp Gly Gln Gly Thr Leu
            100                 105                 110 gtc acc gtc tca agc                                                  351
Val Thr Val Ser Ser
        115
```

<210> SEQ ID NO 158
<211> LENGTH: 117
<212> TYPE: PRT
<213> ORGANISM: Artificial Sequence
<220> FEATURE:
<223> OTHER INFORMATION: heavy chain variable region

<400> SEQUENCE: 158

```
Glu Val Gln Leu Val Gln Ser Gly Gly Gly Val Val Gln Pro Gly Thr
1               5                   10                  15

Ser Leu Arg Leu Ser Cys Ala Ala Ser Gly Phe Ser Phe Arg Ser His
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ile Gly Pro Gly Gly Phe Asp Tyr Trp Gly Gln Gly Thr Leu
            100                 105                 110

Val Thr Val Ser Ser
        115
```

<210> SEQ ID NO 159
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 159

```
cag gtg cag ctg cag gag tcc ggc cca gga ctg gtg aag cct tcg gag       48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc att aga aat tac       96
Thr Leu Ser Leu Thr Cys Thr Val Ser Gly Gly Ser Ile Arg Asn Tyr
            20                  25                  30 tac tgg agt tgg atc cgg cag ccc cca ggg aag gga ctg gag tgg att      144
Tyr Trp Ser Trp Ile Arg Gln Pro Pro Gly Lys Gly Leu Glu Trp Ile
        35                  40                  45 ggg tat att tct gac agt ggg aat acc aac tac aat ccc tcc ctc aag      192
Gly Tyr Ile Ser Asp Ser Gly Asn Thr Asn Tyr Asn Pro Ser Leu Lys
    50                  55                  60 agt cga gtc acc ata tca gta gac acg tcc aag aac cag ttc tcc cta      240
Ser Arg Val Thr Ile Ser Val Asp Thr Ser Lys Asn Gln Phe Ser Leu
65                  70                  75                  80
```

-continued

| | |
|---|---|
| aag ctg acc tct gtg acc gcc aca gac acg gct gcg tat ttc tgt gcg<br>Lys Leu Thr Ser Val Thr Ala Thr Asp Thr Ala Ala Tyr Phe Cys Ala<br>                85                          90                          95 | 288 |
| aga cat cga agc agc tgg gca tgg tac ttc gat ctc tgg ggc cgt ggc<br>Arg His Arg Ser Ser Trp Ala Trp Tyr Phe Asp Leu Trp Gly Arg Gly<br>            100                        105                        110 | 336 |
| acc ctg gtc acc gtc tca agc<br>Thr Leu Val Thr Val Ser Ser<br>        115 | 357 |

<210> SEQ ID NO 160
<211> LENGTH: 119
<212> TYPE: PRT
<213> ORGANISM: Artificial Sequence
<220> FEATURE:
<223> OTHER INFORMATION: heavy chain variable region

<400> SEQUENCE: 160

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Tyr Ile Ser Asp Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Thr Asp Thr Ala Ala Tyr Phe Cys Ala
                85                  90                  95

Arg His Arg Ser Ser Trp Ala Trp Tyr Phe Asp Leu Trp Gly Arg Gly
            100                 105                 110

Thr Leu Val Thr Val Ser Ser
        115

<210> SEQ ID NO 161
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 161

| | |
|---|---|
| cag gtg cag ctg cag gag tcg ggc cca gga ctg gtg aag cct tcg gag<br>Gln Val Gln Leu Gln Glu Ser Gly Pro Gly Leu Val Lys Pro Ser Glu<br>1               5                    10                  15 | 48 |
| acc ctg tcc ctc acc tgc gct gtc tct ggt ggc tcc atc agc agt agt<br>Thr Leu Ser Leu Thr Cys Ala Val Ser Gly Gly Ser Ile Ser Ser Ser<br>         20                     25                    30 | 96 |
| aac tgg tgg agt tgg gtc cgc cag ccc cca ggg aag ggg ctg gag tgg<br>Asn Trp Trp Ser Trp Val Arg Gln Pro Pro Gly Lys Gly Leu Glu Trp<br>            35                    40                    45 | 144 |
| att ggg gaa atc tat cat agt ggg agc acc aac tac aac ccg tcc ctc<br>Ile Gly Glu Ile Tyr His Ser Gly Ser Thr Asn Tyr Asn Pro Ser Leu<br>        50                     55                    60 | 192 |
| aag agt cga gtc acc ata tca gta gac aag tcc aag aac cag ttc tcc<br>Lys Ser Arg Val Thr Ile Ser Val Asp Lys Ser Lys Asn Gln Phe Ser<br>65                  70                  75                  80 | 240 |

```
ctg aag ctg agc tct gtg acc gcc gcg gac acg gcc gtg tat tac tgt    288
Leu Lys Leu Ser Ser Val Thr Ala Ala Asp Thr Ala Val Tyr Tyr Cys
                85                  90                  95 gcg aga gtg ggc agt ggc tgg tac gtt gac tac tgg ggc cag gga acc    336
Ala Arg Val Gly Ser Gly Trp Tyr Val Asp Tyr Trp Gly Gln Gly Thr
            100                 105                 110 ctg gtc acc gtc tca agc                                            354
Leu Val Thr Val Ser Ser
        115
```

<210> SEQ ID NO 162
<211> LENGTH: 118
<212> TYPE: PRT
<213> ORGANISM: Artificial Sequence
<220> FEATURE:
<223> OTHER INFORMATION: heavy chain variable region

<400> SEQUENCE: 162

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Gly Ser Gly Trp Tyr Val Asp Tyr Trp Gly Gln Gly Thr
            100                 105                 110

Leu Val Thr Val Ser Ser
        115
```

<210> SEQ ID NO 163
<211> LENGTH: 360
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(360)

<400> SEQUENCE: 163

```
cag gtg cag ctg cag gag tcc ggc cca gga ctg gtg aag cct tcg ggg    48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt    96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg   144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc   192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc   240
Lys Ser Arg Val Thr Ile Ser Val Asp Lys Ser Lys Asn Gln Phe Ser
65                  70                  75                  80
```

```
ctg aag ctg agc tct gtg acc gcc gcg gac acg gcc gtg tat tac tgt    288
Leu Lys Leu Ser Ser Val Thr Ala Ala Asp Thr Ala Val Tyr Tyr Cys
                85                  90                  95 gcg aga gtt tct ggc tac tac tac ggt atg gac gtc tgg ggc caa        336
Ala Arg Val Ser Gly Tyr Tyr Tyr Gly Met Asp Val Trp Gly Gln
            100                 105                 110 ggg acc acg gtc acc gtc tca agc                                    360
Gly Thr Thr Val Thr Val Ser Ser
        115                 120
```

<210> SEQ ID NO 164
<211> LENGTH: 120
<212> TYPE: PRT
<213> ORGANISM: Artificial Sequence
<220> FEATURE:
<223> OTHER INFORMATION: heavy chain variable region

<400> SEQUENCE: 164

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Ser Gly Tyr Tyr Tyr Gly Met Asp Val Trp Gly Gln
            100                 105                 110

Gly Thr Thr Val Thr Val Ser Ser
        115                 120
```

<210> SEQ ID NO 165
<211> LENGTH: 369
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(369)

<400> SEQUENCE: 165

```
gag gtc cag ctg gta cag tct ggg gga ggc gtg gtc cag cct ggg agg    48
Glu Val Gln Leu Val Gln Ser Gly Gly Gly Val Val Gln Pro Gly Arg
1               5                   10                  15 tcc ctg aga ctc tcc tgt gca gcc tct gga ttc acc ttc agt agc tat    96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg    192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80
```

```
ctg caa atg aac agc ctg aga gct gag gac acg gct gtg tat tac tgt       288
Leu Gln Met Asn Ser Leu Arg Ala Glu Asp Thr Ala Val Tyr Tyr Cys
                85                  90                  95 gcg aaa gcg tat agc agt ggc tgg tac gac tac tac ggt atg gac gtc       336
Ala Lys Ala Tyr Ser Ser Gly Trp Tyr Asp Tyr Tyr Gly Met Asp Val
            100                 105                 110 tgg ggc caa ggg acc acg gtc acc gtc tca agc                           369
Trp Gly Gln Gly Thr Thr Val Thr Val Ser Ser
        115                 120
```

<210> SEQ ID NO 166
<211> LENGTH: 123
<212> TYPE: PRT
<213> ORGANISM: Artificial Sequence
<220> FEATURE:
<223> OTHER INFORMATION: heavy chain variable region

<400> SEQUENCE: 166

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Ser Ser Gly Trp Tyr Asp Tyr Tyr Gly Met Asp Val
            100                 105                 110

Trp Gly Gln Gly Thr Thr Val Thr Val Ser Ser
        115                 120
```

<210> SEQ ID NO 167
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)

<400> SEQUENCE: 167

```
cag gtg cag ctg cag gag tcg ggc cca gga ctg gtg aag cct tcg ggg        48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt        96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg       144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc       192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc       240
Lys Ser Arg Val Thr Ile Ser Val Asp Lys Ser Lys Asn Gln Phe Ser
65                  70                  75                  80
```

```
ctg aag ctg agc tct gtg acc gcc gcg gac acg gcc gtg tat tac tgt    288
Leu Lys Leu Ser Ser Val Thr Ala Ala Asp Thr Ala Val Tyr Tyr Cys
                85                  90                  95 gcg aga gcc agc gtt gat gct ttt gat atc tgg ggc caa ggg aca atg    336
Ala Arg Ala Ser Val Asp Ala Phe Asp Ile Trp Gly Gln Gly Thr Met
            100                 105                 110 gtc acc gtc tca agc                                                351
Val Thr Val Ser Ser
        115

<210> SEQ ID NO 168
<211> LENGTH: 117
<212> TYPE: PRT
<213> ORGANISM: Artificial Sequence
<220> FEATURE:
<223> OTHER INFORMATION: heavy chain variable region

<400> SEQUENCE: 168

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Ser Val Asp Ala Phe Asp Ile Trp Gly Gln Gly Thr Met
            100                 105                 110

Val Thr Val Ser Ser
        115

<210> SEQ ID NO 169
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 169 cag gtg cag ctg cag gag tcc ggc cca gga ctg gtg aag cct tcg ggg    48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt    96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg   144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc   192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc   240
Lys Ser Arg Val Thr Ile Ser Val Asp Lys Ser Lys Asn Gln Phe Ser
65                  70                  75                  80
```

| | |
|---|---|
| ctg aag ctg agc tct gtg acc gct gcg gac acg gcc gtg tac tac tgt<br>Leu Lys Leu Ser Ser Val Thr Ala Ala Asp Thr Ala Val Tyr Tyr Cys<br>                 85                      90                      95 | 288 |
| gcg aga ggg ctg ggg gat agt agt ggt tat atc ctt tgg ggc caa ggg<br>Ala Arg Gly Leu Gly Asp Ser Ser Gly Tyr Ile Leu Trp Gly Gln Gly<br>                 100                     105                    110 | 336 |
| aca atg gtc acc gtc tca agc<br>Thr Met Val Thr Val Ser Ser<br>        115 | 357 |

<210> SEQ ID NO 170
<211> LENGTH: 119
<212> TYPE: PRT
<213> ORGANISM: Artificial Sequence
<220> FEATURE:
<223> OTHER INFORMATION: heavy chain variable region

<400> SEQUENCE: 170

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Leu Gly Asp Ser Ser Gly Tyr Ile Leu Trp Gly Gln Gly
            100                 105                 110

Thr Met Val Thr Val Ser Ser
        115

<210> SEQ ID NO 171
<211> LENGTH: 348
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(348)

<400> SEQUENCE: 171

| | |
|---|---|
| cag gta cag ctg cag cag tca ggc cca gga ctg gtg aag cct tcg ggg<br>Gln Val Gln Leu Gln Gln Ser Gly Pro Gly Leu Val Lys Pro Ser Gly<br>1                 5                     10                  15 | 48 |
| acc ctg tcc ctc acc tgc gct gtc tct ggt ggc tcc atc agc agt agt<br>Thr Leu Ser Leu Thr Cys Ala Val Ser Gly Gly Ser Ile Ser Ser Ser<br>           20                     25                    30 | 96 |
| aac tgg tgg agt tgg gtc cgc cag ccc cca ggg aag ggg ctg gag tgg<br>Asn Trp Trp Ser Trp Val Arg Gln Pro Pro Gly Lys Gly Leu Glu Trp<br>        35                  40                  45 | 144 |
| att ggg gaa atc tat cat agt ggg agc acc aac tac aac ccg tcc ctc<br>Ile Gly Glu Ile Tyr His Ser Gly Ser Thr Asn Tyr Asn Pro Ser Leu<br>    50                  55                  60 | 192 |
| aag agt cga gtc acc ata tca gta gac aag tcc aag aac cag ttc tcc<br>Lys Ser Arg Val Thr Ile Ser Val Asp Lys Ser Lys Asn Gln Phe Ser<br>65                70                75                80 | 240 |

```
ctg aag ctg agc tct gtg act ccc gag gac acg gct gtg tat tac tgt     288
Leu Lys Leu Ser Ser Val Thr Pro Glu Asp Thr Ala Val Tyr Tyr Cys
                85                  90                  95 gca aga gat cac ggc ccc ttt gac tac tgg ggc cgg gga acc ctg gtc     336
Ala Arg Asp His Gly Pro Phe Asp Tyr Trp Gly Arg Gly Thr Leu Val
            100                 105                 110 acc gtc tca agc                                                     348
Thr Val Ser Ser
        115

<210> SEQ ID NO 172
<211> LENGTH: 116
<212> TYPE: PRT
<213> ORGANISM: Artificial Sequence
<220> FEATURE:
<223> OTHER INFORMATION: heavy chain variable region

<400> SEQUENCE: 172

Gln Val Gln Leu Gln Gln Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Pro Glu Asp Thr Ala Val Tyr Tyr Cys
                85                  90                  95

Ala Arg Asp His Gly Pro Phe Asp Tyr Trp Gly Arg Gly Thr Leu Val
            100                 105                 110

Thr Val Ser Ser
        115

<210> SEQ ID NO 173
<211> LENGTH: 360
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(360)

<400> SEQUENCE: 173 cag gtg cag ctg gtg caa tct ggg gga ggc gtg gtc cag cct ggg agg     48
Gln Val Gln Leu Val Gln Ser Gly Gly Gly Val Val Gln Pro Gly Arg
1               5                   10                  15 tcc ctg aga ctc tcc tgt gca gcc tct gga ttc gcc ttc agt agc tat     96
Ser Leu Arg Leu Ser Cys Ala Ala Ser Gly Phe Ala Phe Ser Ser Tyr
            20                  25                  30 ggc atg cac tgg gtc cgc cag gct cca ggg aag ggg ctg gag tgg gtt    144
Gly Met His Trp Val Arg Gln Ala Pro Gly Lys Gly Leu Glu Trp Val
        35                  40                  45 tca tac att agt agt agt agt agt acc ata tac tac gca gac tct gtg    192
Ser Tyr Ile Ser Ser Ser Ser Ser Thr Ile Tyr Tyr Ala Asp Ser Val
    50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80
```

```
ctg caa atg aac agc ctg aga gcc gag gac acg gct gtg tat tac tgt    288
Leu Gln Met Asn Ser Leu Arg Ala Glu Asp Thr Ala Val Tyr Tyr Cys
                85                  90                  95 gcg aga gat cga ttt ggg tcg ggg cac ttg ccc gac tac tgg ggc cag    336
Ala Arg Asp Arg Phe Gly Ser Gly His Leu Pro Asp Tyr Trp Gly Gln
            100                 105                 110 gga acc ctg gtc acc gtc tca agc                                     360
Gly Thr Leu Val Thr Val Ser Ser
        115                 120

<210> SEQ ID NO 174
<211> LENGTH: 120
<212> TYPE: PRT
<213> ORGANISM: Artificial Sequence
<220> FEATURE:
<223> OTHER INFORMATION: heavy chain variable region

<400> SEQUENCE: 174

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Phe Gly Ser Gly His Leu Pro Asp Tyr Trp Gly Gln
            100                 105                 110

Gly Thr Leu Val Thr Val Ser Ser
        115                 120

<210> SEQ ID NO 175
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 175 cag gtg cag cta cag cag tgg ggc gca gga ctg ttg aag cct tcg gag    48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac    96
Thr Leu Ser Leu Thr Cys Ala Val Tyr Gly Gly Ser Phe Ser Gly Tyr
            20                  25                  30 tac tgg agc tgg atc cgc cag ccc cca ggg aag ggg ctg gag tgg att    144
Tyr Trp Ser Trp Ile Arg Gln Pro Pro Gly Lys Gly Leu Glu Trp Ile
        35                  40                  45 ggg gaa atc aat cat agt gga agc acc aac tac aac ccg tcc ctc aag    192
Gly Glu Ile Asn His Ser Gly Ser Thr Asn Tyr Asn Pro Ser Leu Lys
    50                  55                  60 agt cga gtc acc ata tca gta gac acg tcc aag aac cag ttc tcc ctg    240
Ser Arg Val Thr Ile Ser Val Asp Thr Ser Lys Asn Gln Phe Ser Leu
65                  70                  75                  80
```

```
aag ctg agc tct gtg acc gcc gcg gac acg gct gtg tat tac tgt gcg    288
Lys Leu Ser Ser Val Thr Ala Ala Asp Thr Ala Val Tyr Tyr Cys Ala
                85                  90                  95 aga gtt ggg tat agc agt ggc cgt gac gtt gac tac tgg ggc cag ggc    336
Arg Val Gly Tyr Ser Ser Gly Arg Asp Val Asp Tyr Trp Gly Gln Gly
            100                 105                 110 acc ctg gtc acc gtc tca agc                                        357
Thr Leu Val Thr Val Ser Ser
        115

<210> SEQ ID NO 176
<211> LENGTH: 119
<212> TYPE: PRT
<213> ORGANISM: Artificial Sequence
<220> FEATURE:
<223> OTHER INFORMATION: heavy chain variable region

<400> SEQUENCE: 176

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Tyr Ser Ser Gly Arg Asp Val Asp Tyr Trp Gly Gln Gly
            100                 105                 110

Thr Leu Val Thr Val Ser Ser
        115

<210> SEQ ID NO 177
<211> LENGTH: 360
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(360)

<400> SEQUENCE: 177 gag gtc cag ctg gtg gag tct ggc cca gga ctg gtg aag cct tcg ggg    48
Glu Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt    96
Thr Leu Ser Leu Thr Cys Ala Val Ser Gly Gly Ser Ile Ser Ser Ser
            20                  25                  30 aac tgg tgg agt tgg atc cgg cag ccc cca ggg aag ggg ctg gag tgg    144
Asn Trp Trp Ser Trp Ile Arg Gln Pro Pro Gly Lys Gly Leu Glu Trp
        35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
65                  70                  75                  80
```

```
ctg aag ctg agc tct gtg acc gcc gcg gac acg gcc gtg tat tac tgt    288
Leu Lys Leu Ser Ser Val Thr Ala Ala Asp Thr Ala Val Tyr Tyr Cys
                85                  90                  95 gcg aga gat agc agc agc tgg tac tac ggt atg gac gtc tgg ggc caa    336
Ala Arg Asp Ser Ser Ser Trp Tyr Tyr Gly Met Asp Val Trp Gly Gln
            100                 105                 110 ggg acc acg gtc acc gtc tca agc                                    360
Gly Thr Thr Val Thr Val Ser Ser
        115                 120

<210> SEQ ID NO 178
<211> LENGTH: 120
<212> TYPE: PRT
<213> ORGANISM: Artificial Sequence
<220> FEATURE:
<223> OTHER INFORMATION: heavy chain variable region

<400> SEQUENCE: 178

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Ile Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ser Ser Ser Trp Tyr Tyr Gly Met Asp Val Trp Gly Gln
            100                 105                 110

Gly Thr Thr Val Thr Val Ser Ser
        115                 120

<210> SEQ ID NO 179
<211> LENGTH: 348
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(348)

<400> SEQUENCE: 179 gag gtc cag ctg gtg gag tcc ggc cca gga ctg gtg aag cct tcg gag    48
Glu Val Gln Leu Val Glu Ser Gly Pro Gly Leu Val Lys Pro Ser Glu
1               5                   10                  15 acc ctg tcc ctc acc tgc gct gtc tct ggt ggc tcc atc agc agt agt    96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
65                  70                  75                  80
```

```
ctg aag ctg agc tct gtg acc gct gcg gac acg gcc gta tat tat tgt    288
Leu Lys Leu Ser Ser Val Thr Ala Ala Asp Thr Ala Val Tyr Tyr Cys
            85                  90                  95 gcg aga tcg acg tgg tcc ctt gac tac tgg ggc cag ggc acc ctg gtc    336
Ala Arg Ser Thr Trp Ser Leu Asp Tyr Trp Gly Gln Gly Thr Leu Val
            100                 105                 110 acc gtc tca agc                                                    348
Thr Val Ser Ser
        115
```

<210> SEQ ID NO 180
<211> LENGTH: 116
<212> TYPE: PRT
<213> ORGANISM: Artificial Sequence
<220> FEATURE:
<223> OTHER INFORMATION: heavy chain variable region

<400> SEQUENCE: 180

```
Glu Val Gln Leu Val Glu Ser Gly Pro Gly Leu Val Lys Pro Ser Glu
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Ser Thr Trp Ser Leu Asp Tyr Trp Gly Gln Gly Thr Leu Val
            100                 105                 110

Thr Val Ser Ser
        115
```

<210> SEQ ID NO 181
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 181

```
gag gtc cag ctg gtg gag tct ggc cca gga ctg gtg aag cct tcg ggg     48
Glu Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt     96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
65                  70                  75                  80
```

```
ctg aag ctg agc tct gtg acc gct gcg gac acg gcc gta tat tac tgt    288
Leu Lys Leu Ser Ser Val Thr Ala Ala Asp Thr Ala Val Tyr Tyr Cys
                85                  90                  95 gcg aga ctc tcg ttt gcc gat cct ttt gat atc tgg ggc caa ggg aca    336
Ala Arg Leu Ser Phe Ala Asp Pro Phe Asp Ile Trp Gly Gln Gly Thr
                100                 105                 110 atg gtc acc gtc tca agc                                            354
Met Val Thr Val Ser Ser
        115
```

<210> SEQ ID NO 182
<211> LENGTH: 118
<212> TYPE: PRT
<213> ORGANISM: Artificial Sequence
<220> FEATURE:
<223> OTHER INFORMATION: heavy chain variable region

<400> SEQUENCE: 182

```
Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Ser Phe Ala Asp Pro Phe Asp Ile Trp Gly Gln Gly Thr
                100                 105                 110

Met Val Thr Val Ser Ser
        115
```

<210> SEQ ID NO 183
<211> LENGTH: 366
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(366)

<400> SEQUENCE: 183

```
cag gtc cag ctg gtg cag tct ggg gct gag gtg aag aag cct ggg tcc    48
Gln Val Gln Leu Val Gln Ser Gly Ala Glu Val Lys Lys Pro Gly Ser
1               5                   10                  15 tcg gtg aag gtc tcc tgc aag gct tct gga ggc acc ttc agc agc tat    96
Ser Val Lys Val Ser Cys Lys Ala Ser Gly Gly Thr Phe Ser Ser Tyr
            20                  25                  30 gct atc agc tgg gtg cga cag gcc cct gga caa ggg ctt gag tgg atg    144
Ala Ile Ser Trp Val Arg Gln Ala Pro Gly Gln Gly Leu Glu Trp Met
        35                  40                  45 gga agg atc atc ccc atc ctt ggt ata gca aac tac gca cag aag ttc    192
Gly Arg Ile Ile Pro Ile Leu Gly Ile Ala Asn Tyr Ala Gln Lys Phe
    50                  55                  60 cag ggc aga gtc acg att acc gcg gac aaa tcc acg agc aca gcc tac    240
Gln Gly Arg Val Thr Ile Thr Ala Asp Lys Ser Thr Ser Thr Ala Tyr
65                  70                  75                  80
```

```
atg gag ctg agc agc ctg aga tct gag gac acg gcc gtg tat tac tgt    288
Met Glu Leu Ser Ser Leu Arg Ser Glu Asp Thr Ala Val Tyr Tyr Cys
                85                  90                  95 gca tat ggt tcg ggg agt tat tac gac tac tac tac atg gac gtc tgg    336
Ala Tyr Gly Ser Gly Ser Tyr Tyr Asp Tyr Tyr Tyr Met Asp Val Trp
            100                 105                 110 ggc aaa ggg acc acg gtc acc gtc tca agc                            366
Gly Lys Gly Thr Thr Val Thr Val Ser Ser
        115                 120
```

<210> SEQ ID NO 184
<211> LENGTH: 122
<212> TYPE: PRT
<213> ORGANISM: Artificial Sequence
<220> FEATURE:
<223> OTHER INFORMATION: heavy chain variable region

<400> SEQUENCE: 184

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Gly Ser Gly Ser Tyr Tyr Asp Tyr Tyr Tyr Met Asp Val Trp
            100                 105                 110

Gly Lys Gly Thr Thr Val Thr Val Ser Ser
        115                 120
```

<210> SEQ ID NO 185
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 185

```
gag gtc cag ctg gtg cag tct ggg gga ggc ttg gtc cag cct ggg ggg    48
Glu Val Gln Leu Val Gln Ser Gly Gly Gly Leu Val Gln Pro Gly Gly
1               5                   10                  15 tcc ctg aga ctc tcc tgt tca gcc tcc gga ttc acc ttc agt agc tat    96
Ser Leu Arg Leu Ser Cys Ser Ala Ser Gly Phe Thr Phe Ser Ser Tyr
            20                  25                  30 gct atg cac tgg gtc cgc cag gct cca ggg aag gga ctg gaa tat gtt    144
Ala Met His Trp Val Arg Gln Ala Pro Gly Lys Gly Leu Glu Tyr Val
        35                  40                  45 tca act att agt agt aat ggg gat agc aca tac tac gca gac tcc gtg    192
Ser Thr Ile Ser Ser Asn Gly Asp Ser Thr Tyr Tyr Ala Asp Ser Val
    50                  55                  60 aag ggc aga ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80
```

```
ctg caa atg aac agc ctg aga gct gag gac acg gct gtg tat tac tgt      288
Leu Gln Met Asn Ser Leu Arg Ala Glu Asp Thr Ala Val Tyr Tyr Cys
            85                  90                  95 gcg aaa gaa gaa gta tgg cta cag gct ttt gat atc tgg ggc caa ggg      336
Ala Lys Glu Glu Val Trp Leu Gln Ala Phe Asp Ile Trp Gly Gln Gly
            100                 105                 110 aca atg gtc acc gtc tca agc                                          357
Thr Met Val Thr Val Ser Ser
        115
```

<210> SEQ ID NO 186
<211> LENGTH: 119
<212> TYPE: PRT
<213> ORGANISM: Artificial Sequence
<220> FEATURE:
<223> OTHER INFORMATION: heavy chain variable region

<400> SEQUENCE: 186

```
Glu Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Thr Ile Ser Ser Asn Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Glu Glu Val Trp Leu Gln Ala Phe Asp Ile Trp Gly Gln Gly
            100                 105                 110

Thr Met Val Thr Val Ser Ser
        115
```

<210> SEQ ID NO 187
<211> LENGTH: 345
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(345)

<400> SEQUENCE: 187

```
cag ctg cag ctg cag gag tcg ggc cca gga ctg gtg aag cct tcg gag      48
Gln Leu Gln Leu Gln Glu Ser Gly Pro Gly Leu Val Lys Pro Ser Glu
1               5                   10                  15 acc ctg tcc ctc acc tgc act gtc tct ggt ggc tcc atc agt agt aac      96
Thr Leu Ser Leu Thr Cys Thr Val Ser Gly Gly Ser Ile Ser Ser Asn
            20                  25                  30 tgg tgg agt tgg gtc cgc cag ccc cca ggg aag ggg ctg gag tgg att     144
Trp Trp Ser Trp Val Arg Gln Pro Pro Gly Lys Gly Leu Glu Trp Ile
        35                  40                  45 ggg gaa atc tat cat agt ggg agc acc aac tac aac ccc tcc ctc aag     192
Gly Glu Ile Tyr His Ser Gly Ser Thr Asn Tyr Asn Pro Ser Leu Lys
    50                  55                  60 agt cga gtc acc atc tca gta gac acg tcc aag aac cag ttc tcc ctg     240
Ser Arg Val Thr Ile Ser Val Asp Thr Ser Lys Asn Gln Phe Ser Leu
65                  70                  75                  80
```

```
aag ctg agc tct gtg acc gct gcg gac acg gcc gtg tat tac tgt gcg       288
Lys Leu Ser Ser Val Thr Ala Ala Asp Thr Ala Val Tyr Tyr Cys Ala
                85                  90                  95 aga gat aag gga tac atg gac gtc tgg ggc aaa ggg acc acg gtc acc       336
Arg Asp Lys Gly Tyr Met Asp Val Trp Gly Lys Gly Thr Thr Val Thr
            100                 105                 110 gtc tca agc                                                           345
Val Ser Ser
        115

<210> SEQ ID NO 188
<211> LENGTH: 115
<212> TYPE: PRT
<213> ORGANISM: Artificial Sequence
<220> FEATURE:
<223> OTHER INFORMATION: heavy chain variable region

<400> SEQUENCE: 188

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Trp Trp Ser Trp Val Arg Gln Pro Pro Gly Lys Gly Leu Glu Trp Ile
        35                  40                  45

Gly Glu Ile Tyr His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Gly Tyr Met Asp Val Trp Gly Lys Gly Thr Thr Val Thr
            100                 105                 110

Val Ser Ser
        115

<210> SEQ ID NO 189
<211> LENGTH: 363
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(363)

<400> SEQUENCE: 189 cag gta cag ctg cag cag tca ggg gct gag gtg aag aag cct ggg tcc       48
Gln Val Gln Leu Gln Gln Ser Gly Ala Glu Val Lys Lys Pro Gly Ser
1               5                   10                  15 tcg gtg aag gtc tcc tgc aag gct tct gga ggc acc ttc agc agc tat       96
Ser Val Lys Val Ser Cys Lys Ala Ser Gly Gly Thr Phe Ser Ser Tyr
            20                  25                  30 gct atc agc tgg gtg cga cag gcc cct gga caa ggg ctt gag tgg atg       144
Ala Ile Ser Trp Val Arg Gln Ala Pro Gly Gln Gly Leu Glu Trp Met
        35                  40                  45 gga agg atc atc cct atc ctt ggt ata gca aac tac gca cag aag ttc       192
Gly Arg Ile Ile Pro Ile Leu Gly Ile Ala Asn Tyr Ala Gln Lys Phe
    50                  55                  60 cag ggc aga gtc acg att acc gcg gac aaa tcc acg agc aca gcc tac       240
Gln Gly Arg Val Thr Ile Thr Ala Asp Lys Ser Thr Ser Thr Ala Tyr
65                  70                  75                  80
```

```
atg gag ctg agc agc ctg aga tct gag gac acg gcc gtg tat tac tgt    288
Met Glu Leu Ser Ser Leu Arg Ser Glu Asp Thr Ala Val Tyr Tyr Cys
            85                  90                  95 gcg aga gat cat agg ttc gac tac gcc tgg tac ttc gat ctc tgg ggc    336
Ala Arg Asp His Arg Phe Asp Tyr Ala Trp Tyr Phe Asp Leu Trp Gly
            100                 105                 110 cgt ggc acc ctg gtc acc gtc tca agc                                363
Arg Gly Thr Leu Val Thr Val Ser Ser
        115                 120

<210> SEQ ID NO 190
<211> LENGTH: 121
<212> TYPE: PRT
<213> ORGANISM: Artificial Sequence
<220> FEATURE:
<223> OTHER INFORMATION: heavy chain variable region

<400> SEQUENCE: 190

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Arg Phe Asp Tyr Ala Trp Tyr Phe Asp Leu Trp Gly
            100                 105                 110

Arg Gly Thr Leu Val Thr Val Ser Ser
        115                 120

<210> SEQ ID NO 191
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)

<400> SEQUENCE: 191 cag gtg cag ctg cag gag tcg ggc cca gga ctg ctg aag cct tcg ggg    48
Gln Val Gln Leu Gln Glu Ser Gly Pro Gly Leu Leu Lys Pro Ser Gly
1               5                   10                  15 acc ctg tcc ctc acc tgc gct gtc tct ggt ggc tcc atc agc agt agc    96
Thr Leu Ser Leu Thr Cys Ala Val Ser Gly Gly Ser Ile Ser Ser Ser
            20                  25                  30 aac tgg tgg agt tgg gtc cgc cag ccc cca ggg gag ggg ctg gag tgg    144
Asn Trp Trp Ser Trp Val Arg Gln Pro Pro Gly Glu Gly Leu Glu Trp
        35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
65                  70                  75                  80
```

```
ctg aag ctg agc tct gtg acc gcc gcg gac acg gcc gtc tat tac tgt    288
Leu Lys Leu Ser Ser Val Thr Ala Ala Asp Thr Ala Val Tyr Tyr Cys
                85                  90                  95 gcg aga gat cta acg ggg agt ctt gac tac tgg ggc cag gga acc ctg    336
Ala Arg Asp Leu Thr Gly Ser Leu Asp Tyr Trp Gly Gln Gly Thr Leu
            100                 105                 110 gtc acc gtc tca agc                                                351
Val Thr Val Ser Ser
        115
```

<210> SEQ ID NO 192
<211> LENGTH: 117
<212> TYPE: PRT
<213> ORGANISM: Artificial Sequence
<220> FEATURE:
<223> OTHER INFORMATION: heavy chain variable region

<400> SEQUENCE: 192

```
Gln Val Gln Leu Gln Glu Ser Gly Pro Gly Leu Leu Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Glu Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Leu Thr Gly Ser Leu Asp Tyr Trp Gly Gln Gly Thr Leu
            100                 105                 110

Val Thr Val Ser Ser
        115
```

<210> SEQ ID NO 193
<211> LENGTH: 351
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(351)

<400> SEQUENCE: 193

```
cag gtg cag ctg cag gag tcc ggc cca gga ctg gtg aag cct tcg ggg    48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt    96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
65                  70                  75                  80
```

```
ctg aag ctg agc tct gtg acc gcc gcg gac acg gcc gtg tat tac tgt       288
Leu Lys Leu Ser Ser Val Thr Ala Ala Asp Thr Ala Val Tyr Tyr Cys
                85                  90                  95 gcg aga ata cgc tat gat gct ttt gat atc tgg ggc caa ggg aca atg       336
Ala Arg Ile Arg Tyr Asp Ala Phe Asp Ile Trp Gly Gln Gly Thr Met
            100                 105                 110 gtc acc gtc tca agc                                                   351
Val Thr Val Ser Ser
        115

<210> SEQ ID NO 194
<211> LENGTH: 117
<212> TYPE: PRT
<213> ORGANISM: Artificial Sequence
<220> FEATURE:
<223> OTHER INFORMATION: heavy chain variable region

<400> SEQUENCE: 194

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Arg Tyr Asp Ala Phe Asp Ile Trp Gly Gln Gly Thr Met
            100                 105                 110

Val Thr Val Ser Ser
        115

<210> SEQ ID NO 195
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 195 cag gtg cag ctg cag gag tcg ggc cca gga ctg gtg aag cct tcg gag       48
Gln Val Gln Leu Gln Glu Ser Gly Pro Gly Leu Val Lys Pro Ser Glu
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg       144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc       192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc       240
Lys Ser Arg Val Thr Ile Ser Val Asp Lys Ser Lys Asn Gln Phe Ser
65                  70                  75                  80
```

```
ctg aag ctg agc tct gtg acc gct gcg gac acg gcc gtg tat tac tgt     288
Leu Lys Leu Ser Ser Val Thr Ala Ala Asp Thr Ala Val Tyr Tyr Cys
                85                  90                  95 gcc gtg acg gca gcc cat gat gct ttt gat atc tgg ggc caa ggg aca     336
Ala Val Thr Ala Ala His Asp Ala Phe Asp Ile Trp Gly Gln Gly Thr
            100                 105                 110 atg gtc acc gtc tca agc                                             354
Met Val Thr Val Ser Ser
        115

<210> SEQ ID NO 196
<211> LENGTH: 118
<212> TYPE: PRT
<213> ORGANISM: Artificial Sequence
<220> FEATURE:
<223> OTHER INFORMATION: heavy chain variable region

<400> SEQUENCE: 196

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Val Thr Ala Ala His Asp Ala Phe Asp Ile Trp Gly Gln Gly Thr
            100                 105                 110

Met Val Thr Val Ser Ser
        115

<210> SEQ ID NO 197
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 197 cag gtg cag cta cag cag tgg ggc cca gga ctg gtg aag cct tcg ggg      48
Gln Val Gln Leu Gln Gln Trp Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80
```

```
ctg aag ctg agc tct gtg acc gcc gcg gac acg gcc gtg tat tac tgt      288
Leu Lys Leu Ser Ser Val Thr Ala Ala Asp Thr Ala Val Tyr Tyr Cys
                85                  90                  95 gcg aga gac agc agt ggc caa ggg tac ttt gac tac tgg ggc cag ggc      336
Ala Arg Asp Ser Ser Gly Gln Gly Tyr Phe Asp Tyr Trp Gly Gln Gly
            100                 105                 110 acc ctg gtc acc gtc tca agc                                          357
Thr Leu Val Thr Val Ser Ser
        115
```

<210> SEQ ID NO 198
<211> LENGTH: 119
<212> TYPE: PRT
<213> ORGANISM: Artificial Sequence
<220> FEATURE:
<223> OTHER INFORMATION: heavy chain variable region

<400> SEQUENCE: 198

```
Gln Val Gln Leu Gln Gln Trp Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ser Ser Gly Gln Gly Tyr Phe Asp Tyr Trp Gly Gln Gly
            100                 105                 110

Thr Leu Val Thr Val Ser Ser
        115
```

<210> SEQ ID NO 199
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 199

```
gag gtg cag ctg gtg cag tct ggg gct gag gtg aag aag cct ggg gcc       48
Glu Val Gln Leu Val Gln Ser Gly Ala Glu Val Lys Lys Pro Gly Ala
1               5                   10                  15 tca gtg aag gtc tcc tgc aag gct tct gga tac acc ttc act agc tat       96
Ser Val Lys Val Ser Cys Lys Ala Ser Gly Tyr Thr Phe Thr Ser Tyr
            20                  25                  30 gct atg cat tgg gtg cgc cag gcc ccc gga caa agg ctt gag tgg atg      144
Ala Met His Trp Val Arg Gln Ala Pro Gly Gln Arg Leu Glu Trp Met
        35                  40                  45 gga tgg atc aac gct ggc aat ggt aac aca aaa tat tca cag aag ttc      192
Gly Trp Ile Asn Ala Gly Asn Gly Asn Thr Lys Tyr Ser Gln Lys Phe
    50                  55                  60 cag ggc aga gtc acc atg acc agg gac acg tcc acg agc aca gtc tac      240
Gln Gly Arg Val Thr Met Thr Arg Asp Thr Ser Thr Ser Thr Val Tyr
65                  70                  75                  80
```

```
atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95 gct aga cac tcg tac tac tac ggt atg gac gtc tgg ggc caa ggc acc      336
Ala Arg His Ser Tyr Tyr Tyr Gly Met Asp Val Trp Gly Gln Gly Thr
            100                 105                 110 ctg gtc acc gtc tca agc                                              354
Leu Val Thr Val Ser Ser
        115
```

<210> SEQ ID NO 200
<211> LENGTH: 118
<212> TYPE: PRT
<213> ORGANISM: Artificial Sequence
<220> FEATURE:
<223> OTHER INFORMATION: heavy chain variable region

<400> SEQUENCE: 200

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Ser Tyr Tyr Tyr Gly Met Asp Val Trp Gly Gln Gly Thr
            100                 105                 110

Leu Val Thr Val Ser Ser
        115
```

<210> SEQ ID NO 201
<211> LENGTH: 360
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(360)

<400> SEQUENCE: 201

```
cag gtg cag cta cag cag tgg ggc gca gga ctg ttg aag cct tcg gag       48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac       96
Thr Leu Ser Leu Thr Cys Ala Val Tyr Gly Gly Ser Phe Ser Gly Tyr
            20                  25                  30 tac tgg agc tgg atc cgc cag ccc cca ggg aag ggg ctg gag tgg att      144
Tyr Trp Ser Trp Ile Arg Gln Pro Pro Gly Lys Gly Leu Glu Trp Ile
        35                  40                  45 ggg gaa atc aat cat agt gga agc acc aac tac aac ccg tcc ctc aag      192
Gly Glu Ile Asn His Ser Gly Ser Thr Asn Tyr Asn Pro Ser Leu Lys
    50                  55                  60 agt cga gtc acc ata tcg gta gac acg tcc aag aac cag ttc tcc ctg      240
Ser Arg Val Thr Ile Ser Val Asp Thr Ser Lys Asn Gln Phe Ser Leu
65                  70                  75                  80
```

```
aag ctg agc tct gtg acc gcc gcg gac acg gct gtg tat tac tgt gcg      288
Lys Leu Ser Ser Val Thr Ala Ala Asp Thr Ala Val Tyr Tyr Cys Ala
                85                  90                  95 aga gtc ggg tat agc cac ggc gaa gaa gtc ctg gac gtc tgg ggc aaa      336
Arg Val Gly Tyr Ser His Gly Glu Glu Val Leu Asp Val Trp Gly Lys
            100                 105                 110 ggg acc acg gtc acc gtc tca agc                                      360
Gly Thr Thr Val Thr Val Ser Ser
        115                 120

<210> SEQ ID NO 202
<211> LENGTH: 120
<212> TYPE: PRT
<213> ORGANISM: Artificial Sequence
<220> FEATURE:
<223> OTHER INFORMATION: heavy chain variable region

<400> SEQUENCE: 202

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Tyr Ser His Gly Glu Glu Val Leu Asp Val Trp Gly Lys
            100                 105                 110

Gly Thr Thr Val Thr Val Ser Ser
        115                 120

<210> SEQ ID NO 203
<211> LENGTH: 354
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(354)

<400> SEQUENCE: 203 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc ggc aat tat      96
Thr Leu Ser Leu Thr Cys Thr Val Ser Gly Gly Ser Ile Gly Asn Tyr
            20                  25                  30 gac tgg agt tgg atc cgg cag ccc cca ggg aag gga ctg gag tgg att     144
Asp Trp Ser Trp Ile Arg Gln Pro Pro Gly Lys Gly Leu Glu Trp Ile
        35                  40                  45 ggg act atc tac tct agt ggg agt acg tac tac agt ccg tcc ctc aag     192
Gly Thr Ile Tyr Ser Ser Gly Ser Thr Tyr Tyr Ser Pro Ser Leu Lys
    50                  55                  60 agt cga ctc acc ata tca gta gac aag tcc aag aac cgg ttc tcc ctg     240
Ser Arg Leu Thr Ile Ser Val Asp Lys Ser Lys Asn Arg Phe Ser Leu
65                  70                  75                  80
```

```
aag ctg agc tct gtg acc gcc gcg gac acg gcc gtg tat tac tgt gcg      288
Lys Leu Ser Ser Val Thr Ala Ala Asp Thr Ala Val Tyr Tyr Cys Ala
                85                  90                  95 aga gca cga ggg tat agc agc ccc ttc gac ccc tgg ggc cag ggc acc      336
Arg Ala Arg Gly Tyr Ser Ser Pro Phe Asp Pro Trp Gly Gln Gly Thr
            100                 105                 110 ctg gtc acc gtc tca agc                                               354
Leu Val Thr Val Ser Ser
        115
```

<210> SEQ ID NO 204
<211> LENGTH: 118
<212> TYPE: PRT
<213> ORGANISM: Artificial Sequence
<220> FEATURE:
<223> OTHER INFORMATION: heavy chain variable region

<400> SEQUENCE: 204

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Asn Tyr
            20                  25                  30

Asp Trp Ser Trp Ile Arg Gln Pro Pro Gly Lys Gly Leu Glu Trp Ile
        35                  40                  45

Gly Thr Ile Tyr Ser Ser Gly Ser Thr Tyr Tyr Ser Pro Ser Leu Lys
    50                  55                  60

Ser Arg Leu Thr Ile Ser Val Asp Lys Ser Lys Asn Arg Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Tyr Ser Ser Pro Phe Asp Pro Trp Gly Gln Gly Thr
            100                 105                 110

Leu Val Thr Val Ser Ser
        115
```

<210> SEQ ID NO 205
<211> LENGTH: 357
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(357)

<400> SEQUENCE: 205

```
cag gtc cag ctg gta cag tct ggg gct gag gtg aag aag cct ggg tcc       48
Gln Val Gln Leu Val Gln Ser Gly Ala Glu Val Lys Lys Pro Gly Ser
1               5                   10                  15 tcg gtg aag gtc tcc tgc aag gct tct gga ggc acc ttc agc agc tat       96
Ser Val Lys Val Ser Cys Lys Ala Ser Gly Gly Thr Phe Ser Ser Tyr
            20                  25                  30 gct atc agc tgg gtg cga cag gcc cct gga caa ggg ctt gag tgg atg      144
Ala Ile Ser Trp Val Arg Gln Ala Pro Gly Gln Gly Leu Glu Trp Met
        35                  40                  45 gga ata atc aac cct agt ggt ggt agc aca agc tac gca cag aag ttc      192
Gly Ile Ile Asn Pro Ser Gly Gly Ser Thr Ser Tyr Ala Gln Lys Phe
    50                  55                  60 cag ggc aga gtc acc att acc agg gac aca tcc gcg agc aca gcc tac      240
Gln Gly Arg Val Thr Ile Thr Arg Asp Thr Ser Ala Ser Thr Ala Tyr
65                  70                  75                  80
```

```
atg gag ctg agc agc ctg aga tct gaa gac acg gct gtg tat tac tgt         288
Met Glu Leu Ser Ser Leu Arg Ser Glu Asp Thr Ala Val Tyr Tyr Cys
            85                  90                  95 gcg aga gat cgg tgg agg tac gat gct ttt gat atc tgg ggc caa ggg         336
Ala Arg Asp Arg Trp Arg Tyr Asp Ala Phe Asp Ile Trp Gly Gln Gly
           100                 105                 110 aca atg gtc acc gtc tca agc                                             357
Thr Met Val Thr Val Ser Ser
        115
```

<210> SEQ ID NO 206
<211> LENGTH: 119
<212> TYPE: PRT
<213> ORGANISM: Artificial Sequence
<220> FEATURE:
<223> OTHER INFORMATION: heavy chain variable region

<400> SEQUENCE: 206

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Trp Arg Tyr Asp Ala Phe Asp Ile Trp Gly Gln Gly
            100                 105                 110

Thr Met Val Thr Val Ser Ser
        115
```

<210> SEQ ID NO 207
<211> LENGTH: 348
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)..(348)

<400> SEQUENCE: 207

```
gag gtg cag ctg gtg gag tct ggc cca gga ctg gtg aag cct tcg ggg          48
Glu Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt          96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg         144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc         192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc         240
Lys Ser Arg Val Thr Ile Ser Val Asp Lys Ser Lys Asn Gln Phe Ser
65                  70                  75                  80
```

```
ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga gaa aaa tcg ggt atg gac gtc tgg ggc caa ggg acc acg gtc     336
Ala Arg Glu Lys Ser Gly Met Asp Val Trp Gly Gln Gly Thr Thr Val
            100                 105                 110 acc gtc tca agc                                                      348
Thr Val Ser Ser
        115

<210> SEQ ID NO 208
<211> LENGTH: 116
<212> TYPE: PRT
<213> ORGANISM: Artificial Sequence
<220> FEATURE:
<223> OTHER INFORMATION: heavy chain variable region

<400> SEQUENCE: 208

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Lys Ser Gly Met Asp Val Trp Gly Gln Gly Thr Thr Val
            100                 105                 110

Thr Val Ser Ser
        115

<210> SEQ ID NO 209
<211> LENGTH: 321
<212> TYPE: DNA
<213> ORGANISM: Artificial Sequence
<220> FEATURE:
<223> OTHER INFORMATION: light chain constant region
<220> FEATURE:
<221> NAME/KEY: CDS
<222> LOCATION: (1)..(321)

<400> SEQUENCE: 209 cga act gtg gct gca cca tct gtc ttc atc ttc ccg cca tct gat gag     48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc     96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa    144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc    192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag    240
Thr Tyr Ser Leu Ser Ser Thr Leu Thr Leu Ser Lys Ala Asp Tyr Glu
65                  70                  75                  80
```

```
aaa cac aaa gtc tac gcc tgc gaa gtc acc cat cag ggc ctg agc tcg      288
Lys His Lys Val Tyr Ala Cys Glu Val Thr His Gln Gly Leu Ser Ser
                85                  90                  95 ccc gtc aca aag agc ttc aac agg gga gag tgt                          321
Pro Val Thr Lys Ser Phe Asn Arg Gly Glu Cys
            100                 105

<210> SEQ ID NO 210
<211> LENGTH: 107
<212> TYPE: PRT
<213> ORGANISM: Artificial Sequence
<220> FEATURE:
<223> OTHER INFORMATION: light chain constant region

<400> SEQUENCE: 210

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 211
<211> LENGTH: 990
<212> TYPE: DNA
<213> ORGANISM: Artificial Sequence
<220> FEATURE:
<223> OTHER INFORMATION: heavy chain constant region
<220> FEATURE:
<221> NAME/KEY: CDS
<222> LOCATION: (1)..(990)

<400> SEQUENCE: 211 gcc tcc acc aag ggc cca tcg gtc ttc ccc ctg gca ccc tcc tcc aag       48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac       96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110
```

```
cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
            115                 120                 125 aaa ccc aag gac acc ctc atg atc tcc cgg acc cct gag gtc aca tgc      432
Lys Pro Lys Asp Thr Leu Met Ile Ser Arg Thr Pro Glu Val Thr Cys
130                 135                 140 gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag      720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat      768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tct ccg ggt aaa                              990
Gln Lys Ser Leu Ser Leu Ser Pro Gly Lys
                325                 330

<210> SEQ ID NO 212
<211> LENGTH: 330
<212> TYPE: PRT
<213> ORGANISM: Artificial Sequence
<220> FEATURE:
      <223> OTHER INFORMATION: heavy chain constant region

<400> SEQUENCE: 212

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 213
<211> LENGTH: 9
<212> TYPE: PRT
<213> ORGANISM: Artificial Sequence
<220> FEATURE:
<223> OTHER INFORMATION: Light chain CDR3
<220> FEATURE:
<221> NAME/KEY: MISC_FEATURE
<222> LOCATION: (8)..(8)
<223> OTHER INFORMATION: Xaa can be any naturally occuring amino acid

<400> SEQUENCE: 213

Met Gln Ala Leu Gln Thr Pro Xaa Thr
1               5

<210> SEQ ID NO 214
<211> LENGTH: 9
<212> TYPE: PRT
<213> ORGANISM: Artificial Sequence
<220> FEATURE:
<223> OTHER INFORMATION: Light chain CDR3
<220> FEATURE:
<221> NAME/KEY: MISC_FEATURE
<222> LOCATION: (3)..(3)
<223> OTHER INFORMATION: Xaa is arginine or serine
```

```
<220> FEATURE:
<221> NAME/KEY: MISC_FEATURE
<222> LOCATION: (4)..(4)
<223> OTHER INFORMATION: Xaa is asparagine or serine
<220> FEATURE:
<221> NAME/KEY: MISC_FEATURE
<222> LOCATION: (5)..(5)
<223> OTHER INFORMATION: Xaa is serine or asparagine
<220> FEATURE:
<221> NAME/KEY: MISC_FEATURE
<222> LOCATION: (6)..(6)
<223> OTHER INFORMATION: Xaa is glycine, alanine, valine, leucine,
      isoleucine, proline, phenylalinine, methionine, tryptophan or
      cysteine

<400> SEQUENCE: 214

Gln Gln Xaa Xaa Xaa Xaa Pro Leu Thr
1               5

<210> SEQ ID NO 215
<211> LENGTH: 10
<212> TYPE: PRT
<213> ORGANISM: Artificial Sequence
<220> FEATURE:
<223> OTHER INFORMATION: Light chain CDR3
<220> FEATURE:
<221> NAME/KEY: MISC_FEATURE
<222> LOCATION: (8)..(9)
<223> OTHER INFORMATION: Xaa is arginine, valine, or isoleucine or no
      amino acid

<400> SEQUENCE: 215

Gln Ser Tyr Asp Ser Ser Asn Xaa Xaa Val
1               5                   10

<210> SEQ ID NO 216
<211> LENGTH: 8
<212> TYPE: PRT
<213> ORGANISM: Artificial Sequence
<220> FEATURE:
<223> OTHER INFORMATION: Heavy chain CDR3

<400> SEQUENCE: 216

Ser Arg Leu Asp Ala Phe Asp Ile
1               5

<210> SEQ ID NO 217
<211> LENGTH: 10
<212> TYPE: PRT
<213> ORGANISM: Artificial Sequence
<220> FEATURE:
<223> OTHER INFORMATION: Heavy chain CDR3
<220> FEATURE:
<221> NAME/KEY: MISC_FEATURE
<222> LOCATION: (2)..(2)
<223> OTHER INFORMATION: Xaa can be any naturally occurring amino acid

<400> SEQUENCE: 217

Ser Xaa Tyr Asp Tyr Tyr Gly Met Asp Val
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Heavy chain CDR3
<220> FEATURE:
<221> NAME/KEY: MISC_FEATURE
<222> LOCATION: (3)..(3)
<223> OTHER INFORMATION: Xaa can be any naturally occurring amino acid
```

```
<220> FEATURE:
<221> NAME/KEY: MISC_FEATURE
<222> LOCATION: (5)..(5)
<223> OTHER INFORMATION: Xaa can be any naturally occurring amino acid

<400> SEQUENCE: 218

His Arg Xaa Asp Xaa Ala Trp Tyr Phe Asp Leu
1               5                   10

<210> SEQ ID NO 219
<211> LENGTH: 4
<212> TYPE: PRT
<213> ORGANISM: Artificial Sequence
<220> FEATURE:
<223> OTHER INFORMATION: Heavy chain CDR3
<220> FEATURE:
<221> NAME/KEY: MISC_FEATURE
<222> LOCATION: (1)..(4)

<400> SEQUENCE: 219

Asp Ser Ser Gly
1

<210> SEQ ID NO 220
<211> LENGTH: 16
<212> TYPE: PRT
<213> ORGANISM: Artificial Sequence
<220> FEATURE:
<223> OTHER INFORMATION: Light chain CDR1
<220> FEATURE:
<221> NAME/KEY: MISC_FEATURE
<222> LOCATION: (1)..(16)

<400> SEQUENCE: 220

Arg Ser Ser Gln Ser Leu Leu His Ser Asn Gly Tyr Asn Tyr Leu Asp
1               5                   10                  15

<210> SEQ ID NO 221
<211> LENGTH: 11
<212> TYPE: PRT
<213> ORGANISM: Artificial Sequence
<220> FEATURE:
<223> OTHER INFORMATION: Light chain CDR1
<220> FEATURE:
<221> NAME/KEY: MISC_FEATURE
<222> LOCATION: (5)..(5)
<223> OTHER INFORMATION: Xaa is glycine or serine
<220> FEATURE:
<221> NAME/KEY: MISC_FEATURE
<222> LOCATION: (6)..(6)
<223> OTHER INFORMATION: Xaa is isoleucine or valine
<220> FEATURE:
<221> NAME/KEY: MISC_FEATURE
<222> LOCATION: (7)..(7)
<223> OTHER INFORMATION: Xaa is glycine or serine
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is tyrosine or phenylalanine
<220> FEATURE:
<221> NAME/KEY: MISC_FEATURE
<222> LOCATION: (11)..(11)
<223> OTHER INFORMATION: Xaa is alanine or asparagine

<400> SEQUENCE: 221

Arg Ala Ser Gln Xaa Xaa Xaa Xaa Xaa Leu Xaa
1               5                   10
```

```
<210> SEQ ID NO 222
<211> LENGTH: 11
<212> TYPE: PRT
<213> ORGANISM: Artificial Sequence
<220> FEATURE:
<223> OTHER INFORMATION: Light chain CDR1
<220> FEATURE:
<221> NAME/KEY: MISC_FEATURE
<222> LOCATION: (6)..(6)
<223> OTHER INFORMATION: Xaa is leucine or serine
<220> FEATURE:
<221> NAME/KEY: MISC_FEATURE
<222> LOCATION: (7)..(11)
<223> OTHER INFORMATION: Xaa is independently any amino acid

<400> SEQUENCE: 222

Arg Ser Ser Gln Ser Xaa Xaa Xaa Xaa Xaa Xaa
1               5                   10

<210> SEQ ID NO 223
<211> LENGTH: 7
<212> TYPE: PRT
<213> ORGANISM: Artificial Sequence
<220> FEATURE:
<223> OTHER INFORMATION: Light chain CDR2

<400> SEQUENCE: 223

Leu Gly Ser Asn Arg Ala Ser
1               5

<210> SEQ ID NO 224
<211> LENGTH: 7
<212> TYPE: PRT
<213> ORGANISM: Artificial Sequence
<220> FEATURE:
<223> OTHER INFORMATION: Light chain CDR2

<400> SEQUENCE: 224

Ala Ala Ser Thr Leu Gln Ser
1               5

<210> SEQ ID NO 225
<211> LENGTH: 7
<212> TYPE: PRT
<213> ORGANISM: Artificial Sequence
<220> FEATURE:
<223> OTHER INFORMATION: Light chain CDR2
<220> FEATURE:
<221> NAME/KEY: MISC_FEATURE
<222> LOCATION: (4)..(4)
<223> OTHER INFORMATION: Xaa can be any naturally occurring amino acid

<400> SEQUENCE: 225

Glu Asp Asn Xaa Arg Pro Ser
1               5

<210> SEQ ID NO 226
<211> LENGTH: 6
<212> TYPE: PRT
<213> ORGANISM: Artificial Sequence
<220> FEATURE:
<223> OTHER INFORMATION: Heavy chain CDR1

<400> SEQUENCE: 226

Ser Ser Asn Trp Trp Ser
1               5

<210> SEQ ID NO 227
```

```
<211> LENGTH: 5
<212> TYPE: PRT
<213> ORGANISM: Artificial Sequence
<220> FEATURE:
<223> OTHER INFORMATION: Heavy chain CDR1
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 227

Xaa Tyr Tyr Trp Ser
1               5

<210> SEQ ID NO 228
<211> LENGTH: 5
<212> TYPE: PRT
<213> ORGANISM: Artificial Sequence
<220> FEATURE:
<223> OTHER INFORMATION: Heavy chain CDR1
<220> FEATURE:
<221> NAME/KEY: MISC_FEATURE
<222> LOCATION: (5)..(5)
<223> OTHER INFORMATION: Xaa is serine or histidine

<400> SEQUENCE: 228

Ser Tyr Ala Met Xaa
1               5

<210> SEQ ID NO 229
<211> LENGTH: 16
<212> TYPE: PRT
<213> ORGANISM: Artificial Sequence
<220> FEATURE:
<223> OTHER INFORMATION: Heavy chain CDR2
<220> FEATURE:
<221> NAME/KEY: MISC_FEATURE
<222> LOCATION: (1)..(1)
<223> OTHER INFORMATION: Xaa = glutamic acid or isoleucine
<220> FEATURE:
<221> NAME/KEY: MISC_FEATURE
<222> LOCATION: (2)..(2)
<223> OTHER INFORMATION: Xaa = isoleucine or valine
<220> FEATURE:
<221> NAME/KEY: MISC_FEATURE
<222> LOCATION: (3)..(3)
<223> OTHER INFORMATION: Xaa = tyrosine or asparagine
<220> FEATURE:
<221> NAME/KEY: MISC_FEATURE
<222> LOCATION: (4)..(4)
<223> OTHER INFORMATION: Xaa = histidine or tyrosine
<220> FEATURE:
<221> NAME/KEY: MISC_FEATURE
<222> LOCATION: (9)..(9)
<223> OTHER INFORMATION: Xaa = asparagine or tyrosine

<400> SEQUENCE: 229

Xaa Xaa Xaa Xaa Ser Gly Ser Thr Xaa Tyr Asn Pro Ser Leu Lys Ser
1               5                   10                  15

<210> SEQ ID NO 230
<211> LENGTH: 17
<212> TYPE: PRT
<213> ORGANISM: Artificial Sequence
<220> FEATURE:
<223> OTHER INFORMATION: Heavy chain CDR2
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (4)..(4)
```

```
<223> OTHER INFORMATION: Xaa = glycine or serine
<220> FEATURE:
<221> NAME/KEY: MISC_FEATURE
<222> LOCATION: (7)..(7)
<223> OTHER INFORMATION: Xaa = glycine or serine

<400> SEQUENCE: 230

Xaa Ile Ser Xaa Ser Gly Xaa Ser Thr Tyr Tyr Ala Asp Ser Val Lys
 1               5                  10                  15

Gly

<210> SEQ ID NO 231
<211> LENGTH: 1162
<212> TYPE: PRT
<213> ORGANISM: Artificial Sequence
<220> FEATURE:
<223> OTHER INFORMATION: huIGF-1R:Fc
<220> FEATURE:
<221> NAME/KEY: MISC_FEATURE
<222> LOCATION: (1)..(1162)

<400> SEQUENCE: 231

Met Lys Ser Gly Ser Gly Gly Ser Pro Thr Ser Leu Trp Gly Leu
 1               5                  10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285
```

-continued

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
            405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
            645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
690                 695                 700

```
Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
            725                 730                 735

Arg Lys Arg Arg Asp Val Met Gln Val Ala Asn Thr Thr Met Ser Ser
        740                 745                 750

Arg Ser Arg Asn Thr Thr Ala Ala Asp Thr Tyr Asn Ile Thr Asp Pro
    755                 760                 765

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Asp Glu Val Asp Gly Cys Lys Pro
930                 935                 940

Cys Ile Cys Thr Val Pro Glu Val Ser Ser Val Phe Ile Phe Pro Pro
945                 950                 955                 960

Lys Pro Lys Asp Val Leu Thr Ile Thr Leu Thr Pro Lys Val Thr Cys
                965                 970                 975

Val Val Val Asp Ile Ser Lys Asp Asp Pro Glu Val Gln Phe Ser Trp
            980                 985                 990

Phe Val Asp Asp Val Glu Val His Thr Ala Gln Thr Gln Pro Arg Glu
        995                 1000                1005

Glu Gln Phe Asn Ser Thr Phe Arg Ser Val Ser Glu Leu Pro Ile
    1010                1015                1020

Met His Gln Asp Trp Leu Asn Gly Lys Glu Phe Lys Cys Arg Val
    1025                1030                1035

Asn Ser Ala Ala Phe Pro Ala Pro Ile Glu Lys Thr Ile Ser Lys
    1040                1045                1050

Thr Lys Gly Arg Pro Lys Ala Pro Gln Val Tyr Thr Ile Pro Pro
    1055                1060                1065

Pro Lys Glu Gln Met Ala Lys Asp Lys Val Ser Leu Thr Cys Met
    1070                1075                1080

Ile Thr Asp Phe Phe Pro Glu Asp Ile Thr Val Glu Trp Gln Trp
    1085                1090                1095

Asn Gly Gln Pro Ala Glu Asn Tyr Lys Asn Thr Gln Pro Ile Met
    1100                1105                1110

Asp Thr Asp Gly Ser Tyr Phe Val Tyr Ser Lys Leu Asn Val Gln
```

-continued

```
            1115                1120                1125
Lys Ser Asn Trp Glu Ala Gly Asn Thr Phe Thr Cys Ser Val Leu
        1130                1135                1140

His Glu Gly Leu His Asn His His Thr Glu Lys Ser Leu Ser His
    1145                1150                1155

Ser Pro Gly Lys
    1160

<210> SEQ ID NO 232
<211> LENGTH: 1180
<212> TYPE: PRT
<213> ORGANISM: Artificial Sequence
<220> FEATURE:
<223> OTHER INFORMATION: hu INSR:fC
<220> FEATURE:
<221> NAME/KEY: MISC_FEATURE
<222> LOCATION: (1)..(1180)

<400> SEQUENCE: 232

Met Gly Thr Gly Gly Arg Arg Gly Ala Ala Ala Pro Leu Leu Val
1               5                   10                  15

Ala Val Ala Ala Leu Leu Leu Gly Ala Ala Gly His Leu Tyr Pro Gly
            20                  25                  30

Glu Val Cys Pro Gly Met Asp Ile Arg Asn Asn Leu Thr Arg Leu His
        35                  40                  45

Glu Leu Glu Asn Cys Ser Val Ile Glu Gly His Leu Gln Ile Leu Leu
    50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
        115                 120                 125

Lys Glu Leu Gly Leu Tyr Asn Leu Met Asn Ile Thr Arg Gly Ser Val
    130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn His Ile Val Leu Asn Lys
                165                 170                 175

Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
        195                 200                 205

Cys Trp Thr His Ser His Cys Gln Lys Val Cys Pro Thr Ile Cys Lys
    210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
            260                 265                 270

Tyr His Phe Gln Asp Trp Arg Cys Val Asn Phe Ser Phe Cys Gln Asp
        275                 280                 285

Leu His His Lys Cys Lys Asn Ser Arg Arg Gln Gly Cys His Gln Tyr
```

-continued

```
            290                 295                 300
Val Ile His Asn Asn Lys Cys Ile Pro Glu Cys Pro Ser Gly Tyr Thr
305                 310                 315                 320

Met Asn Ser Ser Asn Leu Leu Cys Thr Pro Cys Leu Gly Pro Cys Pro
                325                 330                 335

Lys Val Cys His Leu Leu Glu Gly Glu Lys Thr Ile Asp Ser Val Thr
                340                 345                 350

Ser Ala Gln Glu Leu Arg Gly Cys Thr Val Ile Asn Gly Ser Leu Ile
                355                 360                 365

Ile Asn Ile Arg Gly Gly Asn Asn Leu Ala Ala Glu Leu Glu Ala Asn
370                 375                 380

Leu Gly Leu Ile Glu Glu Ile Ser Gly Tyr Leu Lys Ile Arg Arg Ser
385                 390                 395                 400

Tyr Ala Leu Val Ser Leu Ser Phe Phe Arg Lys Leu Arg Leu Ile Arg
                405                 410                 415

Gly Glu Thr Leu Glu Ile Gly Asn Tyr Ser Phe Tyr Ala Leu Asp Asn
                420                 425                 430

Gln Asn Leu Arg Gln Leu Trp Asp Trp Ser Lys His Asn Leu Thr Thr
                435                 440                 445

Thr Gln Gly Lys Leu Phe Phe His Tyr Asn Pro Lys Leu Cys Leu Ser
                450                 455                 460

Glu Ile His Lys Met Glu Glu Val Ser Gly Thr Lys Gly Arg Gln Glu
465                 470                 475                 480

Arg Asn Asp Ile Ala Leu Lys Thr Asn Gly Asp Lys Ala Ser Cys Glu
                485                 490                 495

Asn Glu Leu Leu Lys Phe Ser Tyr Ile Arg Thr Ser Phe Asp Lys Ile
                500                 505                 510

Leu Leu Arg Trp Glu Pro Tyr Trp Pro Pro Asp Phe Arg Asp Leu Leu
                515                 520                 525

Gly Phe Met Leu Phe Tyr Lys Glu Ala Pro Tyr Gln Asn Val Thr Glu
                530                 535                 540

Phe Asp Gly Gln Asp Ala Cys Gly Ser Asn Ser Trp Thr Val Val Asp
545                 550                 555                 560

Ile Asp Pro Pro Leu Arg Ser Asn Asp Pro Lys Ser Gln Asn His Pro
                565                 570                 575

Gly Trp Leu Met Arg Gly Leu Lys Pro Trp Thr Gln Tyr Ala Ile Phe
                580                 585                 590

Val Lys Thr Leu Val Thr Phe Ser Asp Glu Arg Arg Thr Tyr Gly Ala
                595                 600                 605

Lys Ser Asp Ile Ile Tyr Val Gln Thr Asp Ala Thr Asn Pro Ser Val
610                 615                 620

Pro Leu Asp Pro Ile Ser Val Ser Asn Ser Ser Ser Gln Ile Ile Leu
625                 630                 635                 640

Lys Trp Lys Pro Pro Ser Asp Pro Asn Gly Asn Ile Thr His Tyr Leu
                645                 650                 655

Val Phe Trp Glu Arg Gln Ala Glu Asp Ser Glu Leu Phe Glu Leu Asp
                660                 665                 670

Tyr Cys Leu Lys Gly Leu Lys Leu Pro Ser Arg Thr Trp Ser Pro Pro
                675                 680                 685

Phe Glu Ser Glu Asp Ser Gln Lys His Asn Gln Ser Glu Tyr Glu Asp
                690                 695                 700

Ser Ala Gly Glu Cys Cys Ser Cys Pro Lys Thr Asp Ser Gln Ile Leu
705                 710                 715                 720
```

-continued

Lys Glu Leu Glu Glu Ser Ser Phe Arg Lys Thr Phe Glu Asp Tyr Leu
            725                 730                 735

His Asn Val Val Phe Val Pro Arg Lys Thr Ser Ser Gly Thr Gly Ala
            740                 745                 750

Glu Asp Pro Arg Pro Ser Arg Lys Arg Arg Ser Leu Gly Asp Val Gly
            755                 760                 765

Asn Val Thr Val Ala Val Pro Thr Val Ala Ala Phe Pro Asn Thr Ser
            770                 775                 780

Ser Thr Ser Val Pro Thr Ser Pro Glu Glu His Arg Pro Phe Glu Lys
785                 790                 795                 800

Val Val Asn Lys Glu Ser Leu Val Ile Ser Gly Leu Arg His Phe Thr
            805                 810                 815

Gly Tyr Arg Ile Glu Leu Gln Ala Cys Asn Gln Asp Thr Pro Glu Glu
            820                 825                 830

Arg Cys Ser Val Ala Ala Tyr Val Ser Ala Arg Thr Met Pro Glu Ala
            835                 840                 845

Lys Ala Asp Asp Ile Val Gly Pro Val Thr His Glu Ile Phe Glu Asn
850                 855                 860

Asn Val Val His Leu Met Trp Gln Glu Pro Lys Glu Pro Asn Gly Leu
865                 870                 875                 880

Ile Val Leu Tyr Glu Val Ser Tyr Arg Arg Tyr Gly Asp Glu Glu Leu
            885                 890                 895

His Leu Cys Val Ser Arg Lys His Phe Ala Leu Glu Arg Gly Cys Arg
            900                 905                 910

Leu Arg Gly Leu Ser Pro Gly Asn Tyr Ser Val Arg Ile Arg Ala Thr
            915                 920                 925

Ser Leu Ala Gly Asn Gly Ser Trp Thr Glu Pro Thr Tyr Phe Tyr Val
            930                 935                 940

Thr Asp Tyr Leu Asp Val Pro Ser Asn Ile Ala Lys Val Asp Gly Cys
945                 950                 955                 960

Lys Pro Cys Ile Cys Thr Val Pro Glu Val Ser Ser Val Phe Ile Phe
            965                 970                 975

Pro Pro Lys Pro Lys Asp Val Leu Thr Ile Thr Leu Thr Pro Lys Val
            980                 985                 990

Thr Cys Val Val Val Asp Ile Ser Lys Asp Asp Pro Glu Val Gln Phe
            995                1000                1005

Ser Trp Phe Val Asp Asp Val Glu Val His Thr Ala Gln Thr Gln
    1010                1015                1020

Pro Arg Glu Glu Gln Phe Asn Ser Thr Phe Arg Ser Val Ser Glu
    1025                1030                1035

Leu Pro Ile Met His Gln Asp Trp Leu Asn Gly Lys Glu Phe Lys
    1040                1045                1050

Cys Arg Val Asn Ser Ala Ala Phe Pro Ala Pro Ile Glu Lys Thr
    1055                1060                1065

Ile Ser Lys Thr Lys Gly Arg Pro Lys Ala Pro Gln Val Tyr Thr
    1070                1075                1080

Ile Pro Pro Pro Lys Glu Gln Met Ala Lys Asp Lys Val Ser Leu
    1085                1090                1095

Thr Cys Met Ile Thr Asp Phe Phe Pro Glu Asp Ile Thr Val Glu
    1100                1105                1110

Trp Gln Trp Asn Gly Gln Pro Ala Glu Asn Tyr Lys Asn Thr Gln
    1115                1120                1125

```
<210> SEQ ID NO 233
<211> LENGTH: 1062
<212> TYPE: PRT
<213> ORGANISM: Artificial Sequence
<220> FEATURE:
<223> OTHER INFORMATION: hu IGF-1R:avidin

<400> SEQUENCE: 233
```

Pro Ile Met Asp Thr Asp Gly Ser Tyr Phe Val Tyr Ser Lys Leu
    1130                1135                1140

Asn Val Gln Lys Ser Asn Trp Glu Ala Gly Asn Thr Phe Thr Cys
    1145                1150                1155

Ser Val Leu His Glu Gly Leu His Asn His His Thr Glu Lys Ser
    1160                1165                1170

Leu Ser His Ser Pro Gly Lys
    1175                1180

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

-continued

```
Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
    530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
    610                 615                 620

Ser Gln Leu Ile Val Lys Trp Asn Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
    690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
```

```
                    725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
            805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
            850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
            885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Ala Ala Ala Arg Lys Cys Ser Leu Thr Gly Lys Trp
            930                 935                 940

Thr Asn Asp Leu Gly Ser Asn Met Thr Ile Gly Ala Val Asn Ser Lys
945                 950                 955                 960

Gly Glu Phe Thr Gly Thr Tyr Thr Thr Ala Val Thr Ala Thr Ser Asn
            965                 970                 975

Glu Ile Lys Glu Ser Pro Leu His Gly Thr Gln Asn Thr Ile Asn Lys
            980                 985                 990

Arg Thr Gln Pro Thr Phe Gly Phe Thr Val Asn Trp Lys Phe Ser Glu
            995                 1000                1005

Ser Thr Thr Val Phe Thr Gly Gln Cys Phe Ile Asp Arg Asn Gly
    1010                1015                1020

Lys Glu Val Leu Lys Thr Met Trp Leu Leu Arg Ser Ser Val Asn
    1025                1030                1035

Asp Ile Gly Asp Asp Trp Lys Ala Thr Arg Val Gly Ile Asn Ile
    1040                1045                1050

Phe Thr Arg Leu Arg Thr Gln Lys Glu
    1055                1060

<210> SEQ ID NO 234
<211> LENGTH: 107
<212> TYPE: PRT
<213> ORGANISM: Artificial Sequence
<220> FEATURE:
<223> OTHER INFORMATION: human kappa light chain constant region

<400> SEQUENCE: 234

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

-continued

```
                    20                  25                  30
Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
             100                 105

<210> SEQ ID NO 235
<211> LENGTH: 330
<212> TYPE: PRT
<213> ORGANISM: Artificial Sequence
<220> FEATURE:
<223> OTHER INFORMATION: heavy chain constant region

<400> SEQUENCE: 235

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                    275                 280                 285
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 236
<211> LENGTH: 16
<212> TYPE: PRT
<213> ORGANISM: Artificial Sequence
<220> FEATURE:
<223> OTHER INFORMATION: light chain CDR1
<220> FEATURE:
<221> NAME/KEY: MISC_FEATURE
<222> LOCATION: (9)..(9)
<223> OTHER INFORMATION: Xaa is serine or threonine residue
<220> FEATURE:
<221> NAME/KEY: MISC_FEATURE
<222> LOCATION: (10)..(10)
<223> OTHER INFORMATION: Xaa is asparagine, serine or histidine residue
<220> FEATURE:
<221> NAME/KEY: MISC_FEATURE
<222> LOCATION: (14)..(14)
<223> OTHER INFORMATION: Xaa is tyrosine or phenylalanine residue
<220> FEATURE:
<221> NAME/KEY: MISC_FEATURE
<222> LOCATION: (16)..(16)
<223> OTHER INFORMATION: Xaa is aspartate or asparagine residue

<400> SEQUENCE: 236

Arg Ser Ser Gln Ser Leu Leu His Xaa Xaa Gly Tyr Asn Xaa Leu Xaa
1               5                   10                  15

<210> SEQ ID NO 237
<211> LENGTH: 13
<212> TYPE: PRT
<213> ORGANISM: Artificial Sequence
<220> FEATURE:
<223> OTHER INFORMATION: light chain CDR1
<220> FEATURE:
<221> NAME/KEY: MISC_FEATURE
<222> LOCATION: (6)..(6)
<223> OTHER INFORMATION: Xaa is serine or aspartate residue
<220> FEATURE:
<221> NAME/KEY: MISC_FEATURE
<222> LOCATION: (8)..(8)
<223> OTHER INFORMATION: Xaa is alanine or aspartate residue
<220> FEATURE:
<221> NAME/KEY: MISC_FEATURE
<222> LOCATION: (9)..(9)
<223> OTHER INFORMATION: Xaa is serine or asparagine residue

<400> SEQUENCE: 237

Thr Arg Ser Ser Gly Xaa Ile Xaa Xaa Asn Tyr Val Gln
1               5                   10

<210> SEQ ID NO 238
<211> LENGTH: 11
<212> TYPE: PRT
<213> ORGANISM: Artificial Sequence
<220> FEATURE:
<223> OTHER INFORMATION: light chain CDR1
<220> FEATURE:
<221> NAME/KEY: MISC_FEATURE
<222> LOCATION: (5)..(5)
<223> OTHER INFORMATION: Xaa is glycine or serine residue
<220> FEATURE:
<221> NAME/KEY: MISC_FEATURE
<222> LOCATION: (6)..(6)
```

```
<223> OTHER INFORMATION: Xaa is isoleucine, valine or proline residue
<220> FEATURE:
<221> NAME/KEY: MISC_FEATURE
<222> LOCATION: (7)..(7)
<223> OTHER INFORMATION: Xaa is serine, glycine or tyrosine residue
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is phenylalanine, tyrosine, asparagine or
      tryptophan residue
<220> FEATURE:
<221> NAME/KEY: MISC_FEATURE
<222> LOCATION: (11)..(11)
<223> OTHER INFORMATION: Xaa is alanine or asparagine residue

<400> SEQUENCE: 238

Arg Ala Ser Gln Xaa Xaa Xaa Xaa Xaa Leu Xaa
1               5                   10

<210> SEQ ID NO 239
<211> LENGTH: 7
<212> TYPE: PRT
<213> ORGANISM: Artificial Sequence
<220> FEATURE:
<223> OTHER INFORMATION: light chain CDR2
<220> FEATURE:
<221> NAME/KEY: MISC_FEATURE
<222> LOCATION: (2)..(2)
<223> OTHER INFORMATION: Xaa is glycine or valine residue
<220> FEATURE:
<221> NAME/KEY: MISC_FEATURE
<222> LOCATION: (3)..(3)
<223> OTHER INFORMATION: Xaa is serine or phenylalanine residue
<220> FEATURE:
<221> NAME/KEY: MISC_FEATURE
<222> LOCATION: (4)..(4)
<223> OTHER INFORMATION: Xaa is asparagine, tyrosine or threonine
      residue
<220> FEATURE:
<221> NAME/KEY: MISC_FEATURE
<222> LOCATION: (6)..(6)
<223> OTHER INFORMATION: Xaa is alanine or aspartate residue

<400> SEQUENCE: 239

Leu Xaa Xaa Xaa Arg Xaa Ser
1               5

<210> SEQ ID NO 240
<211> LENGTH: 7
<212> TYPE: PRT
<213> ORGANISM: Artificial Sequence
<220> FEATURE:
<223> OTHER INFORMATION: light chain CDR2
<220> FEATURE:
<221> NAME/KEY: MISC_FEATURE
<222> LOCATION: (2)..(2)
<223> OTHER INFORMATION: Xaa is alanine or threonine residue
<220> FEATURE:
<221> NAME/KEY: MISC_FEATURE
<222> LOCATION: (4)..(4)
<223> OTHER INFORMATION: Xaa is threonine or glycine residue
<220> FEATURE:
<221> NAME/KEY: MISC_FEATURE
<222> LOCATION: (6)..(6)
<223> OTHER INFORMATION: Xaa is glutamine or glutamate residue

<400> SEQUENCE: 240

Ala Xaa Ser Xaa Leu Xaa Ser
1               5
```

```
<210> SEQ ID NO 241
<211> LENGTH: 7
<212> TYPE: PRT
<213> ORGANISM: Artificial Sequence
<220> FEATURE:
<223> OTHER INFORMATION: light chain CDR2
<220> FEATURE:
<221> NAME/KEY: MISC_FEATURE
<222> LOCATION: (1)..(1)
<223> OTHER INFORMATION: Xaa is glutamate, glutamine or glycine residue
<220> FEATURE:
<221> NAME/KEY: MISC_FEATURE
<222> LOCATION: (2)..(2)
<223> OTHER INFORMATION: Xaa is aspartate or lysine residue
<220> FEATURE:
<221> NAME/KEY: MISC_FEATURE
<222> LOCATION: (4)..(4)
<223> OTHER INFORMATION: Xaa is any amino acid residue

<400> SEQUENCE: 241

Xaa Xaa Asn Xaa Arg Pro Ser
1               5

<210> SEQ ID NO 242
<211> LENGTH: 9
<212> TYPE: PRT
<213> ORGANISM: Artificial Sequence
<220> FEATURE:
<223> OTHER INFORMATION: light chain CDR3
<220> FEATURE:
<221> NAME/KEY: MISC_FEATURE
<222> LOCATION: (2)..(2)
<223> OTHER INFORMATION: Xaa is glutamine or glutamate residue
<220> FEATURE:
<221> NAME/KEY: MISC_FEATURE
<222> LOCATION: (3)..(3)
<223> OTHER INFORMATION: Xaa is alanine, glycine, serine or threonine
      residue
<220> FEATURE:
<221> NAME/KEY: MISC_FEATURE
<222> LOCATION: (4)..(4)
<223> OTHER INFORMATION: Xaa is leucine or threonine residue
<220> FEATURE:
<221> NAME/KEY: MISC_FEATURE
<222> LOCATION: (5)..(5)
<223> OTHER INFORMATION: Xaa is glutamine, glutamate or histidine
      residue
<220> FEATURE:
<221> NAME/KEY: MISC_FEATURE
<222> LOCATION: (6)..(6)
<223> OTHER INFORMATION: Xaa is threonine, tryptophan, methionine or
      valine residue
<220> FEATURE:
<221> NAME/KEY: MISC_FEATURE
<222> LOCATION: (8)..(8)
<223> OTHER INFORMATION: Xaa is nonpolar side chain
<220> FEATURE:
<221> NAME/KEY: MISC_FEATURE
<222> LOCATION: (9)..(9)
<223> OTHER INFORMATION: Xaa is threonine, serine or alanine residue

<400> SEQUENCE: 242

Met Xaa Xaa Xaa Xaa Xaa Pro Xaa Xaa
1               5

<210> SEQ ID NO 243
<211> LENGTH: 9
<212> TYPE: PRT
<213> ORGANISM: Artificial Sequence
<220> FEATURE:
<223> OTHER INFORMATION: light chain CDR3
<220> FEATURE:
<221> NAME/KEY: MISC_FEATURE
<222> LOCATION: (3)..(3)
```

```
<223> OTHER INFORMATION: Xaa is arginine, serine, leucine or alanine
      residue
<220> FEATURE:
<221> NAME/KEY: MISC_FEATURE
<222> LOCATION: (4)..(4)
<223> OTHER INFORMATION: Xaa is asparagine, serine or histidine residue
<220> FEATURE:
<221> NAME/KEY: MISC_FEATURE
<222> LOCATION: (5)..(5)
<223> OTHER INFORMATION: Xaa is serine or asparagine residue
<220> FEATURE:
<221> NAME/KEY: MISC_FEATURE
<222> LOCATION: (6)..(6)
<223> OTHER INFORMATION: Xaa is nonpolar side chain
<220> FEATURE:
<221> NAME/KEY: MISC_FEATURE
<222> LOCATION: (8)..(8)
<223> OTHER INFORMATION: Xaa is leucine, isoleucine, tyrosine or
      tryptophan residue

<400> SEQUENCE: 243

Gln Gln Xaa Xaa Xaa Xaa Pro Xaa Thr
1               5

<210> SEQ ID NO 244
<211> LENGTH: 10
<212> TYPE: PRT
<213> ORGANISM: Artificial Sequence
<220> FEATURE:
<223> OTHER INFORMATION: light chain CDR3
<220> FEATURE:
<221> NAME/KEY: MISC_FEATURE
<222> LOCATION: (4)..(4)
<223> OTHER INFORMATION: Xaa is aspartate or glutamine residue
<220> FEATURE:
<221> NAME/KEY: MISC_FEATURE
<222> LOCATION: (6)..(6)
<223> OTHER INFORMATION: Xaa is serine or aspartate residue
<220> FEATURE:
<221> NAME/KEY: MISC_FEATURE
<222> LOCATION: (8)..(8)
<223> OTHER INFORMATION: Xaa is glutamine, valine or tryptophan residue
<220> FEATURE:
<221> NAME/KEY: MISC_FEATURE
<222> LOCATION: (9)..(9)
<223> OTHER INFORMATION: Xaa is arginine residue or no residue

<400> SEQUENCE: 244

Gln Ser Tyr Xaa Ser Xaa Asn Xaa Xaa Val
1               5                   10

<210> SEQ ID NO 245
<211> LENGTH: 6
<212> TYPE: PRT
<213> ORGANISM: Artificial Sequence
<220> FEATURE:
<223> OTHER INFORMATION: heavy chain CDR1
<220> FEATURE:
<221> NAME/KEY: MISC_FEATURE
<222> LOCATION: (1)..(1)
<223> OTHER INFORMATION: Xaa is serine residue or no residue
<220> FEATURE:
<221> NAME/KEY: MISC_FEATURE
<222> LOCATION: (2)..(2)
<223> OTHER INFORMATION: Xaa is serine or asparagine residue
<220> FEATURE:
<221> NAME/KEY: MISC_FEATURE
<222> LOCATION: (3)..(3)
<223> OTHER INFORMATION: Xaa is asparagine and isoleucine residue

<400> SEQUENCE: 245

Xaa Xaa Xaa Trp Trp Ser
1               5
```

```
<210> SEQ ID NO 246
<211> LENGTH: 5
<212> TYPE: PRT
<213> ORGANISM: Artificial Sequence
<220> FEATURE:
<223> OTHER INFORMATION: heavy chain CDR1
<220> FEATURE:
<221> NAME/KEY: MISC_FEATURE
<222> LOCATION: (1)..(1)
<223> OTHER INFORMATION: Xaa is glycine, asparagine or aspartate residue
<220> FEATURE:
<221> NAME/KEY: MISC_FEATURE
<222> LOCATION: (2)..(2)
<223> OTHER INFORMATION: Xaa is tyrosine or phenylalanine residue

<400> SEQUENCE: 246

Xaa Xaa Tyr Trp Ser
1               5

<210> SEQ ID NO 247
<211> LENGTH: 5
<212> TYPE: PRT
<213> ORGANISM: Artificial Sequence
<220> FEATURE:
<223> OTHER INFORMATION: heavy chain CDR1
<220> FEATURE:
<221> NAME/KEY: MISC_FEATURE
<222> LOCATION: (3)..(3)
<223> OTHER INFORMATION: Xaa is alanine or glycine residue
<220> FEATURE:
<221> NAME/KEY: MISC_FEATURE
<222> LOCATION: (4)..(4)
<223> OTHER INFORMATION: Xaa is methionine or isoleucine residue
<220> FEATURE:
<221> NAME/KEY: MISC_FEATURE
<222> LOCATION: (5)..(5)
<223> OTHER INFORMATION: Xaa is serine or histidine residue

<400> SEQUENCE: 247

Ser Tyr Xaa Xaa Xaa
1               5

<210> SEQ ID NO 248
<211> LENGTH: 16
<212> TYPE: PRT
<213> ORGANISM: Artificial Sequence
<220> FEATURE:
<223> OTHER INFORMATION: heavy chain CDR2
<220> FEATURE:
<221> NAME/KEY: MISC_FEATURE
<222> LOCATION: (1)..(1)
<223> OTHER INFORMATION: Xaa is glutamate, tyrosine or serine residue
<220> FEATURE:
<221> NAME/KEY: MISC_FEATURE
<222> LOCATION: (2)..(2)
<223> OTHER INFORMATION: Xaa is isoleucine or valine residue
<220> FEATURE:
<221> NAME/KEY: MISC_FEATURE
<222> LOCATION: (3)..(3)
<223> OTHER INFORMATION: Xaa is tyrosine, asparagine or serine residue
<220> FEATURE:
<221> NAME/KEY: MISC_FEATURE
<222> LOCATION: (4)..(4)
<223> OTHER INFORMATION: Xaa is histidine, tyrosine, aspartate, or
      proline residue
<220> FEATURE:
<221> NAME/KEY: MISC_FEATURE
<222> LOCATION: (5)..(5)
<223> OTHER INFORMATION: Xaa is serine or arginine residue
<220> FEATURE:
<221> NAME/KEY: MISC_FEATURE
<222> LOCATION: (7)..(7)
<223> OTHER INFORMATION: Xaa is serine or arginine residue
<220> FEATURE:
```

```
<221> NAME/KEY: MISC_FEATURE
<222> LOCATION: (9)..(9)
<223> OTHER INFORMATION: Xaa is asparagine or tyrosine residue
<220> FEATURE:
<221> NAME/KEY: MISC_FEATURE
<222> LOCATION: (15)..(15)
<223> OTHER INFORMATION: Xaa is lysine or glutamate residue

<400> SEQUENCE: 248

Xaa Xaa Xaa Xaa Xaa Gly Xaa Thr Xaa Tyr Asn Pro Ser Leu Xaa Ser
1               5                   10                  15

<210> SEQ ID NO 249
<211> LENGTH: 17
<212> TYPE: PRT
<213> ORGANISM: Artificial Sequence
<220> FEATURE:
<223> OTHER INFORMATION: heavy chain CDR2
<220> FEATURE:
<221> NAME/KEY: MISC_FEATURE
<222> LOCATION: (1)..(1)
<223> OTHER INFORMATION: Xaa is threonine, alanine, valine or tyrosine
      residue
<220> FEATURE:
<221> NAME/KEY: MISC_FEATURE
<222> LOCATION: (4)..(4)
<223> OTHER INFORMATION: Xaa is glycine, serine or tyrosine residue
<220> FEATURE:
<221> NAME/KEY: MISC_FEATURE
<222> LOCATION: (5)..(5)
<223> OTHER INFORMATION: Xaa is serine, asparagine or aspartate residue
<220> FEATURE:
<221> NAME/KEY: MISC_FEATURE
<222> LOCATION: (6)..(6)
<223> OTHER INFORMATION: Xaa is glycine or serine residue
<220> FEATURE:
<221> NAME/KEY: MISC_FEATURE
<222> LOCATION: (7)..(7)
<223> OTHER INFORMATION: Xaa is glycine, serine or aspartate residue
<220> FEATURE:
<221> NAME/KEY: MISC_FEATURE
<222> LOCATION: (8)..(8)
<223> OTHER INFORMATION: Xaa is serine, threonine or asparagine residue
<220> FEATURE:
<221> NAME/KEY: MISC_FEATURE
<222> LOCATION: (9)..(9)
<223> OTHER INFORMATION: Xaa is threonine, lysine or isoleucine residue

<400> SEQUENCE: 249

Xaa Ile Ser Xaa Xaa Xaa Xaa Xaa Xaa Tyr Tyr Ala Asp Ser Val Lys
1               5                   10                  15

Gly

<210> SEQ ID NO 250
<211> LENGTH: 12
<212> TYPE: PRT
<213> ORGANISM: Artificial Sequence
<220> FEATURE:
<223> OTHER INFORMATION: heavy chain CDR3
<220> FEATURE:
<221> NAME/KEY: MISC_FEATURE
<222> LOCATION: (1)..(1)
<223> OTHER INFORMATION: Xaa is glutamate or no residue
<220> FEATURE:
<221> NAME/KEY: MISC_FEATURE
<222> LOCATION: (2)..(2)
<223> OTHER INFORMATION: Xaa is tyrosine, glycine or serine or no
      residue
<220> FEATURE:
<221> NAME/KEY: MISC_FEATURE
<222> LOCATION: (3)..(3)
<223> OTHER INFORMATION: Xaa is serine, asparagine, tryptophan or
      glutamate or no residue
<220> FEATURE:
```

-continued

```
<221> NAME/KEY: MISC_FEATURE
<222> LOCATION: (4)..(4)
<223> OTHER INFORMATION: Xaa is serine, aspartate, tryptophan, alanine,
      arginine, threonine, glutamine, leucine or glutamate or no residue
<220> FEATURE:
<221> NAME/KEY: MISC_FEATURE
<222> LOCATION: (5)..(5)
<223> OTHER INFORMATION: Xaa is serine, glycine, asparagine, threonine,
      tryptophan, alanine, valine or isoleucine residue
<220> FEATURE:
<221> NAME/KEY: MISC_FEATURE
<222> LOCATION: (6)..(6)
<223> OTHER INFORMATION: Xaa is arginine, glutamine, tyrosine, valine,
      alanine, glycine, serine, phenylalanine or tryptophan residue
<220> FEATURE:
<221> NAME/KEY: MISC_FEATURE
<222> LOCATION: (7)..(7)
<223> OTHER INFORMATION: Xaa is leucine, asparagine, aspartate,
      threonine, tryptophan, tyrosine, valine, alanine, or histidine
      residue
<220> FEATURE:
<221> NAME/KEY: MISC_FEATURE
<222> LOCATION: (8)..(8)
<223> OTHER INFORMATION: Xaa is aspartate, serine, asparagine or
      glutamine residue
<220> FEATURE:
<221> NAME/KEY: MISC_FEATURE
<222> LOCATION: (9)..(9)
<223> OTHER INFORMATION: Xaa is alanine or proline residue

<400> SEQUENCE: 250

Xaa Xaa Xaa Xaa Xaa Xaa Xaa Xaa Xaa Phe Asp Ile
1               5                   10

<210> SEQ ID NO 251
<211> LENGTH: 14
<212> TYPE: PRT
<213> ORGANISM: Artificial Sequence
<220> FEATURE:
<223> OTHER INFORMATION: heavy chain CDR3
<220> FEATURE:
<221> NAME/KEY: MISC_FEATURE
<222> LOCATION: (1)..(1)
<223> OTHER INFORMATION: Xaa is alanine or no residue
<220> FEATURE:
<221> NAME/KEY: MISC_FEATURE
<222> LOCATION: (2)..(2)
<223> OTHER INFORMATION: Xaa is glutamate, tryosine or glycine or no
      residue
<220> FEATURE:
<221> NAME/KEY: MISC_FEATURE
<222> LOCATION: (3)..(3)
<223> OTHER INFORMATION: Xaa is serine, asparagine, tryptophan,
      glutamate or no residue
<220> FEATURE:
<221> NAME/KEY: MISC_FEATURE
<222> LOCATION: (4)..(4)
<223> OTHER INFORMATION: Xaa is aspartate, glycine, serine, or valine
      residue, or no residue
<220> FEATURE:
<221> NAME/KEY: MISC_FEATURE
<222> LOCATION: (5)..(5)
<223> OTHER INFORMATION: Xaa is serine, glycine, or aspartate residue,
      or no residue
<220> FEATURE:
<221> NAME/KEY: MISC_FEATURE
<222> LOCATION: (6)..(6)
<223> OTHER INFORMATION: Xaa is glycine, phenylalanine, aspartate,
      serine, tryptophan, or tyrosine residue, or no residue
<220> FEATURE:
<221> NAME/KEY: MISC_FEATURE
<222> LOCATION: (7)..(7)
<223> OTHER INFORMATION: Xaa is a tyrosine, tryptophan, serine, or
      aspartate residue, or no residue
<220> FEATURE:
<221> NAME/KEY: MISC_FEATURE
<222> LOCATION: (8)..(8)
```

```
<223> OTHER INFORMATION: Xaa is aspartate, arginine, serine, glycine,
      tyrosine, or tryptophan residue
<220> FEATURE:
<221> NAME/KEY: MISC_FEATURE
<222> LOCATION: (9)..(9)
<223> OTHER INFORMATION: Xaa is tyrosine, isoleucine, leucine,
      phenylalanine, or lysine residue
<220> FEATURE:
<221> NAME/KEY: MISC_FEATURE
<222> LOCATION: (10)..(10)
<223> OTHER INFORMATION: Xaa is tyrosine, phenylalanine, aspartate, or
      glycine residue
<220> FEATURE:
<221> NAME/KEY: MISC_FEATURE
<222> LOCATION: (11)..(11)
<223> OTHER INFORMATION: Xaa is glycine, tyrosine, or asparagine residue

<400> SEQUENCE: 251

Xaa Xaa Xaa Xaa Xaa Xaa Xaa Xaa Xaa Xaa Xaa Met Asp Val
1               5                   10

<210> SEQ ID NO 252
<211> LENGTH: 11
<212> TYPE: PRT
<213> ORGANISM: Artificial Sequence
<220> FEATURE:
<223> OTHER INFORMATION: heavy chain CDR3
<220> FEATURE:
<221> NAME/KEY: MISC_FEATURE
<222> LOCATION: (1)..(1)
<223> OTHER INFORMATION: Xaa is aspartate or valine residue, or no
      residue
<220> FEATURE:
<221> NAME/KEY: MISC_FEATURE
<222> LOCATION: (2)..(2)
<223> OTHER INFORMATION: Xaa is glycine, tyrosine, arginine, or
      aspartate residue, or no residue,
<220> FEATURE:
<221> NAME/KEY: MISC_FEATURE
<222> LOCATION: (3)..(3)
<223> OTHER INFORMATION: Xaa is asparagine, leucine, glycine,
      isoleucine, serine, valine, phenylalanine, or tyrosine residue, or
      no residue
<220> FEATURE:
<221> NAME/KEY: MISC_FEATURE
<222> LOCATION: (4)..(4)
<223> OTHER INFORMATION: Xaa is leucine, serine, tryptophan, alanine,
      tyrosine, isoleucine, glycine, or aspartate residue, or no residue
<220> FEATURE:
<221> NAME/KEY: MISC_FEATURE
<222> LOCATION: (5)..(5)
<223> OTHER INFORMATION: Xaa is glycine, alanine, tyrosine, serine,
      aspartate, or leucine residue
<220> FEATURE:
<221> NAME/KEY: MISC_FEATURE
<222> LOCATION: (6)..(6)
<223> OTHER INFORMATION: Xaa is valine, alanine, glycine, threonine,
      proline, histidine, or glutamine residue
<220> FEATURE:
<221> NAME/KEY: MISC_FEATURE
<222> LOCATION: (7)..(7)
<223> OTHER INFORMATION: Xaa is glutamate, glycine, serine, aspartate,
      glycine, valine, tryptophan, histidine, or arginine residue
<220> FEATURE:
<221> NAME/KEY: MISC_FEATURE
<222> LOCATION: (8)..(8)
<223> OTHER INFORMATION: Xaa is glutamine, alanine, glycine, tyrosine,
      proline, leucine, aspartate, or serine residue
<220> FEATURE:
<221> NAME/KEY: MISC_FEATURE
<222> LOCATION: (9)..(9)
<223> OTHER INFORMATION: Xaa is nonpolar side chain residue
<220> FEATURE:
<221> NAME/KEY: MISC_FEATURE
<222> LOCATION: (10)..(10)
<223> OTHER INFORMATION: Xaa is aspartate or alanine residue
```

<400> SEQUENCE: 252

Xaa Xaa Xaa Xaa Xaa Xaa Xaa Xaa Xaa Xaa Tyr
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Heavy chain CDR3
<220> FEATURE:
<221> NAME/KEY: MISC_FEATURE
<222> LOCATION: (1)..(1)
<223> OTHER INFORMATION: Xaa is glycine residue, or no residue
<220> FEATURE:
<221> NAME/KEY: MISC_FEATURE
<222> LOCATION: (2)..(2)
<223> OTHER INFORMATION: Xaa is proline residue, or no residue
<220> FEATURE:
<221> NAME/KEY: MISC_FEATURE
<222> LOCATION: (3)..(3)
<223> OTHER INFORMATION: Xaa is arginine or aspartate residue, or no
      residue
<220> FEATURE:
<221> NAME/KEY: MISC_FEATURE
<222> LOCATION: (4)..(4)
<223> OTHER INFORMATION: Xaa is histidine or proline residue
<220> FEATURE:
<221> NAME/KEY: MISC_FEATURE
<222> LOCATION: (5)..(5)
<223> OTHER INFORMATION: Xaa is arginine or glycine residue
<220> FEATURE:
<221> NAME/KEY: MISC_FEATURE
<222> LOCATION: (6)..(6)
<223> OTHER INFORMATION: Xaa is arginine, serine, or phenylalanine
      residue
<220> FEATURE:
<221> NAME/KEY: MISC_FEATURE
<222> LOCATION: (7)..(7)
<223> OTHER INFORMATION: Xaa is aspartate or serine residue
<220> FEATURE:
<221> NAME/KEY: MISC_FEATURE
<222> LOCATION: (8)..(8)
<223> OTHER INFORMATION: Xaa is glycine, tryptophan, or tyrosine residue
<220> FEATURE:
<221> NAME/KEY: MISC_FEATURE
<222> LOCATION: (9)..(9)
<223> OTHER INFORMATION: Xaa is tyrosine or alanine residue
<220> FEATURE:
<221> NAME/KEY: MISC_FEATURE
<222> LOCATION: (10)..(10)
<223> OTHER INFORMATION: Xaa is asparagine or tryptophan residue
<220> FEATURE:
<221> NAME/KEY: MISC_FEATURE
<222> LOCATION: (14)..(14)
<223> OTHER INFORMATION: Xaa is asparagine or leucine residue

<400> SEQUENCE: 253

Xaa Xaa Xaa Xaa Xaa Xaa Xaa Xaa Xaa Tyr Phe Asp Xaa
1               5                   10

<210> SEQ ID NO 254
<211> LENGTH: 15
<212> TYPE: PRT
<213> ORGANISM: Artificial Sequence
<220> FEATURE:
<223> OTHER INFORMATION: heavy chain CDR3
<220> FEATURE:
<221> NAME/KEY: MISC_FEATURE
<222> LOCATION: (1)..(1)
<223> OTHER INFORMATION: Xaa is phenylalanine residue, or no residue
<220> FEATURE:
<221> NAME/KEY: MISC_FEATURE
<222> LOCATION: (2)..(2)
<223> OTHER INFORMATION: Xaa is asparagine or glycine residue, or no

```
                residue
<220> FEATURE:
<221> NAME/KEY: MISC_FEATURE
<222> LOCATION: (3)..(3)
<223> OTHER INFORMATION: Xaa is tyrosine or a leucine residue, or no
      residue
<220> FEATURE:
<221> NAME/KEY: MISC_FEATURE
<222> LOCATION: (4)..(4)
<223> OTHER INFORMATION: Xaa is a tyrosine or glycine residue, or no
      residue
<220> FEATURE:
<221> NAME/KEY: MISC_FEATURE
<222> LOCATION: (8)..(8)
<223> OTHER INFORMATION: Xaa is a glycine, serine, or valine residue
<220> FEATURE:
<221> NAME/KEY: MISC_FEATURE
<222> LOCATION: (9)..(9)
<223> OTHER INFORMATION: Xaa is tyrosine, phenylalanine, tryptophan,
      or glutamine residue,
      or no residue
<220> FEATURE:
<221> NAME/KEY: MISC_FEATURE
<222> LOCATION: (10)..(10)
<223> OTHER INFORMATION: Xaa is tyrosine, glycine, or isoleucine
      residue, or no residue
<220> FEATURE:
<221> NAME/KEY: MISC_FEATURE
<222> LOCATION: (11)..(11)
<223> OTHER INFORMATION: Xaa is tyrosine, leucine, or glycine residue,
      or no residue
<220> FEATURE:
<221> NAME/KEY: MISC_FEATURE
<222> LOCATION: (12)..(12)
<223> OTHER INFORMATION: Xaa is methionine,  glycine, or phenylalanine
      residue, or no residue
<220> FEATURE:
<221> NAME/KEY: MISC_FEATURE
<222> LOCATION: (13)..(13)
<223> OTHER INFORMATION: Xaa is  aspartate or methionine residue, or no
      residue
<220> FEATURE:
<221> NAME/KEY: MISC_FEATURE
<222> LOCATION: (14)..(14)
<223> OTHER INFORMATION: Xaa is a valine, aspartate, or tyrosine
      residue, or no residue
<220> FEATURE:
<221> NAME/KEY: MISC_FEATURE
<222> LOCATION: (15)..(15)
<223> OTHER INFORMATION: Xaa is a valine residue, or no residue

<400> SEQUENCE: 254

Xaa Xaa Xaa Xaa Asp Ser Ser Xaa Xaa Xaa Xaa Xaa Xaa Xaa Xaa
1               5                   10                  15

<210> SEQ ID NO 255
<211> LENGTH: 8
<212> TYPE: DNA
<213> ORGANISM: Artificial Sequence
<220> FEATURE:
<223> OTHER INFORMATION: polypeptide

<400> SEQUENCE: 255 dykddddk                                                            8

<210> SEQ ID NO 256
<211> LENGTH: 37
<212> TYPE: DNA
<213> ORGANISM: Artificial Sequence
<220> FEATURE:
<223> OTHER INFORMATION: nucleic acid

<400> SEQUENCE: 256
agcaagcttc caccatgaag tctggctccg gaggagg                            37
```

<210> SEQ ID NO 257
<211> LENGTH: 36
<212> TYPE: DNA
<213> ORGANISM: Artificial Sequence
<220> FEATURE:
<223> OTHER INFORMATION: nucleic acid

<400> SEQUENCE: 257
atttgtcgac ttcgtccaga tggatgaagt tttcat 36

<210> SEQ ID NO 258
<211> LENGTH: 3486
<212> TYPE: DNA
<213> ORGANISM: Artificial Sequence
<220> FEATURE:
<223> OTHER INFORMATION: nucleic acid

<400> SEQUENCE: 258

| | |
|---|---|
| atgaagtctg gctccggagg agggtccccg acctcgctgt gggggctcct gtttctctcc | 60 |
| gccgcgctct cgctctggcc gacgagtgga gaaatctgcg gccaggcat cgacatccgc | 120 |
| aacgactatc agcagctgaa gcgcctggag aactgcacgg tgatcgaggg ctacctccac | 180 |
| atcctgctca tctccaaggc cgaggactac cgcagctacc gcttccccaa gctcacggtc | 240 |
| attaccgagt acttgctgct gttccgagtg gctggcctcg agagcctcgg agacctcttc | 300 |
| cccaacctca cggtcatccg cggctggaaa ctcttctaca actacgccct ggtcatcttc | 360 |
| gagatgacca atctcaagga tattgggctt tacaacctga ggaacattac tcgggggggcc | 420 |
| atcaggattg agaaaaatgc tgacctctgt tacctctcca ctgtggactg gtccctgatc | 480 |
| ctggatgcgg tgtccaataa ctacattgtg ggaataagc ccccaaagga atgtgggggac | 540 |
| ctgtgtccag ggaccatgga ggagaagccg atgtgtgaga agaccaccat caacaatgag | 600 |
| tacaactacc gctgctggac cacaaaccgc tgccagaaaa tgtgcccaag cacgtgtggg | 660 |
| aagcgggcgt gcaccgagaa caatgagtgc tgccaccccg agtgcctggg cagctgcagc | 720 |
| gcgcctgaca cgacacggc ctgtgtagct tgccgccact actactatgc cggtgtctgt | 780 |
| gtgcctgcct gcccgcccaa cacctacagg tttgagggct ggcgctgtgt ggaccgtgac | 840 |
| ttctgcgcca acatcctcag cgccgagagc agcgactccg aggggtttgt gatccacgac | 900 |
| ggcgagtgca tgcaggagtg cccctcgggc ttcatccgca acggcagcca gagcatgtac | 960 |
| tgcatcccct tgtgaaggtcc ttgcccgaag gtctgtgagg aagaaaagaa acaaagacc | 1020 |
| attgattctg ttacttctgc tcagatgctc caaggatgca ccatcttcaa gggcaatttg | 1080 |
| ctcattaaca tccgacgggg gaataacatt gcttcagagc tggagaactt catgggggctc | 1140 |
| atcgaggtgg tgacgggcta cgtgaagatc cgccattctc atgccttggt ctccttgtcc | 1200 |
| ttcctaaaaa accttcgcct catcctagga gaggagcagc tagaagggaa ttactccttc | 1260 |
| tacgtcctcg acaaccagaa cttgcagcaa ctgtgggact gggaccaccg caacctgacc | 1320 |
| atcaaagcag ggaaaatgta ctttgctttc aatcccaaat tatgtgttc cgaaatttac | 1380 |
| cgcatggagg aagtgacggg gactaaaggg cgccaaagca aggggacat aaacaccagg | 1440 |
| aacaacgggg agagagcctc ctgtgaaagt gacgtcctgc atttcacctc caccaccacg | 1500 |
| tcgaagaatc gcatcatcat aacctggcac cggtaccggc ccctgactac cagggatctc | 1560 |
| atcagcttca ccgtttacta caaggaagca ccctttaaga atgtcacaga gtatgatggg | 1620 |
| caggatgcct gcggctccaa cagctggaac atggtggacg tggacctccc gcccaacaag | 1680 |

-continued

```
gacgtggagc cggcatctt actacatggg ctgaagccct ggactcagta cgccgtttac   1740
gtcaaggctg tgaccctcac catggtggag aacgaccata tccgtgggc caagagtgag   1800 atcttgtaca ttcgcaccaa tgcttcagtt ccttccattc ccttggacgt tctttcagca   1860
tcgaactcct cttctcagtt aatcgtgaag tggaaccctc cctctctgcc caacggcaac   1920
ctgagttact acattgtgcg ctggcagcgg cagcctcagg acggctacct ttaccggcac   1980
aattactgct ccaaagacaa atccccatc aggaagtatg ccgacggcac catcgacatt   2040
gaggaggtca cagagaaccc caagactgag gtgtgtggtg gggagaaagg gccttgctgc   2100
gcctgcccca aaactgaagc cgagaagcag gccgagaagg aggaggctga ataccgcaaa   2160
gtctttgaga atttcctgca caactccatc ttcgtgccca gacctgaaag gaagcggaga   2220
gatgtcatgc aagtggccaa caccaccatg tccagccgaa gcaggaacac cacggccgca   2280
gacacctaca acatcactga cccggaagag ctggagacag agtacccttt ctttgagagc   2340
agagtggata caaggagag aactgtcatt tctaaccttc ggcctttcac attgtaccgc   2400
atcgatatcc acagctgcaa ccacgaggct gagaagctgg gctgcagcgc ctccaacttc   2460
gtctttgcaa ggactatgcc cgcagaagga gcagatgaca ttcctgggcc agtgacctgg   2520
gagccaaggc ctgaaaactc catcttttta aagtggccgg aacctgagaa tcccaatgga   2580
ttgattctaa tgtatgaaat aaaatacgga tcacaagttg aggatcagcg agaatgtgtg   2640
tccagacagg aatacaggaa gtatggaggg gccaagctaa accggctaaa cccggggaac   2700
tacacagccc ggattcaggc cacatctctc tctgggaatg ggtcgtggac agatcctgtg   2760
ttcttctatg tccaggccaa aacaggatat gaaaacttca tccatctgga cgaagtcgac   2820
ggttgtaagc cttgcatatg tacagtccca gaagtatcat ctgtcttcat cttcccccca   2880
aagcccaagg atgtgctcac cattactctg actcctaagg tcacgtgtgt tgtggtagac   2940
atcagcaagg atgatcccga ggtccagttc agctggtttg tagatgatgt ggaggtgcac   3000
acagctcaga cgcaaccccg ggaggagcag ttcaacagca ctttccgctc agtcagtgaa   3060
cttcccatca tgcaccagga ctggctcaat ggcaaggagt tcaaatgcag gtaaacagt   3120 gcagctttcc ctgcccccat cgagaaaacc atctccaaaa ccaaaggcag accgaaggct   3180
ccacaggtgt acaccattcc acctcccaag gagcagatgg ccaaggataa agtcagtctg   3240
acctgcatga taacagactt cttccctgaa gacattactg tggagtggca gtggaatggg   3300
cagccagcgg agaactacaa gaacactcag cccatcatgg acacagatgg ctcttacttc   3360
gtctacagca agctcaatgt gcagaagagc aactgggagg caggaaatac tttcacctgc   3420
tctgtgttac atgagggcct gcacaaccac catactgaga agagcctctc ccactctcct   3480
ggtaaa                                                             3486
```

<210> SEQ ID NO 259
<211> LENGTH: 32
<212> TYPE: DNA
<213> ORGANISM: Artificial Sequence
<220> FEATURE:
<223> OTHER INFORMATION: nucleic acid

<400> SEQUENCE: 259

```
agcaagcttc caccatgggc accgggggcc gg                                32
```

<210> SEQ ID NO 260
<211> LENGTH: 37
<212> TYPE: DNA
<213> ORGANISM: Artificial Sequence

```
<220> FEATURE:
<223> OTHER INFORMATION: nucleic acid

<400> SEQUENCE: 260
atttgtcgac ttttgcaata tttgacggga cgtctaa                              37

<210> SEQ ID NO 261
<211> LENGTH: 3540
<212> TYPE: DNA
<213> ORGANISM: Artificial Sequence
<220> FEATURE:
<223> OTHER INFORMATION: nucleic acid

<400> SEQUENCE: 261
atgggcaccg ggggccggcg gggggcggcg gccgcgccgc tgctggtggc ggtggccgcg    60
ctgctactgg gcgccgcggg ccacctgtac cccggagagg tgtgtcccgg catggatatc   120
cggaacaacc tcactaggtt gcatgagctg gagaattgct ctgtcatcga aggacacttg   180
cagatactct tgatgttcaa aacgaggccc gaagatttcc gagacctcag tttccccaaa   240
ctcatcatga tcactgatta cttgctgctc ttccgggtct atgggctcga gagcctgaag   300
gacctgttcc ccaacctcac ggtcatccgg ggatcacgac tgttctttaa ctacgcgctg   360
gtcatcttcg agatggttca cctcaaggaa ctcggcctct acaacctgat gaacatcacc   420
cggggttctg tccgcatcga gaagaacaat gagctctgtt acttggccac tatcgactgg   480
tcccgtatcc tggattccgt ggaggataat cacatcgtgt tgaacaaaga tgacaacgag   540
gagtgtggag acatctgtcc gggtaccgcg aagggcaaga ccaactgccc cgccaccgtc   600
atcaacgggc agtttgtcga cgatgttgg actcatagtc actgccagaa agtttgcccg   660
accatctgta agtcacacgg ctgcaccgcc gaaggcctct gttgccacag cgagtgcctg   720
ggcaactgtt ctcagcccga cgaccccacc aagtgcgtgg cctgccgcaa cttctacctg   780
gacggcaggt gtgtggagac ctgcccgccc ccgtactacc acttccagga ctggcgctgt   840
gtgaacttca gcttctgcca ggacctgcac cacaaatgca gaactcgcg gaggcagggc   900 tgccaccagt acgtcattca aacaacaag tgcatccctg agtgtcctc cgggtacacg   960 atgaattcca gcaacttgct gtgcaccca tgcctgggtc cctgtccaa ggtgtgccac  1020 ctcctagaag gcgagaagac catcgactcg gtgacgtctg cccaggagct ccgaggatgc  1080
accgtcatca acgggagtct gatcatcaac attcgaggag gcaacaatct ggcagctgag  1140
ctagaagcca acctcggcct cattgaagaa atttcagggt atctaaaaat ccgccgatcc  1200
tacgctctgg tgtcactttc cttcttccgg aagttacgtc tgattcgagg agagaccttg  1260
gaaattggga actactcctt ctatgccttg gacaaccaga acctaaggca gctctgggac  1320
tggagcaaac acaacctcac caccactcag gggaaactct ctttccacta taccccaaa  1380 ctctgcttgt cagaaatcca aagatgaa gaagtttcag gaaccaaggg cgccaggag  1440 agaaacgaca ttgccctgaa gaccaatggg gacaaggcat cctgtgaaaa tgagttactt  1500 aaatttctctt acattcggac atctttgac aagatcttgc tgagatggga gccgtactgg  1560 cccccgact tccgagacct cttggggttc atgctgttct acaaagaggc cccttatcag  1620
aatgtgacgg agttcgatgg gcaggatgcg tgtggttcca acagtggac ggtggtagac  1680 attgacccac ccctgaggtc caacgacccc aaatcacaga ccacccagg tggctgatg  1740 cggggtctca gccctggac ccagtatgcc atctttgtga agaccctggt cacccttttcg  1800 gatgaacgcc ggacctatgg ggccaagagt gacatcattt atgtccagac agatgccacc  1860
```

| | |
|---|---|
| aacccctctg tgcccctgga tccaatctca gtgtctaact catcatccca gattattctg | 1920 |
| aagtggaaac caccctccga ccccaatggc aacatcaccc actacctggt tttctgggag | 1980 |
| aggcaggcgg aagacagtga gctgttcgag ctggattatt gcctcaaagg gctgaagctg | 2040 |
| ccctcgagga cctggtctcc accattcgag tctgaagatt ctcagaagca caaccagagt | 2100 |
| gagtatgagg attcggccgg cgaatgctgc tcctgtccaa agacagactc tcagatcctg | 2160 |
| aaggagctgg aggagtcctc gtttaggaag acgtttgagg attacctgca caacgtggtt | 2220 |
| ttcgtcccca gaaaaacctc ttcaggcact ggtgccgagg accctaggcc atctcggaaa | 2280 |
| cgcaggtccc ttggcgatgt tgggaatgtg acggtggccg tgcccacggt ggcagctttc | 2340 |
| cccaacactt cctcgaccag cgtgcccacg agtccggagg agcacaggcc ttttgagaag | 2400 |
| gtggtgaaca aggagtcgct ggtcatctcc ggcttgcgac acttcacggg ctatcgcatc | 2460 |
| gagctgcagg cttgcaacca ggacaccccct gaggaacggt gcagtgtggc agcctacgtc | 2520 |
| agtgcgagga ccatgcctga agccaaggct gatgacattg ttggccctgt gacgcatgaa | 2580 |
| atctttgaga caacgtcgt ccacttgatg tggcaggagc cgaaggagcc caatggtctg | 2640 |
| atcgtgctgt atgaagtgag ttatcggcga tatggtgatg aggagctgca tctctgcgtc | 2700 |
| tcccgcaagc acttcgctct ggaacggggc tgcaggctgc gtgggctgtc accggggaac | 2760 |
| tacagcgtgc gaatccgggc cacctcccctt gcgggcaacg gctcttggac ggaacccacc | 2820 |
| tatttctacg tgacagacta tttagacgtc ccgtcaaata ttgcaaaagt cgacggttgt | 2880 |
| aagccttgca tatgtacagt cccagaagta tcatctgtct tcatcttccc cccaaagccc | 2940 |
| aaggatgtgc tcaccattac tctgactcct aaggtcacgt gtgttgtggt agacatcagc | 3000 |
| aaggatgatc ccgaggtcca gttcagctgg tttgtagatg atgtggaggt gcacacagct | 3060 |
| cagacgcaac cccgggagga gcagttcaac agcacttttcc gctcagtcag tgaacttccc | 3120 |
| atcatgcacc aggactggct caatggcaag gagttcaaat gcagggtaaa cagtgcagct | 3180 |
| ttccctgccc ccatcgagaa aaccatctcc aaaaccaaag gcagaccgaa ggctccacag | 3240 |
| gtgtacacca ttccacctcc caaggagcag atggccaagg ataaagtcag tctgacctgc | 3300 |
| atgataacag acttcttccc tgaagacatt actgtggagt ggcagtggaa tgggcagcca | 3360 |
| gcggagaact acaagaacac tcagcccatc atggacacag atggctctta cttcgtctac | 3420 |
| agcaagctca atgtgcagaa gagcaactgg gaggcaggaa atactttcac ctgctctgtg | 3480 |
| ttacatgagg gcctgcacaa ccaccatact gagaagagcc tctcccactc tcctggtaaa | 3540 |

<210> SEQ ID NO 262
<211> LENGTH: 1409
<212> TYPE: DNA
<213> ORGANISM: Artificial Sequence
<220> FEATURE:
<223> OTHER INFORMATION: nucleic acid

<400> SEQUENCE: 262

| | |
|---|---|
| tctagaccac catggacatc aggctcagct tagttttcct tgtccttttc ataaaaggtg | 60 |
| tccagtgtga ggtagaactg gtggagtctg ggggcggctt agtacaacct ggaaggtcca | 120 |
| tgacactctc ctgtgcagcc tcgggattca ctttcagaac ctatggcatg gcctgggtcc | 180 |
| gccaggccca acgaagggt ctggagtggg tctcatcaat tactgctagt ggtggtacca | 240 |
| cctactatcg agactccgtg aagggccgct tcactatttt tagggataat gcaaaaagta | 300 |
| ccctatacct gcagatggac agtccgaggc tgaggacac ggccactat ttctgtacat | 360 |
| caatttcgga atactgggc cacggagtca tggtcaccgt ctctagtgcc tccaccaagg | 420 |

```
gcccatcggt cttcccctg gcaccctcct ccaagagcac ctctgggggc acagcggccc    480
tgggctgcct ggtcaaggac tacttccccg aaccggtgac ggtgtcgtgg aactcaggcg    540
ccctgaccag cggcgtgcac accttcccgg ctgtcctaca gtcctcagga ctctactccc    600
tcagcagcgt ggtgaccgtg ccctccagca gcttgggcac ccagacctac atctgcaacg    660
tgaatcacaa gcccagcaac accaaggtgg acaagaaagt tgagcccaaa tcttgtgaca    720
aaactcacac atgcccaccg tgcccagcac ctgaactcct ggggggaccg tcagtcttcc    780 tcttccccc aaaacccaag gacaccctca tgatctcccg gacccctgag gtcacatgcg    840
tggtggtgga cgtgagccac gaagaccctg aggtcaagtt caactggtac gtggacggcg    900
tggaggtgca taatgccaag acaaagccgc gggaggagca gtacaacagc acgtaccgtg    960
tggtcagcgt cctcaccgtc ctgcaccagg actggctgaa tggcaaggag tacaagtgca    1020
aggtctccaa caaagccctc ccagccccca tcgagaaaac catctccaaa gccaaagggc    1080
agccccgaga accacaggtg tacaccctgc ccccatcccg ggatgagctg accaagaacc    1140
aggtcagcct gacctgcctg gtcaaaggct tctatcccag cgacatcgcc gtggagtggg    1200
agagcaatgg gcagccggag aacaactaca agaccacgcc tcccgtgctg gactccgacg    1260
gctccttctt cctctatagc aagctcaccg tggacaagag caggtggcag caggggaacg    1320
tcttctcatg ctccgtgatg catgaggctc tgcacaacca ctacacgcag aagagcctct    1380
ccctgtctcc gggtaaatga taagtcgac                                      1409
```

<210> SEQ ID NO 263
<211> LENGTH: 22
<212> TYPE: PRT
<213> ORGANISM: Artificial Sequence
<220> FEATURE:
<223> OTHER INFORMATION: protein

<400> SEQUENCE: 263

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 264
<211> LENGTH: 22
<212> TYPE: PRT
<213> ORGANISM: Artificial Sequence
<220> FEATURE:
<223> OTHER INFORMATION: protein

<400> SEQUENCE: 264

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 265
<211> LENGTH: 28
<212> TYPE: DNA
<213> ORGANISM: Artificial Sequence
<220> FEATURE:
<223> OTHER INFORMATION: nucleic acid

<400> SEQUENCE: 265
gcaagcttgg gagaaatctg cgggccag                                        28

<210> SEQ ID NO 266
<211> LENGTH: 32
<212> TYPE: DNA
<213> ORGANISM: Artificial Sequence
<220> FEATURE:
<223> OTHER INFORMATION: nucleic acid

<400> SEQUENCE: 266
attgcggccg cttcatatcc tgttttggcc tg                                    32

<210> SEQ ID NO 267
<211> LENGTH: 30
<212> TYPE: DNA
<213> ORGANISM: Artificial Sequence
<220> FEATURE:
<223> OTHER INFORMATION: nucleic acid

<400> SEQUENCE: 267
attgcggccg ccccacattc ctttgggggc                                       30

<210> SEQ ID NO 268
<211> LENGTH: 28
<212> TYPE: DNA
<213> ORGANISM: Artificial Sequence
<220> FEATURE:
<223> OTHER INFORMATION: nucleic acid

<400> SEQUENCE: 268
agcaagcttg gacctgtgtc cagggacc                                         28

<210> SEQ ID NO 269
<211> LENGTH: 30
<212> TYPE: DNA
<213> ORGANISM: Artificial Sequence
<220> FEATURE:
<223> OTHER INFORMATION: nucleic acid

<400> SEQUENCE: 269
attgcggccg cgcaaggacc ttcacaaggg                                       30

<210> SEQ ID NO 270
<211> LENGTH: 29
<212> TYPE: DNA
<213> ORGANISM: Artificial Sequence
<220> FEATURE:
<223> OTHER INFORMATION: nucleic acid

<400> SEQUENCE: 270
agcaagcttg ccgaaggtct gtgaggaag                                        29

<210> SEQ ID NO 271
<211> LENGTH: 30
<212> TYPE: DNA
<213> ORGANISM: Artificial Sequence
<220> FEATURE:
<223> OTHER INFORMATION: nucleic acid

<400> SEQUENCE: 271
attgcggccg cactttcaca ggaggctctc                                       30

<210> SEQ ID NO 272
<211> LENGTH: 30
<212> TYPE: DNA
<213> ORGANISM: Artificial Sequence
<220> FEATURE:
<223> OTHER INFORMATION: nucleic acid

```
<400> SEQUENCE: 272
agcaagcttg gacgtcctgc atttcacctc                                    30

<210> SEQ ID NO 273
<211> LENGTH: 32
<212> TYPE: DNA
<213> ORGANISM: Artificial Sequence
<220> FEATURE:
<223> OTHER INFORMATION: nucleic acid

<400> SEQUENCE: 273
attgcggccg cggtgcgaat gtacaagatc tc                                 32

<210> SEQ ID NO 274
<211> LENGTH: 32
<212> TYPE: DNA
<213> ORGANISM: Artificial Sequence
<220> FEATURE:
<223> OTHER INFORMATION: nucleic acid

<400> SEQUENCE: 274
agcaagcttg aatgcttcag ttccttccat tc                                 32

<210> SEQ ID NO 275
<211> LENGTH: 33
<212> TYPE: DNA
<213> ORGANISM: Artificial Sequence
<220> FEATURE:
<223> OTHER INFORMATION: nucleic acid

<400> SEQUENCE: 275
attgcggccg cagtccttgc aaagacgaag ttg                                33

<210> SEQ ID NO 276
<211> LENGTH: 29
<212> TYPE: DNA
<213> ORGANISM: Artificial Sequence
<220> FEATURE:
<223> OTHER INFORMATION: nucleic acid

<400> SEQUENCE: 276
agcaagcttg atgcccgcag aaggagcag                                     29

<210> SEQ ID NO 277
<211> LENGTH: 32
<212> TYPE: DNA
<213> ORGANISM: Artificial Sequence
<220> FEATURE:
<223> OTHER INFORMATION: nucleic acid

<400> SEQUENCE: 277
attgcggccg ctttaatggc cactctggtt tc                                 32

<210> SEQ ID NO 278
<211> LENGTH: 29
<212> TYPE: DNA
<213> ORGANISM: Artificial Sequence
<220> FEATURE:
<223> OTHER INFORMATION: nucleic acid

<400> SEQUENCE: 278
agcaagcttg ggagaaatct gcgggccag                                     29

<210> SEQ ID NO 279
```

```
-continued
<211> LENGTH: 29
<212> TYPE: DNA
<213> ORGANISM: Artificial Sequence
<220> FEATURE:
<223> OTHER INFORMATION: nucleic acid

<400> SEQUENCE: 279
agcaagcttg ggagaaatct gcgggccag                                            29
```